United States Patent
Tonogaki et al.

(10) Patent No.: US 9,133,186 B2
(45) Date of Patent: *Sep. 15, 2015

(54) HETERO RING-FUSED IMIDAZOLE DERIVATIVE HAVING AMPK ACTIVATING EFFECT

(75) Inventors: Keisuke Tonogaki, Osaka (JP); Akira Ino, Osaka (JP); Eiichi Kojima, Osaka (JP); Manabu Katou, Osaka (JP); Masafumi Iwatsu, Osaka (JP); Nobuyuki Tanaka, Osaka (JP); Masahiko Fujioka, Osaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/822,189

(22) PCT Filed: Sep. 8, 2011

(86) PCT No.: PCT/JP2011/070429
§ 371 (c)(1),
(2), (4) Date: Mar. 11, 2013

(87) PCT Pub. No.: WO2012/033149
PCT Pub. Date: Mar. 15, 2012

(65) Prior Publication Data
US 2013/0184240 A1    Jul. 18, 2013

(30) Foreign Application Priority Data

Sep. 10, 2010  (JP) .............................. 2010-203029
Dec. 9, 2010   (JP) .............................. 2010-274179
Jul. 1, 2011   (JP) .............................. 2011-147266

(51) Int. Cl.
*C07D 487/04* (2006.01)
*C07D 471/04* (2006.01)
(Continued)

(52) U.S. Cl.
CPC ............ *C07D 471/04* (2013.01); *C07D 473/00* (2013.01); *C07D 473/06* (2013.01); *C07D 473/28* (2013.01); *C07D 473/30* (2013.01);
(Continued)

(58) Field of Classification Search
CPC ... C07D 417/04; C07D 487/04; C07D 471/04
USPC .............. 514/393, 230.5; 546/118; 548/303.1
See application file for complete search history.

(56) References Cited

U.S. PATENT DOCUMENTS 8,563,575 B2 * 10/2013 Taniguchi et al. ............ 514/301
2003/0069257 A1 * 4/2003 Li et al. .......................... 514/256
(Continued)

FOREIGN PATENT DOCUMENTS

JP         5 339224      12/1993
JP       2005 533067     11/2005
(Continued)

OTHER PUBLICATIONS

Oguchi et al. "Molecular design, Synthesis, and Hypoglycemic Activity of a Series of Thiazolidine-2,4-diones" J. Med. Chem., 2000, vol. 43, pp. 3052-3066.*
(Continued)

*Primary Examiner* — Kendra D Carter
(74) *Attorney, Agent, or Firm* — Oblon, McClelland, Maier & Neustadt, L.L.P.

(57) ABSTRACT

Disclosed is a compound which is useful as an AMPK activator. A compound represented by the formula:

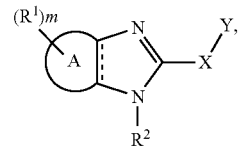

its pharmaceutically acceptable salt, or a solvate thereof, wherein
a group represented by the formula:

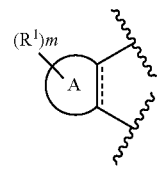

is a group represented by the formula:

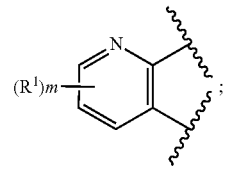

$R^1$ is each independently halogen, hydroxy, cyano, nitro, carboxy, substituted or unsubstituted alkyl, substituted or unsubstituted alkenyl or the like;
m is an integer of 0 to 3;
$R^2$ is hydrogen, or substituted or unsubstituted alkyl;
X is —O—; and
Y is substituted or unsubstituted aryl, or substituted or unsubstituted heteroaryl.

18 Claims, No Drawings

(51) Int. Cl.
*C07D 473/00* (2006.01)
*C07D 473/06* (2006.01)
*C07D 473/28* (2006.01)
*C07D 491/048* (2006.01)
*C07D 495/04* (2006.01)
*C07D 513/04* (2006.01)
*C07D 473/30* (2006.01)
*C07D 491/08* (2006.01)
*C07D 519/00* (2006.01)

(52) U.S. Cl.
CPC .......... *C07D 487/04* (2013.01); *C07D 491/048* (2013.01); *C07D 491/08* (2013.01); *C07D 495/04* (2013.01); *C07D 513/04* (2013.01); *C07D 519/00* (2013.01)

(56) References Cited

U.S. PATENT DOCUMENTS

| | | | |
|---|---|---|---|
| 2004/0014766 | A1 | 1/2004 | Dunten et al. |
| 2004/0186127 | A1 | 9/2004 | Daun et al. |
| 2004/0198725 | A1 | 10/2004 | Sun et al. |
| 2005/0124649 | A1 | 6/2005 | Daun et al. |
| 2006/0069117 | A1 | 3/2006 | Rault et al. |
| 2007/0037809 | A1 | 2/2007 | Nunes et al. |
| 2007/0037810 | A1 | 2/2007 | Nunes et al. |
| 2007/0037827 | A1 | 2/2007 | Nunes et al. |
| 2007/0037865 | A1 | 2/2007 | Nunes et al. |
| 2007/0043050 | A1 | 2/2007 | Nunes et al. |
| 2007/0123553 | A1 | 5/2007 | Huesca et al. |
| 2007/0173527 | A1 | 7/2007 | Bressi et al. |
| 2008/0103137 | A1 | 5/2008 | Daun et al. |
| 2008/0207682 | A1 | 8/2008 | Staehle et al. |
| 2008/0255085 | A1 | 10/2008 | Arvidsson et al. |
| 2008/0255106 | A1 | 10/2008 | Arvidsson et al. |
| 2008/0275038 | A1 | 11/2008 | Vidal Juan et al. |
| 2009/0023763 | A1 | 1/2009 | Vidal Juan et al. |
| 2010/0009992 | A1 | 1/2010 | Birnberg et al. |
| 2010/0081643 | A1 | 4/2010 | Bookser et al. |
| 2010/0234593 | A1 | 9/2010 | Arvidsson et al. |
| 2011/0021532 | A1 | 1/2011 | Powell et al. |
| 2011/0046132 | A1 | 2/2011 | Hocutt et al. |
| 2011/0081315 | A1* | 4/2011 | Buckman et al. ............ 424/85.5 |
| 2011/0105427 | A1* | 5/2011 | Daun et al. ...................... 514/63 |
| 2011/0319394 | A1 | 12/2011 | Taniguchi et al. |
| 2013/0172292 | A1 | 7/2013 | Raker et al. |
| 2013/0172328 | A1 | 7/2013 | Taniguchi et al. |

FOREIGN PATENT DOCUMENTS

| | | |
|---|---|---|
| JP | 2006 507273 | 3/2006 |
| JP | 2007 511504 | 5/2007 |
| JP | 2008 515935 | 5/2008 |
| JP | 2009 503117 | 1/2009 |
| JP | 2009 510152 | 3/2009 |
| JP | 2009 510161 | 3/2009 |
| JP | 2009 510162 | 3/2009 |
| JP | 2010 523490 | 7/2010 |
| WO | WO 03/057696 A1 | 7/2003 |
| WO | WO 2005/100353 A1 | 10/2005 |
| WO | 2008 019309 | 2/2008 |
| WO | 2009 100130 | 8/2009 |
| WO | 2009 129625 | 10/2009 |
| WO | 2009 134750 | 11/2009 |
| WO | 2010 036613 | 4/2010 |
| WO | 2010 047982 | 4/2010 |
| WO | 2010 051176 | 5/2010 |
| WO | 2010 051206 | 5/2010 |
| WO | 2011 038293 | 3/2011 |
| WO | 2011 106273 | 9/2011 |
| WO | WO 2011/163355 A1 | 12/2011 |
| WO | WO 2012/018909 A1 | 2/2012 |
| WO | 2012 116145 | 8/2012 |
| WO | 2013 011932 | 1/2013 |

OTHER PUBLICATIONS

Supplementary European Search Report issued Sep. 27, 2013, in European Patent Application No. 11 82 3623.

Compound Summary, Database PubChem Compound [Online] NCBI; Database Accession No. CID 22570423 Abstract, XP-002713727, Dec. 5, 2007, 4 pages.

Lipka, E., et al., "Enantioseparation of chiral benzimidazole derivatives by electrokinetic chromatography using sulfated cyclodextrins," Journal of Separation Science, vol. 32, No. 11, pp. 1907-1915, (2009).

Bavetsias, V., et al., "Imidazo[4,5-*b*]pyridine Derivatives As Inhibitors of Aurora Kinases: Lead Optimization Studies toward the Identification of an Orally Bioavailable Preclinical Development Candidate," Journal of Medicinal Chemistry, vol. 53, No. 14, pp. 5213-5228, (Jun. 21, 2010).

International Search Report Issued Oct. 11, 2011 in PCT/JP11/70429 Filed Sep. 8, 2011.

Kim, S.A., et al., "Structure-Activity Relationships at Human and Rat A2B Adenosine Receptors of Xanthine Derivatives Substituted at the 1-, 3-, 7- and 8-Positions," Journal of Medicinal Chemistry, vol. 45, No. 11, pp. 2131-2138, (Apr. 25, 2002).

Oguchi, M., et al., "Molecular Design, Synthesis, and Hypoglycemic Activity of a Series of Thiazolidine-2,4-diones," Journal of Medicinal Chemistry, vol. 43, No. 16, pp. 3052-3066, (Jul. 26, 2000).

Li, Y., et al., "Automatic Tailoring and Transplanting: A Practical Method that Makes Virtual Screening More Useful," Journal of Chemical Information and Modeling, vol. 51, No. 6, pp. 1474-1491, (Apr. 26, 2011).

Zhang, B.B., et al., "AMPK: An Emerging Drug Target for Diabetes and the Metabolic Syndrome," Cell Metabolism, vol. 9, No. 5, pp. 407-416, (May 6, 2009).

Lbonard Kuczynski et al. "Synthesis and Biological Properties of Imidazo-[4,5-b]-Pyridine Derivatives", Polish Journal of Pharmacology and Pharmacy, (1982), 34(4), 229-238.

* cited by examiner

HETERO RING-FUSED IMIDAZOLE DERIVATIVE HAVING AMPK ACTIVATING EFFECT

FIELD OF THE INVENTION

The present invention relates to a compound which has an activating effect on adenosine monophosphate-activated protein kinase (hereinafter referred to as AMPK) and is useful as a medicine.

BACKGROUND ART

AMPK is a serine-threonine kinase, which is activated by AMP, and has three subunits, α, β and γ. In each subunit, there exist multiple isoforms (α1, α2, β1, β2, γ1, γ2 and γ3).

AMPK is involved in various physiological functions, such as suppression of gluconeogenesis and inhibition of fatty acid synthesis in liver and incorporation of sugars and an increase in fatty acid oxidation in skeletal muscles, as an energy sensor in living organisms, and has attracted attention as a target molecule of a therapeutic agent for diabetes. Therefore, an AMPK activator is expected to be effective in the treatment of diabetes as an insulin resistance improving drug, which has an insulin independent hypoglycemic effect and a lipid improving effect (Non-Patent Document 1).

Patent Documents 1 to 4 disclose a variety of compounds having an AMPK activating effect; however, a hetero ring-fused imidazole derivative like a compound of the present invention is not disclosed in any of the documents.

Patent Document 5 describes the following imidazopyridine derivatives having highly active foliar treatment ability as herbicides.

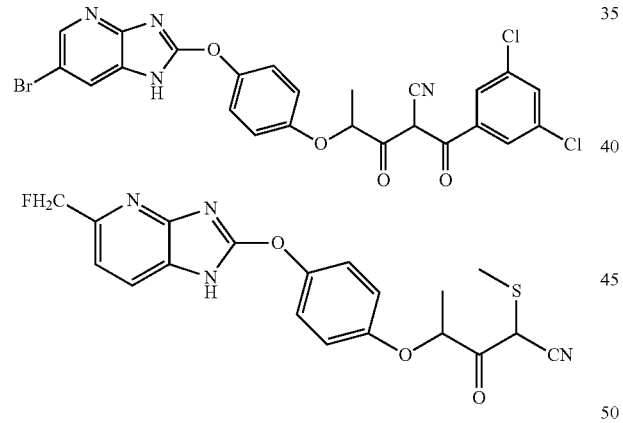

In Patent Document 5, however, an AMPK activating effect is not described.

PRIOR ART DOCUMENT

Patent Document

Patent Document 1: WO2010/036613
Patent Document 2: WO2010/047982
Patent Document 3: WO2010/051176
Patent Document 4: WO2010/051206
Patent Document 5: JP05-339224

Non-Patent Document

Non-Patent Document 1: Cell Metabolism Vol. 9, Issue 5, 407-416, 2009

DISCLOSURE OF INVENTION

Problems to be Solved by the Invention

The present invention provides a useful AMPK activator.

Means for Solving the Problem

The present inventors have intensively studied to synthesize the excellent compounds having an AMPK activating effect.

That is, the present invention relates to the following.

[1]

A compound represented by the formula (I):

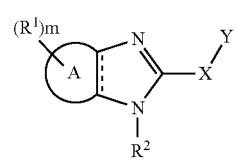

its pharmaceutically acceptable salt, or a solvate thereof, wherein a group represented by the formula:

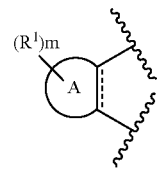

is a group represented by the formula:

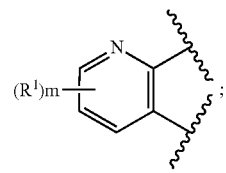

$R^1$ is each independently halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

m is an integer of 0 to 3;

$R^2$ is hydrogen, or substituted or unsubstituted alkyl;

X is —O—; and

Y is substituted or unsubstituted aryl, or substituted or unsubstituted heteroaryl; with the proviso that compounds shown below are excluded:

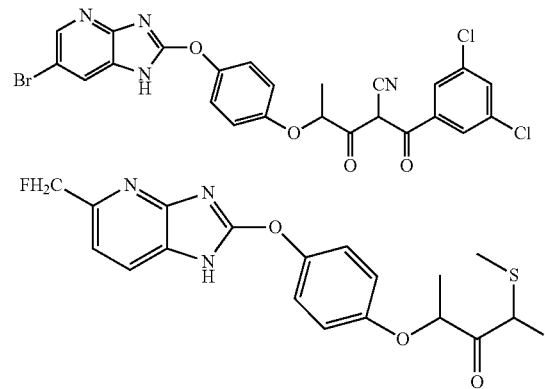

[2]

The compound according to the above [1], its pharmaceutically acceptable salt, or a solvate thereof, wherein Y is

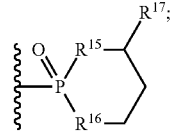

wherein $R^4$ is a group represented by the formula: —$(CR^6R^7)_q$-Z;

$R^6$ is each independently hydrogen, hydroxy, substituted or unsubstituted alkyl, or substituted or unsubstituted amino;

$R^7$ is each independently hydrogen, hydroxy, substituted or unsubstituted alkyl, or substituted or unsubstituted amino;

q is an integer of 0 to 4;

Z is (1) —COOH,
(2) —COOR$^8$,
(3) —OH,
(4) —C(=O)—NR$^9$R$^{10}$,
(5) —NR$^9$—C(=O)—R$^{11}$,
(6) —NR$^9$—SO$_2$—R$^8$,
(7) —SO$_2$—NR$^9$R$^{10}$,
(8) —SO$_2$—NR$^9$—C(=O)—R$^8$,
(9) —SO$_2$—NR$^9$—COOR$^8$,
(10) —SO$_2$—NR$^9$—C(=O)—NR$^9$R$^{10}$,
(11) —C(=O)—NR$^9$—SO$_2$—R$^8$,
(12) —NR$^9$—C(=O)—NR$^9$R$^{10}$,
(13) —P(=O)(—OH)$_2$,
(14) —P(=O)H(—OH),
(15) —P(=O)(—R$^{11}$)$_2$,
(16) —P(=O)(—OR$^{11}$)$_2$,
(17) —P(=O)(—OH)(—R$^{11}$),
(18) —P(=O)(—OH)(—OR$^{11}$),
(19) —P(=O)(—R$^{11}$)(—OR$^{11}$),
(20) —P(=O)(—OH)(—O—(CR$^6$R$^7$)$_{0-4}$—R$^{12}$),
(21) —P(=O)(—NR$^9$—CR$^{13}$R$^{14}$—COOH)$_2$,
(22) —P(=O)(—NR$^9$—CR$^{13}$R$^{14}$—COOR$^{11}$)$_2$,
(23) —P(=O)(—OH)(—NR$^9$—CR$^{13}$R$^{14}$—COOH)$_2$,
(24) —P(=O)(—OH)(—NR$^9$—CR$^{13}$R$^{14}$—COOR$^{11}$),
(25) —P(=O)(—NR$^9$—CR$^{13}$R$^{14}$—COOR$^{11}$)(—O—R$^8$),
(26) —P(=O)(—O—CR$^{13}$R$^{14}$—O—C(=O)—R$^{11}$)$_2$,
(27) —P(=O)(—OH)(—O—CR$^{13}$R$^{14}$—O—C(=O)—R$^{11}$),
(28) —P(=O)(—OH)(—O—(CR$^6$R$^7$)$_{1-4}$—S(=O)—R$^{11}$),
(29) —P(=O)(—O—(CR$^6$R$^7$)$_{1-4}$—S(=O)—R$^{11}$)$_2$,
(30) —P(=O)(—OH)(—O—(CR$^6$R$^7$)$_{1-4}$—S—C(=O)—R$^{11}$),
(31) —P(=O)(—O—(CR$^6$R$^7$)$_{1-4}$—S—C(=O)—R$^{11}$)$_2$,
(32) —NR$^9$—C(=O)—O—R$^{11}$
or

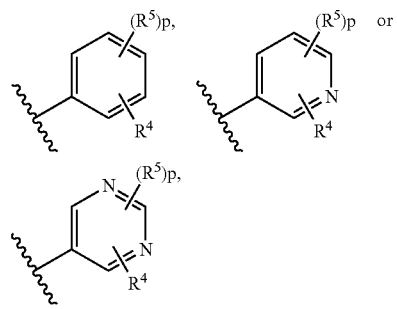

$R^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^9$ and $R^{10}$ are each independently hydrogen, or substituted or unsubstituted alkyl;

$R^{11}$ and $R^{12}$ are each independently substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^{13}$ and $R^{14}$ are each independently hydrogen, or substituted or unsubstituted alkyl;

$R^{15}$ and $R^{16}$ are each independently —O— or —NH—;

$R^{17}$ is substituted or unsubstituted aryl, or substituted or unsubstituted heteroaryl;

$R^5$ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and p is an integer of 0 to 2.

[3]

The compound according to the above [2], its pharmaceutically acceptable salt, or a solvate thereof, wherein q is 1.

[4]

The compound according to the above [3], its pharmaceutically acceptable salt, or a solvate thereof, wherein $R^6$ and $R^7$ are each independently substituted or unsubstituted alkyl.

[5]
The compound according to any one of the above [2] to [4], its pharmaceutically acceptable salt, or a solvate thereof, wherein Z is —NR⁹—C(=O)—R¹¹.
[6]
The compound according to any one of the above [1] to [5], its pharmaceutically acceptable salt, or a solvate thereof, wherein a group represented by the formula:

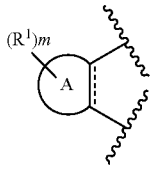

is a group represented by the formula:

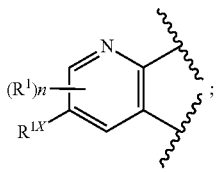

$R^1$ has the same meaning as in the above [1]; n is an integer of 0 to 2; and $R^{1X}$ is halogen.
[7]
The compound according to any one of the above [1] to [6], its pharmaceutically acceptable salt, or a solvate thereof, wherein m is an integer of 1 to 3 or n is 1 or 2; and at least one of $R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.
[8]
The compound according to any one of the above [1] to [7], its pharmaceutically acceptable salt, or a solvate thereof, wherein m is an integer of 1 to 3 or n is 1 or 2; and at least one of $R^1$ is substituted or unsubstituted aryl.
[9]
The compound according to any one of the above [1] to [8], its pharmaceutically acceptable salt, or a solvate thereof, wherein a group represented by the formula:

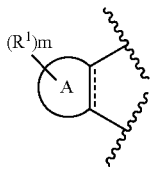

is a group represented by the formula:

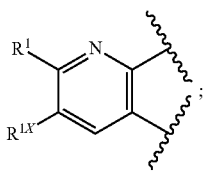

$R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl; and $R^{1X}$ is halogen.
[10]
The compound according to the above [9], its pharmaceutically acceptable salt, or a solvate thereof, wherein $R^1$ is substituted or unsubstituted aryl.
[11]
A pharmaceutical composition having an activating effect on adenosine monophosphate-activated protein kinase, which comprises a compound represented by the formula (I):

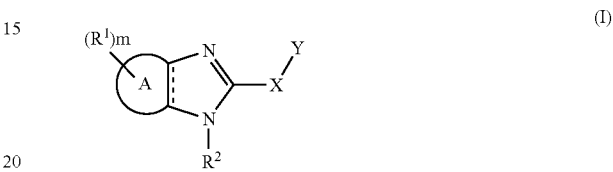

its pharmaceutically acceptable salt, or a solvate thereof,
wherein
Ring A is an aromatic heterocycle or a non aromatic heterocycle;
a dashed line represents the presence or absence of a bond;
$R^1$ is each independently halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
m is an integer of 0 to 7;
$R^2$ is hydrogen, or substituted or unsubstituted alkyl;
X is a single bond, —S—, —O—, —NR³—, —C(=O)—, —NR³C(=O)—, —C(=O)NR³—, —NR³—SO₂—, —SO₂—NR³— or —C(=O)—O—;
$R^3$ is hydrogen, or substituted or unsubstituted alkyl; and
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

[12]
The pharmaceutical composition according to the above [11], wherein, in the formula (I), a group represented by the formula:

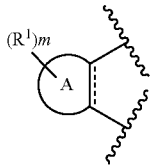

is a group represented by the formula:

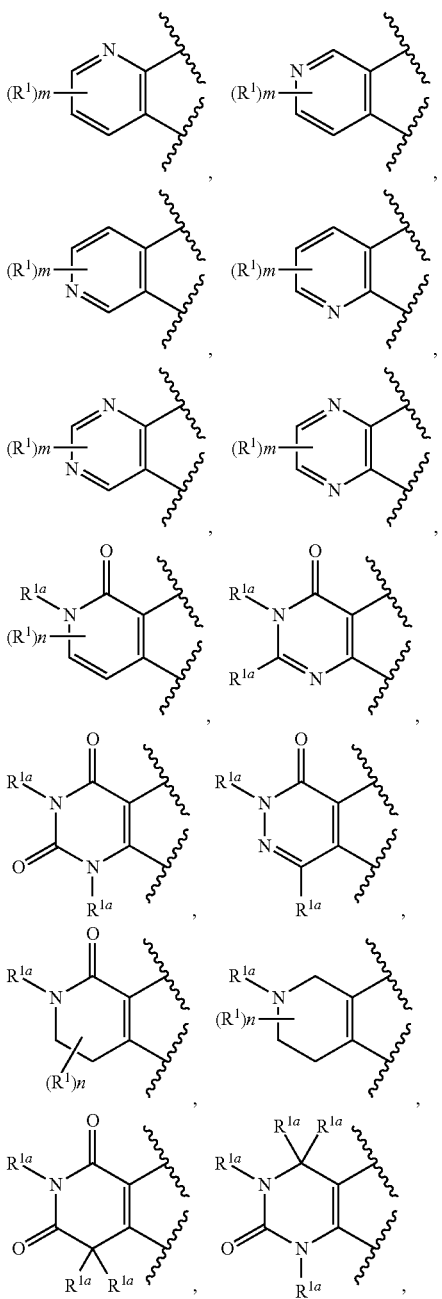

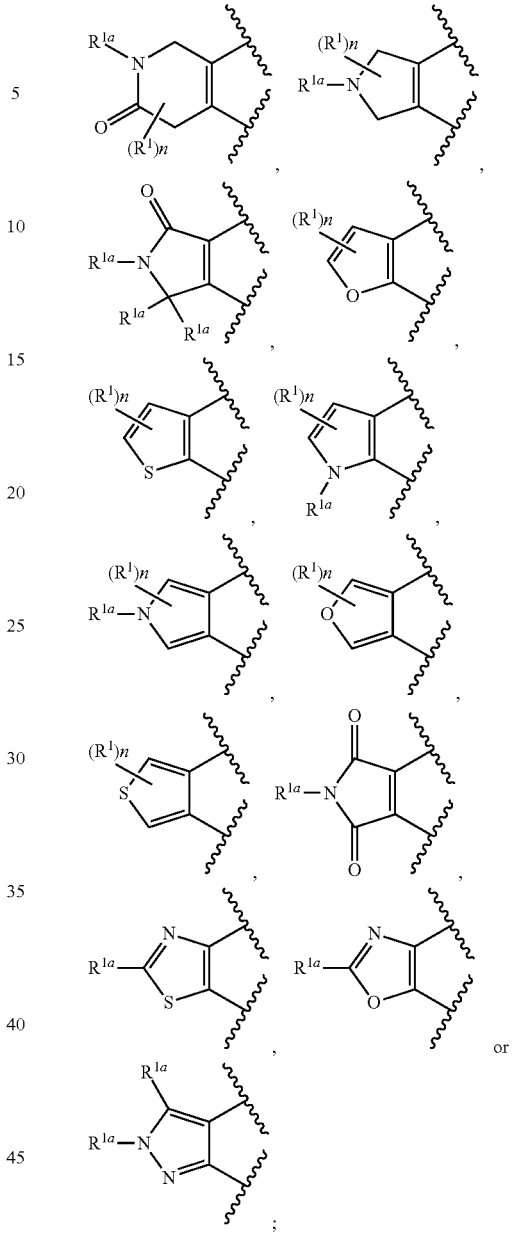

R¹ has the same meaning as in the above [11], m is an integer of 0 to 3;
R$^{1a}$ is each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; and n is an integer of 0 to 6.

[13]

The pharmaceutical composition according to the above [12], wherein, in the formula (I), a group represented by the formula:

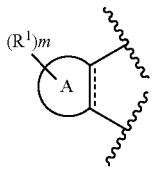

is a group represented by the formula:

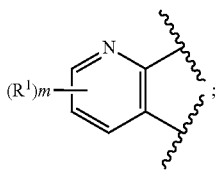

and $R^1$ and m have the same meaning as in the above [12].

[14]

The pharmaceutical composition according to any one of the above [11] to [13], wherein X is a single bond, —S—, —O— or —NR$^3$—.

[15]

The pharmaceutical composition according to the above [14], wherein X is —S— or —O—.

[16]

The pharmaceutical composition according to the above [15], wherein X is —O—.

[17]

The pharmaceutical composition according to any one of the above [11] to [16], wherein Y is substituted or unsubstituted aryl, or substituted or unsubstituted heteroaryl.

[18]

The pharmaceutical composition according to the above [17], wherein Y is substituted or unsubstituted aryl.

[19]

The pharmaceutical composition according to the above [17], wherein Y is a group represented by the formula:

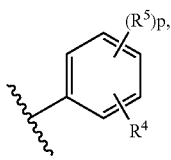 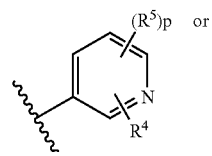 or

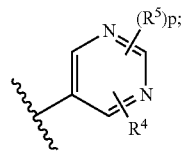

$R^4$ is a group represented by the formula: —(CR$^6$R$^7$)q-Z;

$R^6$ is each independently hydrogen, hydroxy, substituted or unsubstituted alkyl, or substituted or unsubstituted amino;

$R^7$ is each independently hydrogen, hydroxy, substituted or unsubstituted alkyl, or substituted or unsubstituted amino;

q is an integer of 0 to 4;

Z is (1) —COOH,
(2) —COOR$^8$,
(3) —OH,
(4) —C(=O)—NR$^9$R$^{10}$,
(5) —NR$^9$—C(=O)—R$^{11}$,
(6) —NR$^9$—SO$_2$—R$^8$,
(7) —SO$_2$—NR$^9$R$^{10}$,
(8) —SO$_2$—NR$^9$—C(=O)—R$^8$,
(9) —SO$_2$—NR$^9$—COOR$^8$,
(10) —SO$_2$—NR$^9$—C(=O)—NR$^9$R$^{10}$,
(11) —C(=O)—NR$^9$—SO$_2$—R$^8$,
(12) —NR$^9$—C(=O)—NR$^9$R$^{10}$,
(13) —P(=O)(—OH)$_2$,
(14) —P(=O)H(—OH),
(15) —P(=O)(—R$^{11}$)$_2$,
(16) —P(=O)(—OR$^{11}$)$_2$,
(17) —P(=O)(—OH)(—R$^{11}$),
(18) —P(=O)(—OH)(—OR$^{11}$),
(19) —P(=O)(—R$^{11}$)(—OR$^{11}$),
(20) —P(=O)(—OH)(—O—(CR$^6$R$^7$)$_{0-4}$—R$^{12}$),
(21) —P(=O)(—NR$^9$—CR$^{13}$R$^{14}$—COOH)$_2$,
(22) —P(=O)(—NR$^9$—CR$^{13}$R$^{14}$—COOR$^{11}$)$_2$,
(23) —P(=O)(—OH)(—NR$^9$—CR$^{13}$R$^{14}$—COOR$^{11}$),
(24) —P(=O)(—OH)(—NR$^9$—CR$^{13}$R$^{14}$—COOR$^{11}$),
(25) —P(=O)(—NR$^9$—CR$^{13}$R$^{14}$—COOR$^{11}$)(—O—R$^8$),
(26) —P(=O)(—O—CR$^{13}$R$^{14}$—O—C(=O)—R$^{11}$)$_2$,
(27) —P(=O)(—OH)(—O—CR$^{13}$R$^{14}$—O—C(=O)—R$^{11}$),
(28) —P(=O)(—OH)(—O—(CR$^6$R$^7$)$_{1-4}$—S(=O)—R$^{11}$),
(29) —P(=O)(—O—(CR$^6$R$^7$)$_{1-4}$—S(=O)—R$^{11}$)$_2$,
(30) —P(=O)(—O—(CR$^6$R$^7$)$_{1-4}$—S—C(=O)—R$^{11}$),
(31) —P(=O)(—O—(CR$^6$R$^7$)$_{1-4}$—S—C(=O)—R$^{11}$)$_2$,
(32) —NR$^9$—C(=O)—O—R$^{11}$ or

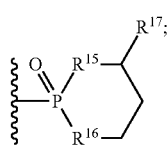

(33)

$R^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^9$ and $R^{10}$ are each independently hydrogen, or substituted or unsubstituted alkyl;

R[11] and R[12] are each independently substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

R[13] and R[14] are each independently hydrogen, or substituted or unsubstituted alkyl;

R[15] and R[16] are each independently —O— or —NH—;

R[17] is substituted or unsubstituted aryl, or substituted or unsubstituted heteroaryl;

R[5] is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and p is an integer of 0 to 2.

[20]

The pharmaceutical composition according to any one of the above [11] to [16], wherein Y is substituted or unsubstituted alkyl.

[21]

The pharmaceutical composition according to any one of the above [11] to [16], wherein Y is substituted or unsubstituted alkyl, wherein the substituted or unsubstituted alkyl is a group represented by the formula: —$(CR^{18}R^{19})_r$—Z;

R[18] is each independently hydrogen, halogen, hydroxy, cyano, nitro, carboxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, or substituted or unsubstituted amino;

R[19] is each independently hydrogen, halogen, hydroxy, cyano, nitro, carboxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, or substituted or unsubstituted amino;

r is an integer of 1 to 4;

Z is (1) —COOH,
(2) —COOR[8],
(3) —OH,
(4) —C(=O)—NR[9]R[10],
(5) —NR[9]—C(=O)—R[11],
(6) —NR[9]—SO$_2$—R[8],
(7) —SO$_2$—NR[9]R[10],
(8) —SO$_2$—NR[9]—C(=O)—R[8],
(9) —SO$_2$—NR[9]—COOR[8],
(10) —SO$_2$—NR[9]—C(=O)—NR[9]R[10],
(11) —C(=O)—NR[9]—SO$_2$—R[8],
(12) —NR[9]—C(=O)—NR[9]R[10],
(13) —P(=O)(—OH)$_2$,
(14) —P(=O)H(—OH),
(15) —P(=O)(—R[11])$_2$,
(16) —P(=O)(—OR[11])$_2$,
(17) —P(=O)(—OH)(—R[11]),
(18) —P(=O)(—OH)(—OR[11]),
(19) —P(=O)(—R[11])(—OR[11]),
(20) —P(=O)(—OH)(—O—$(CR^6R^7)_{0-4}$—R[12]),
(21) —P(=O)(—NR[9]—$CR^{13}R^{14}$—COOH)$_2$,
(22) —P(=O)(—NR[9]—$CR^{13}R^{14}$—COOR[11])$_2$,
(23) —P(=O)(—OH)(—NR[9]—$CR^{13}R^{14}$—COOH),
(24) —P(=O)(—OH)(—NR[9]—$CR^{13}R^{14}$—COOR[11]),
(25) —P(=O)(—NR[9]—$CR^{13}R^{14}$—COOR[11])(—O—R[8]),
(26) —P(=O)(—O—$CR^{13}R^{14}$—O—C(=O)—R[11])$_2$,
(27) —P(=O)(—OH)(—O—$CR^{13}R^{14}$—O—C(=O)—R[11]),
(28) —P(=O)(—OH)(—O—$(CR^6R^7)_{1-4}$—S(=O)—R[11]),
(29) —P(=O)(—O—$(CR^6R^7)_{1-4}$—S(=O)—R[11])$_2$,
(30) —P(=O)(—OH)(—O—$(CR^6R^7)_{1-4}$—S—C(=O)—R[11]),
(31) —P(=O)(—O—$(CR^6R^7)_{1-4}$—S—C(=O)—R[11])$_2$,
(32) —NR[9]—C(=O)—O—R[11]

or

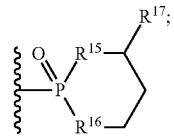

(33)

R[6] is each independently hydrogen, hydroxy, substituted or unsubstituted alkyl, or substituted or unsubstituted amino;

R[7] is each independently hydrogen, hydroxy, substituted or unsubstituted alkyl, or substituted or unsubstituted amino;

R[8] is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

R[9] and R[10] are each independently hydrogen, or substituted or unsubstituted alkyl;

R[11] and R[12] are each independently substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

R[13] and R[14] are each independently hydrogen, or substituted or unsubstituted alkyl;

R[15] and R[16] are each independently —O— or —NH—; and

R[17] is substituted or unsubstituted aryl, or substituted or unsubstituted heteroaryl.

[22]

The pharmaceutical composition according to any one of the above [11] to [21], wherein m is an integer of 1 to 2, and at least one of R[1] is halogen.

[23]

The pharmaceutical composition according to any one of the above [11] to [22], wherein m is an integer of 1 to 2, and at least one of R[1] is substituted or unsubstituted aryl, substituted or unsubstituted heteroaryl, substituted or unsubstituted cycloalkyl, substituted or unsubstituted cycloalkenyl, or substituted or unsubstituted heterocyclyl.

[24]

The pharmaceutical composition according to any one of the above [11] to [23], wherein R[2] is hydrogen.

[25]

The pharmaceutical composition according to the above [11], wherein m is 2; one of R[1] is halogen, and another of R[1] is substituted or unsubstituted aryl;

R[2] is hydrogen;

X is —O—; and

Y is substituted or unsubstituted aryl, or substituted or unsubstituted heteroaryl.

[26]

A pharmaceutical composition comprising the compound according to any one of the above [1] to [10], its pharmaceutically acceptable salt, or a solvate thereof.

[27]
The pharmaceutical composition according to the above [26], which has an activating effect on adenosine monophosphate-activated protein kinase.
[28]
The pharmaceutical composition according to any one of the above [11] to [27], for the treatment and/or prevention of diabetes.
[29]
A method for preventing or treating diabetes, comprising administering the compound according to any one of the above [1] to [25], its pharmaceutically acceptable salt, or a solvate thereof.
[30]
The compound according to any one of the above [1] to [25], its pharmaceutically acceptable salt, or a solvate thereof, for the treatment and/or prevention of diabetes.

Further, the present invention relates to the following.
[1A]
A compound represented by the formula (I):

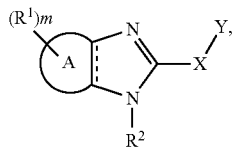

(I)

its pharmaceutically acceptable salt, or a solvate thereof, wherein
a group represented by the formula:

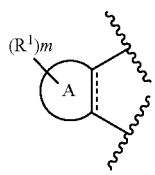

is a group represented by the formula:

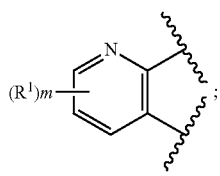

$R^1$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
m is an integer of 0 to 3;
$R^2$ is hydrogen, or substituted or unsubstituted alkyl;
X is —O—; and
Y is substituted or unsubstituted aryl, or substituted or unsubstituted heteroaryl;
with the proviso that compounds shown below are excluded:

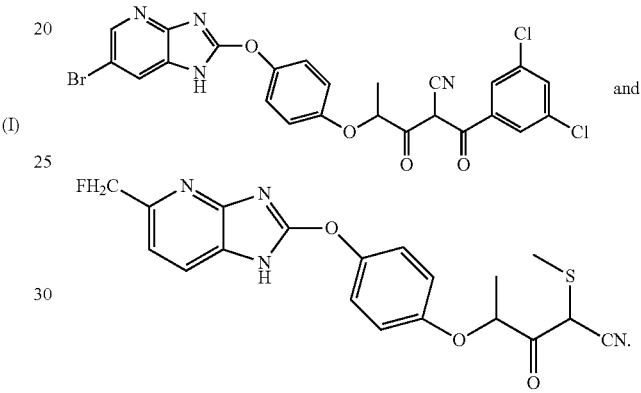

and

[2A]
The compound according to the above [1A], its pharmaceutically acceptable salt, or a solvate thereof, wherein Y is

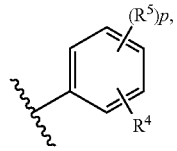

wherein $R^4$ is a group represented by the formula: —$(CR^6R^7)$q-Z;
$R^6$ and $R^7$ are each independently hydrogen, hydroxy, substituted or unsubstituted alkyl, or substituted or unsubstituted amino;
q is an integer of 0 to 4;
Z is
(1) —COON,
(2) —COOR$^8$,
(3) —OH,
(4) —C(O)NHR$^9$,
(5) —NHC(O)R$^{11}$,
(6) —NHSO$_2$R$^8$,
(7) —SO$_2$NHR$^9$,
(8) —SO$_2$NHC(O)R$^8$,
(9) —SO$_2$NHCOOR$^8$,
(10) —SO$_2$NHCONR$^9$R$^{10}$,
(11) —C(O)NHSO$_2$R$^8$,
(12) —NHC(O)NR$^9$R$^{10}$,
(13) —P(O)(OH)$_2$,

(14) —P(O)H(OH),
(15) —P(O)($R^{11}$)$_2$,
(16) —P(O)(OH)$_2$,
(17) —P(O)(OH)($R^{11}$),
(18) —P(O)(OH)(O$R^{11}$),
(19) —P(O)($R^{11}$)(O$R^{11}$),
(20) —P(O)(OH)(O—(C$R^6R^7$)$_{0-4}$—$R^{12}$),
(21) —P(O)(N$R^9$C$R^{13}R^{14}$COOH)$_2$,
(22) —P(O)(N$R^9$C$R^{13}R^{14}$COO$R^{11}$)$_2$,
(23) —P(O)(OH)(N$R^9$C$R^{13}R^{14}$COOH)$_2$,
(24) —P(O)(OH)(N$R^9$C$R^{13}R^{14}$COO$R^{11}$),
(25) —P(O)(N$R^9$C$R^{13}R^{14}$COO$R^{11}$)(O—$R^8$),
(26) —P(O)(OC$R^{13}R^{14}$OC(O)$R^{11}$)$_2$,
(27) —P(O)(OH)(O$R^{13}R^{14}$OC(O)$R^{11}$),
(28) —P(O)(OH)(—O—(C$R^6R^7$)$_{1-4}$—S(O)$R^{11}$),
(29) —P(O)(—O—(C$R^6R^7$)$_{1-4}$—(O)$R^{11}$)$_2$,
(30) —P(O)(OH)(—O—(C$R^6R^7$)$_{1-4}$—SC(O)$R^{11}$),
(31) —P(O)(—O—(C$R^6R^7$)$_{1-4}$—SC(O)$R^{11}$)$_2$

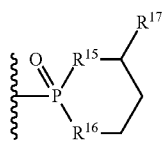

(32)

or
(33) —NHC(O)O$R^{11}$;
$R^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^9$ and $R^{11}$ are each independently hydrogen, or substituted or unsubstituted alkyl;
$R^{11}$ and $R^{12}$ are each independently substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^{13}$ and $R^{14}$ are each independently hydrogen, or substituted or unsubstituted alkyl;
$R^{15}$ and $R^{16}$ are each independently —O— or —NH—;
$R^{17}$ is substituted or unsubstituted aryl, or substituted or unsubstituted heteroaryl;
$R^5$ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and
p is an integer of 0 to 2.

[3A]
The compound according to the above [2A], its pharmaceutically acceptable salt, or a solvate thereof, wherein q is 1.

[4A]
The compound according to the above [3A], its pharmaceutically acceptable salt, or a solvate thereof, wherein $R^6$ and $R^7$ are each independently substituted or unsubstituted alkyl.

[5A]
The compound according to any one of the above [2A] to [4A], its pharmaceutically acceptable salt, or a solvate thereof, wherein Z is —NHC(O)$R^{11}$.

[6A]
The compound according to any one of the above [1A] to [5A], its pharmaceutically acceptable salt, or a solvate thereof, wherein a group represented by the formula:

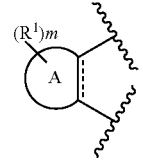

is a group represented by the formula:

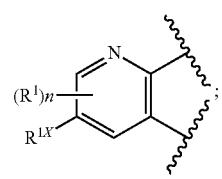

$R^1$ has the same meaning as in the above [1A], n is an integer of 0 to 2, and $R^{1X}$ is halogen.

[7A]
The compound according to any one of the above [1A] to [6A], its pharmaceutically acceptable salt, or a solvate thereof, wherein m is an integer of 1 to 3 or n is 1 or 2; and at least one of $R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

[8A]
The compound according to any one of the above [1A] to [7A], its pharmaceutically acceptable salt, or a solvate thereof, wherein m is an integer of 1 to 3 or n is 1 or 2; and at least one of $R^1$ is substituted or substituted aryl.

[9A]
A pharmaceutical composition having an activating effect on adenosine monophosphate-activated protein kinase, which comprises a compound represented by the formula (I):

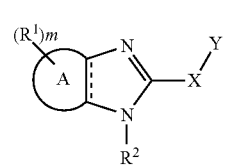

(I)

its pharmaceutically acceptable salt, or a solvate thereof,
wherein
Ring A is an aromatic heterocycle or a non aromatic heterocycle;
a dashed line represents the presence or absence of a bond;
$R^1$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

m is an integer of 0 to 7;

$R^2$ is hydrogen, or substituted or unsubstituted alkyl;

X is a single bond, —S—, —O—, —NR$^3$—, —C(=O)—, —NR$^3$C(=O)—, —C(=O)NR$^3$—, —NR$^3$—SO$_2$—, —SO$_2$—NR$^3$— or —C(=O)—O—;

$R^3$ is hydrogen, or substituted or unsubstituted alkyl; and

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

[10A]

The pharmaceutical composition according to the above [9A], wherein, in the formula (I), a group represented by the formula:

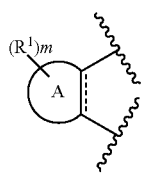

is a group represented by the formula:

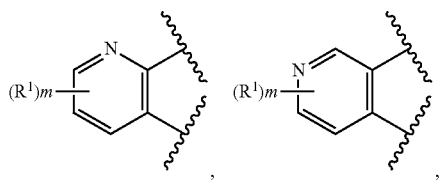

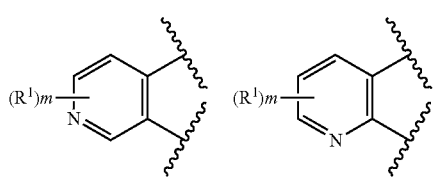

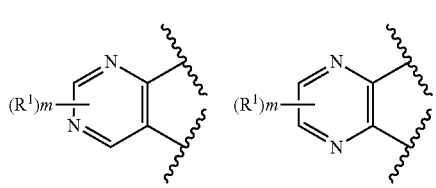

-continued

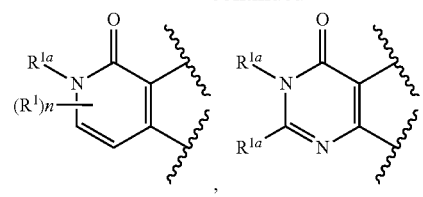

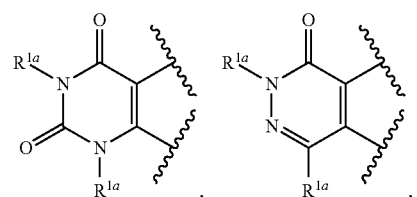

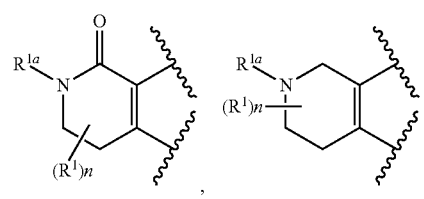

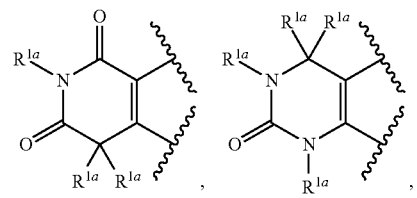

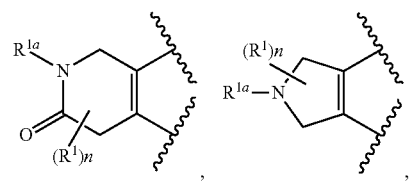

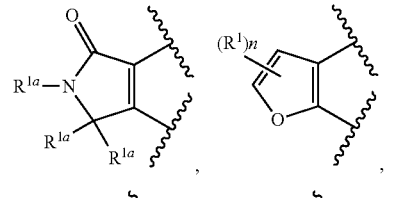

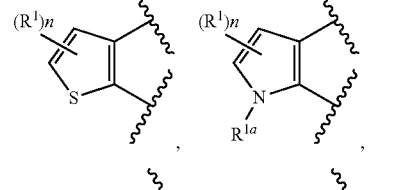

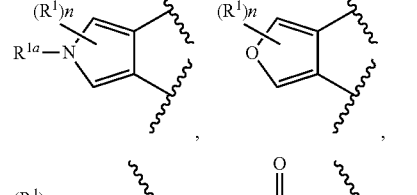

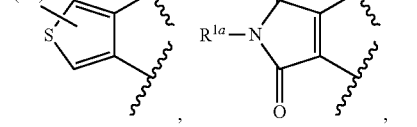

-continued

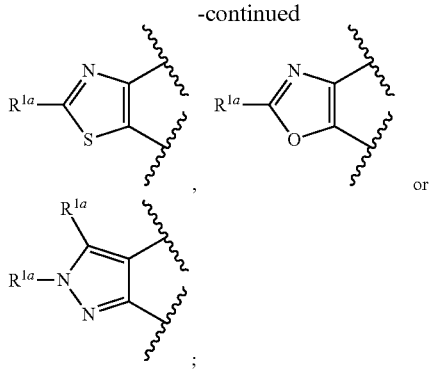

R[1] has the same meaning as in the above [9A], m is an integer of 0 to 3;

R[1a] is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; and n is an integer of 0 to 6.

[11A]
The pharmaceutical composition according to the above [10A], wherein, in the formula (I),
a group represented by the formula:

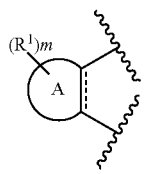

is a group represented by the formula:

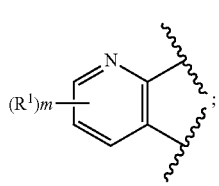

and
R[1] and m have the same meaning as in the above [10A].

[12A]
The pharmaceutical composition according to any one of the above [9A] to [11A], wherein X is a single bond, —S—, —O— or —NR[3]—.

[13A]
The pharmaceutical composition according to the above [12A], wherein X is —S— or —O—.

[14A]
The pharmaceutical composition according to the above [13A], wherein X is —O—.

[15A]
The pharmaceutical composition according to any one of the above [9A] to [14A], wherein Y is substituted or unsubstituted aryl, or substituted or unsubstituted heteroaryl.

[16A]
The pharmaceutical composition according to the above [15A], wherein Y is substituted or unsubstituted aryl.

[17A]
The pharmaceutical composition according to the above [16A], wherein Y is a group represented by the formula:

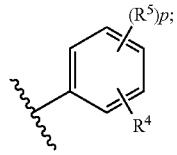

$R^4$ is a group represented by the formula: —$(CR^6R^7)q$-Z;
$R^6$ and $R^7$ are each independently hydrogen, hydroxy, substituted or unsubstituted alkyl, or substituted or unsubstituted amino;
q is an integer of 0 to 4;
Z is
(1) —COOH,
(2) —COORS,
(3) —OH,
(4) —C(O)NHR$^9$,
(5) —NHC(O)R$^{11}$,
(6) —NHSO$_2$R$^8$,
(7) —SO$_2$NHR$^9$,
(8) —SO$_2$NHC(O)R$^8$,
(9) —SO$_2$NHCOOR$^8$,
(10) —SO$_2$NHCONR$^9$R$^{10}$,
(11) —C(O)NHSO$_2$R$^8$,
(12) —NHC(O)NR$^9$R$^{10}$,
(13) —P(O)(OH)$_2$,
(14) —P(O)H(OH),
(15) —P(O)(R$^{11}$)$_2$,
(16) —P(O)(OR$^{11}$)$_2$,
(17) —P(O)(OH)(R$^{11}$),
(18) —P(O)(OH)(OR$^{11}$),
(19) —P(O)(R$^{11}$)(OR$^{11}$),
(20) —P(O)(OH)(O—(CR$^6$R$^7$)$_{0-4}$—R$^{12}$),
(21) —P(O)(NR$^9$CR$^{13}$R$^{14}$COOH)$_2$,
(22) —P(O)(NR$^9$CR$^{13}$R$^{14}$COOR$^{11}$)$_2$,
(23) —P(O)(OH)(NR$^9$CR$^{13}$R$^{14}$COOH)$_2$,
(24) —P(O)(OH)(NR$^9$CR$^{13}$R$^{14}$COOR$^{11}$),
(25) —P(O)(NR$^9$CR$^{13}$R$^{14}$COOR$^{11}$)(P—R$^8$),
(26) —P(O)(OCR$^{13}$R$^{14}$OC(O)R$^{11}$)$_2$,
(27) —P(O)(OH)(OCR$^{13}$R$^{14}$OC(O)R$^{11}$),
(28) —P(O)(OH)(—O—(CR$^6$R$^7$)$_{1-4}$—S(O)R$^{11}$),
(29) —P(O)(—O—(CR$^6$R$^7$)$_{1-4}$—(O)R$^{11}$)$_2$,

(30) —P(O)(OH)(—O—(CR⁶R⁷)₁₋₄—SC(O)R¹¹),
(31) —P(O)(—O—(CR⁶R⁷)₁₋₄—SC(O)R¹¹)₂,

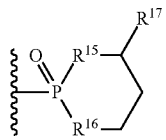
(32)

or
(33) —NHC(O)OR¹¹;
R⁸ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
R⁹ and R¹⁰ are each independently hydrogen, or substituted or unsubstituted alkyl;
R¹¹ and R¹² are each independently substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
R¹³ and R¹⁴ are each independently hydrogen, or substituted or unsubstituted alkyl;
R¹⁵ and R¹⁶ are each independently —O— or —NH—;
R¹⁷ is substituted or unsubstituted aryl, or substituted or unsubstituted heteroaryl;
R⁵ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and
p is an integer of 0 to 2.
[18A]
The pharmaceutical composition according to any one of the above [9A] to [14A], wherein Y is substituted or unsubstituted alkyl.
[19A]
The pharmaceutical composition according to the above [18A], wherein Y is a group represented by the formula: —(CR¹⁸R¹⁹)r—Z;
R¹⁸ and R¹⁹ are each independently hydrogen, halogen, hydroxy, cyano, nitro, carboxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, or substituted or unsubstituted amino;
r is an integer of 0 to 4, and Z has the same meaning as in the above [17A].
[20A]
The pharmaceutical composition according to any one of the above [9A] to [19A], wherein m is an integer of 1 to 2, and at least one of R¹ is halogen.
[21A]
The pharmaceutical composition according to any one of the above [9A] to [20A], wherein m is an integer of 1 to 2, and at least one of R¹ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

[22A]
The pharmaceutical composition according to any one of the above [9A] to [21A], wherein R² is hydrogen.
[23A]
The pharmaceutical composition according to the above [9A], wherein m is 2; one of R¹ is halogen, and another of R¹ is substituted or unsubstituted aryl;
R² is hydrogen;
X is —O—; and
Y is substituted or unsubstituted aryl, or substituted or unsubstituted heteroaryl.
[24A]
A pharmaceutical composition comprising the compound according to any one of the above [1A] to [8A], its pharmaceutically acceptable salt, or a solvate thereof.
[25A]
The pharmaceutical composition according to the above [24A], which has an activating effect on adenosine monophosphate-activated protein kinase.
[26A]
The pharmaceutical composition according to any one of the above [9A] to [23A], and [25A], for the treatment and/or prevention of diabetes.
[27A]
A method for preventing or treating diabetes, comprising administering the compound according to any one of the above [1A] to [23A], its pharmaceutically acceptable salt, or a solvate thereof.
[28A]
The compound according to any one of the above [1A] to [23A], its pharmaceutically acceptable salt, or a solvate thereof, for the treatment and/or prevention of diabetes.
[1B]
A pharmaceutical composition having an activating effect on adenosine monophosphate-activated protein kinase, which comprises a compound represented by the formula (I):

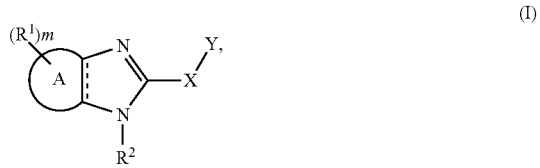
(I)

its pharmaceutically acceptable salt, or a solvate thereof,
wherein
Ring A is an aromatic heterocycle or a non aromatic heterocycle;
a dashed line represents the presence or absence of a bond;
R¹ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

m is an integer of 0 to 7;

$R^2$ is hydrogen, or substituted or unsubstituted alkyl;

X is a single bond, —S—, —O—, —NR$^3$—, —C(=O)—, —NR$^3$C(=O)—, —C(=O)NR$^3$—, —NR$^3$—SO$_2$—, —SO$_2$—NR$^3$— or —C(=O)—O—;

$R^3$ is hydrogen, or substituted or unsubstituted alkyl; and

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

[2B]

The pharmaceutical composition according to the above [1B], wherein, in the formula (I), a group represented by the formula:

is a group represented by the formula:

-continued

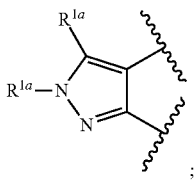
;

R¹ has the same meaning as in the above [1B], m is an integer of 0 to 3;

R¹ᵃ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; and n is an integer of 0 to 6.

[3B]

The pharmaceutical composition according to the above [2B], wherein, in the formula (I),
a group represented by the formula:

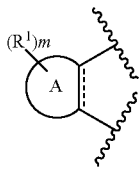

is a group represented by the formula:

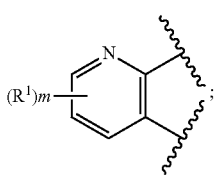

and
R¹ and m have the same meaning as in the above [2B].

[4B]

The pharmaceutical composition according to any one of the above [1B] to [3B], wherein X is a single bond, —S—, —O— or —NR³—.

[5B]

The pharmaceutical composition according to the above [4B], wherein X is —S— or —O—.

[6B]

The pharmaceutical composition according to the above [5B], wherein X is —O—.

[7B]

The pharmaceutical composition according to any one of the above [1B] to [6B], wherein Y is substituted or unsubstituted aryl, or substituted or unsubstituted heteroaryl.

[8B]

The pharmaceutical composition according to the above [7B], wherein Y is substituted or unsubstituted aryl.

[9B]

The pharmaceutical composition according to the above [8B], wherein Y is a group represented by the formula:

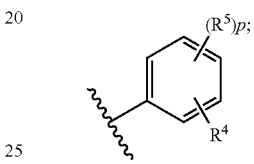

R⁴ is a group represented by the formula: —(CR⁶R⁷)q-Z;

R⁶ and R⁷ are each independently hydrogen, hydroxy, substituted or unsubstituted alkyl, or substituted or unsubstituted amino;

q is an integer of 0 to 4;

Z is (1) —COOH,
(2) —COOR⁸,
(3) —OH,
(4) —C(O)NHR⁹,
(5) —NHC(O)R¹¹,
(6) —NHSO₂R⁸,
(7) —SO₂NHR⁹,
(8) —SO₂NHC(O)R⁸,
(9) —SO₂NHCOOR⁸,
(10) —SO₂NHCONR⁹R¹⁰,
(11) —C(O)NHSO₂R⁸,
(12) —NHC(O)NR⁹R¹⁰,
(13) —P(O)(OH)₂,
(14) —P(O)H(OH),
(15) —P(O)(R¹¹)₂,
(16) —P(O)(OR¹¹)₂,
(17) —P(O)(OH)(R¹¹),
(18) —P(O)(OH)(OR¹¹),
(19) —P(O)(R¹¹)(OR¹¹),
(20) —P(O)(OH)(O—(CR⁶R⁷)₀₋₄—R¹²),
(21) —P(O)(NR⁹CR¹³R¹⁴COOH)₂,
(22) —P(O)(NR⁹CR¹³R¹⁴COOR¹¹)₂,
(23) —P(O)(OH)(NR⁹CR¹³R¹⁴COOH),
(24) —P(O)(OH)(NR⁹CR¹³R¹⁴COOR¹¹),
(25) —P(O)(NR⁹CR¹³R¹⁴COOR¹¹)(O—R⁸),
(26) —P(O)(OCR¹³R¹⁴OC(O)R¹¹)₂,
(27) —P(O)(OH)(OCR¹³R¹⁴OC(O)R¹¹),
(28) —P(O)(OH)(—O—(CR⁶R⁷)₁₋₄—SS(O)R¹¹),
(29) —P(O)(—O—(CR⁶R⁷)₁₋₄—S(O)R¹¹)₂,

(30) —P(O)(OH)(—O—(CR⁶R⁷)₁₋₄—SC(O)R¹¹),
(31) —P(O)(—O—(CR⁶R⁷)₁₋₄—SC(O)R¹¹)₂
or

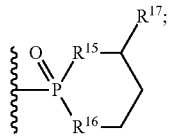
(32)

R⁸ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

R⁹ and R¹⁰ are each independently hydrogen, or substituted or unsubstituted alkyl;

R¹¹ is substituted or unsubstituted alkyl;

R¹² is substituted or unsubstituted aryl;

R¹³ and R¹⁴ are each independently hydrogen, or substituted or unsubstituted alkyl;

R¹⁵ and R¹⁶ are each independently —O— or —NH—;

R¹⁷ is substituted or unsubstituted aryl, or substituted or unsubstituted heteroaryl;

R⁵ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and p is an integer of 0 to 2.

[10B]

The pharmaceutical composition according to any one of the above [1B] to [6B], wherein Y is substituted or unsubstituted alkyl.

[11B]

The pharmaceutical composition according to the above [10B], wherein Y is a group represented by the formula:
—C(R¹⁸R¹⁹)r—Z;

R¹⁸ and R¹⁹ are each independently hydrogen, halogen, hydroxy, cyano, nitro, carboxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, or substituted or unsubstituted amino;

r is an integer of 0 to 4, and Z has the same meaning as in the above [9B].

[12B]

The pharmaceutical composition according to any one of the above [1B] to [11B], wherein m is an integer of 1 to 2, and at least one of R¹ is halogen.

[13B]

The pharmaceutical composition according to any one of the above [1B] to [12B], wherein m is an integer of 1 to 2, and at least one of R¹ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

[14B]

The pharmaceutical composition according to any one of the above [1B] to [13B], wherein R² is hydrogen.

[15B]

A compound represented by the formula (I):

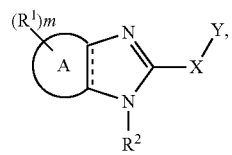
(I)

its pharmaceutically acceptable salt, or a solvate thereof, wherein a group represented by the formula:

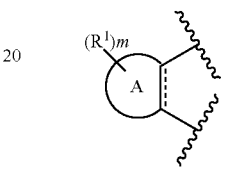

is a group represented by the formula:

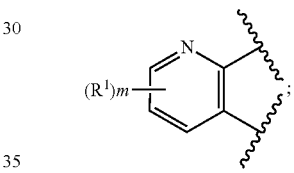

a dashed line represents the presence or absence of a bond;

R¹ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

m is an integer of 0 to 3,

R² is hydrogen, or substituted or unsubstituted alkyl;

X is —O—; and

Y is substituted or unsubstituted aryl; with the proviso that compounds shown below are excluded:

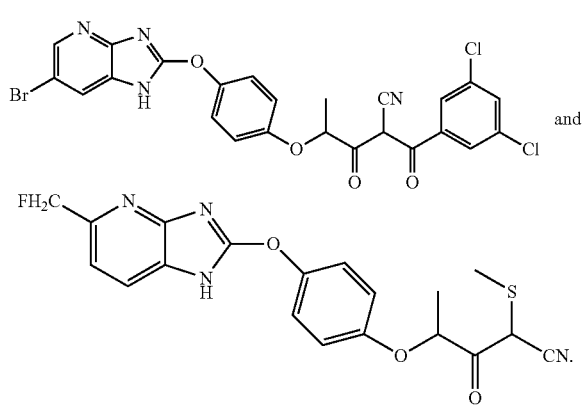 and 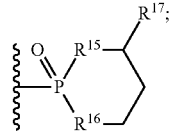

[16B]
The compound according to the above [15B], its pharmaceutically acceptable salt, or a solvate thereof, wherein Y is

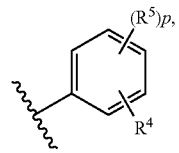

wherein $R^4$ is a group represented by the formula: —$(CR^6R^7)q$-Z;
$R^6$ and $R^7$ are each independently hydrogen, hydroxy, substituted or unsubstituted alkyl, or substituted or unsubstituted amino;
q is an integer of 0 to 4;
Z is
(1) —COON,
(2) —COOR$^8$,
(3) —OH,
(4) —C(O)NHR$^9$,
(5) —NHC(O)R$^{11}$,
(6) —NHSO$_2$R$^8$,
(7) —SO$_2$NHR$^9$,
(8) —SO$_2$NHC(O)R$^8$,
(9) —SO$_2$NHCOOR$^8$,
(10) —SO$_2$NHCONR$^9$R$^{10}$,
(11) —C(O)NHSO$_2$R$^8$,
(12) —NHC(O)NR$^9$R$^{10}$,
(13) —P(O)(OH)$_2$,
(14) —P(O)H(OH),
(15) —P(O)(R$^{11}$)$_2$,
(16) —P(O)(OR$^{11}$)$_2$,
(17) —P(O)(OH)(R$^{11}$),
(18) —P(O)(OH)(OR$^{11}$),
(19) —P(O)(R$^{11}$)(OR$^{11}$)$_2$,
(20) —P(O)(OH)(O—(CR$^6$R$^7$)$_{0-4}$—R$^{12}$),
(21) —P(O)(NR$^9$CR$^{13}$R$^{14}$COOH)$_2$,
(22) —P(O)(NR$^9$CR$^{13}$R$^{14}$COOR$^{11}$)$_2$,
(23) —P(O)(OH)(NR$^9$CR$^{13}$R$^{14}$COOH)$_2$,
(24) —P(O)(OH)(NR$^9$CR$^{13}$R$^{14}$COOR$^{11}$),
(25) —P(O)(NR$^9$CR$^{13}$R$^{14}$COOR$^{11}$)(O—R$^8$),
(26) —P(O)(OCR$^{13}$R$^{14}$OC(O)R$^{11}$)$_2$,
(27) —P(O)(OH)(OCR$^{13}$R$^{14}$OC(O)R$^{11}$),
(28) —P(O)(OH)(—O—(CR$^6$R$^7$)$_{1-4}$—S(O)R$^{11}$),
(29) —P)(O)(—O—(CR$^6$R$^7$)$_{1-4}$—S(O)R$^{11}$)$_2$,
(30) —P(O)(OH)(—O—(CR$^6$R$^7$)$_{1-4}$—SC(O)R$^{11}$),
(31) —P)(O)(—O—(CR$^6$R$^7$)$_{1-4}$—SC(O)R$^{11}$)$_2$
or

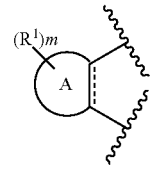

$R^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^9$ and $R^{10}$ are each independently hydrogen, or substituted or unsubstituted alkyl;
$R^{11}$ is substituted or unsubstituted alkyl;
$R^{12}$ is substituted or unsubstituted aryl;
$R^{13}$ and $R^{14}$ are each independently hydrogen, or substituted or unsubstituted alkyl;
$R^{15}$ and $R^{16}$ are each independently —O— or —NH—;
$R^{17}$ is substituted or unsubstituted aryl, or substituted or unsubstituted heteroaryl;
$R^5$ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and
p is an integer of 0 to 2.
[17B]
The compound according to the above [15B] or [16B], its pharmaceutically acceptable salt, or a solvate thereof, wherein a group represented by the formula:

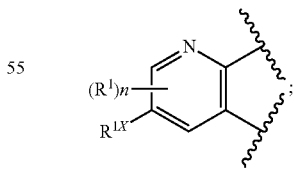

is a group represented by the formula:

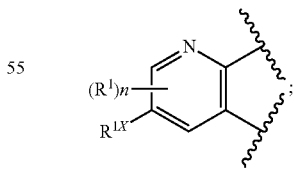

$R^1$ has the same meaning as in the above [15B], n is an integer of 0 to 2, and $R^{1X}$ is halogen.
[18B]
The compound according to any one of the above [15B] to [17B], its pharmaceutically acceptable salt, or a solvate thereof, wherein at least one of $R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.
[19B]
A pharmaceutical composition comprising the compound according to any one of the above [15B] to [18B], its pharmaceutically acceptable salt, or a solvate thereof.
[20B]
The pharmaceutical composition according to the above [19B], which has an activating effect on adenosine monophosphate-activated protein kinase.
[21B]
The pharmaceutical composition according to any one of the above [1B] to [14B], and [20B], for the treatment and/or prevention of diabetes.
[22B]
A method for preventing or treating diabetes, comprising administering the compound according to any one of the above [1B] to [18B], its pharmaceutically acceptable salt, or a solvate thereof.
[23B]
The compound according to any one of the above [1B] to [18B], its pharmaceutically acceptable salt, or a solvate thereof, for the treatment and/or prevention of diabetes.
[1C]
A pharmaceutical composition having an activating effect on adenosine monophosphate-activated protein kinase, which comprises a compound represented by the formula (I):

(I)

its pharmaceutically acceptable salt, or a solvate thereof, wherein
Ring A is an aromatic heterocycle or a non aromatic heterocycle;
a dashed line represents the presence or absence of a bond;
$R^1$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

m is an integer of 0 to 7;
$R^2$ is hydrogen, or substituted or unsubstituted alkyl;
X is a single bond, —S—, —O—, —NR$^3$—, —C(=O)—, —NR$^3$C(=O)—, —C(=O)NR$^3$—, —NR$^3$—SO$_2$—, —SO$_2$——NR$^3$— or —C(=O)—O—;
$R^3$ is hydrogen, or substituted or unsubstituted alkyl; and
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.
[2C]
The pharmaceutical composition according to the above [1C], wherein, in the formula (I),
a group represented by the formula:

is a group represented by the formula;

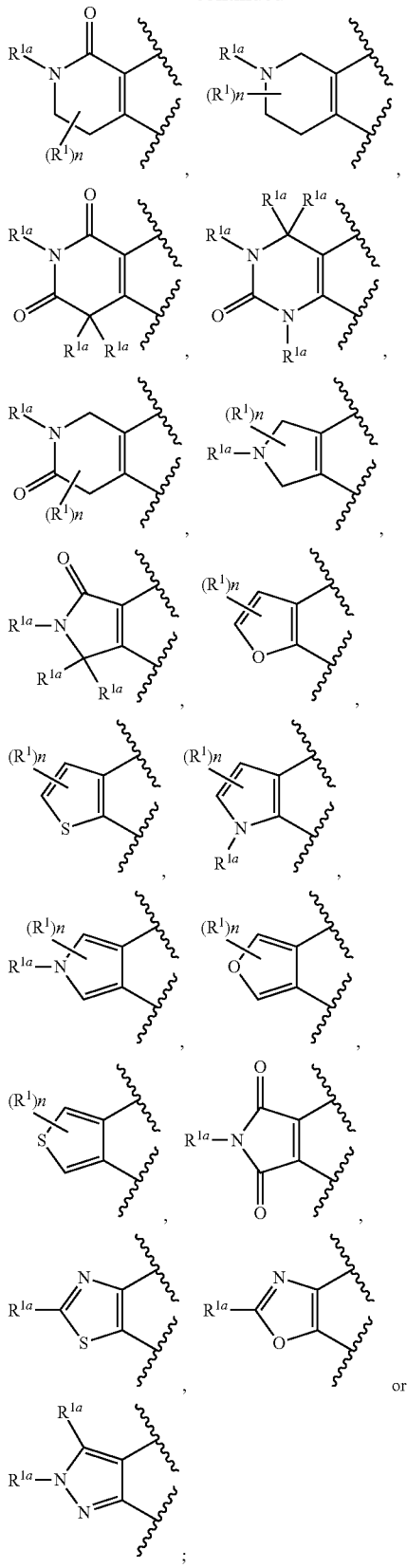

$R^1$ has the same meaning as in the above [1C], m is an integer of 0 to 3;

$R^{1a}$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; and n is an integer of 0 to 6.

[3C]

The pharmaceutical composition according to the above [2C], wherein, in the formula (I), a group represented by the formula:

is a group represented by the formula:

and
$R^1$ and m have the same meaning as in the above [2C].

[4C]

The pharmaceutical composition according to any of the above [1C] to [3C], wherein X is a single bond, —S—, —O— or —NR$^3$—.

[5C]

The pharmaceutical composition according to the above [4C], wherein X is —S— or —O—.

[6C]

The pharmaceutical composition according to the above [5C], wherein X is —O—.

[7C]

The pharmaceutical composition according to any of the above [1C] to [6C], wherein Y is substituted or unsubstituted aryl, or substituted or unsubstituted heteroaryl.

[8C]
The pharmaceutical composition according to the above [7C], wherein Y is substituted or unsubstituted aryl.

[9C]
The pharmaceutical composition according to the above [8C], wherein Y is a group represented by the formula:

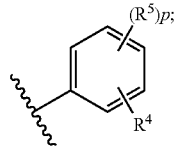

$R^4$ is a group represented by the formula: —$(CR^6R^7)q$-Z;
$R^6$ and $R^7$ are each independently hydrogen, hydroxy, substituted or unsubstituted alkyl, or substituted or unsubstituted amino;
q is an integer of 0 to 4;
Z is
(1) —COOH,
(2) —COOR$^8$,
(3) —OH,
(4) —C(O)NHR$^9$,
(5) —NHC(O)R$^{11}$,
(6) —NHSO$_2$R$^8$,
(7) —SO$_2$NHR$^9$,
(8) —SO$_2$NHC(O)R$^8$,
(9) —SO$_2$NHCOOR$^8$,
(10) —SO$_2$NHCONR$^9$R$^{10}$,
(11) —C(O)NHSO$_2$R$^8$,
(12) —NHC(O)NR$^9$R$^{10}$,
(13) —P(O)(OH)$_2$,
(14) —P(O)H(OH),
(15) —P(O)(R$^{11}$)$_2$,
(16) —P(O)(OR$^{11}$)$_2$,
(17) —P(O)(OH)(R$^{11}$),
(18) —P(O)(OH)(OR$^{11}$),
(19) —P(O)(R$^{11}$)(OR$^{11}$),
(20) —P(O)(OH)(O—(CR$^6$R$^7$)$_{0-4}$—R$^{12}$),
(21) —P(O)(NR$^9$CR$^{13}$R$^{14}$COOH)$_2$,
(22) —P(O)(NR$^9$CR$^{13}$R$^{14}$COOR$^{11}$)$_2$,
(23) —P(O)(OH)(NR$^9$CR$^{13}$R$^{14}$COOH),
(24) —P(O)(OH)(NR$^9$CR$^{13}$R$^{14}$COOR$^{11}$),
(25) —P(O)(NR$^9$CR$^{13}$R$^{14}$COOR$^{11}$)(O—R$^8$),
(26) —P)(O)(OR$^{13}$R$^{14}$OC(O)R$^{11}$)$_2$,
(27) —P(O)(OH)(OR$^{13}$R$^{14}$OC(O)R$^{11}$),
(28) —P(O)(OH)(—O—(CR$^6$R$^7$)$_{1-4}$—S(O)R$^{11}$),
(29) —P(O)(—O—(CR$^6$R$^7$)$_{1-4}$—S(O)R$^{11}$)$_2$,
(30) —P)(O)(OH)(—O—(CR$^6$R$^7$)$_{1-4}$—SC(O)R$^{11}$),
(31) —P(O)(—O—(CR$^6$R$^7$)$_{1-4}$—SC(O)R$^{11}$)$_2$
or (32)

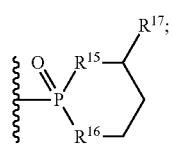

$R^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^9$ and $R^{10}$ are each independently hydrogen, or substituted or unsubstituted alkyl;
$R^{11}$ is substituted or unsubstituted alkyl;
$R^{12}$ is substituted or unsubstituted aryl;
$R^{13}$ and $R^{14}$ are each independently hydrogen, or substituted or unsubstituted alkyl;

$R^{15}$ and $R^{18}$ are each independently —O— or —NH—;
$R^{17}$ is substituted or unsubstituted aryl, or substituted or unsubstituted heteroaryl;
$R^5$ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and
p is an integer of 0 to 2.

[10C]
The pharmaceutical composition according to any of the above [1C] to [6C], wherein Y is substituted or unsubstituted alkyl.

[11C]
The pharmaceutical composition according to the above [10C], wherein Y is a group represented by the formula: —(CR$^{18}$R$^{19}$)r-Z;
$R^{18}$ and $R^{19}$ are each independently hydrogen, halogen, hydroxy, cyano, nitro, carboxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, or substituted or unsubstituted amino;
r is an integer of 0 to 4, and Z has the same meaning as in the above [9C].

[12C]
The pharmaceutical composition according to any of the above [1C] to [11C], wherein m is an integer of 1 to 2, and at least one of $R^1$ is halogen.

[13C]
The pharmaceutical composition according to any of the above [1C] to [12C], wherein m is an integer of 1 to 2, and at least one of $R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

[14C]
The pharmaceutical composition according to any of the above [1C] to [13C], wherein $R^2$ is hydrogen.

[15C]
A compound represented by the formula (I):

[Chem. 57]

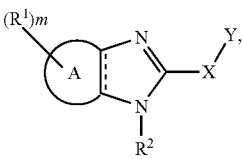

(I)

its pharmaceutically acceptable salt, or a solvate thereof, wherein
a group represented by the formula:

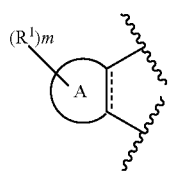

is a group represented by the formula;

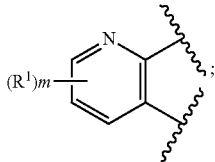

a dashed line represents the presence or absence of a bond;

R$^1$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

m is an integer of 0 to 3,

R$^2$ is hydrogen, or substituted or unsubstituted alkyl;

X is —O—; and

Y is substituted or unsubstituted aryl; with the proviso that compounds shown below are excluded:

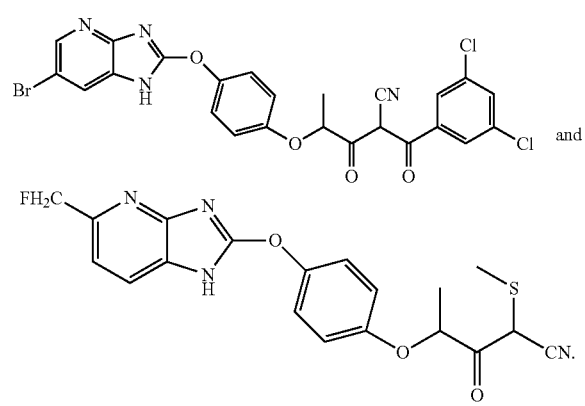

[16C]

The compound according to the above [15C], its pharmaceutically acceptable salt, or a solvate thereof, wherein Y is a group represented by the formula:

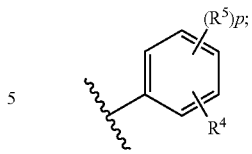

wherein R$^4$ is a group represented by the formula: —(CR$^6$R$^7$)q-Z;

R$^6$ and R$^7$ are each independently hydrogen, hydroxy, substituted or unsubstituted alkyl, or substituted or unsubstituted amino;

q is an integer of 0 to 4;

Z is
(1) —COOH,
(2) —COOR$^8$,
(3) —OH,
(4) —C(O)NHR$^9$,
(5) —NHC(O)R$^{11}$,
(6) —NHSO$_2$R$^8$,
(7) —SO$_2$NHR$^9$,
(8) —SO$_2$NHC(O)R$^8$,
(9) —SO$_2$NHCOOR$^8$,
(10) —SO$_2$NHCONR$^9$R$^{10}$,
(11) —C(O)NHSO$_2$R$^8$,
(12) —NHC(O)NR$^9$R$^{10}$,
(13) —P(O)(OH)$_2$,
(14) —P(O)H(OH),
(15) —P(O)(R$^{11}$)$_2$,
(16) —P(O)(OR$^{11}$)$_2$,
(17) —P(O)(OH)(R$^{11}$),
(18) —P(O)(OH)(OR$^{11}$),
(19) —P(O)(R$^{11}$)(OR$^{11}$),
(20) —P(O)(OH)(O—(CR$^6$R$^7$)$_{0-4}$—R$^{12}$),
(21) —P)(O)(NR$^9$CR$^{13}$R$^{14}$COOH)$_2$,
(22) —P(O)(NR$^9$CR$^{13}$R$^{14}$COOR$^{11}$)$_2$,
(23) —P(O)(OH)(NR$^9$CR$^{13}$R$^{14}$COOH)$_2$,
(24) —P(O)(OH)(NR$^9$CR$^{13}$R$^{14}$COOR$^{11}$),
(25) —P(O)(NR$^9$CR$^{13}$R$^{14}$COOR$^{11}$)(O—R$^8$),
(26) —P(O)(OCR$^{13}$R$^{14}$OC(O)R$^{11}$)$_2$,
(27) —P(O)(OH)(OCR$^{13}$R$^{14}$OC(O)R$^{11}$),
(28) —P)(O)(OH)(—O—(CR$^6$R$^7$)$_{1-4}$—S(O)R$^{11}$),
(29) —P(O)(—O—(CR$^6$R$^7$)$_{1-4}$—S(O)R$^{11}$)$_2$,
(30) —P(O)(OH)(—O—(CR$^6$R$^7$)$_{1-4}$—SC(O)R$^{11}$),
(31) —P)(O)(—O—(CR$^6$R$^7$)$_{1-4}$—SC(O)R$^{11}$)$_2$
or (32)

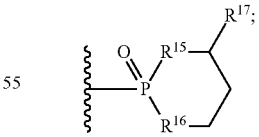

R$^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

R$^9$ and R$^{10}$ are each independently hydrogen, or substituted or unsubstituted alkyl;

R$^{11}$ is substituted or unsubstituted alkyl;

R$^{12}$ is substituted or unsubstituted aryl;

$R^{13}$ and $R^{14}$ are each independently hydrogen, or substituted or unsubstituted alkyl;

$R^{15}$ and $R^{16}$ are each independently —O— or —NH—;

$R^{17}$ is substituted or unsubstituted aryl, or substituted or unsubstituted heteroaryl;

$R^5$ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and p is an integer of 0 to 2.

[17C]

A pharmaceutical composition comprising the compound according to the above [15C] or [16C], its pharmaceutically acceptable salt, or a solvate thereof.

[18C]

The pharmaceutical composition according to the above [17C], which has an activating effect on adenosine monophosphate-activated protein kinase.

[19C]

The pharmaceutical composition according to any one of the above [1C] to [14C], and [18C], for the treatment and/or prevention of diabetes.

[20C]

A method for preventing or treating diabetes, comprising administering the compound according to any one of the above [1C] to [16C], its pharmaceutically acceptable salt, or a solvate thereof.

[21C]

The compound according to any one of the above [1C] to [16C], its pharmaceutically acceptable salt, or a solvate thereof, for the treatment and/or prevention of diabetes.

Effect of the Invention

Since the present compound has an AMPK activating effect, pharmaceutical compositions comprising the present compound are very useful as medicaments, especially, as medicaments for treatment and/or prevention of type II diabetes, hyperglycemia, metabolic syndrome, obesity, hypercholesterolemia and/or hypertension. Furthermore, the present compound has an efficiency as a medicament. Here, the efficiency as a medicament includes high metabolic stability, a weak drug-metabolizing enzyme induction, a weak inhibition of drug metabolizing enzyme that metabolizes other drug, a high oral absorption, a low clearance, a long half-life period enough to exhibit drug efficacy, a high enzyme activity, a high maximal activation rate, a low protein binding rate, high penetration into target tissue, high solubility, high safety and so on.

MODE FOR CARRYING OUT THE INVENTION

In the following, meanings of terms used in the present specification will be explained. Each term has the same meaning when used alone or in combination with other term in this description.

"Halogen" includes fluorine, chlorine, bromine or iodine.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like. Furthermore, "Alkynyl" may have a double bond.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, Spiro hydrocarbon group or the like. Preferable is cyclopropyl, cyclobutyl, cyclopentyl, cyclohexyl or bridged cyclic hydrocarbon group.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group which is derived by excluding one hydrogen from a cycle which consists of two hydrocarbon rings that share one carbon atom. Example includes spiro[3.4]octyl or the like.

"Cycloalkenyl" means C3 to C10 cyclic unsaturated aliphatic hydrocarbon group, and example includes cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl or 3-cyclopenten-1-yl), cyclohexenyl (e.g.: 1-cyclohexen-1-yl, 2-cyclohexen-1-yl or 3-cyclohexen-1-yl), cycloheptenyl (e.g.: 1-cycloheptenyl), cyclooctenyl (e.g.: 1-cyclooctenyl) or the like. Preferable is cyclopropenyl, cyclobutenyl, cyclopentenyl or cyclohexenyl. Cycloalkenyl also includes bridged cyclic hydrocarbon group and spiro hydrocarbon group which have an unsaturated bond in the ring.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group and a fused aromatic heterocyclic group.

The "monocyclic aromatic heterocyclic group" means a group which is induced from a 5 to 8-membered aromatic ring which has one or more, the same or different, hetero atoms optionally selected from oxygen, sulfur and nitrogen atoms in the ring, which group may have a bond at any substitutable position.

The "fused aromatic heterocyclic group" means a group in which a 5 to 8-membered aromatic ring which has one or more, the same or different, hetero atoms optionally selected from oxygen, sulfur and nitrogen atoms in the ring is fused with one to four 5 to 8-membered aromatic carbocyclic rings or another 5 to 8-membered aromatic hetero ring, which group may have a bond at any substitutable position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), dibenzofuryl, benzoxazolyl, benzothiazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocyclyl" means a non aromatic heterocyclic group, which may have a bond at any substitutable position of a ring which has at least one or more nitrogen, oxygen or sulfur atoms in the ring, or a ring in which such ring is fused with a cycloalkane (preferably 5 to 6-membered), a benzene ring and/or a ring which has at least one or more nitrogen, oxygen or sulfur atoms in the ring. "Nonaromatic heterocyclic group" can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperadino, 2-piperidinyl, 3-piperidinyl, 4-piperidinyl, 1-piperadinyl, 2-piperadinyl, 2-morpholinyl, 3-morpholinyl, morpholino, tetrahydropyranyl, 1,2,3,4-tetrahydroisoquinolinyl, 1,2,3,4-tetrahydroquinolinyl, 1,3-dihydro-2H-isoindol-5-yl or the like.

"Heterocyclyl" further contains a bridged group or a spiro ring forming group shown below.

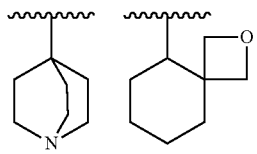

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl.

The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl" and the heterocyclyl part of "heterocyclylcarbonyl" respectively mean the above "alkyl", the above "alkenyl", the above "cycloalkyl", the above "cycloalkenyl", the above "aryl", the above "heteroaryl" and the above "heterocyclyl".

The alkyl part of "alkyloxy", "alkylthio", "alkylsulfonyl" and "alkyloxycarbonyl" means the above "alkyl".

The aryl part of "aryloxy", "arylthio" and "arylsulfonyl" means the above "aryl".

The heteroaryl part of "heteroaryloxy", "heteroarylthio" and "heteroarylsulfonyl" means the above "heteroaryl".

The cycloalkyl part of "cycloalkyloxy", "cycloalkylthio" and "cycloalkylsulfonyl" means the above "cycloalkyl".

The cycloalkenyl part of "cycloalkenyloxy", "cycloalkenylthio" and "cycloalkenylsulfonyl" means the above "cycloalkenyl".

The heterocyclyl part of "heterocyclyloxy", "heterocyclylthio" and "heterocyclylsulfonyl" means the above "heterocyclyl".

"Aromatic hetero ring" means a aromatic ring which contains one or more heteroatom(s) selected from the group consisting of nitrogen atom, sulfur atom and oxygen atom other than the carbon atom in the ring. The ring includes a monocycle or a fused ring.

As the "aromatic hetero ring", example includes a ring derived from the above "heteroaryl", and especially a 6-membered ring is preferable. An example includes pyridine, pyridazine, pyrimidine, pyrazine or the like.

"Nonaromatic hetero ring" means a nonaromatic ring which contains one or more heteroatom(s) selected from the group consisting of nitrogen atom, sulfur atom and oxygen atom other than the carbon atom in the ring. The ring means a 5 to 10 membered ring which may have a saturated or an unsaturated bond partially and may be fused with aryl or aromatic hetero ring.

"Substituted alkyl", "substituted alkenyl", "substituted alkynyl", "substituted aryl", "substituted heteroayl", "substituted cycloalkyl", "substituted cycloalkenyl", "substituted heterocyclyl", "substituted alkyloxy", "substituted aryloxy", "substituted heteroaryloxy", "substituted cycloalkyloxy", "substituted cycloalkenyloxy", "substituted heterocyclyloxy", "substituted alkylthio", "substituted arylthio", "substituted heteroarylthio", "substituted cycloalkylthio", "substituted cycloalkenylthio", "substituted heterocyclylthio", "substituted alkylsulfonyl", "substituted arylsulfonyl", "substituted heteroarylsulfonyl", "substituted cycloalkylsulfonyl", "substituted cycloalkenylsulfonyl", "substituted heterocyclylsulfonyl", "substituted acyl", "substituted carbamoyl", "substituted sulfamoyl", "substituted amino" or "substituted alkyloxycarbonyl" may be substituted with 1 to 4 substituent(s) selected from a group consisting of, for example, halogen; hydroxy; carboxy; nitro; cyano;

substituted or unsubstituted alkyl (an example of a substituent of substituted alkyl includes halogen, hydroxy, carboxy, nitro, cyano, alkyl, aryl, cycloalkyl, cycloalkenyl, heteroaryl, heterocyclyl, substituted or unsubstituted amino (an example of a substituent of substituted amino includes alkyl, alkylsulfonyl, acyl or alkyloxycarbonyl.), substituted or unsubstituted carbamoyl (an example of a substituent of substituted carbamoyl includes hydroxyalkyl, alkyloxyalkyl or alkyloxy.), substituted or unsubstituted alkylcarbamoyl (an example of a substituent of substituted alkylcarbamoyl includes hydroxy or alkylamino.), alkyloxycarbamoyl, substituted or unsubstituted acylamino (an example of a substituent of substituted acylamino includes hydroxy, cyano, alkyloxy, substituted or unsubstituted amino (an example of a substituent of substituted amino includes alkyl.)), alkyloxy, alkylsulfonylamino, alkyloxycarbonylamino, hydroxyimino or alkyloxyimino. e.g. methyl, ethyl, isopropyl, tert-butyl or $CF_3$);

substituted or unsubstituted alkenyl (an example of a substituent of substituted alkenyl includes halogen, hydroxy, carboxy, nitro, cyano, alkyl, aryl, cycloalkyl, cycloalkenyl, heteroaryl or heterocyclyl. e.g. vinyl);

substituted or unsubstituted alkynyl (an example of a substituent of substituted alkynyl includes halogen, hydroxy, carboxy, nitro, cyano, alkyl, aryl, cycloalkyl, cycloalkenyl, heteroaryl or heterocyclyl. e.g. ethynyl);

substituted or unsubstituted aryl (an example of a substituent of substituted aryl includes halogen, hydroxy, carboxy, nitro, cyano, substituted or unsubstituted alkyl (an example of a substituent of substituted alkyl includes hydroxy or alkyloxy.), aryl, cycloalkyl, cycloalkenyl, heteroaryl, heterocyclyl, alkyloxy, aryloxy, arylalkyl, carbamoyl, acylamino, alkylsulfonylamino or amino. e.g. phenyl or naphthyl);

substituted or unsubstituted cycloalkyl (an example of a substituent of substituted cycloalkyl includes halogen, hydroxy, carboxy, nitro, cyano, substituted or unsubstituted alkyl (an example of a substituent of substituted alkyl includes halogen, hydroxy, alkyloxy, acylamino, alkylamino or alkylcarbonyloxy.), aryl, cycloalkyl, cycloalkenyl, heteroaryl, heterocyclyl, carbamoyloxyalkyl, acylamino, carbamoyl or alkylsulfonylamino. e.g. cyclopropyl or cyclobutyl.);

substituted or unsubstituted cycloalkenyl (an example of a substituent of substituted cycloalkenyl includes halogen, hydroxy, carboxy, nitro, cyano, alkyl, aryl, cycloalkyl, cycloalkenyl, heteroaryl, heterocyclyl, amino or acylamino. e.g. cyclopropenyl);

substituted or unsubstituted heteroaryl (an example of a substituent of substituted heteroaryl includes halogen, hydroxy, carboxy, nitro, cyano, substituted or unsubstituted alkyl (an example of a substituent of substituted alkyl includes carboxy.), aryl, cycloalkyl, cycloalkenyl, heteroaryl, heterocyclyl or alkyloxy.);

substituted or unsubstituted heterocyclyl (an example of a substituent of substituted heterocyclyl includes halogen, hydroxy, carboxy, nitro, cyano, substituted or unsubstituted alkyl (an example of a substituent of substituted alkyl includes hydroxy.), aryl, cycloalkyl, cycloalkenyl, heteroaryl, heterocyclyl, acyl, alkylamino, alkyloxy or acylamino.);

substituted or unsubstituted alkyloxy (an example of a substituent of substituted alkyloxy includes halogen, hydroxy, carboxy, nitro, cyano, alkyl, aryl, cycloalkyl, cycloalkenyl, heteroaryl, heterocyclyl, alkyloxy, alkyloxycarbonyl, acylamino, substituted or unsubstituted carbamoylamino (an example of a substituent of substituted carbamoylamino includes alkyl.) or acyl. e.g. methoxy or ethoxy);

substituted or unsubstituted aryloxy (an example of a substituent of substituted aryloxy includes halogen, hydroxy, carboxy, nitro, cyano, alkyl, aryl, cycloalkyl, cycloalkenyl, heteroaryl or heterocyclyl. e.g. phenyloxy);

substituted or unsubstituted cycloalkyloxy (an example of a substituent of substituted cycloalkyloxy includes halogen, hydroxy, carboxy, nitro, cyano, alkyl, aryl, cycloalkyl, cycloalkenyl, heteroaryl or heterocyclyl.);

substituted or unsubstituted cycloalkenyloxy (an example of a substituent of substituted cycloalkenyloxy includes halogen, hydroxy, carboxy, nitro, cyano, alkyl, aryl, cycloalkyl, cycloalkenyl, heteroaryl or heterocyclyl.);

substituted or unsubstituted heteroaryloxy (an example of a substituent of substituted heteroaryloxy includes halogen, hydroxy, carboxy, nitro, cyano, alkyl, aryl, cycloalkyl, cycloalkenyl, heteroaryl or heterocyclyl.);

substituted or unsubstituted heterocyclyloxy (an example of a substituent of substituted heterocyclyloxy includes halogen, hydroxy, carboxy, nitro, cyano, alkyl, aryl, cycloalkyl, cycloalkenyl, heteroaryl or heterocyclyl.);

substituted or unsubstituted arylalkyl (an example of a substituent of substituted arylalkyl includes halogen, hydroxy, carboxy, nitro, cyano, alkyl, aryl, cycloalkyl, cycloalkenyl, heteroaryl or heterocyclyl. e.g. benzyl);

substituted or unsubstituted arylalkyloxy (an example of a substituent of substituted arylalkyloxy includes halogen, hydroxy, carboxy, nitro, cyano, alkyl, aryl, cycloalkyl, cycloalkenyl, heteroaryl or heterocyclyl. e.g. benzyloxy);

substituted or unsubstituted cycloalkylalkyloxy (an example of a substituent of substituted cycloalkylalkyloxy includes halogen, hydroxy, carboxy, nitro, cyano, alkyl, aryl, cycloalkyl, cycloalkenyl, heteroaryl or heterocyclyl.);

substituted or unsubstituted silyloxy;

substituted or unsubstituted amino (e.g. substituted or unsubstituted alkylamino (an example of a substituent of substituted alkylamino includes alkyloxy, heterocyclyl, cycloalkyl or hydroxy. e.g. methylamino, ethylamino, dimethylamino), substituted or unsubstituted acylamino (an example of a substituent of substituted acylamino includes carboxy. e.g. acetylamino or benzoylamino), arylamino, arylalkylamino (e.g. benzylamino or tritylamino), hydroxyamino, alkyloxycarbonylamino, alkylsulfonylamino, substituted or unsubstituted carbamoylamino (an example of a substituent of substituted carbamoylamino includes benzyl.), heterocyclylcarbonylamino, arylsulfonylamino, heteroarylsulfonylamino or substituted or unsubstituted sulfamoylamino (an example of a substituent of substituted sulfamoylamino includes alkyl.));

substituted or unsubstituted carbamoyl (an example of a substituent of substituted carbamoyl includes hydroxy, cyano, substituted or unsubstituted alkyl (an example of a substituent of substituted alkyl includes hydroxy, alkyloxy, alkylamino or dimethylamino.), aryl, cycloalkyl, cycloalkenyl, heteroaryl, heterocyclyl, heterocyclylalkyl, $C_2H_4OH$ or alkyloxy. e.g. alkylcarbamoyl (e.g. methylcarbamoyl, ethylcarbamoyl, dimethylcarbamoyl, phenylethylcarbamoyl, dimethylaminoethylcarbamoyl, isopropylcarbamoyl or hydroxyethylcarbamoyl), alkylsulfonylcarbamoyl, heteroarylalkylcarbamoyl or substituted or unsubstituted alkyloxycarbamoyl);

substituted or unsubstituted carbamoyloxy (an example of a substituent of substituted carbamoyloxy includes halogen, alkyl, aryl, cycloalkyl, cycloalkenyl, heteroaryl or heterocyclyl.);

substituted or unsubstituted acyl (an example of a substituent of substituted acyl includes halogen, hydroxy, carboxy, nitro, cyano, alkyl, aryl, cycloalkyl, cycloalkenyl, heteroaryl or heterocyclyl. e.g. alkylcarbonyl, arylcarbonyl, heteroarylcarbonyl, heterocyclylcarbonyl, formyl or acetyl);

substituted or unsubstituted alkylsulfonyl (an example of a substituent of substituted alkylsulfonyl includes halogen, hydroxy, carboxy, nitro, cyano, alkyl, aryl, cycloalkyl, cycloalkenyl, heteroaryl or heterocyclyl. e.g. methanesulfonyl or ethanesulfonyl);

- substituted or unsubstituted arylsulfonyl (an example of a substituent of substituted arylsulfonyl includes halogen, hydroxy, carboxy, nitro, cyano, alkyl, aryl, cycloalkyl, cycloalkenyl, heteroaryl or heterocyclyl.);
- substituted or unsubstituted cycloalkylsulfonyl (an example of a substituent of substituted cycloalkylsulfonyl includes halogen, hydroxy, carboxy, nitro, cyano, alkyl, aryl, cycloalkyl, cycloalkenyl, heteroaryl or heterocyclyl.);
- substituted or unsubstituted cycloalkenylsulfonyl (an example of a substituent of substituted cycloalkenylsulfonyl includes halogen, hydroxy, carboxy, nitro, cyano, alkyl, aryl, cycloalkyl, cycloalkenyl, heteroaryl or heterocyclyl.);
- substituted or unsubstituted heteroarylsulfonyl (an example of a substituent of substituted heteroarylsulfonyl includes halogen, hydroxy, carboxy, nitro, cyano, alkyl, aryl, cycloalkyl, cycloalkenyl, heteroaryl or heterocyclyl.);
- substituted or unsubstituted heterocyclylsulfonyl (an example of a substituent of substituted heterocyclylsulfonyl includes halogen, hydroxy, carboxy, nitro, cyano, alkyl, aryl, cycloalkyl, cycloalkenyl, hetaroaryl or heterocyclyl.);
- substituted or unsubstituted sulfamoyl (an example of a substituent of substituted sulfamoyl includes halogen, substituted or unsubstituted alkyl (an example of a substituent of substituted alkyl includes hydroxy.), aryl, cycloalkyl, cycloalkenyl, heteroaryl, heterocyclyl, acyl or $C_2H_4OH$.);
- substituted or unsubstituted alkyloxycarbonyl (an example of a substituent of substituted alkyloxycarbonyl includes halogen, hydroxy, carboxy, nitro, cyano, alkyl, aryl, cycloalkyl, cycloalkenyl, heteroaryl or heterocyclyl. e.g. methoxycarbonyl, ethoxycarbonyl or tert-butoxycarbonyl);
- substituted or unsubstituted aryloxycarbonyl (an example of a substituent of substituted aryloxycarbonyl includes halogen, hydroxy, carboxy, nitro, cyano, alkyl, aryl, cycloalkyl, cycloalkenyl, heteroaryl or heterocyclyl.);
- substituted or unsubstituted cycloalkyloxycarbonyl (an example of a substituent of substituted cycloalkyloxycarbonyl includes halogen, hydroxy, carboxy, nitro, cyano, alkyl, aryl, cycloalkyl, cycloalkenyl, heteroaryl or heterocyclyl.);
- substituted or unsubstituted cycloalkenyloxycarbonyl (an example of a substituent of substituted cycloalkenyloxycarbonyl includes halogen, hydroxy, carboxy, nitro, cyano, alkyl, aryl, cycloalkyl, cycloalkenyl, hetaroaryl or heterocyclyl.);
- substituted or unsubstituted heteroaryloxycarbonyl (an example of a substituent of substituted heteroaryloxycarbonyl includes halogen, hydroxy, carboxy, nitro, cyano, alkyl, aryl, cycloalkyl, cycloalkenyl, heteroaryl or heterocyclyl.);
- substituted or unsubstituted heterocyclyloxycarbonyl (an example of a substituent of substituted heterocyclyloxycarbonyl includes halogen, hydroxy, carboxy, nitro, cyano, alkyl, aryl, cycloalkyl, cycloalkenyl, heteroaryl or heterocyclyl.);
- substituted or unsubstituted alkyloxyaryl (an example of a substituent of substituted alkyloxyaryl includes acylamino.);
- alkylsulfinyl; cycloalkylsulfinyl; arylsulfinyl; heteroarylsulfinyl; heterocyclylsulfinyl;
- nitroso;
- alkenyloxy (e.g. vinyloxy or allyloxy);
- azido;
- isocyano; isocyanato; thiocyanato; isothiocyanato; mercapto; alkylthio (e.g. methylthio);
- $P(=O)(OH)_2$,
- $P(=O)(OCH_2CH_3)_2$,
- $C(=O)C(=O)OH$,
- $C(CH_3)=N-O-CH_3$,
- $C(CH_3)=N-OH$,
- formyloxy; haloformyl; oxalo; thioformyl; thiocarboxy; dithiocarboxy; thiocarbamoyl; sulfino; sulfo; sulfoamino; hydrazine; ureido; amidino; guanidine; phthalimido; oxo and the like.

Preferred example of a substituent of "substituted carbamoyl", "substituted sulfamoyl" or "substituted amino" includes

- substituted or unsubstituted alkyl (an example of a substituent of substituted alkyl includes halogen, hydroxy, carboxy, nitro, cyano, alkyl, aryl, cycloalkyl, cycloalkenyl, heteroaryl or heterocyclyl.);
- substituted or unsubstituted alkenyl (an example of a substituent of substituted alkenyl includes halogen, hydroxy, carboxy, nitro, cyano, alkyl, aryl, cycloalkyl, cycloalkenyl, heteroaryl or heterocyclyl.);
- substituted or unsubstituted aryl (an example of a substituent of substituted aryl includes halogen, hydroxy, carboxy, nitro, cyano, alkyl, aryl, cycloalkyl, cycloalkenyl, heteroaryl or heterocyclyl.);
- substituted or unsubstituted heteroaryl (an example of a substituent of substituted heteroaryl includes halogen, hydroxy, carboxy, nitro, cyano, alkyl, aryl, cycloalkyl, cycloalkenyl, heteroaryl or heterocyclyl.);
- substituted or unsubstituted cycloalkyl (an example of a substituent of substituted cycloalkyl includes halogen, hydroxy, carboxy, nitro, cyano, alkyl, aryl, cycloalkyl, cycloalkenyl, heteroaryl or heterocyclyl.);
- substituted or unsubstituted cycloalkenyl (an example of a substituent of substituted cycloalkenyl includes halogen, hydroxy, carboxy, nitro, cyano, alkyl, aryl, cycloalkyl, cycloalkenyl, heteroaryl or heterocyclyl.);
- substituted or unsubstituted heterocyclyl (an example of a substituent of substituted heterocyclyl includes halogen, hydroxy, carboxy, nitro, cyano, alkyl, aryl, cycloalkyl, cycloalkenyl, heteroaryl or heterocyclyl.);
- substituted or unsubstituted arylalkyl (an example of a substituent of substituted arylalkyl includes halogen, hydroxy, carboxy, nitro, cyano, alkyl, aryl, cycloalkyl, cycloalkenyl, heteroaryl or heterocyclyl.);
- substituted or unsubstituted alkyloxy (an example of a substituent of substituted alkyloxy includes halogen, hydroxy, carboxy, nitro, cyano, alkyl, aryl, cycloalkyl, cycloalkenyl, heteroaryl or heterocyclyl.);
- substituted or unsubstituted aryloxy (an example of a substituent of substituted aryloxy includes halogen, hydroxy, carboxy, nitro, cyano, alkyl, aryl, cycloalkyl, cycloalkenyl, heteroaryl or heterocyclyl.);
- substituted or unsubstituted cycloalkyloxy (an example of a substituent of substituted cycloalkyloxy includes halogen, hydroxy, carboxy, nitro, cyano, alkyl, aryl, cycloalkyl, cycloalkenyl, heteroaryl or heterocyclyl.)
- substituted or unsubstituted cycloalkenyloxy (an example of a substituent of substituted cycloalkenyloxy includes halogen, hydroxy, carboxy, nitro, cyano, alkyl, aryl, cycloalkyl, cycloalkenyl, heteroaryl or heterocyclyl.);
- substituted or unsubstituted heteroaryloxy (an example of a substituent of substituted heteroaryloxy includes halogen, hydroxy, carboxy, nitro, cyano, alkyl, aryl, cycloalkyl, cycloalkenyl, heteroaryl or heterocyclyl.);
- substituted or unsubstituted heterocyclyloxy (an example of a substituent of substituted heterocyclyloxy includes halogen, hydroxy, carboxy, nitro, cyano, alkyl, aryl, cycloalkyl, cycloalkenyl, heteroaryl or heterocyclyl.);

substituted or unsubstituted acyl (an example of a substituent of substituted acyl includes halogen, hydroxy, carboxy, nitro, cyano, alkyl, aryl, cycloalkyl, cycloalkenyl, heteroaryl or heterocyclyl.);

substituted or unsubstituted alkyloxycarbonyl (an example of a substituent of substituted alkyloxycarbonyl includes halogen, hydroxy, carboxy, nitro, cyano, alkyl, aryl, cycloalkyl, cycloalkenyl, heteroaryl or heterocyclyl.);

aryloxycarbonyl; cycloalkyloxycarbonyl; cycloalkenyloxycarbonyl; heteroaryloxycarbonyl; heterocyclyloxycarbonyl;

substituted or unsubstituted sulfamoyl (an example of a substituent of substituted sulfamoyl includes halogen, hydroxy, carboxy, nitro, cyano, alkyl, aryl, cycloalkyl, cycloalkenyl, heteroaryl or heterocyclyl.);

substituted or unsubstituted alkylsulfonyl (an example of a substituent of substituted alkylsulfonyl includes halogen, hydroxy, carboxy, nitro, cyano, alkyl, aryl, cycloalkyl, cycloalkenyl, heteroaryl or heterocyclyl.);

substituted or unsubstituted arylsulfonyl (an example of a substituent of substituted arylsulfonyl includes halogen, hydroxy, carboxy, nitro, cyano, alkyl, aryl, cycloalkyl, cycloalkenyl, heteroary or heterocyclyl.);

substituted or unsubstituted heteroarylsulfonyl (an example of a substituent of substituted heteroarylsulfonyl includes halogen, hydroxy, carboxy, nitro, cyano, alkyl, aryl, cycloalkyl, cycloalkenyl, heteroaryl or heterocyclyl.);

substituted or unsubstituted cycloalkylsulfonyl (an example of a substituent of substituted cycloalkylsulfonyl includes halogen, hydroxy, carboxy, nitro, cyano, alkyl, aryl, cycloalkyl, cycloalkenyl, heteroaryl or heterocyclyl.);

substituted or unsubstituted cycloalkenylsulfonyl (an example of a substituent of substituted cycloalkenylsulfonyl includes halogen, hydroxy, carboxy, nitro, cyano, alkyl, aryl, cycloalkyl, cycloalkenyl, heteroaryl or heterocyclyl.);

substituted or unsubstituted heterocyclylsulfonyl (an example of a substituent of substituted heterocyclylsulfonyl includes halogen, hydroxy, carboxy, nitro, cyano, alkyl, aryl, cycloalkyl, cycloalkenyl, heteroaryl or heterocyclyl.);

substituted or unsubstituted carbamoyl (an example of a substituent of substituted carbamoyl includes halogen, hydroxy, carboxy, nitro, cyano, alkyl, aryl, cycloalkyl, cycloalkenyl, heteroaryl or heterocyclyl.);

halogen; hydroxy; carboxy; nitro; cyano; alkylsulfinyl; cycloalkylsulfinyl; cycloalkenylsulfinyl; arylsulfinyl; heteroarylsulfinyl; heterocyclylsulfinyl; amino or the like.

The alkyl part of "alkylamino", "arylalkylamino", "alkyloxycarbonylamino", "alkylsulfonylamino", "alkylcarbamoyl", "alkylsulfonylcarbamoyl", "heteroarylalkylcarbamoyl", "alkyloxycarbamoyl", "alkylcarbonyl", "hydroxyalkyl", "alkyloxyalkyl", "alkyloxyimino", "carbamoyloxyalkyl", "alkyloxyaryl", "alkylcarbonyloxy", and "alkylsulfinyl" means the above-described "alkyl".

The alkenyl part of "alkenyloxy" means the above-described "alkenyl".

The aryl part of "arylalkyl", "arylalkyloxy", "arylamino", "arylalkylamino", "arylsulfonylamino", "arylcarbonyl", "aryloxycarbonyl", "alkyloxyaryl" and "arylsulfinyl" means the above-described "aryl".

The heteroaryl part of "heteroarylsulfonylamino", "heteroarylalkylcarbamoyl", "hetaroarylcarbonyl", "heteroaryloxycarbonyl" and "heteroarylsulfinyl" means the above-described "heteroaryl".

The cycloalkyl part of "cycloalkylsulfinyl" and "cycloalkyloxycarbonyl" means the above-described "cycloalkyl".

The cycloalkenyl part of "cycloalkenyloxycarbonyl" means the above-described "cycloalkenyl".

The heterocyclyl part of "heterocyclylcarbonylamino", "heterocyclylalkyl", "heterocyclylcarbonyl", "heterocyclyloxycarbonyl" and "heterocyclylsulfinyl" means the above-described "heterocyclyl".

Among the compounds of the present invention, the following embodiments are preferable.

Ring A includes an aromatic heterocycle or a non aromatic heterocycle, which is fused with a 5-membered ring adjacent thereto.

Ring A in the formula (I) includes an aromatic heterocycle or a non aromatic heterocycle, which is fused with a 5-membered ring adjacent thereto. Although Ring A contains not only a monocycle but also a fused ring (2 to 3 fused ring), particularly preferred is a monocycle. A substitutable arbitrary position in Ring A may be substituted with 1 to 7 of $R^1$.

As a preferred embodiment, examples of Ring A include the following rings. A substitutable arbitrary position in Ring A may be substituted with 1 to 3 of $R^1$.

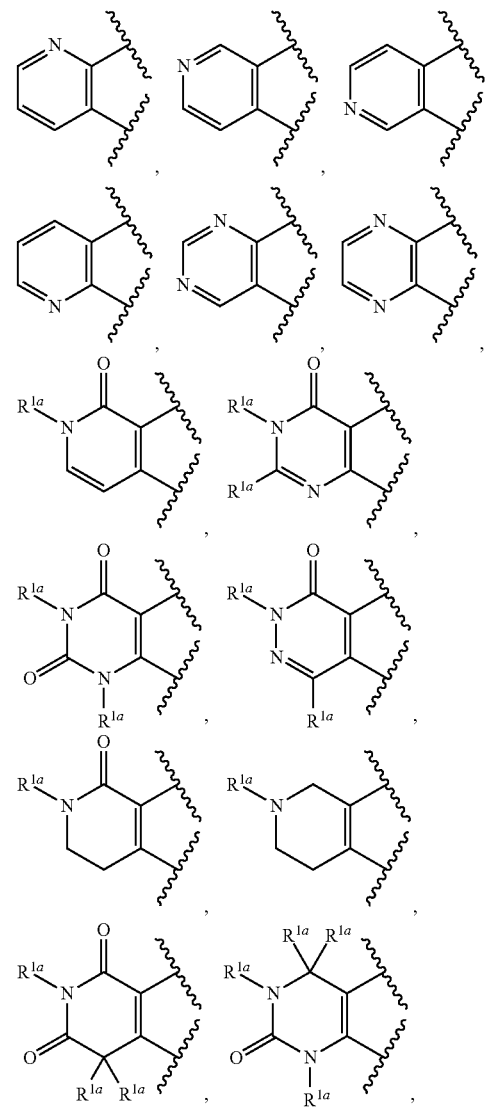

-continued

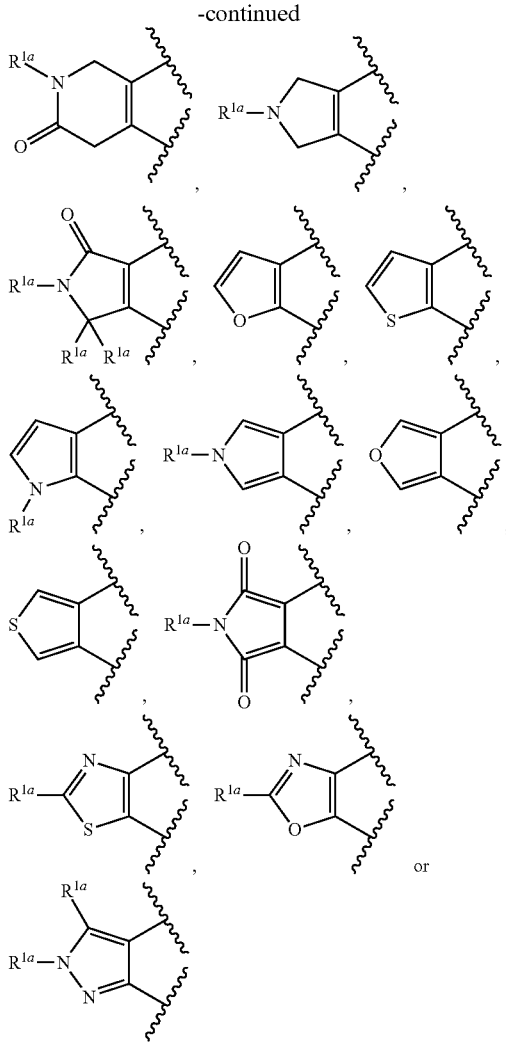

Wherein, $R^{1a}$ has the same meaning as the above.

$R^1$ is each independently halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

m is an integer of 0 to 7. Preferably, m is an integer of 0 to 3. It is particularly preferred when m is an integer of 1 to 2 and at least one of $R^1$ is halogen, and when m is an integer of 1 to 2 and at least one of $R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl. In addition, it is preferred when m is 2, one of $R^1$ is halogen and the other of $R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

$R^2$ is hydrogen, or substituted or unsubstituted alkyl, and preferably hydrogen.

X is a single bond, —S—, —O—, —NR$^3$—, —C(=O)—, —NR$^3$C(=O)—, —C(=O)NR$^3$—, —NR$^3$—SO$_2$—, —SO$_2$—NR$^3$— or —C(=O)—O—, and preferably a single bond, —S— or —O—. Further preferably, X is —O—.

$R^3$ is hydrogen, or substituted or unsubstituted alkyl, and preferably hydrogen.

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, Y is substituted or unsubstituted alkyl, substituted or unsubstituted aryl, or substituted or unsubstituted heteroaryl.

Further preferably, Y is substituted or unsubstituted aryl, or substituted or unsubstituted heteroaryl.

$R^{1a}$ is each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

n is an integer of 0 to 6. Preferably, n is an integer of 0 to 2.

$R^4$ is a group represented by the formula: —(CR$^6$R$^7$)q-Z.

$R^6$ is each independently hydrogen, hydroxy, substituted or unsubstituted alkyl, or substituted or unsubstituted amino.

$R^7$ is each independently hydrogen, hydroxy, substituted or unsubstituted alkyl, or substituted or unsubstituted amino.

Preferably, $R^6$ is each independently substituted or unsubstituted alkyl.

Preferably, $R^7$ is each independently substituted or unsubstituted alkyl.

q is an integer of 0 to 4. Preferably, q is 0 or 1, and further preferably, q is 1.

Z is
(1) —COOH,
(2) —COOR$^8$,
(3) —OH,
(4) —C(=O)—NR$^9$R$^{10}$,
(5) —NR$^9$—C(=O)—R$^{11}$,
(6) —NR$^9$—SO$_2$—R$^8$, (7) —SO$_2$—NR$^9$R$^{10}$,
(8) —SO$_2$—NR$^9$—C(=O)—R$^8$,
(9) —SO$_2$—NR$^9$—COOR$^8$,
(10) —SO$_2$—NR$^9$—C(=O)—NR$^9$R$^{10}$,
(11) —C(=O)—NR$^9$—SO$_2$—R$^8$,
(12) —NR$^9$—C(=O)—NR$^9$R$^{10}$,
(13) —P(=O)(—OH)$_2$,
(14) —P(=O)H(—OH),
(15) —P(=O)(—R$^{11}$)$_2$,
(16) —P(=O)(—OR$^{11}$)$_2$,
(17) —P(=O)(—OH)(—R$^{11}$),
(18) —P(=O)(—OH)(—OR$^{11}$),
(19) —P(=O)(—R$^{11}$)(—OR$^{11}$),
(20) —P(=O)(—OH)(—O—(CR$^6$R$^7$)$_{0-4}$—R$^{12}$),
(21) —P(=O)(—NR$^9$—CR$^{13}$R$^{14}$—COOH)$_2$,
(22) —P(=O)(—NR$^9$—CR$^{13}$R$^{14}$—COOR$^{11}$)$_2$,
(23) —P(=O)(—OH)(—NR$^9$—CR$^{13}$R$^{14}$—COOH),
(24) —P(=O)(—OH)(—NR$^9$—CR$^{13}$R$^{14}$—COOR$^{11}$),
(25) —P(=O)(—NR$^9$—CR$^{13}$R$^{14}$—COOR$^{11}$)(—O—R$^8$),
(26) —P(=O)(—O—CR$^{13}$R$^{14}$—O—C(=O)—R$^{11}$)$_2$,
(27) —P(=O)(—OH)(—O—CR$^{13}$R$^{14}$—O—C(=O)—R$^{11}$),
(28) —P(=O)(—OH)(—O—(CR$^6$R$^7$)$_{1-4}$—S(=O)—R$^{11}$),
(29) —P(=O)(—O—(CR$^6$R$^7$)$_{1-4}$—S(=O)—R$^{11}$)$_2$,
(30) —P(=O)(—OH)(—O—(CR$^6$R$^7$)$_{1-4}$—S—C(=O)—R$^{11}$),
(31) —P(=O)(—O—(CR$^6$R$^7$)$_{1-4}$—S—C(=O)—R$^{11}$)$_2$,
(32) —NR$^9$—C(=O)—O—R$^{11}$
or

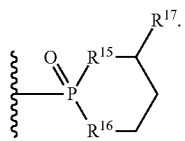

(33)

Preferred is,
(1) —COOH,
(3) —OH,
(4) —C(=O)—NR$^9$R$^{10}$, or
(5) —NR$^9$—C(=O)—R$^{11}$.

R$^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

R$^9$ and R$^{10}$ are each independently hydrogen, or substituted or unsubstituted alkyl.

Preferably, R$^9$ and R$^{10}$ are hydrogen.

R$^{11}$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, R$^{11}$ is substituted or unsubstituted alkyl.

R$^{12}$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

R$^{13}$ and R$^{14}$ are each independently hydrogen, or substituted or unsubstituted alkyl.

R$^{15}$ and R$^{16}$ are each independently —O— or —NH—.

R$^{17}$ is substituted or unsubstituted aryl, or substituted or unsubstituted heteroaryl.

R$^5$ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino.

Preferably, R$^5$ is substituted or unsubstituted alkyl.

p is an integer of 0 to 2.

R$^{18}$ is each independently hydrogen, halogen, hydroxy, cyano, nitro, carboxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, or substituted or unsubstituted amino.

R$^{19}$ is each independently hydrogen, halogen, hydroxy, cyano, nitro, carboxy, substituted or unsubstituted alkyl, substituted or unsubstituted alkyloxy, substituted or unsubstituted alkyloxycarbonyl, substituted or unsubstituted alkylsulfonyl, substituted or unsubstituted carbamoyl, or substituted or unsubstituted amino.

r is an integer of 1 to 4. Preferably, r is 1.

R$^{1X}$ is halogen.

Among the compounds of the present invention, when R$^2$ is hydrogen, a compound represented by the formula (I) is a compound represented by the formula (I') or a compound represented by the formula (I").

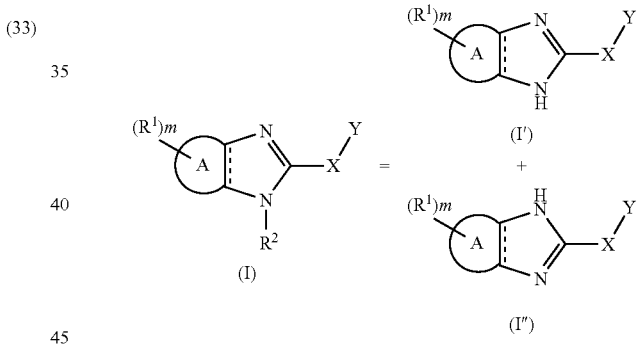

One or more hydrogen, carbon or other atoms of the compound of formula (I) of the present invention can be replaced by an isotope of the hydrogen, carbon or other atoms.

For example, compounds of formula (I) include all radiolabeled forms of compounds of formula (I). The "radiolabeled," "radiolabeled form" and the like of the compound of formula (I) are encompassed by the present invention and useful as a research and/or diagnostic tool in metabolism pharmacokinetic studies and in binding assays.

Examples of isotopes that can be incorporated into the compound of formula (I) of the present invention include isotopes of hydrogen, carbon, nitrogen, oxygen, phosphorous, sulfur, fluorine and chlorine, such as 2H, 3H, 13C, 14C, 15N, 18O, 17O, 31P, 32P, 35S, 18F and 36Cl, respectively. Radiolabeled compounds of the present invention can be prepared by methods known in the art. For example, tritiated compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). 14C-labeled compounds can be prepared by employing starting materials having a 14C carbon.

As a pharmaceutically acceptable salt of the present compound, the following salts can be included.

As a basic salt, example includes alkali metal salt such as sodium salt or potassium salt; alkaline earth metal salt such as calcium salt or strontium salt; metal salt such as beryllium salt, magnesium salt, zinc salt or transition metal salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

The term "solvate" means a solvate of a compound of the present invention or a pharmaceutically acceptable salt thereof, and example includes alcohol (e.g., ethanol) solvate, hydrate or the like. Example of hydrate includes monohydrate, dihydrate or the like.

A compound represented by the formula (I) in the present invention, its pharmaceutically acceptable salt or a solvate thereof can form a prodrug, and the present invention also contains such various types of prodrug. The prodrugs are a derivative of a compound of the present invention, which has a chemically or metabolically decomposable group, and a compound which is changed into a compound of the present invention, which is pharmaceutically active, by solvolysis or in vivo under physiological conditions. The prodrugs contain a compound which is converted into a compound represented by the formula (I) by enzymatic oxidation, reduction, hydrolysis and the like in living organisms under physiological conditions; a compound which is converted into a compound represented by the formula (I) by hydrolysis by e.g. gastric acid; and the like. A method for selecting and a method for producing a proper prodrug derivative are described in e.g. Design of Prodrugs, Elsevier, Amsterdam 1985. Prodrugs can have activity in theirself.

When a compound represented by the formula (I), its pharmaceutically acceptable salt or a solvate thereof has a hydroxyl group, prodrugs such as an acyloxy derivative and a sulfonyloxy derivative are exemplified, which derivatives are produced, for example, by a reaction of a compound having a hydroxy group and a proper acyl halide, a proper acid anhydride, a proper sulfonyl chloride, a proper sulfonyl anhydride and a mixed anhydride, or a reaction using a condensing agent. Examples thereof include $CH_3COO-$, $C_2H_5COO-$, t-BuCOO—, $C_{15}H_{31}COO-$, PhCOO—, (m-NaOOCP)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$—O—$PhSO_3-$, $PhSO_3-$ and p-$CH_3PhSO_3-$.

The term "activating" means that a compound of the present invention activates the function of AMPK.

The term "pharmaceutically acceptable" means preventively or therapeutically harmless.

A general method for producing a compound of the present invention will be illustrated below. For extraction, purification and the like, treatment which is carried out in common experiments in organic chemistry may be carried out.

A compound represented by the formula (I-H) can be synthesized as follows.

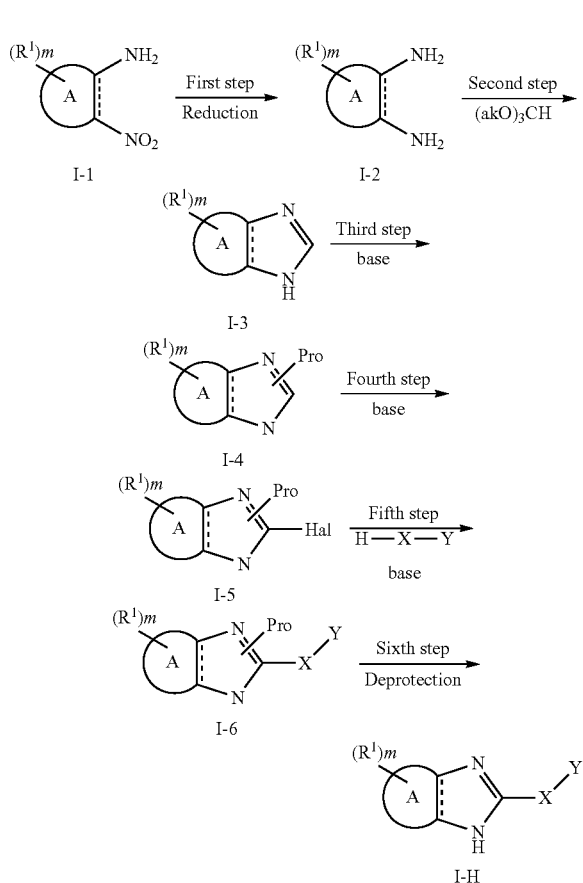

wherein, each symbol has the same meaning as above, and as a compound represented by the formula (I-1), a known compound can be used and a compound which is derived from a known compound by a conventional method can be used. "ak" is C1 to C3 alkyl, "Hal" is halogen, Pro is a protecting group. Pro includes a benzyl group, a benzoyl group and SEM (trimethylsilylethoxymethyl) and the like.

First Step

The first step is the step for producing a compound represented by the formula (I-2) by reduction of a compound represented by the formula (I-1).

As a solvent, example includes N,N-dimethylformamide, dimethylsulfoxide, aromatic hydrocarbons (e.g. toluene, benzene, xylene etc.), saturated hydrocarbons (e.g. cyclohexane, hexane etc.), halogenated hydrocarbons (e.g. dichloromethane, chloroform, 1,2-dichloroethane etc.), ethers (e.g. tetrahydrofuran, diethyl ether, dioxane, 1,2-dimethoxyethane etc.), esters (e.g. methyl acetate, ethyl acetate etc.), ketones (e.g. acetone, methylethylketone etc.), nitriles (e.g. acetonitrile etc.), alcohols (e.g. methanol, ethanol, t-butanol etc.), water, a mixed solvent thereof or the like.

Preferably, halogenated hydrocarbons (e.g. dichloromethane, chloroform, 1,2-dichloroethane etc.), ethers (e.g. tetrahydrofuran, diethylether, dioxane, 1,2-dimethoxyethane etc.), esters (e.g. methyl acetate, ethyl acetate etc.), nitriles (e.g. acetonitrile etc.), alcohols (e.g. methanol, ethanol, t-butanol etc.) or water can be used.

The reaction can be carried out in the presence of Fe, Pd/C, Sn or the like at room temperature to 100° C. for 0.5 to 12 hours.

Although an acid can be used, there is no need to use it. Preferably, an acid includes hydrochloric acid, ammonium chloride or the like.

This step can be carried out using conditions for a reaction which is known as a hydrogenation reaction. The reduction, for example, can be carried out in the presence of Pd/C.

This step can be also carried out using an organic chemical reaction, which is known as a reduction method of a nitro group.

This step can be carried out under a condition in which a substituent on the ring A is suitably protected.

Second Step

The second step is the step for producing a compound represented by the formula (I-3) by reacting a compound represented by the formula (I-2) and a compound represented by the formula: $(akO)_3CH$.

As a solvent, a solvent described in the first step can be used. Preferably, halogenated hydrocarbons (e.g. dichloromethane, chloroform, 1,2-dichloroethane etc.), alcohols (e.g. methanol, ethanol, t-butanol etc.) or the like can be used.

Although an acid can be used, there is no need to use it. Preferably, an acid includes hydrochloric acid, $NH_3SO_3$ or the like.

The reaction can be carried out at room temperature to 150° C. for 0.5 to 12 hours.

As a compound represented by the formula: $(akO)_3CH$, example includes $(MeO)_3CH$, $(EtO)_3CH$ or the like.

Third Step

The third step is the step for producing a compound represented by the formula (I-4) from a compound represented by the formula (I-3).

As a solvent, a solvent described in the first step can be used. Preferably, N,N-dimethylformamide, ethers (e.g. tetrahydrofuran, diethyl ether, dioxane, 1,2-dimethoxyethane etc.), halogenated hydrocarbons (e.g. dichloromethane, chloroform, 1,2-dichloroethane etc.), nitriles (e.g. acetonitrile etc.) or the like can be used.

As a base, example includes metal hydrides (e.g. sodium hydride etc.), metal hydroxides (e.g. sodium hydroxide, potassium hydroxide, lithium hydroxide, barium hydroxide etc.), metal carbonates (e.g. sodium carbonate, calcium carbonate, cesium carbonate etc.), metal alkoxides (e.g. sodium methoxide, sodium ethoxide, potassium t-butoxide etc.), sodium hydrogen carbonate, metal sodium, metal amides, organic amines (e.g. triethylamine, diisopropylethylamine, DBU, 2,6-lutidine etc.), pyridine, alkyllithiums (n-BuLi, sec-BuLi, tert-BuLi), or the like.

Preferably, metal sodium, organic amines (e.g. triethylamine, diisopropylethylamine, DBU, 2,6-lutidine etc.), pyridine or the like can be used.

The reaction can be carried out at 0 to 100° C. for 0.5 to 12 hours.

Fourth Step

The fourth step is the step for producing a compound represented by the formula (I-5) by halogenation of a compound represented by the formula (I-4).

As a solvent, a solvent described in the first step can be used. Preferably, N-dimethylformamide, halogenated hydrocarbons (e.g. dichloromethane, chloroform, 1,2-dichloroethane etc.), ethers (e.g. tetrahydrofuran, diethylether, dioxane, 1,2-dimethoxyethane etc.), nitriles (e.g. acetonitrile etc.) or the like can be used. Further preferably, alcohols (e.g. methanol, ethanol, t-butanol etc.) can be used.

As a base, a base described in the third step can be used. Preferably, metal hydrides (e.g. sodium hydride etc.), metal amides, alkyllithiums (n-BuLi, sec-BuLi, tert-BuLi) or the like can be used.

The reaction can be carried out at −78 to 50° C. for 0.5 to 24 hours.

As a halogenating agent, $I_2$, $Br_2$, NIS (N-iodosuccinimide), NBS (N-bromosuccinimide) or NCS(N-chlorosuccinimide) can be used.

Among compounds represented by the formula (I-6), a compound, wherein X is —S—, —O— or —NR$^3$, can be synthesized as follows.

Fifth Step

The fifth step is the step for producing a compound represented by the formula (I-6) by reacting a compound represented by the formula (I-5) and a compound represented by the formula: H—X—Y.

When X is —O—, example of a compound represented by the formula: H—O—Y includes phenol, methanol, ethanol or the like.

When X is —S—, example of a compound represented by the formula: H—S—Y includes thiophenol, methanethiol, ethanethiol or the like.

When X is —NR$^3$—, example of a compound represented by the formula: H—NR$^3$—Y includes aniline, methylamine, ethylamine or the like.

As a solvent, a solvent described in the first step can be used. Preferably, N-dimethylformamide, dimethylsulfoxide, ethers (e.g. tetrahydrofuran, diethyl ether, dioxane, 1,2-dimethoxyethane etc.), nitriles (e.g. acetonitrile etc.) or the like can be used.

As a base, a base described in the third step can be used. Preferably, metal hydrides (e.g. sodium hydride etc.), metal carbonates (e.g. sodium carbonate, calcium carbonate, cesium carbonate etc.), metal amides, organic amines (e.g. triethylamine, diisopropylethylamine, DBU, 2,6-lutidine etc.), pyridine, alkyllithiums (n-BuLi, sec-BuLi, tert-BuLi) or the like can be used.

Further preferably, metal hydrides (e.g. sodium hydride etc.) or metal carbonates (e.g. sodium carbonate, calcium carbonate, cesium carbonate etc.) can be used.

The reaction can be carried out at 0 to 100° C. for 0.5 to 12 hours.

(When Hal is Bromine or Iodine)

The reaction can be carried out using conditions for a reaction which is known as the Ullmann reaction.

As a solvent, a solvent described in the first step can be used. Preferably, N-dimethylformamide, dimethylsulfoxide, ethers (e.g. tetrahydrofuran, diethyl ether, dioxane, 1,2-dimethoxyethane etc.), nitriles (e.g. acetonitrile etc.) or the like can be used.

As a base, a bases described in the third step can be used. Preferably, metal hydrides (e.g. sodium hydride etc.), metal carbonates (e.g. sodium carbonate, calcium carbonate, cesium carbonate etc.), metal amides, organic amines (e.g.

triethylamine, diisopropylethylamine, DBU, 2,6-lutidine etc.), pyridine, alkyllithiums (n-BuLi, sec-BuLi, tert-BuLi) or the like can be used.

Further preferably, metal carbonates (e.g. sodium carbonate, calcium carbonate, cesium carbonate etc.) can be used.

As a catalyst, copper iodide can be used.

The reaction can be carried out at room temperature to 100° C. for 0.5 to 12 hours.

Sixth Step

The sixth step is the step for producing a compound represented by the formula (I-H) by deprotection of a compound represented by the formula (I-6).

As a solvent, a solvent described in the first step can be used. Preferably, N-dimethylformamide, halogenated hydrocarbons (e.g. dichloromethane, chloroform, 1,2-dichloroethane etc.), ethers (e.g. tetrahydrofuran, diethyl ether, dioxane, 1,2-dimethoxyethane etc.), esters (e.g. methyl acetate, ethyl acetate etc.), nitriles (e.g. acetonitrile etc.), alcohols (e.g. methanol, ethanol, t-butanol etc.) or the like can be used.

The reaction can be carried out in the presence of hydrochloric acid, TFA (trifluoroacetic acid), TBAF (tetrabutylammoniumfluoride) or the like at 0 to 100° C. for 0.5 to 24 hours.

Among compounds represented by the formula (I), a compound, wherein $R^2$ is substituted or unsubstituted alkyl, can be synthesized, for example, from a compound represented by the formula (I-H) by an alkylation reaction using sodium hydride and an alkylhalide.

A compound represented by the formula (I-12) can be synthesized as follows.

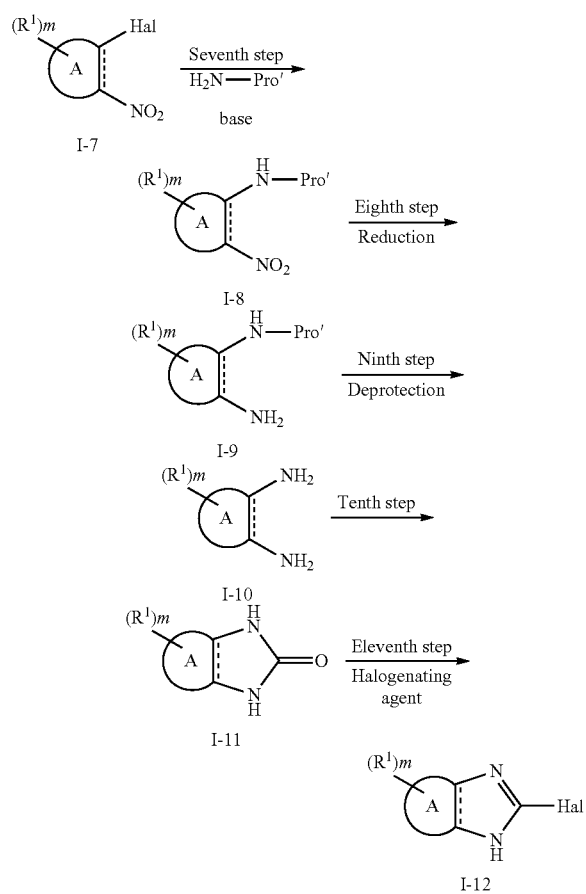

wherein, each symbol has the same meaning as above, and as a compound represented by the formula (I-7), a known compound can be used and a compound which is derived from a known compound by a conventional method can be used. "Hal" is halogen, and Pro' is a protecting group. Pro' includes a benzyl group and the like.

Seventh Step

The seventh step is the step for producing a compound represented by the formula (I-8) by reacting a compound represented by the formula (I-7) and a compound represented by the formula: $H_2N$-Pro'.

As a solvent, a solvent described in the first step can be used. Preferably, N,N-dimethylformamide, ethers (e.g. tetrahydrofuran, diethyl ether, dioxane, 1,2-dimethoxyethane etc.), alcohols (e.g. methanol, ethanol, t-butanol etc.) or the like can be used.

As a base, a base described in the third step can be used. Preferably, metal hydrides (e.g. sodium hydride etc.), metal carbonates (e.g. sodium carbonate, calcium carbonate, cesium carbonate etc.), organic amines (e.g. triethylamine, diisopropylethylamine, DBU, 2,6-lutidine etc.) or the like can be used.

The reaction can be carried out at room temperature to a temperature at which a solvent being used is refluxed, for 0.5 to 24 hours.

Example of a compound represented by the formula: $H_2N$-Pro' includes benzylamine or the like.

Eighth Step

The eighth step is the step for producing a compound represented by the formula (I-9) by reduction of a compound represented by the formula (I-8).

As a solvent, a solvent described in the first step can be used. Preferably, ethers (e.g. tetrahydrofuran, diethyl ether, dioxane, 1,2-dimethoxyethane etc.), alcohols (e.g. methanol, ethanol, t-butanol etc.), a mixed solvent thereof or the like can be used.

The amount of a solvent to be used is not restricted, and any amount can be used, by which a solution capable of the reaction can be formed. To a solution thus prepared, a heterogeneous catalyst is added, and catalytic reduciton can be carried out in the presence of hydrogen gas.

As a heterogeneous catalyst, for example, palladium hydroxide, a palladium/carbon catalyst, platinum oxide, a platinum/carbon catalyst or the like can be used.

The reaction can be carried out at room temperature to 100° C. for 0.5 to 24 hours.

Ninth Step

The ninth step is the step for producing a compound represented by the formula (I-10) by deprotection of a compound represented by the formula (I-9).

As a solvent, a solvent described in the first step can be used. Preferably, ethers (e.g. tetrahydrofuran, diethyl ether, dioxane, 1,2-dimethoxyethane etc.), alcohols (e.g. methanol, ethanol, t-butanol etc.), a mixed solvent thereof or the like can be used.

The amount of a solvent to be used is not restricted, and any amount can be used, by which a solution capable of the reaction can be formed. To a solution thus prepared, a heterogeneous catalyst is added, and catalytic reduciton can be carried out in the presence of hydrogen gas.

As a heterogeneous catalyst, for example, palladium hydroxide, a palladium/carbon catalyst, platinum oxide, a platinum/carbon catalyst or the like can be used.

The reaction can be carried out at room temperature to 100° C. for 0.5 to 24 hours.

Tenth Step

The tenth step is the step for producing a compound represented by the formula (I-11) by reacting a compound represented by the formula (I-10) and carbonyldiimidazole (CDI).

In the reaction, phosgene, triphosgene or the like can be used in place of carbonyldiimidazole (CDI).

As a solvent, a solvent described in the first step can be used. Preferably, N,N-dimethylformamide, halogenated hydrocarbons (e.g. dichloromethane, chloroform, 1,2-dichloroethane etc.), ethers (e.g. tetrahydrofuran, diethylether, dioxane, 1,2-dimethoxyethane etc.), nitriles (e.g. acetonitrile etc.) or the like can be used.

The reaction can be carried out at 0 to 100° C. for 0.5 to 12 hours.

Eleventh Step

The eleventh step is the step for producing a compound represented by the formula (I-12) by reacting a compound represented by the formula (I-11) and a halogenating agent.

Although a solvent described in the first step can be used as a solvent, any solvent is not required to be used.

The halogenating agent includes phosphorus oxychloride, phosphorus pentachloride, oxalyl chloride, thionyl chloride, sulfuryl chloride, dichlorotriphenyl phosphorane or the like. Particularly preferred halogenating agent is phosphorus oxychloride, phosphorus pentachloride, oxalyl chloride or thionyl chloride.

The reaction can be carried out at 0 to 120° C. for 0.5 to 24 hours.

The substituent $R^1$ on the ring A can be introduced as follows. The substituent $R^1$ can be introduced in any step of the above-described first to eleventh steps.

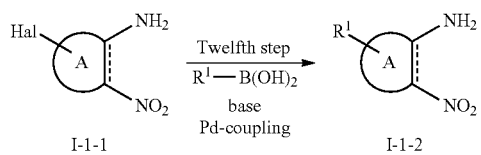

wherein, each symbol has the same meaning as above, and as a compound represented by the formula (I-1-1), a known compound can be used and a compound which is derived from a known compound by a conventional method can be used. "Hal" is halogen.

Twelfth Step

The twelfth step is the step for producing a compound represented by the formula (I-1-2) by reacting a compound represented by the formula (I-1-1) and a compound represented by the formula: $R^1$—$B(OH)_2$ in the presence of a palladium catalyst. As a compound represented by the formula: $R^1$—$B(OH)_2$, boronic acid ester can be used.

As a solvent, a solvent described in the first step can be used. Preferably, N-dimethylformamide, aromatic hydrocarbons (e.g. toluene, benzene, xylene etc.) or ethers (e.g. tetrahydrofuran, diethyl ether, dioxane, 1,2-dimethoxyethane etc.) can be used.

As a base, a base described in the third step can be used. Preferably, metal carbonates (e.g. sodium carbonate, calcium carbonate, cesium carbonate etc.) or organic amines (e.g. triethylamine, diisopropylethylamine, DBU, 2,6-lutidine etc.) can be used.

The reaction may be carried out in the presence of a palladium catalyst (e.g. $Pd(PPh_3)_4$, $PdCl_2$, $Pd(OAc)_2$, $Pd(dba)_2$ etc.) and a phosphine ligand (e.g. $PPh_3$, BINAP etc.) at a temperature, at which a solvent to be used is refluxed, for 0.5 to 12 hours.

When using microwave, the reaction can be carried out at 80 to 200° C. for 5 minutes to one hour.

Example of a compound represented by the formula: $R^1$—$B(OH)_2$ includes phenylboronic acid or the like.

Various types of substituent of the compounds of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS or the like.

The compound of the present invention has an excellent AMPK activating effect. Therefore, the compound can be used for the treatment or prevention of a disease concerning AMPK, particularly disease such as type II diabetes, hyperglycemia, metabolic syndrome, obesity, hypercholesterolemia and/or hypertension. Particularly, the compound is useful in the treatment or prevention of type II diabetes, hyperglycemia, metabolic syndrome or obesity.

A compound used in the present invention can be orally or parenterally administered. For oral administration, a compound used in the present invention can be used in any dosage form of normal formulations, for example, solid formulations such as a tablet, powder, granule, capsule or the like; aqueous formulations; oleaginous suspensions; or liquid formulations such as syrup or elixir. For parenteral administration, a compound used in the present invention can be used as an aqueous or oleaginous suspension for injection or nasal solution. In preparation of such formulations, a conventional excipient, binder, lubricant, aqueous solvent, oleaginous solvent, emulsifying agent, suspending agent, preservative, stabilizer and the like can be optionally used. Especially, using in a form of an oral formulation is preferred.

A formulation of a compound used in the present invention can be produced by combining (e.g. mixing) a compound used in the present invention in a therapeutically effective amount with a pharmaceutically acceptable carrier or diluent. A formulation of a compound used in the present invention can be produced using a well-known and easily-available ingredient by a known method.

A dose of a compound used in the present invention is different depending on an administration method, a patient's age, a body weight, the condition of a patient and a kind of a disease, and commonly for oral administration, usually about 0.05 mg to 3000 mg, preferably about 0.1 mg to 1000 mg per a day for adult person may be administered, if necessary, in divided doses. For parenteral administration, about 0.01 mg to 1000 mg, preferably about 0.05 mg to 500 mg per a day for adult person may be administered. When a compound used in the present invention is administered, it can be used together with other therapeutic agents.

A compound of the present invention can be used in combination with an insulin secretagogue (e.g. a sulfonylurea (SU) drug), a fast-acting insulin secretagogue (e.g. a phenylalanine derivative), a glucose uptake inhibitor (e.g. an α-glucosidase inhibitor (α-GI drug)), an insulin resistance improving drug (e.g. a biguanide drug (BG drug), a thiazolidine derivative (TZD drug)), an insulin formulation, a peptidyl peptidase IV (DPP-IV) inhibitor, a GLP-1 receptor agonist, a sodium-dependent glucose transporter 1 (SGLT1) inhibitor, a sodium-dependent glucose transporter 2 (SGLT 2) inhibitor and the like (hereinafter, abbreviated as concomitant drugs) for the purpose of an increase in the effect of the compound, a decrease in a dose of the compound or the like. In this case, the time when a compound of the present invention and a concomitant drug are administered is not restricted, and they can be administered to a subject of administration simultaneously or at intervals. Further, a compound of the present invention and a concomitant drug can be administered as two kinds of formulation comprising each active ingredient and as a single formulation comprising both active ingredients.

The dose of a concomitant drug can be suitably selected on the basis of a dosage which is clinically used. In addition, the mixing ratio of a compound of the present invention and a concomitant drug can be suitably selected depending on a subject of administration, an administration route, a target disease, symptoms, combination and the like. When a subject of administration is a human, for example, 0.01 to 100 parts by weight of a concomitant drug can be used per part by weight of a compound of the present invention.

The present invention is further explained by the following Examples, which are not intended to limit the scope of the present invention.

NMR spectrum data of the compounds of the present invention and intermediates thereof were shown. NMR analysis obtained in each example was measured by 300 MHz or 400 MHz, and measured using $CDCl_3$ or dimethylsulfoxide (d6-DMSO).

LC/MS was measured under the following conditions.
(Method A)
Column: ACQUITY UPLC BEH C18 (1.7 μm i.d. 2.1×50 mm) (made by Waters)
Flow rate: 0.8 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3.5 minutes and the solvent [B] at 100% was maintained for 0.5 minutes.
(Method B)
Column: Shim-pack XR-ODS (2.2 μm, i.d. 50×3.0 mm) (made by Shimadzu)
Flow rate: 1.6 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3 minutes and the solvent [B] at 100% was maintained for 1 minute.

The meaning of each term in Examples is as follows.
SEMCl: trimethylsilyl ethoxymethyl chloride
THF: tetrahydrofuran
LiHMDS: lithium hexamethyldisilazide
$PdCl_2(PPh_3)_2$: dichloro bistriphenylphosphine palladium
$Pd_2(dba)_3$: tris(dibenzylideneacetone)dipalladium
RuPhos: 2-dicyclohexylphosphino-2',6'-diisopropoxy-1,1'-biphenyl
DMF: dimethylformamide
TBAF: tetrabutylammonium fluoride
TBS: t-butyldimethylsilyl
TFA: trifluoroacetic acid
NaHMDS: sodium hexamethyldisilazide
DPPA: diphenylphosphoryl azide
DIPEA: diisopropylethylamine
$TMSCH_2CH_2OH$: 2-trimethylsilylethanol
DCM: dichloromethane
AcCl: acetylchloride
DOX: 1,4-dioxane
CDI: carbonyldiimidazole Example 1

-continued

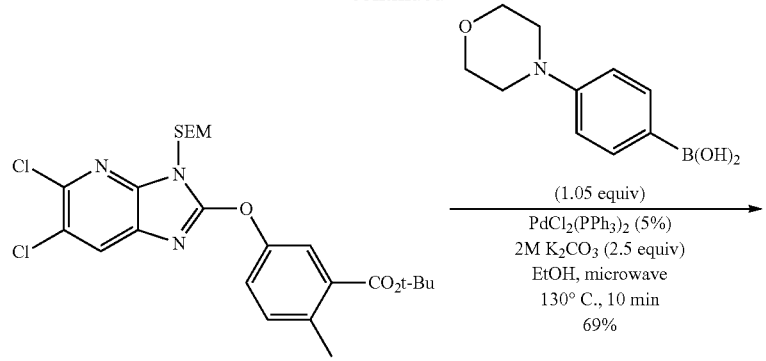

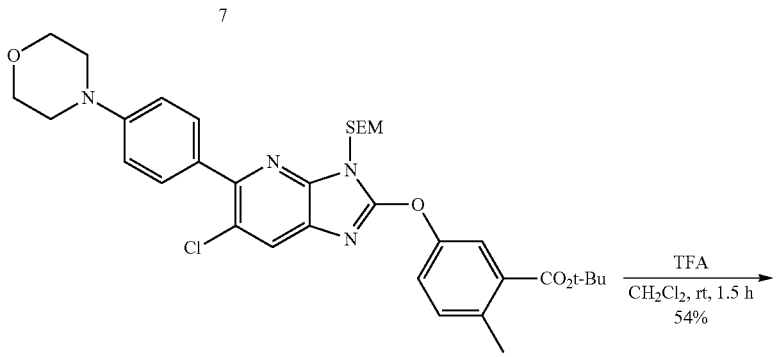

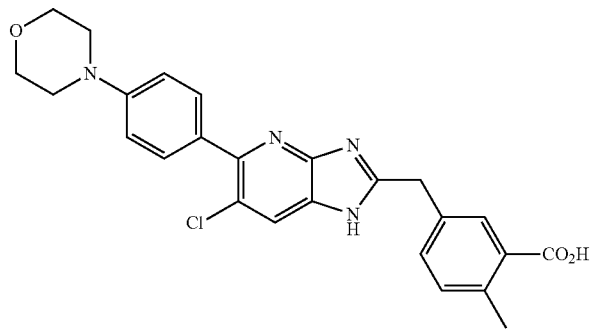

A suspension of 6-chloro-3-nitropyridine-2-amine 1 (20 g, 115 mmol) in anhydrous ethanol (970 mL) was subjected to bubbling with chlorine gas while stirring at 0° C. over one hour. Thereafter, the reaction mixture was subjected to bubbling with nitrogen gas while stirring at room temperature over one hour, and then stirred at 0° C. for 30 minutes. The reaction suspension was filtered, and the obtained residue was washed with diisopropyl ether to obtain a solid. The solvent of the resulting filtrate was removed under reduced pressure, and the precipitated solid was filtered and the obtained solid was then washed with diisopropyl ether to further obtain a solid. The above-described two collected solids were combined to obtain Compound 2 (18.1 g, 76%) as a yellow solid.

Compound 2; $^1$H-NMR (DMSO-d6) δ: 8.33 (brs, 2H), 8.59 (s, 1H).

To a solution of Compound 2 (36.2 g, 174 mmol) in ethanol (775 mL) and water (310 mL) were added iron (48.6 g, 870 mmol) and ammonium chloride (46.5 g, 870 mmol), and the reaction mixture was stirred at 60° C. for 3 hours. The reaction suspension was filtered with Celite, followed by washing with ethanol, and ethanol of the filtrate was removed under reduced pressure. The obtained residue was extracted with ethyl acetate. The organic layer was washed with water and brine, and dried over magnesium sulfate. The solvent was removed under reduced pressure. To the residue was added hexane, followed by filtration. The obtained residue was washed with hexane to obtain Compound 3 (28.46 g, 92%) as a brown solid.

Compound 3; $^1$H-NMR (DMSO-d6) δ: 5.10 (s, 2H), 6.02 (s, 2H), 6.82 (s, 1H).

To a solution of Compound 3 (28.1 g, 158 mmol) in methanol (840 mL) were successively added sulfamic acid (765 mg, 7.88 mmol) and ortho formic acid triethyl (39.3 mL, 236 mmol), and the reaction mixture was stirred at room temperature for 7.5 hours. The reaction suspension was filtered, followed by washing with methanol, and the solvent of the filtrate was removed under reduced pressure. To the residue was added hexane, followed by filtration. The obtained residue was washed with hexane to obtain Compound 4 (24.3 g, 82%) as a gray solid.

Compound 4; $^1$H-NMR (DMSO-d$_6$) δ: 8.40 (s, 1H), 8.58 (s, 1H).

To a solution of Compound 4 (15 g, 80 mmol) in N,N-dimethylformamide (150 ml) were successively added diisopropylethylamine (20.9 mL, 120 mmol) and SEMCl (17.0 mL, 96 mmol), and the reaction mixture was stirred at 80° C. for 2 hours. The reaction solution was extracted with water and ethyl acetate. The organic layer was washed with water and brine, and dried over magnesium sulfate. The solvent was removed under reduced pressure, and the residue was purified by silica gel column chromatography to obtain Compound 5 (11.6 g, 46%).

Compound 5; $^1$H-NMR (DMSO-d$_6$) δ: 0.00 (s, 9H), 0.94 (t, J=8.0 Hz, 2H), 3.68 (t, J=8.0 Hz, 2H), 5.71 (s, 2H), 8.64 (s, 1H), 8.83 (s, 1H).

To a solution of Compound 5 (6.5 g, 20.4 mmol) in anhydrous THF (65 mL) was added dropwise a solution of LiHMDS in THF (1M, 42.8 mL, 42.8 mmol) under nitrogen atmosphere at −60° C. over 20 minutes. Thereafter, the reaction mixture was stirred at −60° C. for 30 minutes, and iodine (25.9 g, 102 mmol) was then added thereto. The reaction mixture was stirred at −60° C. for 30 minutes. The reaction solution was extracted with a saturated aqueous solution of ammonium chloride and ethyl acetate. The organic layer was washed with a 10% aqueous solution of sodium thiosulfate, water and brine, and dried over magnesium sulfate. The solvent was removed under reduced pressure to obtain Compound 6 as a crude brown solid product.

Compound 6; $^1$H-NMR (DMSO-d$_6$) δ: 0.00 (s, 9H), 0.95 (t, J=8.0 Hz, 2H), 3.69 (t, J=8.0 Hz, 2H), 5.61 (s, 2H), 8.57 (s, 1H).

To a solution of the crude product of Compound 6 obtained above in 1,4-dioxane (90 ml) were successively added 5-hydroxyl-2-methylbenzoic acid t-butyl ester (4.67 g, 22.4 mmol), copper(I) iodide (582 mg, 3.1 mmol), 2-dimethylaminoacetic acid (1.26 g, 12.2 mmol) and cesium carbonate (13.3 g, 40.8 mmol), and the reaction mixture was stirred at 90° C. for 3.5 hours. The reaction suspension was extracted with water and ethyl acetate. The organic layer was washed with water and brine, and dried over magnesium sulfate. The solvent was removed under reduced pressure, and the residue was purified by silica gel column chromatography to obtain Compound 7 (5.33 g, 50%, 2 steps) as a white solid.

Compound 7; $^1$H-NMR (DMSO-d$_6$) δ: 0.00 (s, 9H), 0.98 (t, J=8.0 Hz, 2H), 1.61 (s, 9H), 2.59 (s, 3H), 3.79 (t, J=8.0 Hz, 21T), 5.64 (s, 2H), 7.51 (d, J=8.0 Hz, 1H), 7.61 (dd, J=8.0, 2.4 Hz, 1H), 7.79 (d, J=2.4 Hz, 1H), 8.31 (s, 1H).

To a solution of Compound 7 (300 mg, 0.57 mmol) in ethanol (3 mL) were added 4-morpholinobenzeneboronic acid (130 mg, 0.63 mmol), PdCl$_2$(PPh$_3$)$_2$ (20.1 mg, 0.029 mmol) and an aqueous solution of potassium carbonate (2 M, 0.72 ml, 1.43 mmol), and the reaction mixture was stirred under microwave irradiation at 130° C. for 10 minutes. The reaction suspension was extracted with water and ethyl acetate. The organic layer was washed with water and brine, and dried over magnesium sulfate. The solvent was removed under reduced pressure, and the residue was purified by silica gel column chromatography to obtain Compound 8 (258 mg, 69%) as a yellow solid.

Compound 8; $^1$H-NMR (DMSO-d$_6$) δ: 0.00 (s, 9H), 1.00 (t, J=8.0 Hz, 2H), 1.64 (s, 9H), 2.62 (s, 3H), 3.30 (t, J=4.8 Hz, 4H), 3.81-3.88 (m, 6H), 5.69 (s, 2H), 7.13 (d, J=8.4 Hz, 2H), 7.54 (d, J=8.4 Hz, 1H), 7.65 (dd, J=8.4, 2.4 Hz, 1H), 7.70 (d, J=8.4 Hz, 2H), 7.83 (d, J=2.4 Hz, 1H), 8.13 (s, 1H).

To a solution of Compound 8 (250 mg, 0.38 mmol) in methylene chloride (1.3 mL) was added trifluoroacetic acid (1.3 ml), and the reaction mixture was stirred at room temperature for 1.5 hours. The solvent was removed under reduced pressure. To the residue was added a 2N aqueous solution of sodium hydroxide to obtain pH 10. The aqueous layer was washed with ethyl acetate, and 2N hydrochloric acid was then added to the aqueous layer to obtain pH 4. The precipitated solid was filtered, and the obtained solid was successively washed with water and ethyl acetate to obtain Compound A-1 (97 mg, 54%) as a white solid.

Compound A-1; $^1$H-NMR (DMSO-d$_6$) δ: 2.56 (s, 3H), 3.19 (t, J=4.8 Hz, 4H), 3.76 (t, J=4.8 Hz, 4H), 7.02 (d, J=8.4 Hz, 2H), 7.42 (d, J=8.4 Hz, 1H), 7.53 (dd, J=8.4, 2.4 Hz, 1H), 7.57 (d, J=8.4 Hz, 2H), 7.83 (d, J=2.4 Hz, 1H), 7.94 (s, 1H), 13.2 (brs, 2H).

A compound shown below was synthesized in the same manner.

Example 2

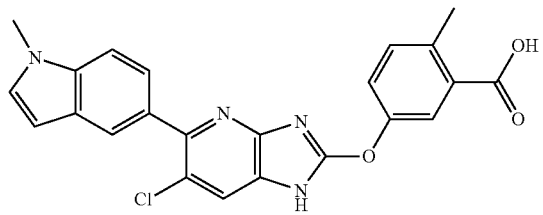 [SMILES: Cc1ccc(Oc2nc3nc(-c4ccc5c(ccn5C)c4)c(Cl)cc3[nH]2)cc1C(=O)O]

Compound A-2; $^1$H-NMR (DMSO-d$_6$) δ: 2.56 (s, 3H), 3.84 (s, 3H), 6.51 (d, J=4.0 Hz, 1H), 7.38-7.45 (m, 3H), 7.49-7.51 (m, 2H), 7.82 (s, 2H), 7.96 (s, 1H).

Example 3

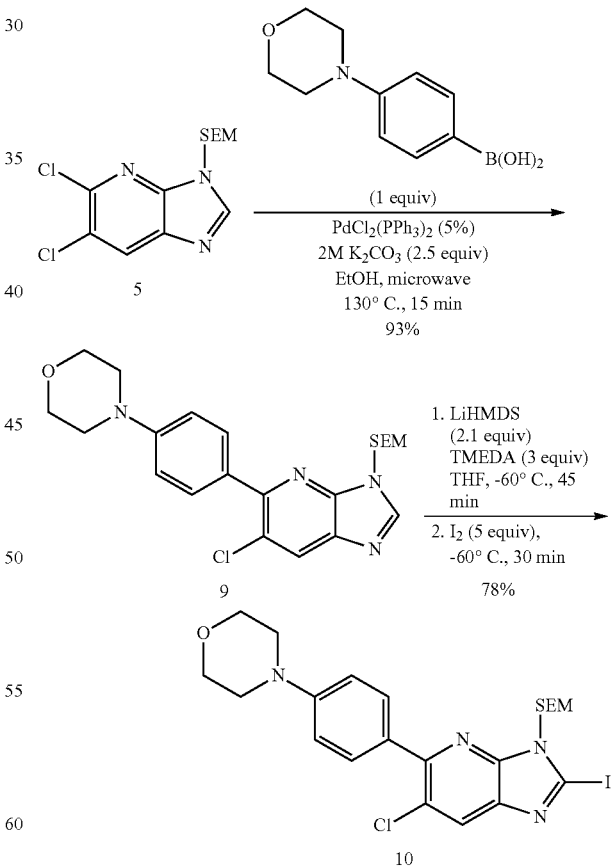

To a solution of Compound 5 (4.23 g, 13.29 mmol) in ethanol (43 mL) were added 4-morpholinobenzeneboronic acid (2.75 g, 13.29 mmol), PdCl$_2$(PPh$_3$)$_2$ (467 mg, 0.67 mmol) and an aqueous solution of potassium carbonate (2 M, 16.6 ml, 33.23 mmol), and the reaction mixture was stirred under microwave irradiation at 130° C. for 15 minutes. The reaction suspension was extracted with water and ethyl acetate. The organic layer was washed with water and brine, and dried over magnesium sulfate. The solvent was removed under reduced pressure, and the residue was purified by silica gel column chromatography to obtain Compound 9 (5.51 g, 93%) as a yellow solid.

Compound 9; $^1$H-NMR (DMSO-$d_6$) δ: 0.00 (s, 9H), 0.97 (t, J=8.0 Hz, 2H), 3.32 (t, J=4.8 Hz, 4H), 3.74 (t, J=8.0 Hz, 2H), 3.88 (t, J=4.8 Hz, 4H), 5.75 (s, 2H), 7.15 (d, J=8.4 Hz, 2H), 7.73 (d, J=8.4 Hz, 2H), 8.45 (s, 1H), 8.78 (s, 1H).

To a solution of Compound 9 (4.7 g, 10.56 mmol) in anhydrous THF (47 mL) was added TMEDA (4.8 ml, 31.70 mmol). To the reaction mixture was added dropwise a solution of LiHMDS in THF (1M, 22.2 mL, 22.2 mmol) under nitrogen atmosphere at −60° C. over 15 minutes. Thereafter, the reaction mixture was stirred at −60° C. for 45 minutes, and iodine (13.4 g, 52.8 mmol) was then added thereto. The reaction mixture was stirred at −60° C. for 30 minutes. The reaction suspension was extracted with a saturated aqueous solution of ammonium chloride and ethyl acetate. The organic layer was washed with a 10% aqueous solution of sodium thiosulfate, water and a saturated sodium chloride solution and dried over magnesium sulfate. The solvent was removed under reduced pressure, and the residue was purified by silica gel column chromatography. The solvent was removed under reduced pressure, and to the residue, hexane was added, followed by filtration. The obtained residue was washed with hexane to obtain Compound 10 (4.69 g, 78%) as a yellow solid.

Compound 10; $^1$H-NMR (DMSO-$d_6$) δ: 0.00 (s, 9H), 0.98 (t, J=8.0 Hz, 2H), 3.32 (t, J=4.8 Hz, 4H), 3.75 (t, J=8.0 Hz, 2H), 3.88 (t, J=4.8 Hz, 4H), 5.68 (s, 2H), 7.15 (d, J=8.4 Hz, 2H), 7.74 (d, J=8.4 Hz, 2H), 8.40 (s, 1H).

Example 4

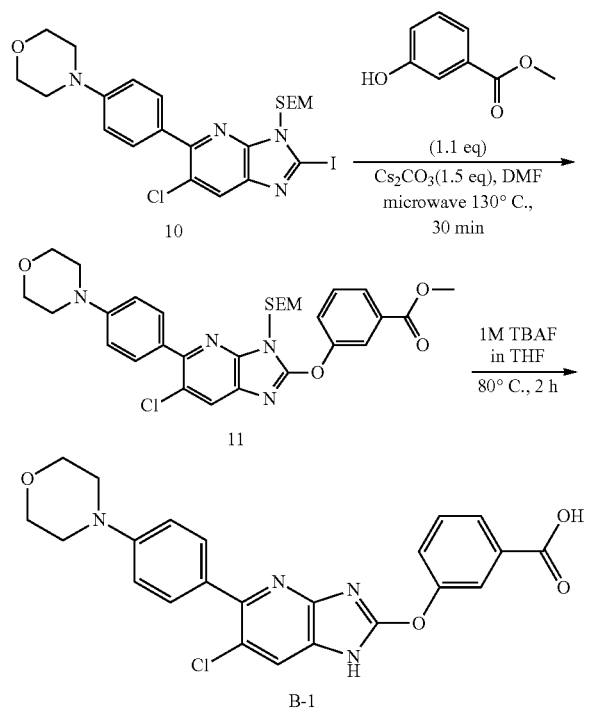

To a solution of Compound 10 (25.0 mg, 0.044 mmol) in anhydrous DMF (0.5 ml) were added cesium carbonate (21.4 mg, 0.066 mmol) and methyl 3-hydroxybenzoate (7.33 mg, 0.048 mmol), and the reaction mixture was stirred under microwave irradiation at 130° C. for 30 minutes. The reaction suspension was extracted with water and ethyl acetate. The organic layer was washed with water and brine, and dried over sodium sulfate. The solvent was removed under reduced pressure to obtain Compound 11 as a colorless oil. The following reaction was carried out without purification.

To the above-described Compound 11 was added 1M TBAF in THF (0.439 ml, 0.439 mmol), and the reaction mixture was stirred under nitrogen atmosphere at 80° C. for 2 hours. The reaction solution was extracted with a saturated aqueous solution of KHSO4 and ethyl acetate. The organic layer was washed with water and brine and dried over sodium sulfate. The solvent was removed under reduced pressure, and the residue was purified by reverse-phase preparative liquid chromatography (a 10 mM ammonium carbonate containing aqueous solution/acetonitrile; gradient 15-35%, 10 min) to obtain Compound B-1 (3.3 mg, 0.007 mmol, 17%) as a white solid.

Compound B-1;
MS (ESI) m/z=450.9 (M+H)$^+$.
LC/MS retension time=1.74 min.
Method B Example 5

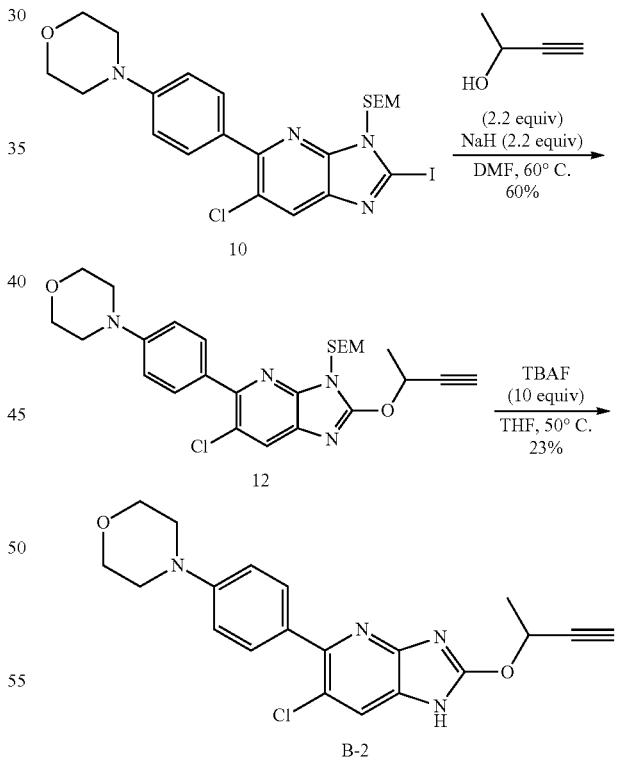

To a suspension of sodium hydride (60 wt %, 15.4 mg, 0.39 mmol) in N,N-dimethylformamide (150 ml) was added 3-butyn-2-ol (30 μL, 0.39 mmol) under nitrogen atmosphere at 0° C., and the reaction mixture was stirred at room temperature for 5 minutes. Thereafter, Compound 10 (100 mg, 0.18 mmol) was added thereto at room temperature, and the reaction mixture was stirred at room temperature for 30 minutes. The reaction solution was extracted with a saturated aqueous solution of ammonium chloride and ethyl acetate. The organic layer was washed with brine, and dried over magnesium sulfate. The solvent was removed under reduced pressure, and the residue was purified by silica gel column chromatography to obtain Compound 12 (54 mg, 60%) as a yellow oily substance.

To Compound 12 (52 mg, 0.10 mmol) was added a solution of tetrabutylammoniumfluoride in THF (1M, 1 mL, 1.0 mmol) at room temperature, and the reaction mixture was stirred at 50° C. for 6 hours. The reaction solution was extracted with a saturated aqueous solution of ammonium chloride and chloroform. The organic layer was dried over magnesium sulfate. The solvent was removed under reduced pressure, and the residue was purified by silica gel column chromatography to obtain Compound B-2 (9 mg, 23%) as a yellow solid.

Compound B-2; $^1$H-NMR (DMSO-$d_6$) δ: 1.64 (d, J=6.6 Hz, 3H), 3.18 (m, 4H), 3.68 (d, J=2.0 Hz, 1H), 3.77 (m, 4H), 5.78 (qd, J=6.6, 2.0 Hz, 1H), 7.01 (d, J=8.9 Hz, 2H), 7.56 (d, J=8.9 Hz, 2H), 7.91 (s, 1H), 12.8 (s, 1H).

Example 6

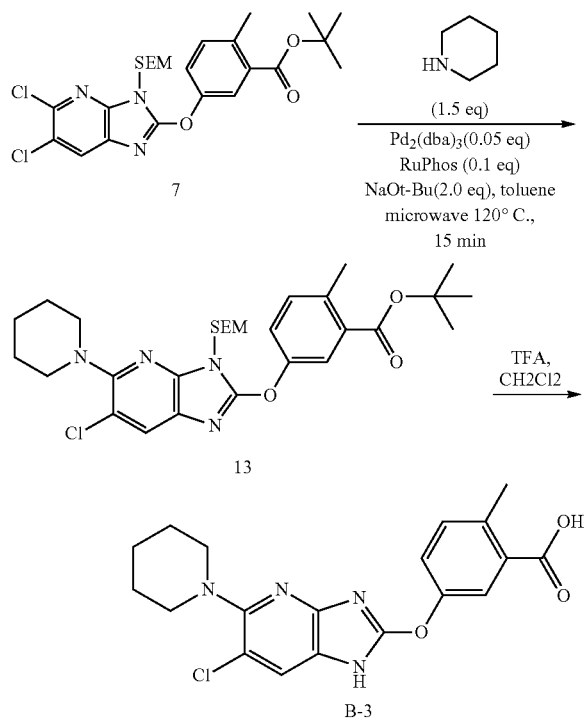

To a solution of Compound 7 (15.0 mg, 0.029 mmol) in anhydrous toluene (0.5 mL) were added piperidine (0.0042 ml, 0.043 mmol), Pd$_2$(dba)$_3$ (1.3 mg, 0.0014 mmol), RuPhos (1.3 mg, 0.0028 mmol) and NaOtBu (5.5 mg, 0.057 mmol), and the reaction mixture was stirred under microwave irradiation at 120° C. for 15 minutes. The reaction suspension was extracted with water and ethyl acetate. The organic layer was washed with water and brine, and dried over sodium sulfate. The solvent was removed under reduced pressure to obtain Compound 13 as a colorless oil. The following reaction was carried out without purification.

To a solution of the above-described Compound 13 in methylene chloride (0.500 ml) was added TFA (0.500 ml, 6.49 mmol), and the reaction mixture was stirred under nitrogen atmosphere at room temperature for one hour. The reaction solution was concentrated under reduced pressure, and the residue was purified by reverse-phase preparative liquid chromatography (a 10 mM ammonium carbonate containing aqueous solution/acetonitrile; gradient 20-40%, 10 min) to obtain Compound B-3 (2.0 mg, 0.005 mmol, 18%) as a white solid.

Compound B-3;
MS (ESI) m/z=386.9 (M+H)$^+$.
LC/MS retension time=2.04 min.
Method B Example 7

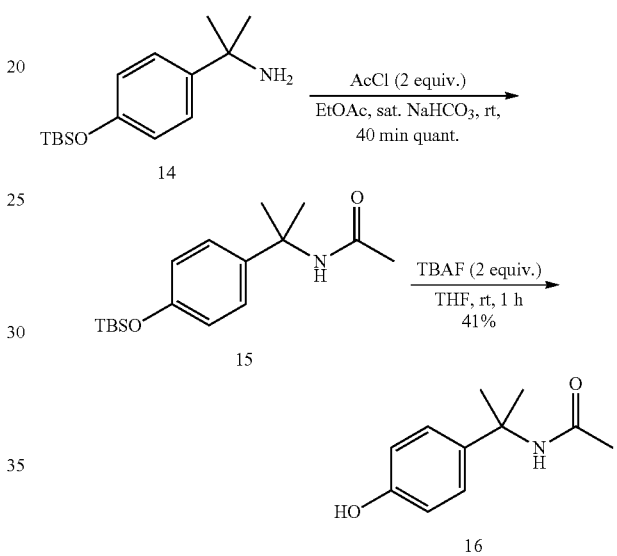

Compound 14 is described as Compound 52 in J. Med. Chem. 1996, 39, 2795-2811.

To a solution of Compound 14 (9 g, 33.9 mmol) in ethyl acetate (180 mL) was added a saturated aqueous solution of sodium hydrogen carbonate (180 mL). To the reaction mixture was added dropwise acetyl chloride (4.84 mL, 67.8 mmol) while vigorously stirring, and the reaction mixture was stirred at room temperature for 40 minutes.

The reaction solution was fractionated, followed by drying over magnesium sulfate. The solvent was removed under reduced pressure to obtain Compound 15 (11.7 g, quant.) as a pale yellow oil.

Compound 15; 1H-NMR (CDCl3) δ: 0.19 (6H, s), 0.98 (9H, s), 1.69 (6H, s), 1.95 (3H, s), 5.62 (1H, s), 6.78 (2H, d, J=8.62 Hz), 7.25 (3H, d, J=5.58 Hz).

To a solution of Compound 15 (9.26 g, 30.1 mmol) in THF (90 mL) was added tetrabutylammoniumfluoride (15.75 g, 60.2 mmol), and the reaction mixture was stirred at room temperature for one hour. The reaction solution was extracted with 1 M HCl and ethyl acetate. The aqueous layer was extracted once with 200 mL of ethyl acetate and twice with 100 mL of ethyl acetate. The organic layer was dried over magnesium sulfate, and the solvent was removed under reduced pressure. To the resulting solid, hexane was added, followed by filtration, and the obtained residue was washed with hexane to obtain Compound 16 (3.92 g, 41%) as a white solid.

Compound 16; 1H-NMR (DMSO-d6) δ: 1.49 (6H, s), 1.79 (3H, s), 6.65 (2H, d, J=8.62 Hz), 7.09 (2H, d, J=8.62 Hz), 9.13 (1H, s).

Example 8

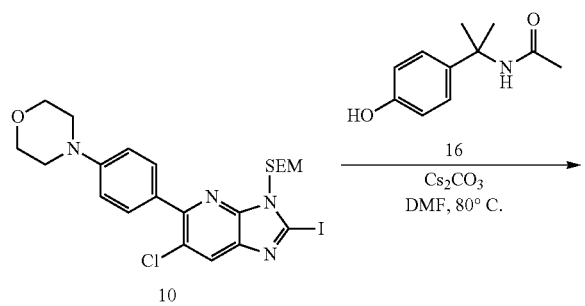

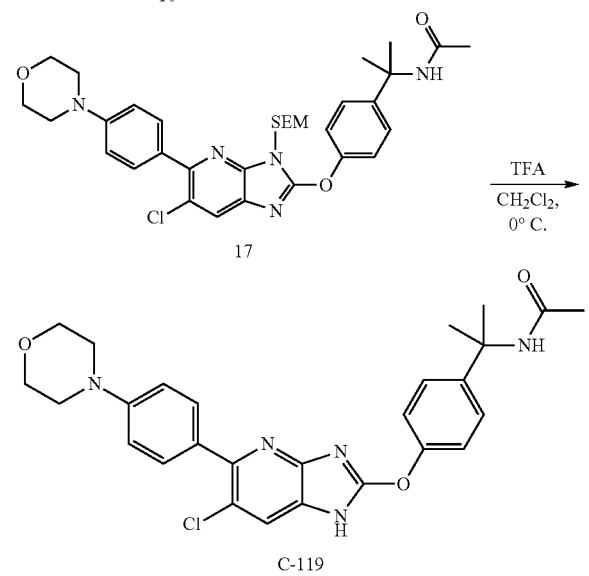

To a solution of Compound 10 (1 g, 1.75 mmol) in N,N-dimethylformamide (100 ml) were added cesium carbonate (0.856 g, 2.63 mmol) and Compound 16 (0.406 g, 2.10 mmol), and the reaction mixture was stirred at room temperature for one hour. The reaction solution was extracted with water and ethyl acetate. The organic layer was dried over anhydrous magnesium sulfate and concentrated under reduced pressure. The residue was purified by silica gel column chromatography to obtain Compound 17 (1.10 g, 99%).

Compound 17; 1H-NMR (DMSO-d6) δ: −0.09 (s, 9H), 0.91 (t, J=7.9 Hz, 2H), 1.57 (s, 6H), 1.64 (s, 4H), 1.85 (s, 3H), 3.25 (t, J=5.1 Hz, 4H), 3.74 (t, J=7.9 Hz, 2H), 5.58 (s, 2H), 7.00 (d, J=9.1 Hz, 2H), 7.31 (d, J=8.6 Hz, 2H), 7.42 (d, J=8.6 Hz, 2H), 7.58 (d, J=8.6 Hz, 2H), 8.02 (s, 1H), 8.10 (s, 1H).

To a solution of Compound 17 (1 g, 1.75 mmol) in methylene chloride (5 ml) was added trifluoroacetic acid (5 ml, 54.9 mmol), and the reaction mixture was stirred at room temperature for one hour. The reaction solution was added to a saturated sodium bicarbonate water, followed by extraction with ethyl acetate. The organic layer was dried over anhydrous magnesium sulfate and then concentrated under reduced pressure. The residue was washed with ethyl acetate/hexane to obtain Compound C-119 (0.78 g, 89%).

Compound C-119; 1H-NMR (DMSO-d6) δ: 1.57 (s, 6H), 1.84 (s, 3H), 3.19 (t, J=4.8 Hz, 4H), 3.76 (t, J=4.6 Hz, 4H), 7.02 (d, J=9.1 Hz, 2H), 7.31 (d, J=8.6 Hz, 2H), 7.40 (d, J=8.6 Hz, 2H), 7.57 (d, J=8.6 Hz, 2H), 7.92 (s, 1H), 8.09 (s, 1H), 13.18 (s, 1H).

Example 9

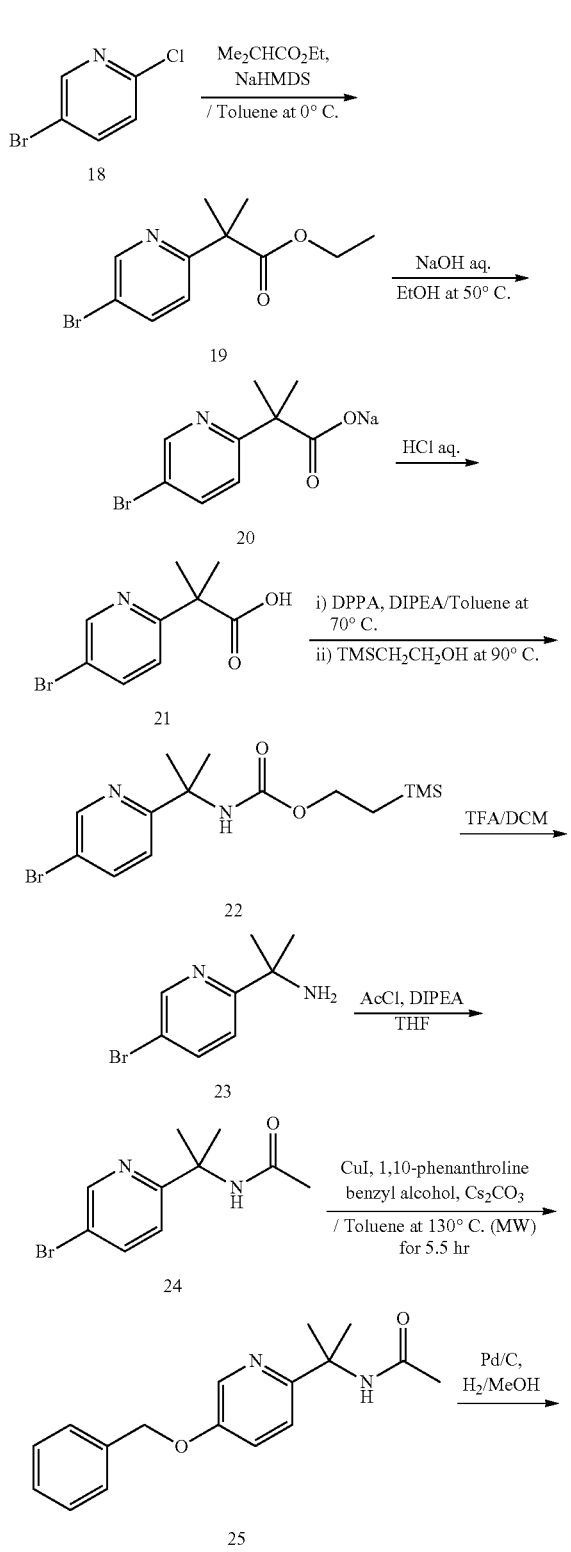

-continued

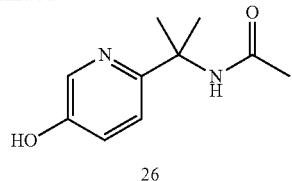

26

To a solution of ethyl isobutyrate (3.86 ml, 28.6 mmol) in toluene (50 mL) was added dropwise a 1.9 M solution of NaHMDS in toluene (27.3 ml, 52.0 mmol) under ice-cooling, and the reaction mixture was stirred for 15 minutes. Thereafter, Compound 18 (5 g, 26.0 mmol), which remained in the form of powder, was added thereto, and the reaction mixture was stirred at 0° C. for another 5 hours. Quenching was carried out with a saturated aqueous solution of ammonium chloride, followed by extraction with ethyl acetate. The organic layer was washed with brine and dried over magnesium sulfate. The solvent was removed under reduced pressure, and the residue was then purified twice by silica gel column chromatography (hexane/EtOAc=10:1) to obtain Compound 19 (6.18 g, 87%) as a yellow oil.

Compound 19; 1H-NMR (CDCl$_3$) δ: 1.19 (t, J=7.10 Hz, 3H), 1.59 (s, 6H), 4.14 (q, J=7.10 Hz, 2H), 7.20 (d, J=8.11 Hz, 1H), 7.76 (dd, J=8.11, 2.03 Hz, 1H), 8.59 (d, J=2.03 Hz, 1H).

To a solution of Compound 19 (2.09 g, 7.68 mmol) in ethanol (20 mL) was added a 2 N NaOH aqueous solution (4.22 ml, 8.45 mmol), and the reaction mixture was stirred at 50° C. for 3 hours. The solvent was removed under reduced pressure, and to the residue, 20 ml of chloroform was added and suspended. The obtained suspension was filtered to obtain Compound 20 (1.81 g, 89%) as a white solid.

The resulting Na salt 20 (1.81 g, 6.80 mmol) was dissolved in 15 ml of distilled water, and a 2 N HCl aqueous solution (3.4 ml, 6.80 mmol) was then added dropwise thereto under ice-cooling. The reaction mixture was stirred at room temperature for 10 minutes. The resulting solid was filtered, and the obtained solid was washed three times with ice-cold water to obtain Compound 21 (1.5 g, 90%).

Compound 21; 1H-NMR (CDCl$_3$) δ: 1.65 (s, 6H), 7.37 (d, J=8.62 Hz, 1H), 7.90 (dd, J=8.62, 2.53 Hz, 1H), 8.62 (d, J=2.53 Hz, 1H).

To a solution of Compound 21 (1.49 g, 6.10 mmol) in toluene (15 ml) were successively added DPPA (1.44 ml, 6.71 mmol) and DIPEA (2.35 ml, 13.43 mmol) at room temperature. The reaction mixture was stirred for 20 minutes and then heated to 70° C., and stirred for another 1.5 hours. The reaction mixture was allowed to cool to room temperature, and 2-trimethylsilylethanol (8.75 ml, 61 mmol) was then added thereto, and the reaction mixture was stirred at 110° C. for 10 hours. The reaction mixture was allowed to cool to room temperature, and 20 ml of distilled water was added thereto, followed by extraction with ethyl acetate, washing with brine and drying with sodium sulfate. The solvent was removed under reduced pressure. The concentrated residue was purified by silica gel column chromatography (hexane/ethyl acetate=1:4) to obtain Compound 22 (1.44 g, 66%) as a colorless oil.

Compound 22; 1H-NMR (CDCl$_3$) δ: 0.03 (s, 9H), 0.96 (t, J=8.11 Hz, 2H), 1.68 (s, 6H), 4.10 (t, J=8.11 Hz, 2H), 6.02 (s, 1H), 7.32 (d, J=8.62 Hz, 1H), 7.78 (dd, J=8.62, 2.53 Hz, 1H), 8.57 (d, J=2.53 Hz, 1H).

To a solution of Compound 22 (600 mg, 1.67 mmol) in DCM (3 ml) was added TFA (3 ml, 38.9 mmol), and the reaction mixture was stirred at room temperature for one hour. TFA was removed by azeotropic distillation with toluene, and the residue was then diluted with distilled water and neutralized with a saturated sodium bicarbonate water. The mixture was extracted three times with chloroform, followed by drying over sodium sulfate. The solvent was removed under reduced pressure. The concentrated residue was dissolved in THF (3 ml), and DIPEA (0.437 ml, 2.51 mmol) and AcCl (0.125 ml, 1.75 mmol) were successively added thereto under ice-cooling, and the reaction mixture was stirred at 0° C. for one hour. The reaction solution was extracted with distilled water and ethyl acetate, followed by washing with brine and drying over sodium sulfate. The solvent was removed under reduced pressure. The concentrated residue was purified by silica gel column chromatography (chloroform/methanol=10:1) to obtain Compound 24 (385 mg, 90%) as a white solid.

Compound 24; 1H-NMR (CDCl$_3$) δ: 1.72 (s, 6H), 2.03 (s, 3H), 7.15 (s, 1H), 7.31 (d, J=8.62 Hz, 1H), 7.81 (dd, J=8.62, 2.53 Hz, 1H), 8.56 (d, J=2.03 Hz, 1H).

To a solution of Compound 24 (340 mg, 1.32 mmol) in toluene (3 ml) were added copper(I) iodide (25.2 mg, 0.13 mmol), cesium carbonate (646 mg, 1.98 mmol), benzyl alcohol (1.38 ml, 13.22 mmol) and 1,10-phenanthroline (48 mg, 0.26 mmol), and the reaction mixture was stirred under microwave irradiation at 130° C. for 5.5 hours. To the reaction liquid, distilled water was added, and a aqueous layer was extracted with ethyl acetate, followed by washing with brine and drying over sodium sulfate. The solvent was removed under reduced pressure. The concentrated residue was purified by silica gel column chromatography (hexane:ethyl acetate=1:4, and chloroform:methanol=10:1 for a second time) to obtain Compound 25 as a mixture with approximately 10% of Compound 24 (376 mg, 100%).

Compound 25; 1H-NMR (CDCl$_3$) δ: 1.72 (s, 6H), 2.03 (s, 3H), 5.11 (s, 2H), 7.28-7.51 (m, 8H), 8.25 (d, J=2.03 Hz, 1H).

To a solution of Compound 25 (376 mg, 1.32 mmol) in methanol (4 ml) was added 10% Pd/C (50% wet) (281 mg, 0.132 mmol), and the reaction mixture was stirred under a hydrogen atmosphere at room temperature for 2 hours. The reaction mixture was filtered with Celite, and the solvent was then removed under reduced pressure to obtain a crude crystal 26. The crystal was used for the following reaction without further purification.

Example 10

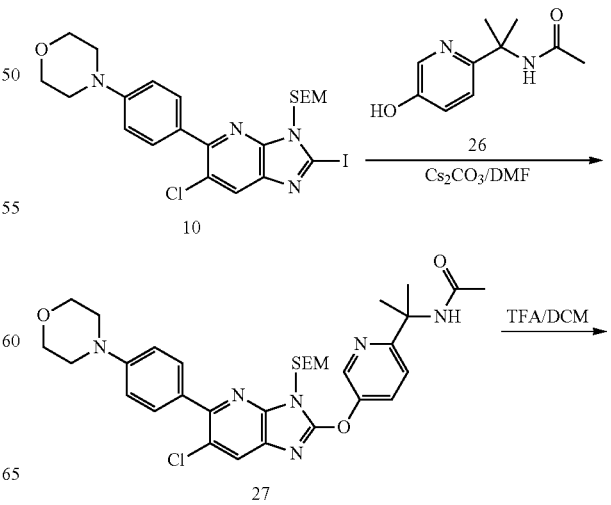

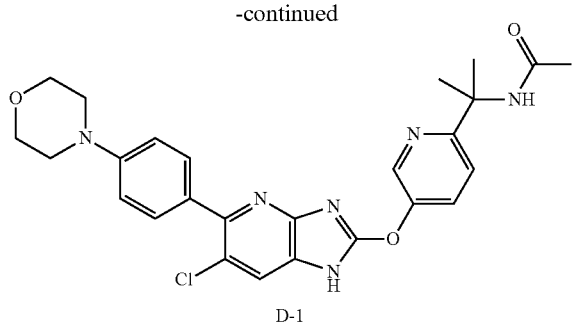

D-1

To a solution of Compound 10 (100 mg, 0.175 mmol) in DMF (1 ml) were added Compound 26 (45 mg, 0.210 mmol (tentatively calculated as 90% Wt)) and cesium carbonate (74.2 mg, 0.228 mmol), and the reaction mixture was stirred at 80° C. for 2 hours. To the reaction mixture, distilled water was added, followed by extraction with ethyl acetate, washing three times with distilled water and once with a saturated sodium bicarbonate water and drying over sodium sulfate. The solvent was removed under reduced pressure. The concentrated residue was purified by silica gel column chromatography (chloroform:methanol=10:1) to obtain Compound 27 (112 mg, 100%) as a colorless amorphous.

Compound 27; 1H-NMR (CDCl$_3$) δ: −0.03 (s, 9H), 0.99 (t, J=8.11 Hz, 2H), 1.79 (s, 6H), 2.05 (s, 3H), 3.26 (t, J=4.82 Hz, 4H), 3.80 (t, J=8.11 Hz, 2H), 3.89 (t, J=4.82 Hz, 4H), 5.67 (s, 2H), 6.99 (d, J=8.62 Hz, 2H), 7.39 (s, 1H), 7.53 (d, J=9.12 Hz, 1H), 7.72 (d, J=8.62 Hz, 2H), 7.83-7.89 (m, 2H), 8.63 (d, J=3.04 Hz, 1H).

To a solution of Compound 27 (110 mg, 0.173 mmol) in DCM (0.5 ml) was added TFA (0.5 ml, 6.49 mmol), and the reaction mixture was stirred at room temperature for 3 hours. Thereafter, methanol (0.5 ml) was added thereto, and the reaction mixture was stirred for another one hour. TFA was removed by azeotropic distillation with toluene. The obtained residue was neutralized with 2N NaOH aq., followed by extraction twice with ethyl acetate, washing with brine and drying over sodium sulfate. The solvent was removed under reduced pressure. The concentrated residue was purified by silica gel column chromatography (chloroform:methanol=10:1) and crystallized with chloroform/hexane to obtain Compound D-1 (53 mg, 61%) as a white solid.

Compound D-1; 1H-NMR (DMSO-d6) δ: 1.58 (s, 6H), 1.86 (s, 3H), 3.19 (t, J=4.82 Hz, 4H), 3.76 (t, J=4.82 Hz, 4H), 7.02 (d, J=8.62 Hz, 2H), 7.47 (d, J=8.62 Hz, 1H), 7.57 (d, J=8.62 Hz, 2H), 7.84 (dd, J=8.62, 3.04 Hz, 1H), 7.96 (s, 1H), 8.20 (s, 1H), 8.58 (d, J=3.04 Hz, 1H), 13.35 (s, 1H).

Example 11

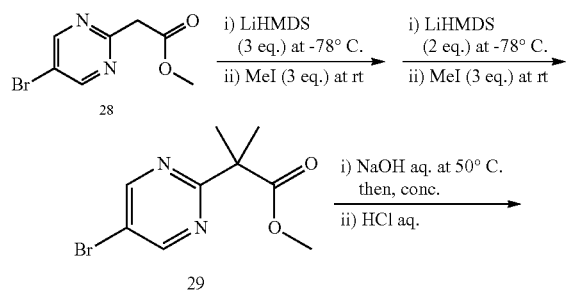

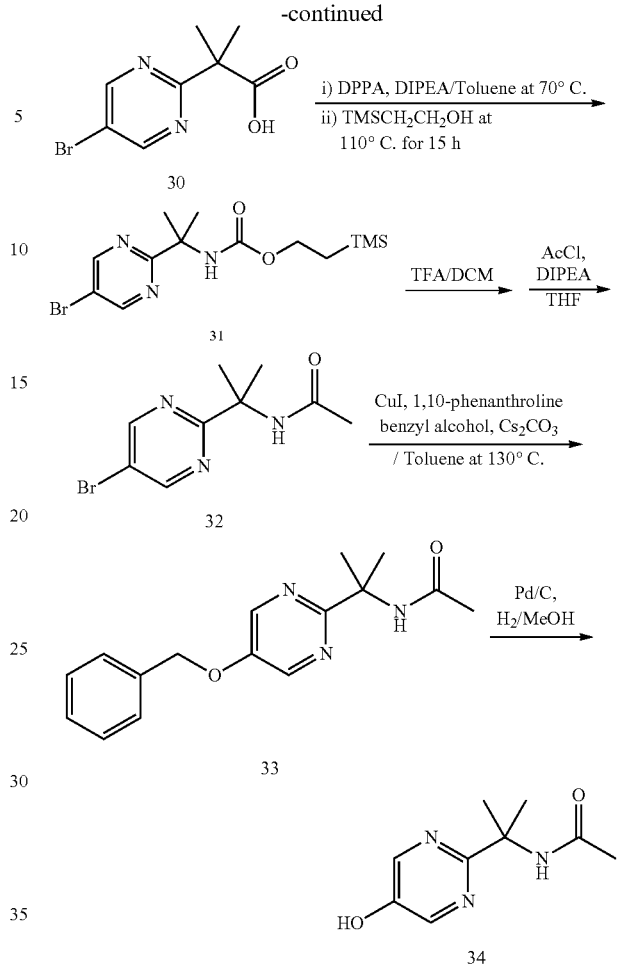

Compound 28 is described as Compound 23a in Tetrahedron 65 (2009) 757-764.

To a solution of Compound 28 (3.7 g, 16.0 mmol) in THF (40 ml) was added dropwise a 1M solution of LiHMDS in THF (48 ml, 48.0 mmol) at −60° C., and the reaction mixture was stirred for 30 minutes. Thereafter, MeI (3.0 ml, 48.0 mmol) was added thereto, and the reaction mixture was stirred for 2 hours with warming to room temperature. The reaction mixture was cooled to −60° C. again, and a 1M solution of LiHMDS in THF (32 ml, 32.0 mmol) was then added dropwise thereto, and the reaction mixture was stirred for 30 minutes. Thereafter, MeI (3.0 ml, 48.0 mmol) was added thereto, and the reaction mixture was stirred for 2 hours with heating to room temperature. The reaction mixture was cooled to 0° C., and quenching was carried out with a saturated aqueous solution of ammonium chloride, followed by extraction with ethyl acetate, washing with brine and drying over sodium sulfate. The solvent was removed under reduced pressure. The concentrated residue was purified by silica gel column chromatography (hexane:ethyl acetate=5:1) to obtain Compound 29 (3.85 g, 93%) as a yellow oil.

Compound 29; 1H-NMR (CDCl$_3$) δ: 1.63 (s, 6H), 3.70 (s, 3H), 8.73 (s, 2H).

To a solution of Compound 29 (3.8 g, 14.67 mmol) in MeOH (40 ml) was added a 2N NaOH aqueous solution (8.07 ml, 16.13 mmol), and the reaction mixture was stirred at 50° C. After 3 hours, a 2N NaOH aqueous solution (1.5 ml, 3.0 mmol) was added thereto, and the reaction mixture was stirred at 50° C. for another 3 hours. The solvent was removed under reduced pressure to dryness, and resulting solid was dissolved in 20 ml of distilled water. The obtained solution was adjusted to pH=5 with a 2 N HCl aqueous solution under ice-cooling. The resulting solid was filtered, and the obtained solid was washed three times with water to obtain Compound 30 (3.35 g, 93%) as a white solid.

Compound 30; 1H-NMR (DMSO-d6) δ: 1.51 (s, 6H), 8.97 (s, 2H), 12.45 (s, 1H).

To a suspension of Compound 30 (2 g, 8.16 mmol) in toluene (20 ml) were added DIPEA (3.14 ml, 17.95 mmol) and DPPA (1.93 ml, 8.98 mmol), and the reaction mixture was stirred at room temperature for 50 minutes, and then heated to 70° C. and stirred for another 90 minutes. The reaction mixture was allowed to cool to room temperature, and 2-trimethylsilylethanol (11.7 ml, 82 mmol) was then added thereto, and the reaction mixture was heated to 110° C. and stirred for 40 hours. The solvent was removed under reduced pressure, and the concentrated residue was purified by silica gel column chromatography (hexane:ethyl acetate=5:1×2) to obtain Compound 31 (1.95 g, 66%) as a colorless oil.

Compound 31; 1H-NMR (CDCl$_3$) δ: 0.03 (s, 9H), 0.97 (t, J=8.62 Hz, 2H), 1.73 (s, 6H), 4.11 (t, J=8.62 Hz, 2H), 6.06 (s, 1H), 8.75 (s, 2H).

To a solution of Compound 31 (800 mg, 2.22 mmol) in DCM (4 ml) was added TFA (4 ml, 51.9 mmol), and the reaction mixture was stirred at room temperature for one hour. TFA was removed by azeotropic distillation with toluene, and the residue was then diluted with distilled water and neutralized with a saturated sodium bicarbonate water. The mixture was extracted three times with chloroform, followed by drying over sodium sulfate. The solvent was removed under reduced pressure. The concentrated residue was dissolved in THF (4 ml), and DIPEA (0.437 ml, 2.51 mmol) and AcCl (0.125 ml, 1.75 mmol) were successively added thereto under ice-cooling. The reaction mixture was stirred at 0° C. for one hour. The reaction solution was extracted with distilled water and ethyl acetate, followed by washing with brine and drying over sodium sulfate. The solvent was removed under reduced pressure. The concentrated residue was purified by silica gel column chromatography (chloroform/methanol=10:1) to obtain Compound 32 (488 mg, 85%) as a white solid.

Compound 32; 1H-NMR (CDCl$_3$) δ: 1.76 (s, 6H), 2.03 (s, 3H), 6.91 (s, 1H), 8.75 (s, 2H).

To a solution of Compound 32 (450 mg, 1.74 mmol) in toluene (7.5 ml) were added copper(I) iodide (33.2 mg, 0.17 mmol), cesium carbonate (852 mg, 2.62 mmol), benzyl alcohol (0.90 ml, 8.72 mmol) and 1,10-phenanthroline (63 mg, 0.35 mmol), and the reaction mixture was stirred under microwave irradiation at 130° C. for 2.5 hours. To the reaction solution, distilled water was added, and the aqueous layer was extracted with ethyl acetate, followed by washing with brine and drying over sodium sulfate. The solvent was removed under reduced pressure. The concentrated residue was purified by silica gel column chromatography (hexane:ethyl acetate=1:10, and chloroform:methanol=10:1 for a second time) to obtain Compound 33 as a mixture with approximately 10% of Compound 32 (448 mg, 81%).

Compound 33; 1H-NMR (CDCl$_3$) δ: 1.76 (s, 6H), 2.03 (s, 3H), 5.15 (s, 2H), 7.35-7.47 (m, 5H), 8.43 (s, 2H).

To a solution of Compound 33 (440 mg, 1.54 mmol) in methanol (5 ml) was added 10% Pd/C (50% wet) (328 mg, 0.154 mmol), and the reaction mixture was stirred under a hydrogen atmosphere at room temperature for 3 hours. The reaction mixture was filtered with Celite, and the solvent was then removed under reduced pressure to obtain a crude crystal 34. The crystal was used for the following reaction without further purification.

Example 12

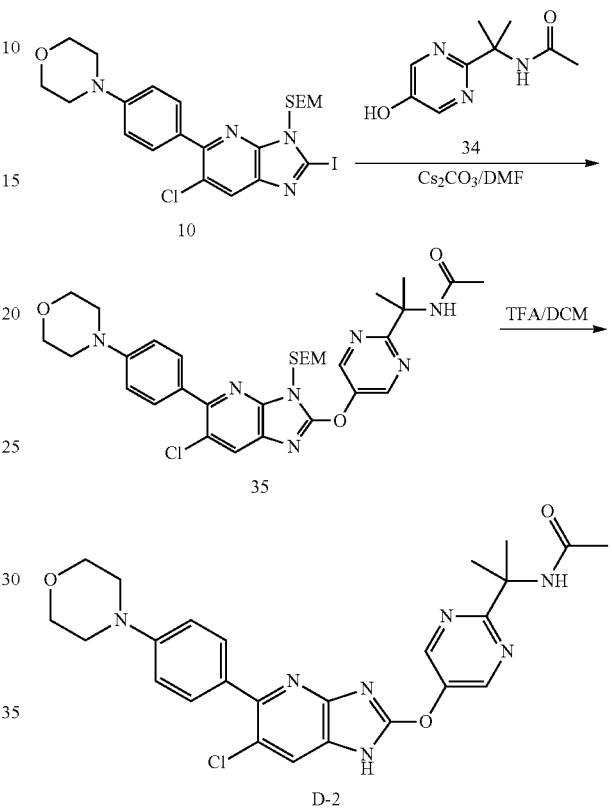

To a solution of Compound 10 (100 mg, 0.175 mmol) in DMF (1 ml) were added Compound 34 (51 mg, 0.210 mmol (tentatively calculated as 80% Wt)) and cesium carbonate (74.2 mg, 0.228 mmol), and the reaction mixture was stirred under microwave irradiation at 130° C. for 30 minutes. Compound 34 (51 mg, 0.210 mmol (tentatively calculated as 80% Wt)) was added thereto, and the reaction mixture was stirred under microwave irradiation at 130° C. for another 20 minutes. To the reaction solution, distilled water was added, followed by extraction with ethyl acetate, washing three times with distilled water and once with a saturated sodium bicarbonate water and drying over sodium sulfate. The solvent was removed under reduced pressure. The concentrated residue was purified by silica gel column chromatography (chloroform:methanol=10:1) to obtain Compound 35 (75 mg, 67%) as a yellow amorphous.

Compound 35; 1H-NMR (CDCl$_3$) δ: −0.03 (s, 9H), 0.98 (t, J=8.36 Hz, 2H), 1.83 (s, 6H), 2.06 (s, 3H), 3.26 (t, J=4.82 Hz, 4H), 3.79 (t, J=8.36 Hz, 2H), 3.89 (t, J=4.82 Hz, 4H), 5.68 (s, 2H), 6.99 (d, J=8.62 Hz, 2H), 7.20 (s, 1H), 7.72 (d, J=8.62 Hz, 2H), 7.87 (s, 1H), 8.94 (s, 2H).

To a solution of Compound 35 (70 mg, 0.110 mmol) in DCM (0.5 ml) was added TFA (0.5 ml, 6.49 mmol), and the reaction mixture was stirred at room temperature for one hour. Thereafter, methanol (0.5 ml) was added thereto, and the reaction mixture was stirred for another one hour. TFA was removed by azeotropic distillation with toluene. The obtained residue was neutralized with a saturated sodium bicarbonate water, followed by extraction three times with chloroform, washing with brine and drying over sodium sulfate. The solvent was removed under reduced pressure. The concentrated residue was purified by silica gel column chromatography (chloroform:methanol=10:1) and crystallized with chloroform/hexane to obtain Compound D-2 (39 mg, 70%) as a white solid.

Compound D-2; 1H-NMR (DMSO-d6) δ: 1.61 (s, 6H), 1.80 (s, 3H), 3.20 (t, J=4.82 Hz, 4H), 3.76 (t, J=4.82 Hz, 4H), 7.02 (d, J=8.62 Hz, 2H), 7.57 (d, J=8.62 Hz, 2H), 8.00 (s, 1H), 8.26 (s, 1H), 8.94 (s, 2H), 13.42 (s, 1H).

Example 13

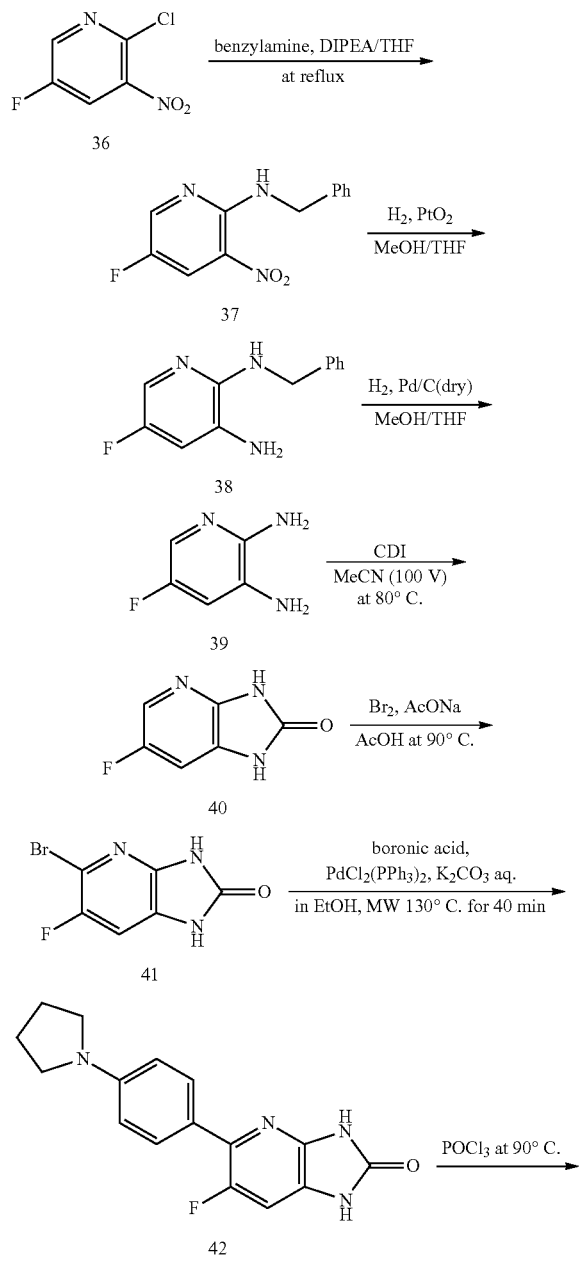

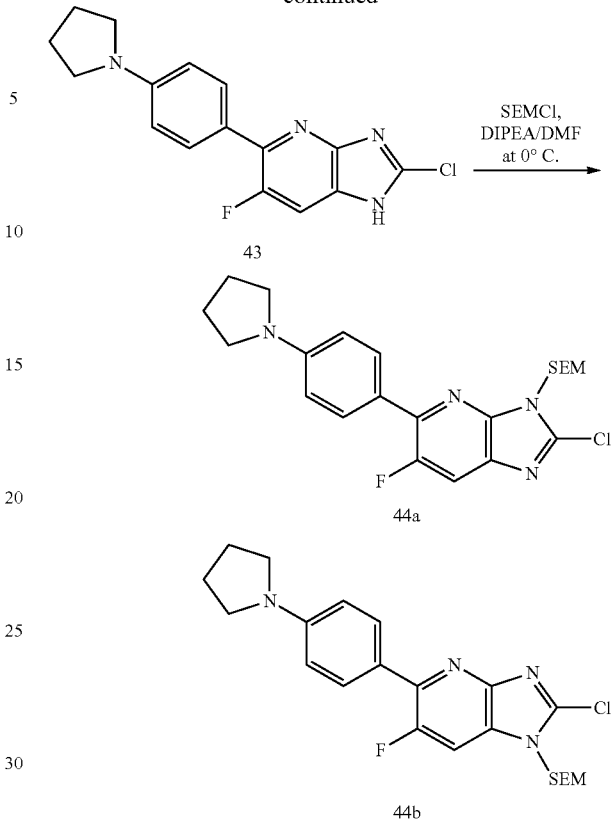

To a solution of 2-chloro-5-fluoro-3-nitropyridine 36 (1.378 g, 7.81 mmol) in THF (10 ml) were successively added DIPEA (4.09 ml, 23.42 mmol) and benzylamine (1.71 ml, 15.61 mmol), and the reaction mixture was stirred under heating to reflux for 7 hours. The reaction mixture was allowed to cool to room temperature, and 20 ml of distilled water was added thereto, followed by extraction three times with 20 ml of ethyl acetate and drying over sodium sulfate. The solvent was removed under reduced pressure. The concentrated residue was purified by silica gel column chromatography (hexane/EtOAc=10:1) to obtain Compound 37 as a mixture with benzylamine.

The concentrated residue after purification was dissolved in a mixed solvent of methanol (10 ml) and THF (10 ml), and platinum oxide (177 mg, 0.781 mmol) was added thereto, and the reaction mixture was stirred under a hydrogen atmosphere for one hour. The reaction solution was filtered with Celite, and the solvent was removed under reduced pressure, followed by purification by silica gel column chromatography (hexane/ethyl acetate=3:1) to obtain Compound 38 (1.52 g, 90%) as a brown solid.

Compound 37; 1H-NMR (DMSO-d6) δ: 4.78 (d, J=6.08 Hz, 2H), 7.20-7.35 (m, 5H), 8.41 (dd, J=8.36, 2.79 Hz, 1H), 8.58 (d, J=2.79 Hz, 1H), 8.90 (t, J=6.08 Hz, 1H).

Compound 38; 1H-NMR (DMSO-d6) δ: 4.51 (d, J=5.58 Hz, 2H), 5.18 (s, 2H), 6.02 (t, J=5.58 Hz, 1H), 6.60 (dd, J=10.65, 2.53 Hz, 1H), 7.19-7.34 (m, 6H).

To a mixed solution of MeOH (10 ml) and THF (10 ml) containing Compound 38 (1.46 g, 6.72 mmol) was added 5% Pd/C (715 mg, 0.336 mmol), and the reaction mixture was stirred under a hydrogen atmosphere for 2 hours. The reaction mixture was allowed to cool to room temperature, and 2-trimethylsilylethanol (8.75 ml, 61 mmol) was then added thereto, and the reaction mixture was stirred at 110° C. for 10 hours. The reaction solution was filtered with Celite, and the solvent was removed under reduced pressure. The obtained residue was suspended with chloroform, and the suspension was filtered to obtain Compound 39 (800 mg, 94%) as a white solid.

Compound 39; 1H-NMR (DMSO-d6) δ: 5.04 (s, 2H), 5.29 (s, 2H), 6.57 (dd, J=10.65, 2.53 Hz, 1H), 7.15 (d, J=2.53 Hz, 1H).

To a solution of Compound 39 (795 mg, 6.25 mmol) in MeCN (70 ml) was added CDT (1.52 g, 9.38 mmol), and the reaction mixture was stirred at 80° C. for 6 hours. The reaction mixture was allowed to cool to room temperature, and the solvent was removed under reduced pressure, followed by the addition of 50 ml of chloroform. The mixture was stirred for 30 minutes, and a solid was filtered to obtain Compound 40 (738 mg, 77%) as a white solid.

Compound 40; 1H-NMR (DMSO-d6) δ: 7.24 (dd, J=8.62, 2.53 Hz, 1.0H), 7.84 (t, J=2.28 Hz, 1.0H), 11.04 (br s, 1.0H), 11.40 (br s, 1.0H).

To a solution of Compound 40 (730 mg, 4.77 mmol) in acetic acid (20 ml) were added sodium acetate (782 mg, 9.54 mmol) and bromine (990 mg, 6.20 mmol), and the reaction mixture was stirred at 90° C. for one hour. The reaction mixture was allowed to cool to room temperature, and 20 ml of distilled water was then added thereto. The mixture was stirred for one hour, and the resulting solid was filtered to obtain Compound 41 (810 mg, 73%) as a brown solid.

Compound 41; 1H-NMR (DMSO-d6) δ: 7.43 (d, J=8.62 Hz, 1H), 11.23 (s, 1H), 11.65 (s, 1H).

To a solution of Compound 41 (400 mg, 1.72 mmol) in ethanol (3 ml) were added 1-(4-(4,4,5,5-tetramethyl-1,3,2-dioxaborolan-2-yl)phenyl)pyrrolidine (565 mg, 2.07 mmol), PdCl$_2$(PPh$_3$)$_2$ (85 mg, 0.121 mmol) and 2 M K$_2$CO$_3$ aq. (2.15 ml, 4.31 mmol), and the reaction mixture was stirred under microwave irradiation at 130° C. for 30 minutes. The reaction solution was diluted in ethyl acetate (300 ml), and the mixture was then stirred at 40° C. for one hour. Insoluble matter was filtered with Celite, followed by washing with brine and drying over sodium sulfate. The solvent was removed under reduced pressure. The concentrated residue was stirred in a mixed solvent of ethyl acetate (10 ml) and chloroform (10 ml) for 30 minutes, and then filtered to obtain Compound 42 (225 mg, 44%) as a brown solid.

Compound 42; 1H-NMR (DMSO-d6) δ: 1.97 (t, J=6.34 Hz, 4H), 3.28 (t, J=6.34 Hz, 4H), 6.61 (d, J=9.12 Hz, 2H), 7.24 (d, J=11.66 Hz, 1H), 7.68 (d, J=7.60 Hz, 2H), 10.94 (s, 1H), 11.33 (s, 1H).

A suspension of Compound 42 (130 mg, 0.436 mmol) in phosphorus oxychloride (2.5 ml, 26.9 mmol) was stirred at 100° C. for 3 hours. The suspension was allowed to cool to room temperature, and tetramethylammonium chloride (47.8 mg, 0.436 mmol) and phosphorus oxychloride (1 ml, 10.76 mmol) were then added thereto, and the reaction mixture was stirred at 100° C. for 7 hours. Quenching was carried out with methanol under ice-cooling. The mixture was diluted with distilled water and neutralized with a 2 N NaOH aqueous solution, followed by extraction three times with chloroform. The organic layer was dried over sodium sulfate, and the solvent was removed under reduced pressure. The concentrated residue was purified by silica gel column chromatography (hexane:ethyl acetate=2:1) to obtain Compound 43 (42 mg, 30%) as a brown solid.

Compound 43; 1H-NMR (DMSO-d6) δ: 1.96-2.01 (m, 4H), 3.28-3.33 (m, 4H), 6.65 (d, J=9.12 Hz, 2H), 7.79 (d, J=9.12 Hz, 2H), 7.96 (br s, 1H), 13.96 (s, 1H).

To a solution of Compound 43 (40 mg, 0.126 mmol) in DMF (0.4 ml) were added DIPEA (28.7 μl, 0.164 mmol) and SEMCl (24 μl 0.133 mmol) under ice-cooling, and the reaction mixture was stirred at 0° C. for 40 minutes. The reaction mixture was diluted with 1 ml of distilled water, followed by extraction with ethyl acetate, washing with brine and drying over sodium sulfate. The solvent was removed under reduced pressure. The concentrated residue was purified by silica gel column chromatography (hexane:ethyl acetate=5:1 to 2:1) to obtain Compound 44a (31.2 mg, 55%) and 44b (9.2 mg, 16%) as a yellow oil and a yellow solid, respectively.

Compound 44a; 1H-NMR (DMSO-d6) δ: −0.12 (s, 9H), 0.90 (t, J=7.86 Hz, 2H), 1.99 (t, J=6.59 Hz, 4H), 3.27-3.33 (m, 4H), 3.68 (t, J=7.86 Hz, 2H), 5.66 (s, 2H), 6.65 (d, J=9.12 Hz, 2H), 7.88 (dd, J=9.12, 1.52 Hz, 2H), 8.08 (d, J=12.17 Hz, 1H).

Compound 44b; 1H-NMR (DMSO-d6) δ: −0.07 (s, 9H), 0.86 (t, J=8.11 Hz, 2H), 1.99 (t, J=6.59 Hz, 4H), 3.29-3.33 (m, 4H), 3.60 (t, J=8.11 Hz, 2H), 5.65 (s, 2H), 6.66 (d, J=9.12 Hz, 2H), 7.80 (d, J=9.12 Hz, 2H), 8.23 (d, J=11.15 Hz, 1H).

Example 14

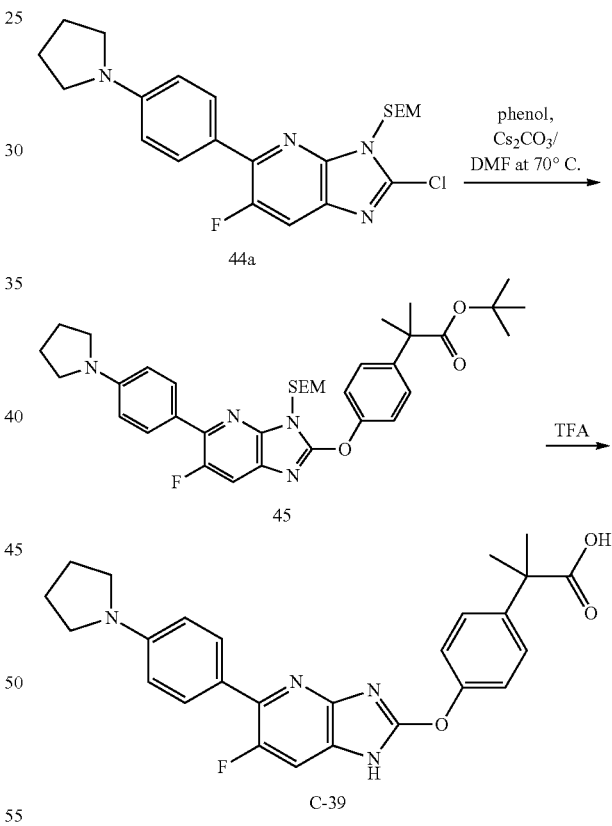

To a solution of Compound 44a (30 mg, 0.067 mmol) in DMF (600 μl) were added cesium carbonate (33 mg, 0.101 mmol) and tert-butyl 2-(4-hydroxyphenyl)-2-methylpropanoate (21 mg, 0.087 mmol), and the reaction mixture was stirred at 70° C. for one hour. The reaction mixture was diluted with 1 ml of distilled water, followed by extraction with ethyl acetate, washing with brine and drying over sodium sulfate. The solvent was removed under reduced pressure. The concentrated residue was purified by silica gel column chromatography (hexane:ethyl acetate=5:1) to obtain Compound 45 (36 mg, 82%) as a white solid.

Compound 45; 1H-NMR (DMSO-d6) δ: −0.10 (s, 9H), 0.93 (t, J=8.11 Hz, 2H), 1.37 (s, 9H), 1.49 (s, 6H), 1.99 (t, J=6.34 Hz, 4H), 3.28-3.33 (m, 4H), 3.76 (t, J=8.11 Hz, 2H), 5.62 (s, 2H), 6.65 (d, J=8.62 Hz, 2H), 7.37-7.46 (m, 4H), 7.79-7.86 (m, 3H).

To a solution of Compound 45 (34 mg, 0.053 mmol) in DCM (600 µl) was added TFA (600 µl, 7.79 mmol), and the reaction mixture was stirred at room temperature for 4 hours. The solvent was removed under reduced pressure, and the obtained residue was diluted with distilled water (1 ml). The mixture was adjusted to pH=5 with a 2 N NaOH aqueous solution, followed by extraction three times with ethyl acetate. The organic layer was washed with brine and dried over sodium sulfate. The solvent was removed under reduced pressure. To the concentrated residue, 15 ml of ethyl acetate was added, and the resulting solid residue was filtered to obtain Compound C-39 (18 mg, 74%) as a yellow solid.

Compound C-39; 1H-NMR (DMSO-d6) δ: 1.51 (s, 6H), 1.98 (t, J=4.39 Hz, 4H), 3.29 (t, J=4.39 Hz, 4H), 6.63 (d, J=9.12 Hz, 2H), 7.37 (d, J=8.62 Hz, 2H), 7.44 (d, J=8.62 Hz, 2H), 7.71 (d, J=12.17 Hz, 1H), 7.76 (d, J=9.12 Hz, 2H), 12.43 (s, 1H), 13.09 (s, 1H).

Compounds shown below were synthesized in the same manner. The measurement results of NMR or LC/MS of each compound were shown.

TABLE 1

| No. | Structure | NMR (δ) | retention time | Mass (M + H) | method |
|---|---|---|---|---|---|
| B-4 | 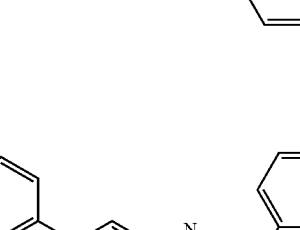 HCl | (DMSO-d6) δ: 2.49 (s, 3H), 2.78-2.82 (m, 1H), 2.94-2.98 (m, 1H), 3.34-3.36 (m, 1H), 3.63-3.66 (m, 1H), 3.91-3.95 (m, 1H), 4.06-4.09 (m, 1H), 4.41-4.50 (m, 3H), 7.30-7.35 (m, 2H), 7.47-7.48 (m, 3H), 7.59-7.60 (m, 1H), 7.64-7.66 (m, 2H),, 11.26 (s, 1H). | | | |
| B-5 | 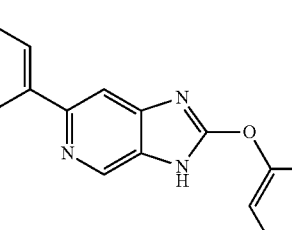 | (DMSO-d6) δ: 2.56 (s, 3H), 3.82 (s, 3H), 6.49 (d, J = 4.0 Hz, 1H), 7.36-7.56 (m, 5H), 7.49-7.51 (m, 2H), 7.84 (s, 2H), 7.97 (s, 1H), 8.48 (s, 1H) 12.75 (brs, 1H) 13.10 (brs, 1H). | | | |
| B-6 | 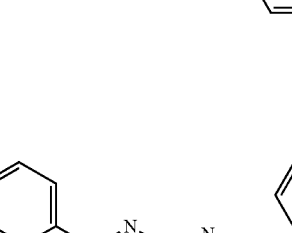 | (DMSO-d6) δ: 2.56 (s, 3H), 3.83 (s, 3H), 6.51 (d, J = 4.0 Hz, 1H), 7.36-7.42 (m, 2H), 7.51-7.53 (m, 2H), 7.81-7.86 (m, 2H), 8.21 (s, 1H), 8.63 (s, 1H), 12.99 (brs, 2H). | | | |
| B-7 | 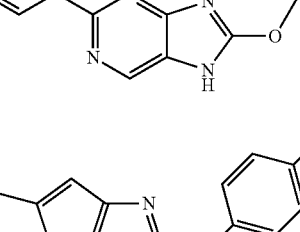 | (DMSO-d6) δ: 2.56 (s, 3H), 3.21 (t, J = 4.8 Hz, 4H), 3.76 (t, J = 4.8 Hz, 4H), 7.04 (d, J = 8.4 Hz, 2H), 7.43 (d, J = 8.4 Hz, 1H), 7.54 (dd, J = 8.4, 2.4 Hz, 1H), 7.86 (d, J = 2.4 Hz, 1H), 8.25 (d, J = 8.4 Hz, 2H), 8.76 (s, 1H), 13.21 (brs, 2H). | | | |
| B-8 | 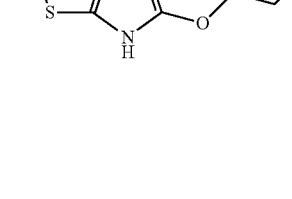 | (DMSO-d6) δ: 2.52 (s, 3H), 7.26 (t, J = 7.35 Hz, 1H), 7.37-7.41 (m, 4H), 7.49 (s, 1H), 7.64 (d, J = 7.10 Hz, 2H), 7.69 (d, J = 2.53 Hz, 1H), 12.72 (s, 1H), 13.06 (br s, 1H). | | | |

TABLE 1-continued

| No. | Structure | NMR (δ) | retention time | Mass (M + H) | method |
|---|---|---|---|---|---|
| B-9 | 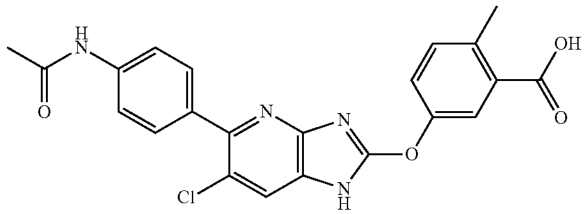 [SMILES: CC(=O)Nc1ccc(-c2nc3nc(Oc4ccc(C)c(C(=O)O)c4)[nH]c3cc2Cl)cc1] | | 1.56 | 436.9 | B |

TABLE 2

| No. | Structure | retention time | Mass (M + H) | method |
|---|---|---|---|---|
| B-10 | 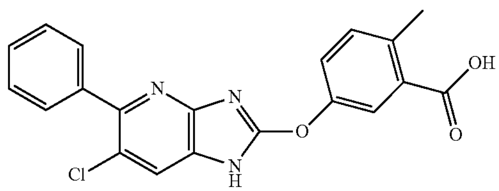 [SMILES: Cc1ccc(Oc2nc3nc(-c4ccccc4)c(Cl)cc3[nH]2)cc1C(=O)O] | 1.98 | 380.18 | A |
| B-11 | 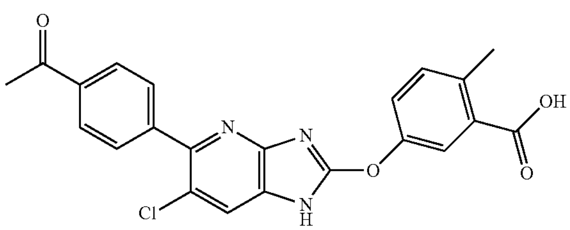 [SMILES: CC(=O)c1ccc(-c2nc3nc(Oc4ccc(C)c(C(=O)O)c4)[nH]c3cc2Cl)cc1] | 1.85 | 422.21 | A |
| B-12 | 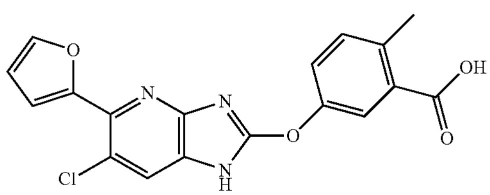 [SMILES: Cc1ccc(Oc2nc3nc(-c4ccco4)c(Cl)cc3[nH]2)cc1C(=O)O] | 1.8 | 370.17 | A |
| B-13 | 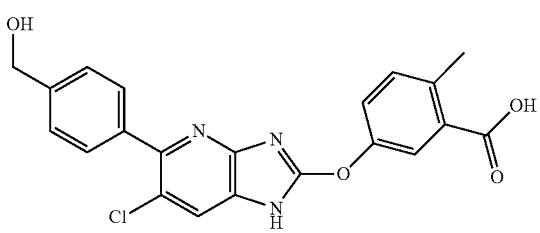 [SMILES: Cc1ccc(Oc2nc3nc(-c4ccc(CO)cc4)c(Cl)cc3[nH]2)cc1C(=O)O] | 1.56 | 410.21 | A |
| B-14 | 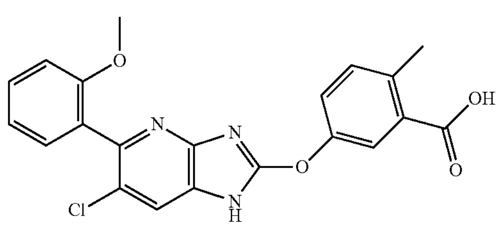 [SMILES: COc1ccccc1-c1nc2nc(Oc3ccc(C)c(C(=O)O)c3)[nH]c2cc1Cl] | 1.88 | 410.2 | A |

TABLE 2-continued

| No. | Structure | retention time | Mass (M + H) | method |
|---|---|---|---|---|
| B-15 | 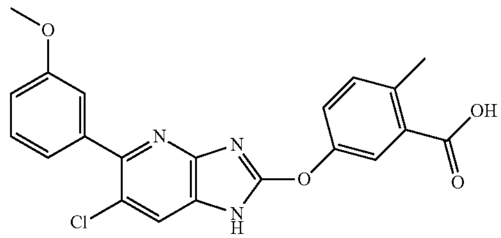 [SMILES: COc1cccc(-c2nc3nc(Oc4ccc(C)c(C(=O)O)c4)[nH]c3cc2Cl)c1] | 1.98 | 410.2 | A |

TABLE 3

| No. | Structure | retention time | Mass (M + H) | method |
|---|---|---|---|---|
| B-16 | 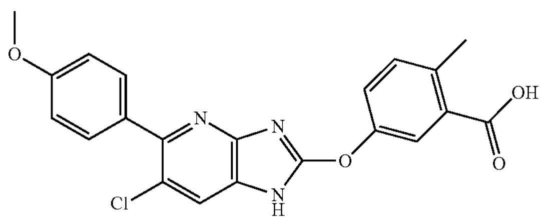 [SMILES: COc1ccc(-c2nc3nc(Oc4ccc(C)c(C(=O)O)c4)[nH]c3cc2Cl)cc1] | 1.97 | 410.2 | A |
| B-17 | 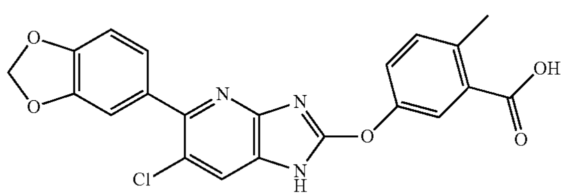 [SMILES: Cc1ccc(Oc2nc3nc(-c4ccc5c(c4)OCO5)c(Cl)cc3[nH]2)cc1C(=O)O] | 1.91 | 424.18 | A |
| B-18 | 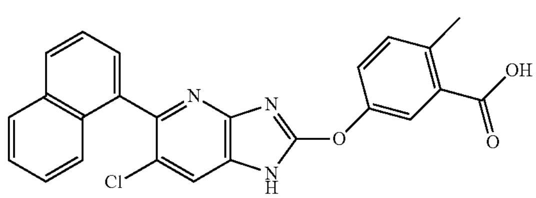 [SMILES: Cc1ccc(Oc2nc3nc(-c4cccc5ccccc45)c(Cl)cc3[nH]2)cc1C(=O)O] | 2.16 | 430.21 | A |
| B-19 | 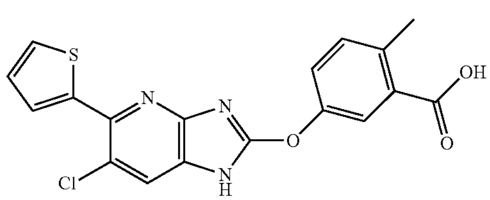 | 2.06 | 386.15 | A |
| B-20 | 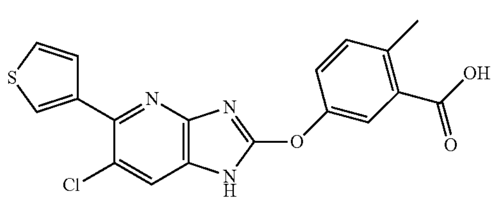 [SMILES: Cc1ccc(Oc2nc3nc(-c4ccsc4)c(Cl)cc3[nH]2)cc1C(=O)O] | 1.97 | 386.15 | A |

TABLE 3-continued

| No. | Structure | retention time | Mass (M + H) | method |
|---|---|---|---|---|
| B-21 | 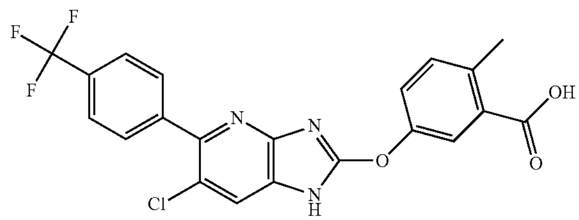 [SMILES: Cc1ccc(Oc2nc3nc(-c4ccc(C(F)(F)F)cc4)c(Cl)cc3[nH]2)cc1C(=O)O] | 2.28 | 448.17 | A |

TABLE 4

| No. | Structure | NMR (δ) | retention time | Mass (M + H) | method |
|---|---|---|---|---|---|
| B-22 | 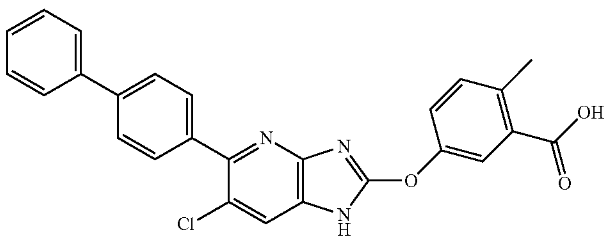 [SMILES: Cc1ccc(Oc2nc3nc(-c4ccc(-c5ccccc5)cc4)c(Cl)cc3[nH]2)cc1C(=O)O] | (DMSO-d$_6$) δ: 2.56 (s, 3H), 7.38-7.44(m, 2H), 7.49-7.57 (m, 3H), 7.74-7.80 (m, 6H), 7.85 (s, 1H), 8.02(s, 1H), 13.13 (bs, 1H) | 2.45 | 456.21 | A |
| B-23 | 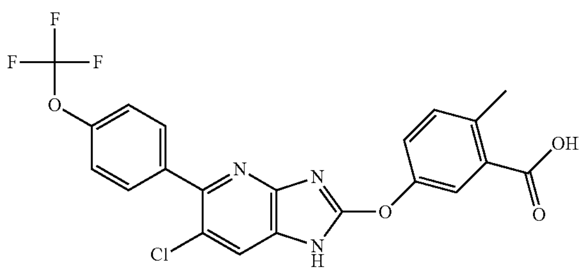 [SMILES: Cc1ccc(Oc2nc3nc(-c4ccc(OC(F)(F)F)cc4)c(Cl)cc3[nH]2)cc1C(=O)O] | | 2.36 | 464.18 | A |
| B-24 | 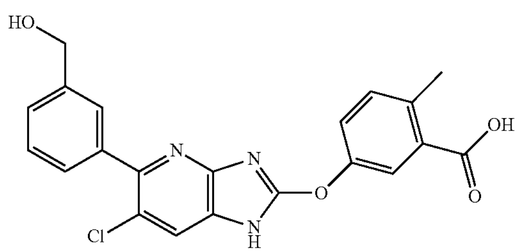 [SMILES: Cc1ccc(Oc2nc3nc(-c4cccc(CO)c4)c(Cl)cc3[nH]2)cc1C(=O)O] | | 1.6 | 410.21 | A |
| B-25 | 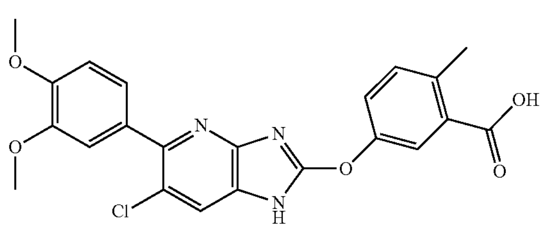 [SMILES: COc1ccc(-c2nc3nc(Oc4ccc(C)c(C(=O)O)c4)[nH]c3cc2Cl)cc1OC] | | 1.82 | 440.22 | A |
| B-26 | 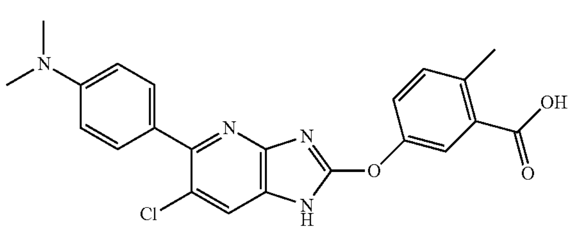 [SMILES: Cc1ccc(Oc2nc3nc(-c4ccc(N(C)C)cc4)c(Cl)cc3[nH]2)cc1C(=O)O] | | 1.74 | 423.23 | A |

TABLE 4-continued

| No. | Structure | NMR (δ) | retention time | Mass (M + H) | method |
|---|---|---|---|---|---|
| B-27 | 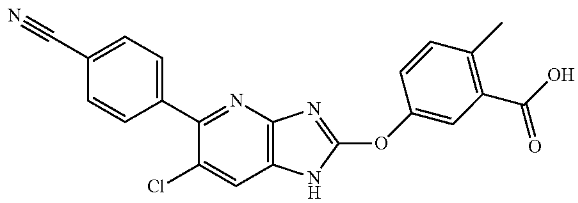 [SMILES: Cc1ccc(Oc2nc3nc(-c4ccc(C#N)cc4)c(Cl)cc3[nH]2)cc1C(=O)O] | | 1.92 | 405.2 | A |

TABLE 5

| No. | Structure | retention time | Mass (M + H) | method |
|---|---|---|---|---|
| B-28 | 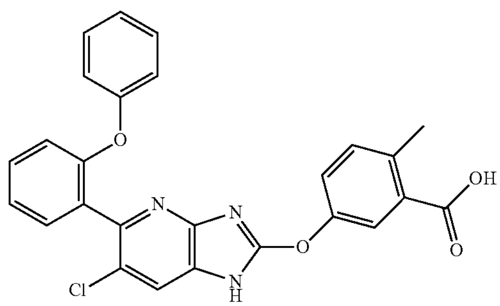 [SMILES: Cc1ccc(Oc2nc3nc(-c4ccccc4Oc4ccccc4)c(Cl)cc3[nH]2)cc1C(=O)O] | 2.27 | 472.22 | A |
| B-29 | 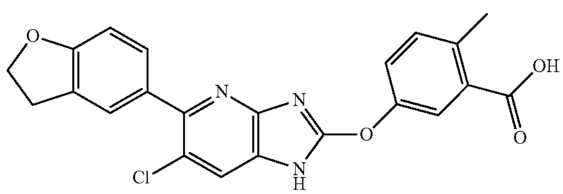 | 1.96 | 422.19 | A |
| B-30 | 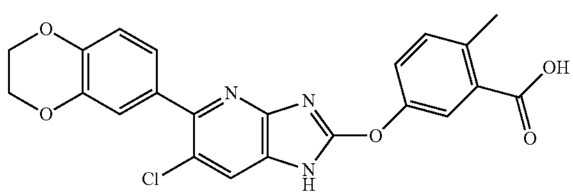 [SMILES: Cc1ccc(Oc2nc3nc(-c4ccc5c(c4)OCCO5)c(Cl)cc3[nH]2)cc1C(=O)O] | 1.92 | 438.2 | A |
| B-31 | 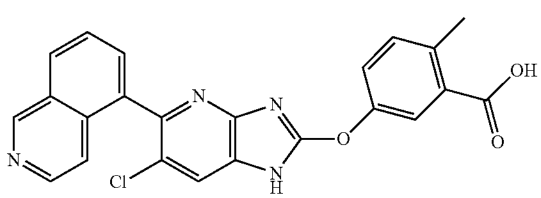 [SMILES: Cc1ccc(Oc2nc3nc(-c4cccc5cnccc45)c(Cl)cc3[nH]2)cc1C(=O)O] | 1.27 | 431.2 | A |
| B-32 | 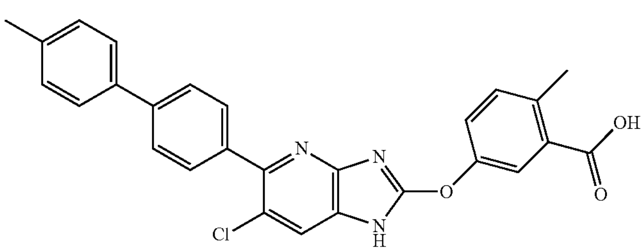 [SMILES: Cc1ccc(-c2ccc(-c3nc4nc(Oc5ccc(C)c(C(=O)O)c5)[nH]c4cc3Cl)cc2)cc1] | 2.6 | 470.23 | A |

TABLE 5-continued

| No. | Structure | retention time | Mass (M + H) | method |
|---|---|---|---|---|
| B-33 | 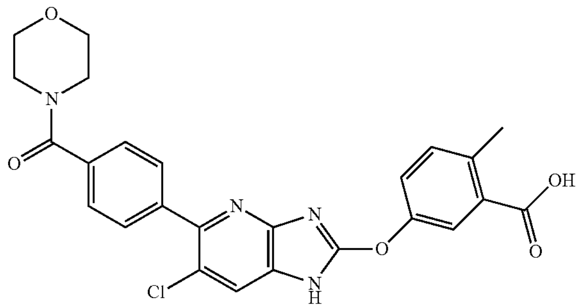 [SMILES: Cc1ccc(Oc2nc3nc(-c4ccc(C(=O)N5CCOCC5)cc4)c(Cl)cc3[nH]2)cc1C(=O)O] | 1.59 | 493.24 | A |

TABLE 6

| No. | Structure | retention time | Mass (M + H) | method |
|---|---|---|---|---|
| B-34 | 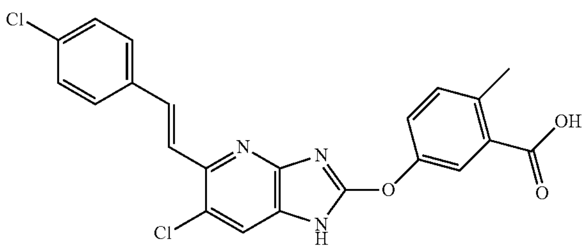 [SMILES: Cc1ccc(Oc2nc3nc(/C=C/c4ccc(Cl)cc4)c(Cl)cc3[nH]2)cc1C(=O)O] | 2.59 | 440.15 | A |
| B-35 | 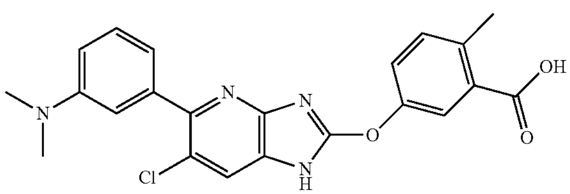 [SMILES: Cc1ccc(Oc2nc3nc(-c4cccc(N(C)C)c4)c(Cl)cc3[nH]2)cc1C(=O)O] | 1.54 | 423.24 | A |
| B-36 | 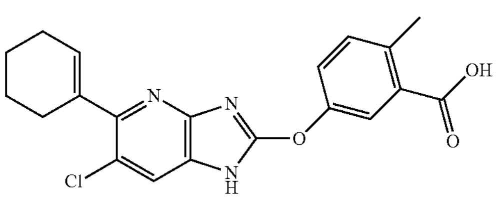 [SMILES: Cc1ccc(Oc2nc3nc(C4=CCCCC4)c(Cl)cc3[nH]2)cc1C(=O)O] | 2.14 | 384.21 | A |
| B-37 | 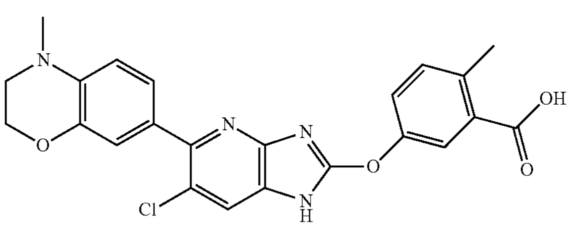 [SMILES: Cc1ccc(Oc2nc3nc(-c4ccc5c(c4)OCCN5C)c(Cl)cc3[nH]2)cc1C(=O)O] | 1.98 | 451.23 | A |
| B-38 | 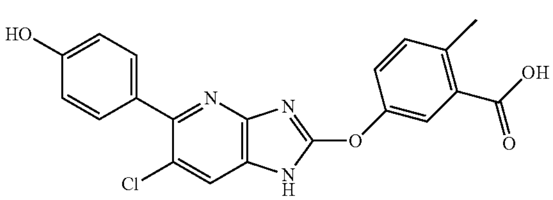 [SMILES: Cc1ccc(Oc2nc3nc(-c4ccc(O)cc4)c(Cl)cc3[nH]2)cc1C(=O)O] | 1.61 | 396.2 | A |

TABLE 6-continued

| No. | Structure | retention time | Mass (M + H) | method |
|---|---|---|---|---|
| B-39 | 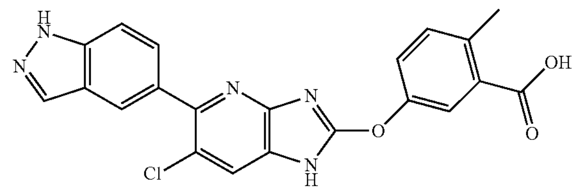 [SMILES: Cc1ccc(Oc2nc3nc(-c4ccc5[nH]ncc5c4)c(Cl)cc3[nH]2)cc1C(=O)O] | 1.56 | 420.2 | A |

TABLE 7

| No. | Structure | retention time | Mass (M + H) | method |
|---|---|---|---|---|
| B-40 | 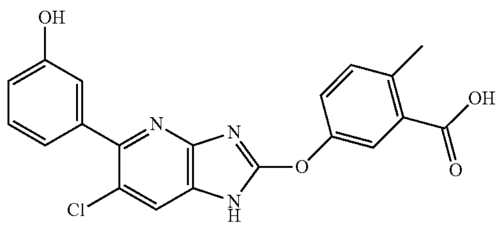 [SMILES: Cc1ccc(Oc2nc3nc(-c4cccc(O)c4)c(Cl)cc3[nH]2)cc1C(=O)O] | 1.66 | 396.19 | A |
| B-41 | 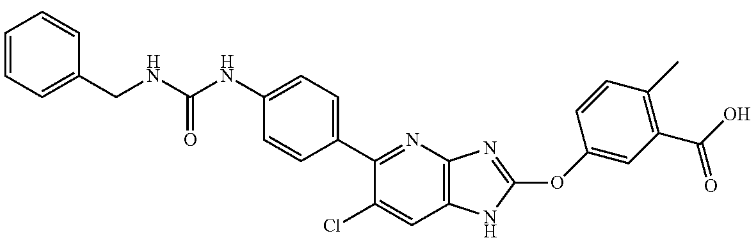 [SMILES: Cc1ccc(Oc2nc3nc(-c4ccc(NC(=O)NCc5ccccc5)cc4)c(Cl)cc3[nH]2)cc1C(=O)O] | 1.95 | 528.23 | A |
| B-42 | 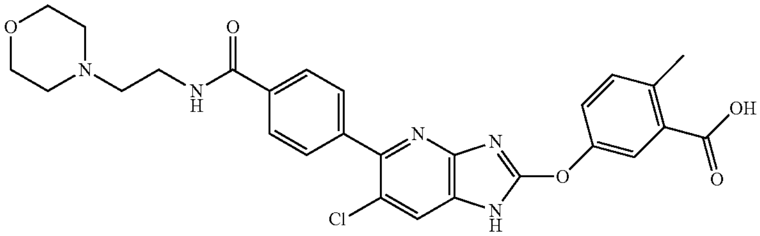 [SMILES: Cc1ccc(Oc2nc3nc(-c4ccc(C(=O)NCCN5CCOCC5)cc4)c(Cl)cc3[nH]2)cc1C(=O)O] | 1.21 | 536.26 | A |
| B-43 | 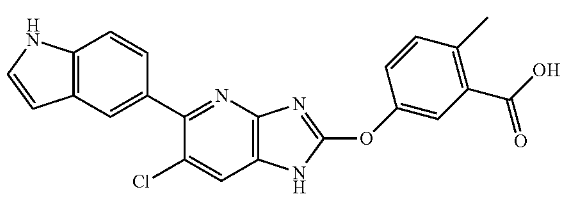 [SMILES: Cc1ccc(Oc2nc3nc(-c4ccc5[nH]ccc5c4)c(Cl)cc3[nH]2)cc1C(=O)O] | 1.85 | 419.19 | A |
| B-44 | 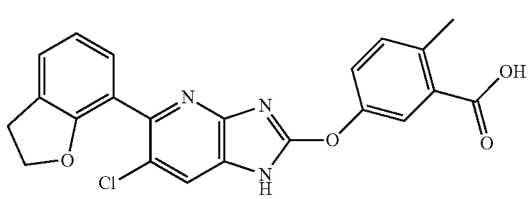 [SMILES: Cc1ccc(Oc2nc3nc(-c4cccc5c4OCC5)c(Cl)cc3[nH]2)cc1C(=O)O] | 1.92 | 422.18 | A |

TABLE 7-continued

| No. | Structure | retention time | Mass (M + H) | method |
|---|---|---|---|---|
| B-45 | 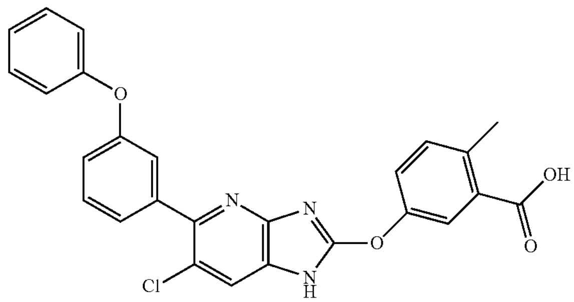 [SMILES: Cc1ccc(Oc2nc3nc(-c4cccc(Oc5ccccc5)c4)c(Cl)cc3[nH]2)cc1C(=O)O] | 2.43 | 472.19 | A |

TABLE 8

| No. | Structure | retention time | Mass (M + H) | method |
|---|---|---|---|---|
| B-46 | 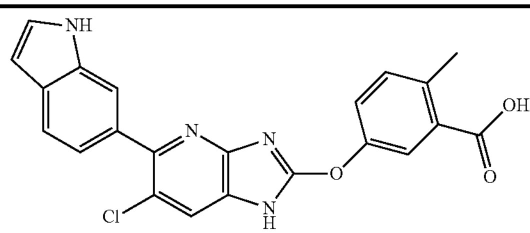 | 1.91 | 419.18 | A |
| B-47 | 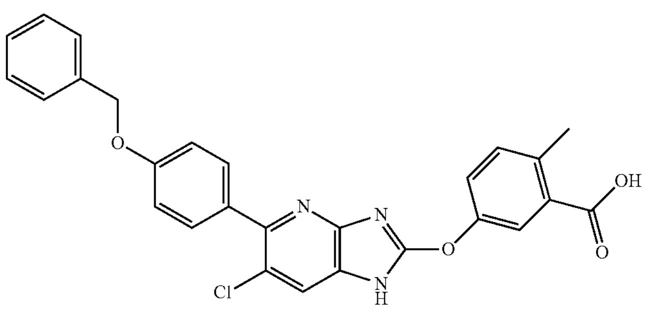 [SMILES: Cc1ccc(Oc2nc3nc(-c4ccc(OCc5ccccc5)cc4)c(Cl)cc3[nH]2)cc1C(=O)O] | 2.43 | 486.2 | A |
| B-48 | 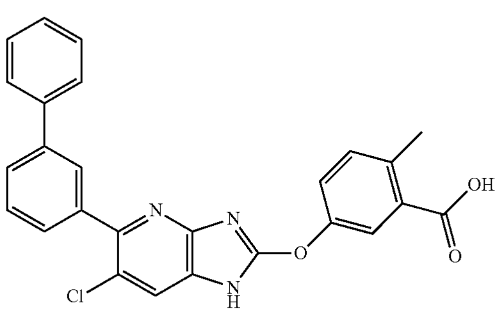 [SMILES: Cc1ccc(Oc2nc3nc(-c4cccc(-c5ccccc5)c4)c(Cl)cc3[nH]2)cc1C(=O)O] | 2.42 | 456.19 | A |
| B-49 | 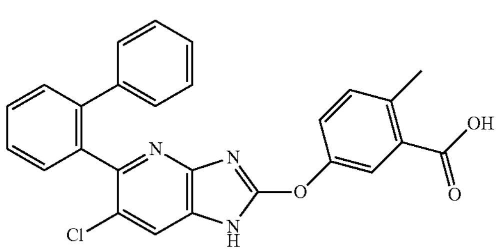 [SMILES: Cc1ccc(Oc2nc3nc(-c4ccccc4-c4ccccc4)c(Cl)cc3[nH]2)cc1C(=O)O] | 2.24 | 456.2 | A |

TABLE 8-continued
| No. | Structure | retention time | Mass (M + H) | method |
|---|---|---|---|---|
| B-50 | 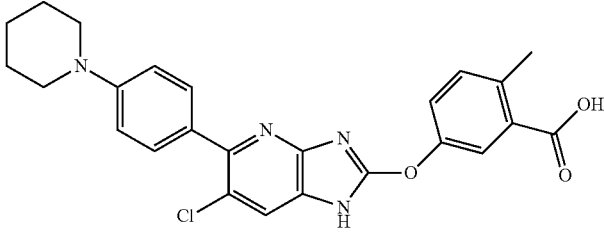 [SMILES: Cc1ccc(Oc2nc3nc(-c4ccc(N5CCCCC5)cc4)c(Cl)cc3[nH]2)cc1C(=O)O] | 1.59 | 463.25 | A |
| B-51 | 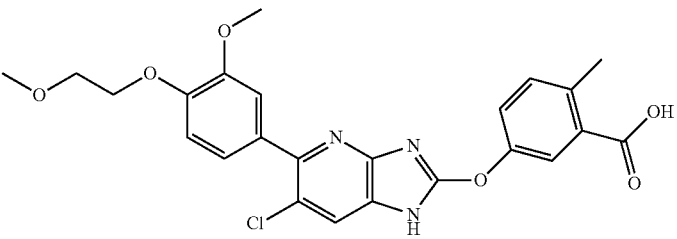 [SMILES: COCCOc1ccc(-c2nc3nc(Oc4ccc(C)c(C(=O)O)c4)[nH]c3cc2Cl)cc1OC] | 1.84 | 484.21 | A |
TABLE 9
| No. | Structure | retention time | Mass (M + H) | method |
|---|---|---|---|---|
| B-52 | 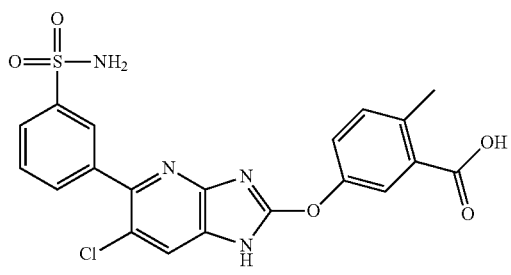 [SMILES: Cc1ccc(Oc2nc3nc(-c4cccc(S(N)(=O)=O)c4)c(Cl)cc3[nH]2)cc1C(=O)O] | 1.55 | 459.14 | A |
| B-53 | 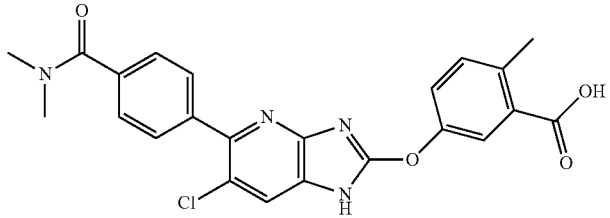 [SMILES: Cc1ccc(Oc2nc3nc(-c4ccc(C(=O)N(C)C)cc4)c(Cl)cc3[nH]2)cc1C(=O)O] | 1.61 | 451.2 | A |
| B-54 | 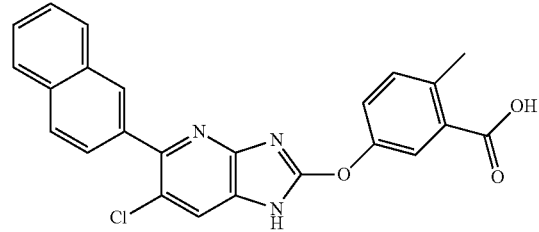 [SMILES: Cc1ccc(Oc2nc3nc(-c4ccc5ccccc5c4)c(Cl)cc3[nH]2)cc1C(=O)O] | 2.29 | 430.19 | A |

TABLE 9-continued

| No. | Structure | retention time | Mass (M + H) | method |
|---|---|---|---|---|
| B-55 | 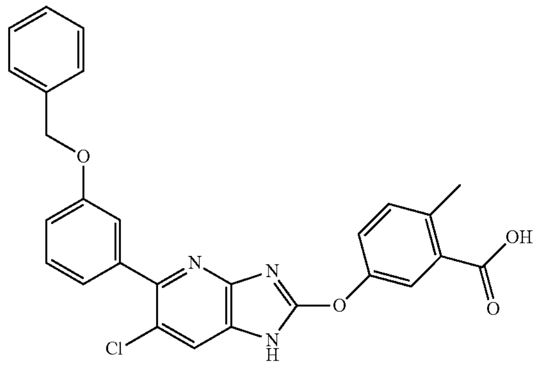 [SMILES: Cc1ccc(Oc2nc3nc(-c4cccc(OCc5ccccc5)c4)c(Cl)cc3[nH]2)cc1C(=O)O] | 2.41 | 486.2 | A |
| B-56 | 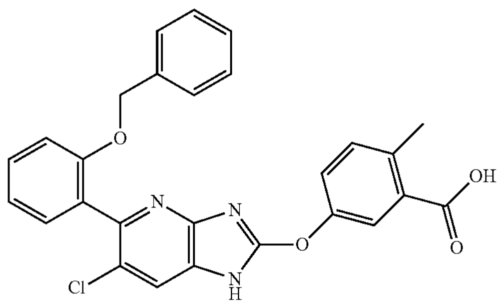 [SMILES: Cc1ccc(Oc2nc3nc(-c4ccccc4OCc4ccccc4)c(Cl)cc3[nH]2)cc1C(=O)O] | 2.26 | 486.21 | A |
| B-57 | 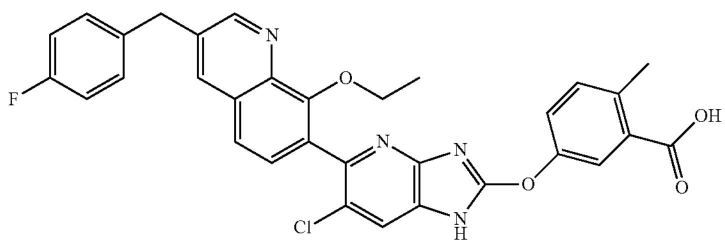 [SMILES: CCOc1c(-c2nc3nc(Oc4ccc(C)c(C(=O)O)c4)[nH]c3cc2Cl)ccc2cc(Cc3ccc(F)cc3)cnc12] | 2.17 | 583.27 | A |

TABLE 10

| No. | Structure | retention time | Mass (M + H) | method |
|---|---|---|---|---|
| B-58 | 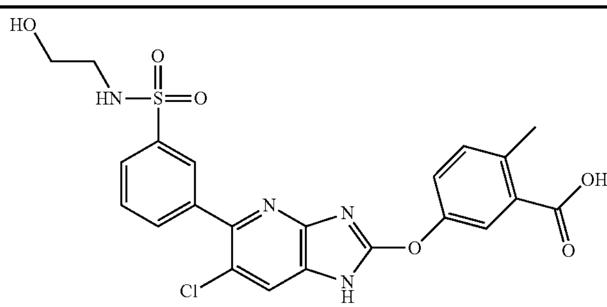 | 1.56 | 503.15 | A |
| B-59 | 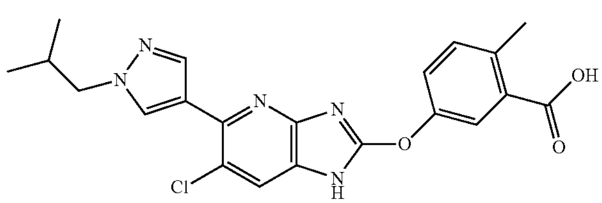 [SMILES: Cc1ccc(Oc2nc3nc(-c4cnn(CC(C)C)c4)c(Cl)cc3[nH]2)cc1C(=O)O] | 1.93 | 426.25 | A |

TABLE 10-continued

| No. | Structure | retention time | Mass (M + H) | method |
|---|---|---|---|---|
| B-60 | 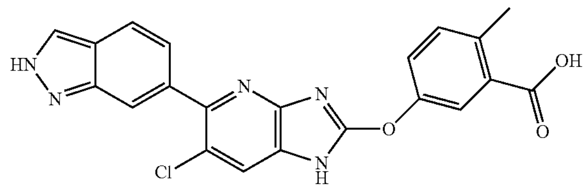 [SMILES: Cc1ccc(Oc2nc3nc(-c4ccc5c[nH]nc5c4)c(Cl)cc3[nH]2)cc1C(=O)O] | 1.61 | 420.19 | A |
| B-61 | 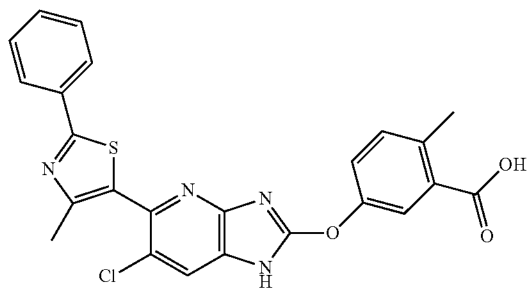 [SMILES: Cc1ccc(Oc2nc3nc(-c4sc(-c5ccccc5)nc4C)c(Cl)cc3[nH]2)cc1C(=O)O] | 2.26 | 477.19 | A |
| B-62 | 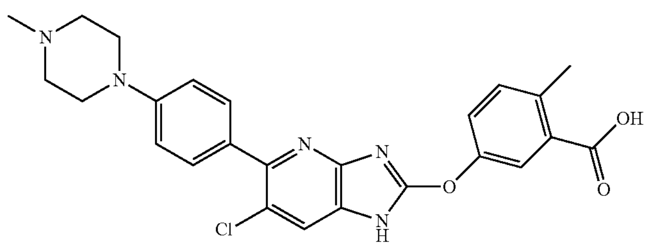 [SMILES: Cc1ccc(Oc2nc3nc(-c4ccc(N5CCN(C)CC5)cc4)c(Cl)cc3[nH]2)cc1C(=O)O] | 1.31 | 478.26 | A |
| B-63 | 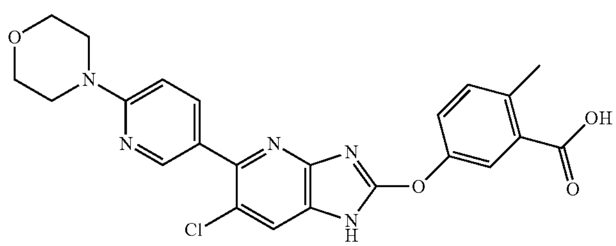 [SMILES: Cc1ccc(Oc2nc3nc(-c4ccc(N5CCOCC5)nc4)c(Cl)cc3[nH]2)cc1C(=O)O] | 1.35 | 466.21 | A |

TABLE 11

| No. | Structure | NMR (δ) | retention time | Mass (M + H) | method |
|---|---|---|---|---|---|
| B-64 | 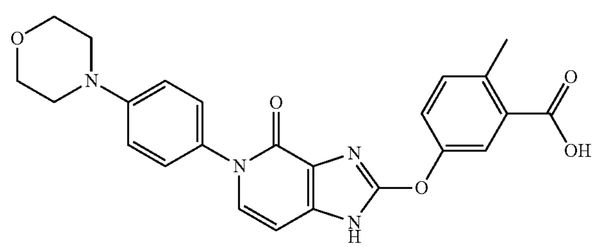 [SMILES: Cc1ccc(Oc2nc3c(=O)n(-c4ccc(N5CCOCC5)cc4)ccc3[nH]2)cc1C(=O)O] | (DMSO-d$_6$) δ: 2.54 (s, 3H), 3.17 (t, J = 4.8 Hz, 4H), 3.76 (t, J = 4.8 Hz, 4H), 6.52 (d, J = 7.2 Hz, 1H), 7.04 (d, J = 8.4 Hz, 2H), 7.24 (d, J = 8.4 Hz, 2H), 7.32 (d, J = 7.2 Hz, 1H), 7.39 (d, J = 8.4 Hz, 1H), 7.45 (dd, J = 8.4, 2.4 Hz, 1H), 7.72 (d, J = 2.4 Hz, 1H), 13.08 (brs, 1H), 13.31 (brs, 1H). | | | |

TABLE 11-continued

| No. | Structure | NMR (δ) | retention time | Mass (M + H) | method |
|---|---|---|---|---|---|
| B-65 | 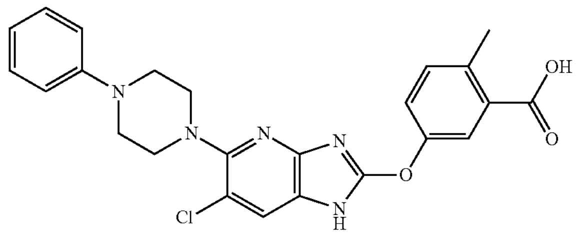 [SMILES: Cc1ccc(Oc2nc3nc(N4CCN(c5ccccc5)CC4)c(Cl)cc3[nH]2)cc1C(=O)O] | | 2.17 | 464.19 | A |
| B-66 | 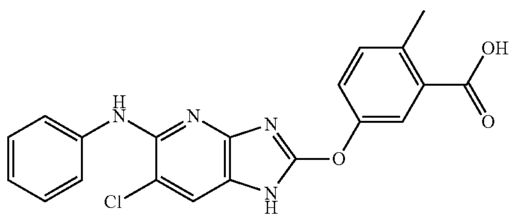 [SMILES: Cc1ccc(Oc2nc3nc(Nc4ccccc4)c(Cl)cc3[nH]2)cc1C(=O)O] | | 2.06 | 395.15 | A |
| B-67 | 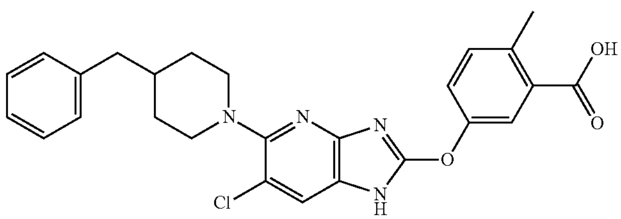 [SMILES: Cc1ccc(Oc2nc3nc(N4CCC(Cc5ccccc5)CC4)c(Cl)cc3[nH]2)cc1C(=O)O] | | 2.67 | 477.2 | A |
| B-68 | 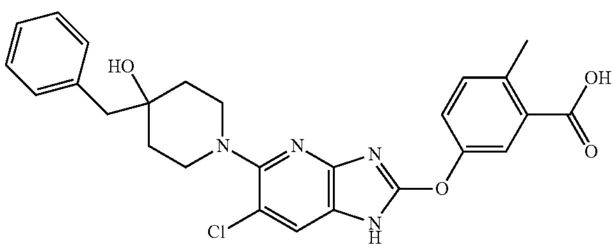 [SMILES: Cc1ccc(Oc2nc3nc(N4CCC(O)(Cc5ccccc5)CC4)c(Cl)cc3[nH]2)cc1C(=O)O] | | 2.09 | 493.21 | A |
| B-69 | 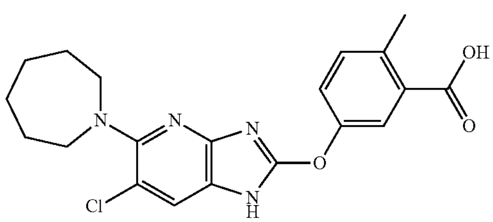 [SMILES: Cc1ccc(Oc2nc3nc(N4CCCCCC4)c(Cl)cc3[nH]2)cc1C(=O)O] | | 2.33 | 401.2 | A |

TABLE 12

| No. | Structure | retention time | Mass (M + H) | method |
|---|---|---|---|---|
| B-70 | 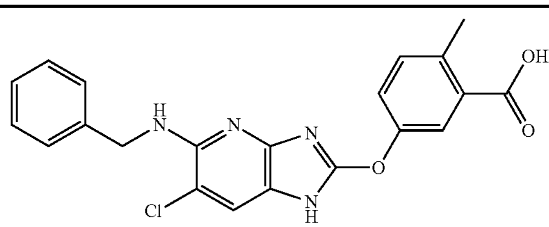 | 2.07 | 409.16 | A |

TABLE 12-continued
| No. | Structure | retention time | Mass (M + H) | method |
|---|---|---|---|---|
| B-71 | 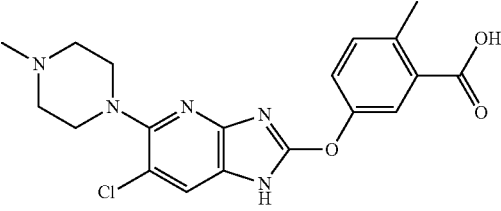 [SMILES: Cc1ccc(Oc2nc3nc(N4CCN(C)CC4)c(Cl)cc3[nH]2)cc1C(=O)O] | 1.03 | 402.21 | A |
| B-72 | 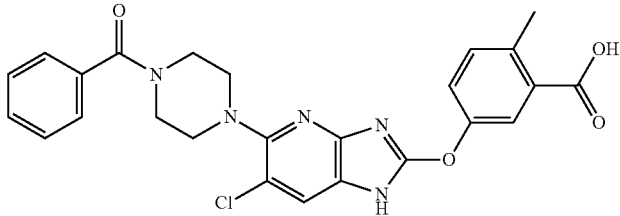 [SMILES: Cc1ccc(Oc2nc3nc(N4CCN(C(=O)c5ccccc5)CC4)c(Cl)cc3[nH]2)cc1C(=O)O] | 1.88 | 492.16 | A |
| B-73 | 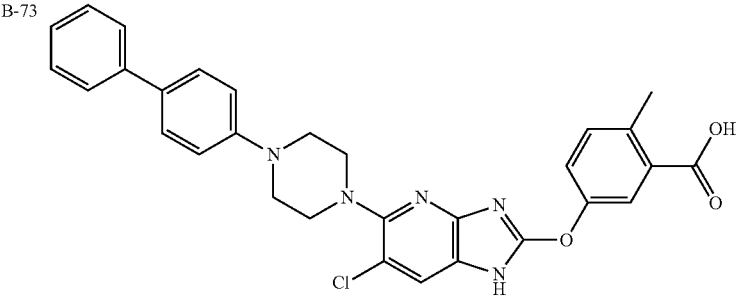 | 2.71 | 540.23 | A |
| B-74 | 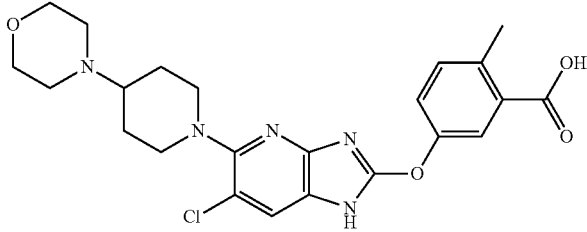 [SMILES: Cc1ccc(Oc2nc3nc(N4CCC(N5CCOCC5)CC4)c(Cl)cc3[nH]2)cc1C(=O)O] | 1.11 | 472.22 | A |
| B-75 | 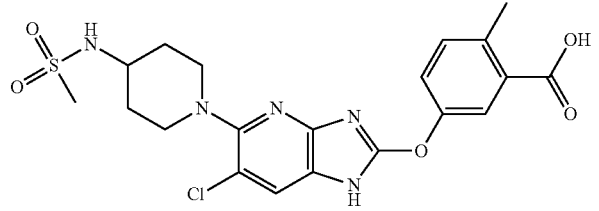 [SMILES: Cc1ccc(Oc2nc3nc(N4CCC(NS(C)(=O)=O)CC4)c(Cl)cc3[nH]2)cc1C(=O)O] | 1.55 | 480.14 | A |

TABLE 13

| No. | Structure | NMR(δ) | retention time | Mass (M + H) | method |
|---|---|---|---|---|---|
| B-76 | 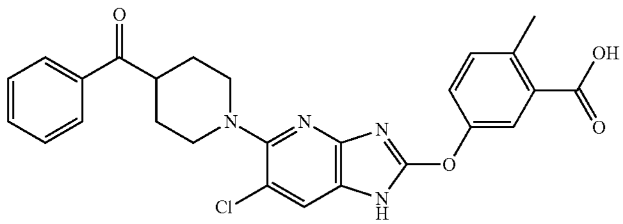 [SMILES: Cc1ccc(Oc2nc3nc(N4CCC(C(=O)c5ccccc5)CC4)c(Cl)cc3[nH]2)cc1C(=O)O] | | 2.26 | 491.19 | A |
| B-77 | 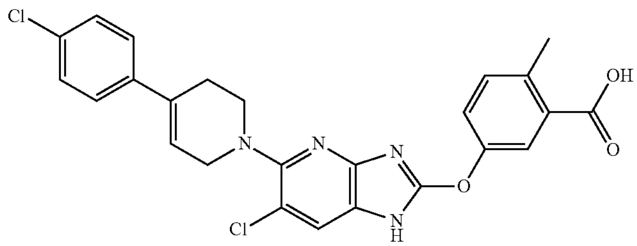 [SMILES: Cc1ccc(Oc2nc3nc(N4CC=C(c5ccc(Cl)cc5)CC4)c(Cl)cc3[nH]2)cc1C(=O)O] | | 2.69 | 495.13 | A |
| B-78 | 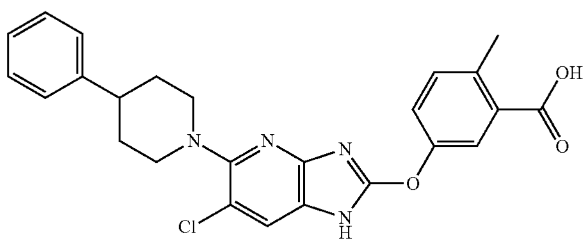 [SMILES: Cc1ccc(Oc2nc3nc(N4CCC(c5ccccc5)CC4)c(Cl)cc3[nH]2)cc1C(=O)O] | | 2.54 | 463.19 | A |
| B-79 | 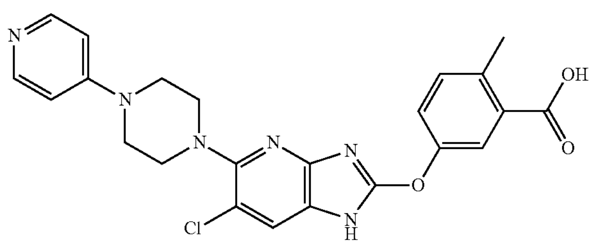 [SMILES: Cc1ccc(Oc2nc3nc(N4CCN(c5ccncc5)CC4)c(Cl)cc3[nH]2)cc1C(=O)O] | | 1.27 | 465.18 | A |
| B-80 | 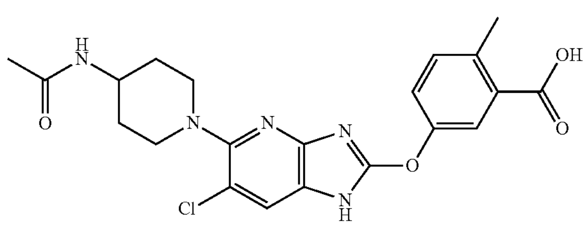 [SMILES: CC(=O)NC1CCN(c2nc3nc(Oc4ccc(C)c(C(=O)O)c4)[nH]c3cc2Cl)CC1] | | 1.42 | 444.18 | A |
| B-81 | 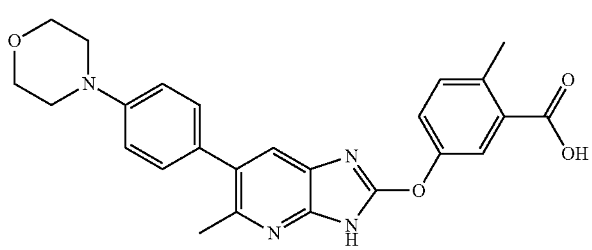 [SMILES: Cc1ccc(Oc2nc3cc(-c4ccc(N5CCOCC5)cc4)c(C)nc3[nH]2)cc1C(=O)O] | (DMSO-d$_6$) δ: 2.43 (s, 3H), 2.55 (s, 3H), 3.16 (t, J = 4.8 Hz, 4H), 3.76 (t, J = 4.8 Hz, 4H), 7.01 (d, J = 8.4 Hz, 2H), 7.25 (d, J = 8.4 Hz, 2H), 7.41 (d, J = 8.4 Hz, 1H), 7.49-7.51 (m, 2H), 7.81 (d, J = 2.4 Hz, 1H), 13.04 (brs, 2H). | | | |

TABLE 14

| No. | Structure | retention time | Mass (M + H) | method |
|---|---|---|---|---|
| B-82 | 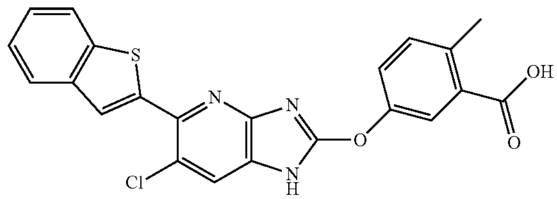 [SMILES: Cc1ccc(Oc2nc3nc(-c4cc5ccccc5s4)c(Cl)cc3[nH]2)cc1C(=O)O] | 2.42 | 436.16 | A |
| B-83 | 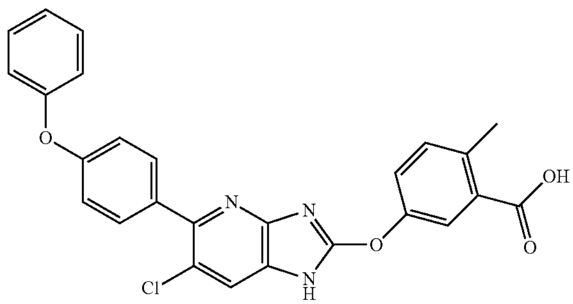 [SMILES: Cc1ccc(Oc2nc3nc(-c4ccc(Oc5ccccc5)cc4)c(Cl)cc3[nH]2)cc1C(=O)O] | 2.45 | 472.22 | A |
| B-84 | 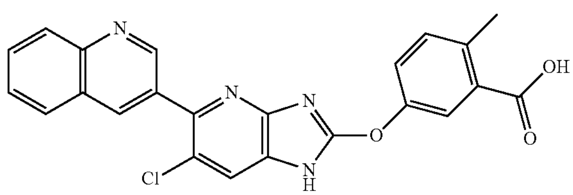 [SMILES: Cc1ccc(Oc2nc3nc(-c4cnc5ccccc5c4)c(Cl)cc3[nH]2)cc1C(=O)O] | 1.68 | 431.2 | A |
| B-85 | 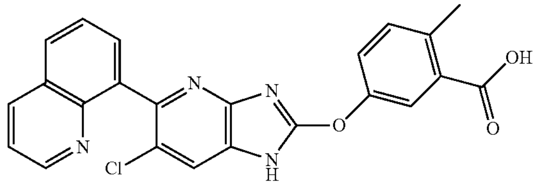 [SMILES: Cc1ccc(Oc2nc3nc(-c4cccc5cccnc45)c(Cl)cc3[nH]2)cc1C(=O)O] | 1.51 | 431.2 | A |
| B-86 | 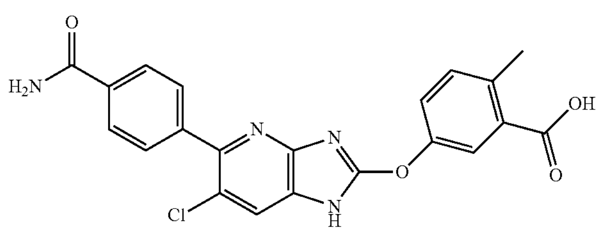 [SMILES: Cc1ccc(Oc2nc3nc(-c4ccc(C(N)=O)cc4)c(Cl)cc3[nH]2)cc1C(=O)O] | 1.42 | 423.19 | A |
| B-87 | 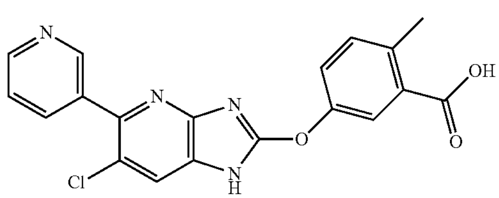 [SMILES: Cc1ccc(Oc2nc3nc(-c4cccnc4)c(Cl)cc3[nH]2)cc1C(=O)O] | 1.18 | 381.18 | A |

TABLE 15

| No. | Structure | retention time | Mass (M + H) | method |
|---|---|---|---|---|
| B-88 | 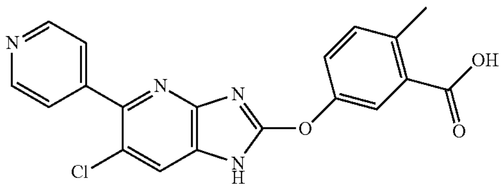 [SMILES: Cc1ccc(Oc2nc3nc(-c4ccncc4)c(Cl)cc3[nH]2)cc1C(=O)O] | 1.11 | 382.19 | A |
| B-89 | 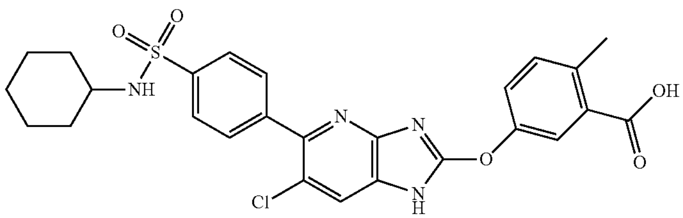 [SMILES: Cc1ccc(Oc2nc3nc(-c4ccc(S(=O)(=O)NC5CCCCC5)cc4)c(Cl)cc3[nH]2)cc1C(=O)O] | 2.22 | 541.23 | A |
| B-90 | 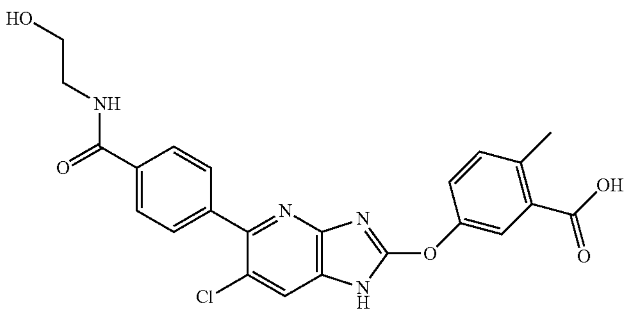 [SMILES: Cc1ccc(Oc2nc3nc(-c4ccc(C(=O)NCCO)cc4)c(Cl)cc3[nH]2)cc1C(=O)O] | 1.39 | 467.18 | A |
| B-91 | 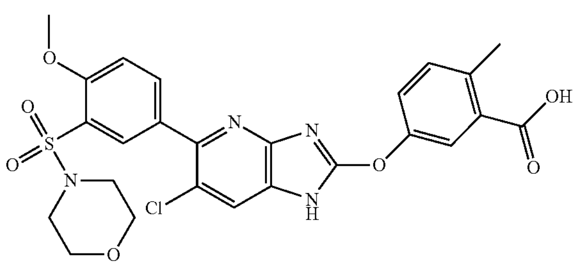 [SMILES: COc1ccc(-c2nc3nc(Oc4ccc(C)c(C(=O)O)c4)[nH]c3cc2Cl)cc1S(=O)(=O)N1CCOCC1] | 1.78 | 559.19 | A |
| B-92 | 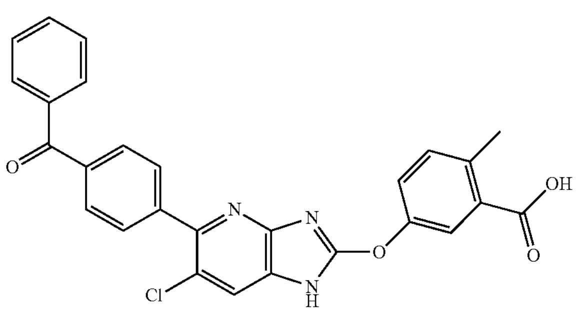 [SMILES: Cc1ccc(Oc2nc3nc(-c4ccc(C(=O)c5ccccc5)cc4)c(Cl)cc3[nH]2)cc1C(=O)O] | 2.27 | 484.17 | A |
| B-93 | 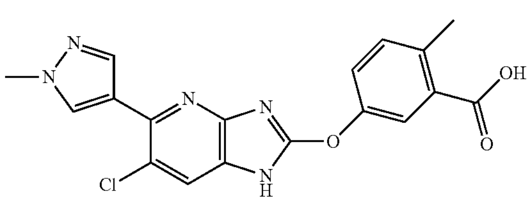 [SMILES: Cc1ccc(Oc2nc3nc(-c4cnn(C)c4)c(Cl)cc3[nH]2)cc1C(=O)O] | 1.49 | 384.17 | A |

TABLE 16
| No. | Structure | retention time | Mass (M + H) | method |
|---|---|---|---|---|
| B-94 | 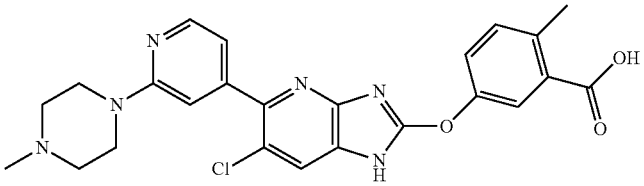 [SMILES: Cc1ccc(Oc2nc3nc(-c4ccnc(N5CCN(C)CC5)c4)c(Cl)cc3[nH]2)cc1C(=O)O] | 1.19 | 479.24 | A |
| B-95 | 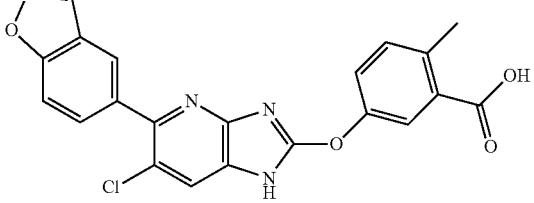 | 1.67 | 421.18 | A |
| B-96 | 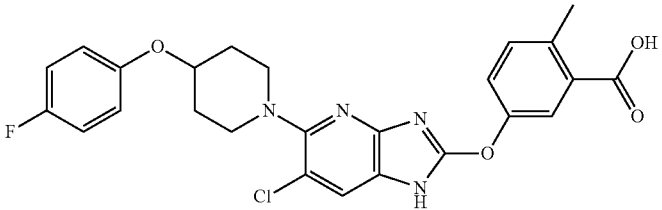 [SMILES: Cc1ccc(Oc2nc3nc(N4CCC(Oc5ccc(F)cc5)CC4)c(Cl)cc3[nH]2)cc1C(=O)O] | 2.45 | 497.17 | A |
| B-97 | 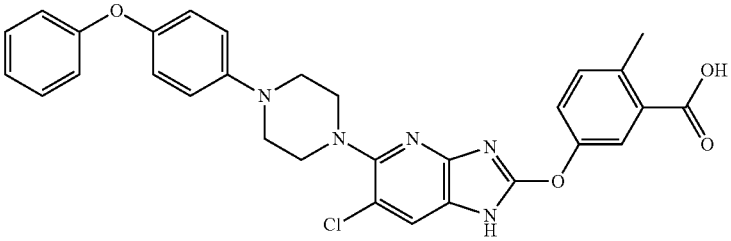 [SMILES: Cc1ccc(Oc2nc3nc(N4CCN(c5ccc(Oc6ccccc6)cc5)CC4)c(Cl)cc3[nH]2)cc1C(=O)O] | 2.59 | 556.22 | A |
| B-98 | 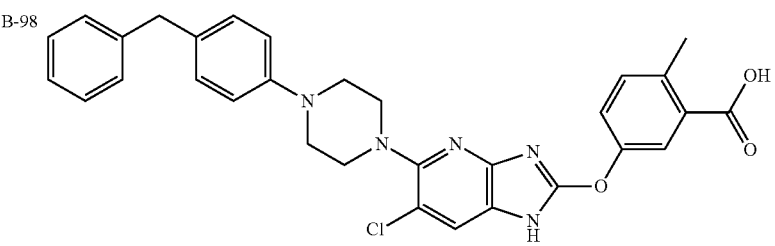 | 2.64 | 554.22 | A |
| B-99 | 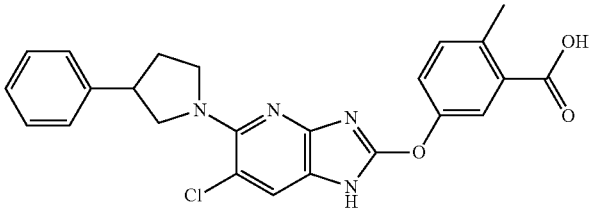 [SMILES: Cc1ccc(Oc2nc3nc(N4CCC(c5ccccc5)C4)c(Cl)cc3[nH]2)cc1C(=O)O] | 2.45 | 449.18 | A |

TABLE 17

| No. | Structure | retention time | Mass (M + H) | method |
|---|---|---|---|---|
| B-100 | 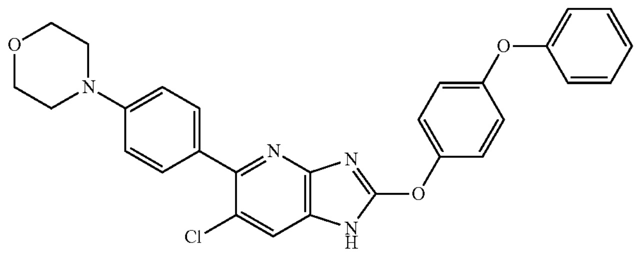 [SMILES: Clc1cc2[nH]c(Oc3ccc(Oc4ccccc4)cc3)nc2nc1-c1ccc(N2CCOCC2)cc1] | 2.49 | 499.18 | A |
| B-101 | 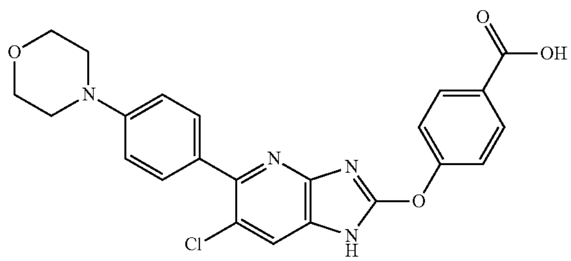 [SMILES: O=C(O)c1ccc(Oc2nc3nc(-c4ccc(N5CCOCC5)cc4)c(Cl)cc3[nH]2)cc1] | 1.7 | 451.17 | A |
| B-102 | 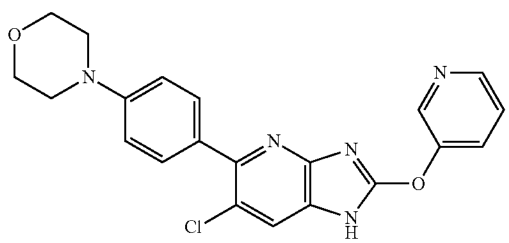 [SMILES: Clc1cc2[nH]c(Oc3cccnc3)nc2nc1-c1ccc(N2CCOCC2)cc1] | 1.52 | 408.18 | A |
| B-103 | 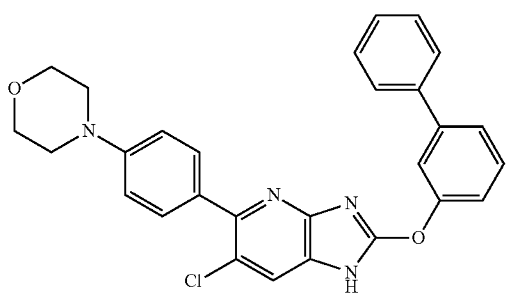 [SMILES: Clc1cc2[nH]c(Oc3cccc(-c4ccccc4)c3)nc2nc1-c1ccc(N2CCOCC2)cc1] | 2.5 | 483.2 | A |
| B-104 | 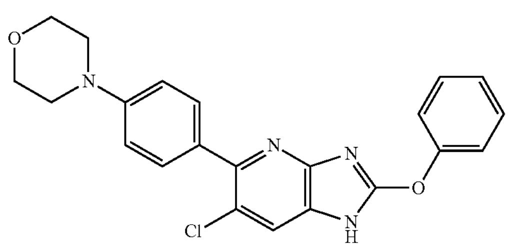 [SMILES: Clc1cc2[nH]c(Oc3ccccn3)nc2nc1-c1ccc(N2CCOCC2)cc1] | 1.99 | 407.21 | A |
| B-105 | 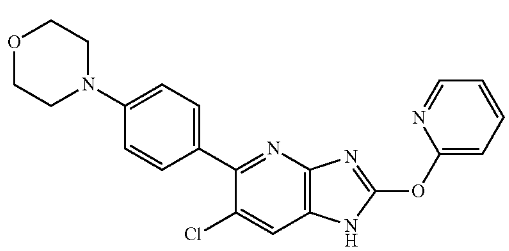 | 1.82 | 408.18 | A |

TABLE 18

| No. | Structure | NMR(δ) | retention time | Mass (M + H) | method |
|---|---|---|---|---|---|
| B-106 | 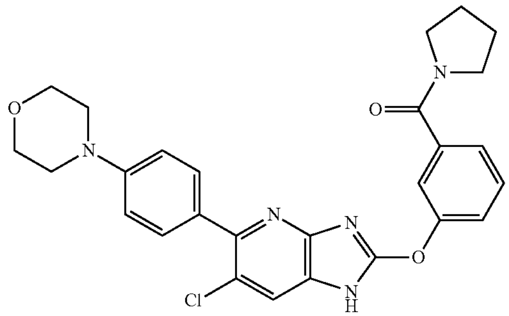 [SMILES: O=C(c1cccc(Oc2nc3nc(-c4ccc(N5CCOCC5)cc4)c(Cl)cc3[nH]2)c1)N1CCCC1] | | 1.8 | 504.26 | A |
| B-107 | 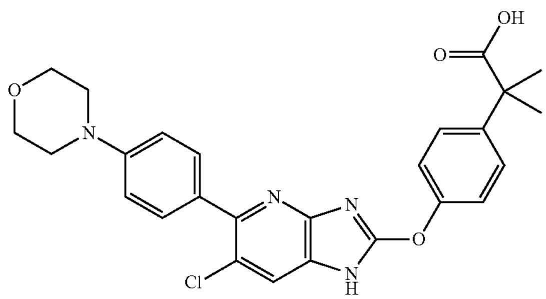 [SMILES: CC(C)(C(=O)O)c1ccc(Oc2nc3nc(-c4ccc(N5CCOCC5)cc4)c(Cl)cc3[nH]2)cc1] | (DMSO-d6) δ: 1.51 (s, 6H), 3.19 (t, J = 4.0 Hz, 4H), 3.76 (t, J = 4.0 Hz, 4H), 7.02(d, J = 8.6 Hz, 2H), 7.35 (d, J = 8.6 Hz, 2H), 7.44 (d, J = 8.6 Hz, 2H), 7.56 (d, J = 8.6 Hz, 2H), 7.86 (s, 1H), | 1.95 | 493.21 | A |
| B-108 | 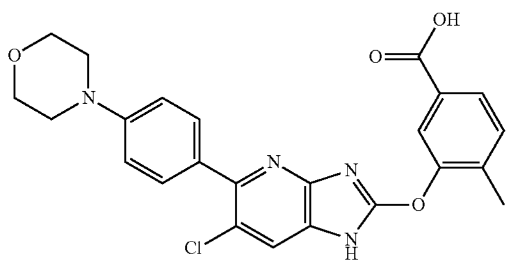 [SMILES: Cc1ccc(C(=O)O)cc1Oc1nc2nc(-c3ccc(N4CCOCC4)cc3)c(Cl)cc2[nH]1] | | 1.79 | 465.2 | A |
| B-109 | 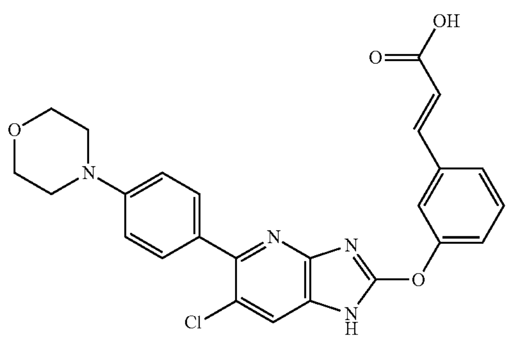 [SMILES: O=C(O)/C=C/c1cccc(Oc2nc3nc(-c4ccc(N5CCOCC5)cc4)c(Cl)cc3[nH]2)c1] | | 1.81 | 477.19 | A |
| B-110 | 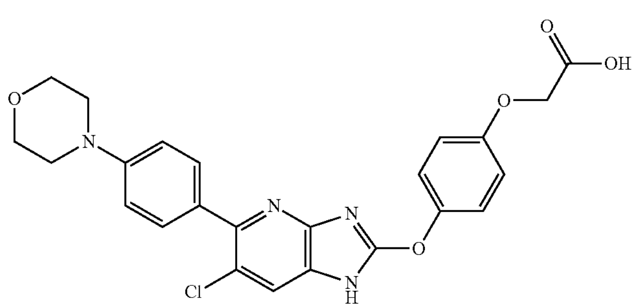 [SMILES: O=C(O)COc1ccc(Oc2nc3nc(-c4ccc(N5CCOCC5)cc4)c(Cl)cc3[nH]2)cc1] | | 1.66 | 481.18 | A |

TABLE 18-continued
| No. | Structure | NMR(δ) | retention time | Mass (M + H) | method |
|---|---|---|---|---|---|
| B-111 | 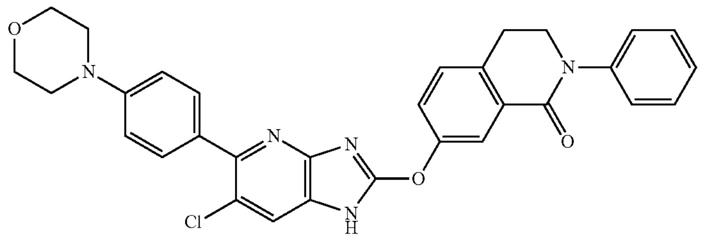 [SMILES: O=C1c2cc(Oc3nc4nc(-c5ccc(N6CCOCC6)cc5)c(Cl)cc4[nH]3)ccc2CCN1c1ccccc1] | | 2.16 | 552.25 | A |
TABLE 19
| No. | Structure | retention time | Mass (M + H) | method |
|---|---|---|---|---|
| B-112 | 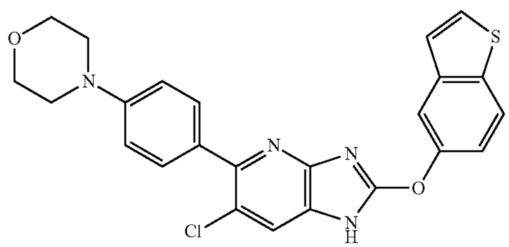 [SMILES: Clc1cc2[nH]c(Oc3ccc4sccc4c3)nc2nc1-c1ccc(N2CCOCC2)cc1] | 2.24 | 463.15 | A |
| B-113 | 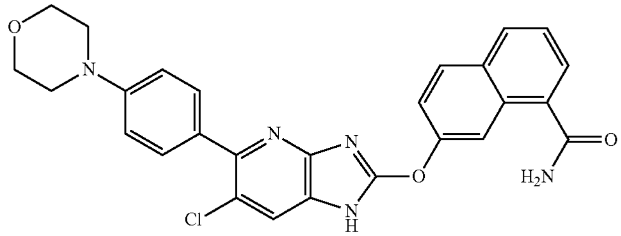 [SMILES: NC(=O)c1cccc2ccc(Oc3nc4nc(-c5ccc(N6CCOCC6)cc5)c(Cl)cc4[nH]3)cc12] | 1.73 | 500.19 | A |
| B-114 | 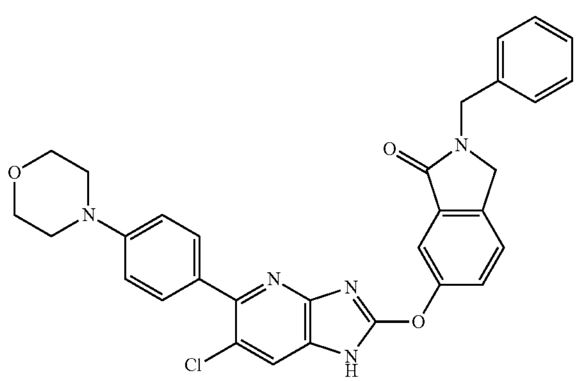 [SMILES: O=C1c2cc(Oc3nc4nc(-c5ccc(N6CCOCC6)cc5)c(Cl)cc4[nH]3)ccc2CN1Cc1ccccc1] | 2.11 | 552.24 | A |
| B-115 | 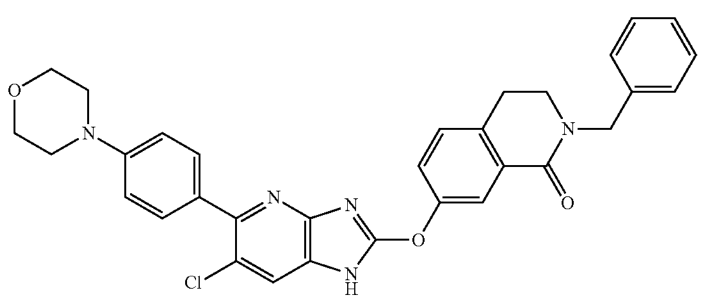 [SMILES: O=C1c2cc(Oc3nc4nc(-c5ccc(N6CCOCC6)cc5)c(Cl)cc4[nH]3)ccc2CCN1Cc1ccccc1] | 2.26 | 566.26 | A |

TABLE 19-continued

| No. | Structure | retention time | Mass (M + H) | method |
|---|---|---|---|---|
| B-116 | 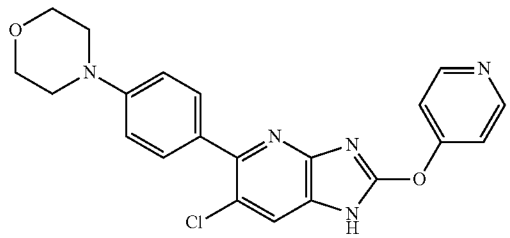 [SMILES: Clc1cc2[nH]c(Oc3ccncc3)nc2nc1-c1ccc(N2CCOCC2)cc1] | 1.44 | 408.2 | A |
| B-117 | 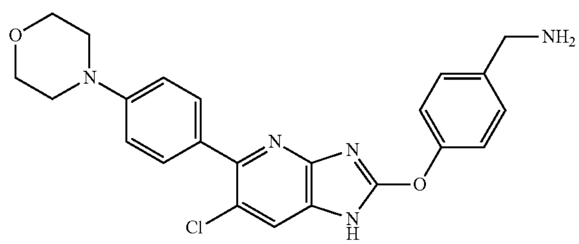 [SMILES: NCc1ccc(Oc2nc3nc(-c4ccc(N5CCOCC5)cc4)c(Cl)cc3[nH]2)cc1] | 1.19 | 436.22 | A |

TABLE 20

| No. | Structure | retention time | Mass (M + H) | method |
|---|---|---|---|---|
| B-118 | 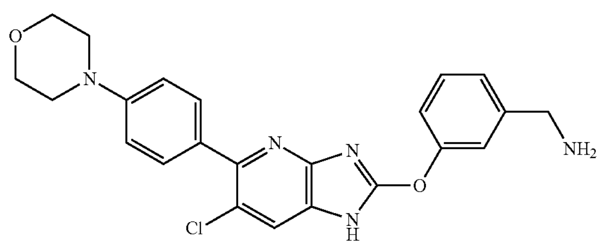 [SMILES: NCc1cccc(Oc2nc3nc(-c4ccc(N5CCOCC5)cc4)c(Cl)cc3[nH]2)c1] | 1.21 | 436.22 | A |
| B-119 | 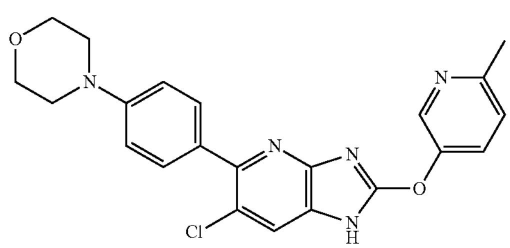 [SMILES: Cc1ccc(Oc2nc3nc(-c4ccc(N5CCOCC5)cc4)c(Cl)cc3[nH]2)cn1] | 1.48 | 422.22 | A |
| B-120 | 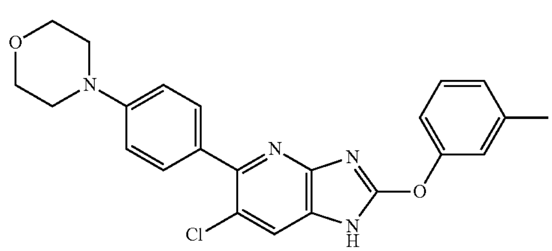 [SMILES: Cc1cccc(Oc2nc3nc(-c4ccc(N5CCOCC5)cc4)c(Cl)cc3[nH]2)c1] | 2.15 | 421.21 | A |

TABLE 20-continued

| No. | Structure | retention time | Mass (M + H) | method |
|---|---|---|---|---|
| B-121 | 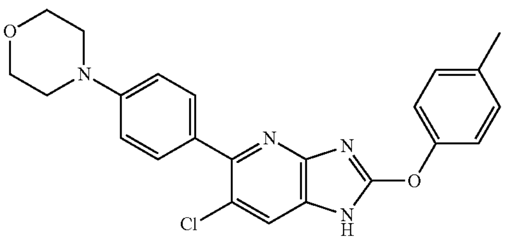 [SMILES: Cc1ccc(Oc2nc3nc(-c4ccc(N5CCOCC5)cc4)c(Cl)cc3[nH]2)cc1] | 2.16 | 421.22 | A |
| B-122 | 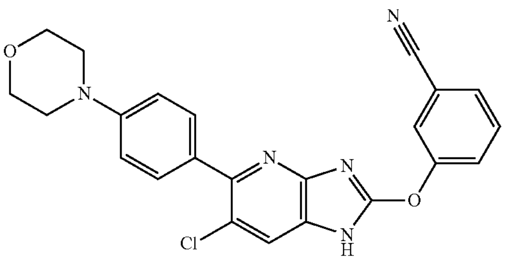 [SMILES: N#Cc1cccc(Oc2nc3nc(-c4ccc(N5CCOCC5)cc4)c(Cl)cc3[nH]2)c1] | 1.95 | 432.19 | A |
| B-123 | 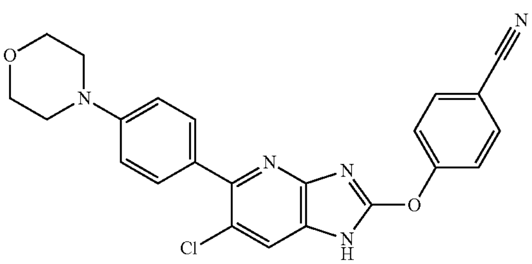 [SMILES: N#Cc1ccc(Oc2nc3nc(-c4ccc(N5CCOCC5)cc4)c(Cl)cc3[nH]2)cc1] | 1.95 | 432.19 | A |

TABLE 21

| No. | Structure | retention time | Mass (M + H) | method |
|---|---|---|---|---|
| B-124 | 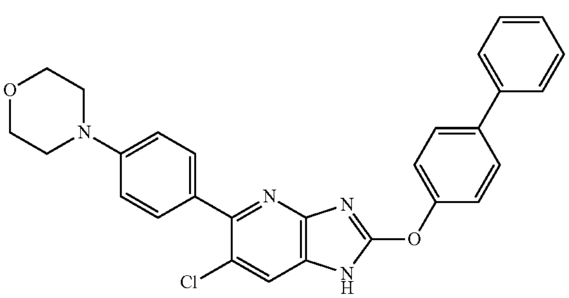 [SMILES: Clc1cc2[nH]c(Oc3ccc(-c4ccccc4)cc3)nc2nc1-c1ccc(N2CCOCC2)cc1] | 2.5 | 483.21 | A |
| B-125 | 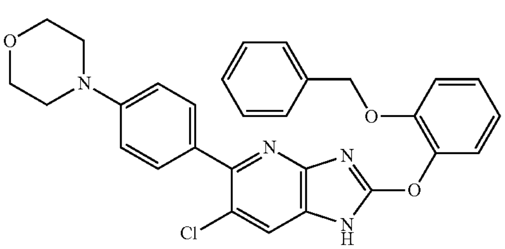 [SMILES: Clc1cc2[nH]c(Oc3ccccc3OCc3ccccc3)nc2nc1-c1ccc(N2CCOCC2)cc1] | 2.31 | 513.24 | A |

TABLE 21-continued

| No. | Structure | retention time | Mass (M + H) | method |
|---|---|---|---|---|
| B-126 | 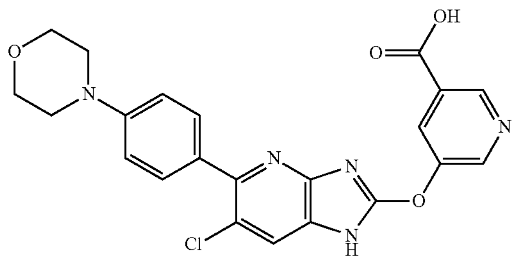 [SMILES: O=C(O)c1cncc(Oc2nc3nc(-c4ccc(N5CCOCC5)cc4)c(Cl)cc3[nH]2)c1] | 1.49 | 452.17 | A |
| B-127 | 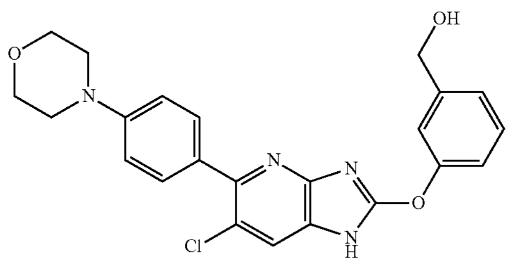 [SMILES: OCc1cccc(Oc2nc3nc(-c4ccc(N5CCOCC5)cc4)c(Cl)cc3[nH]2)c1] | 1.65 | 437.18 | A |
| B-128 | 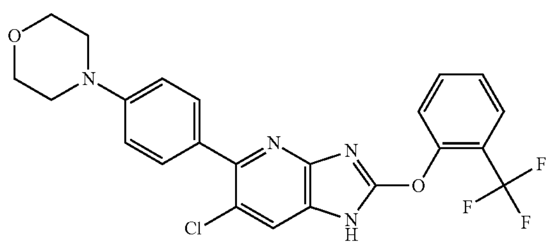 [SMILES: FC(F)(F)c1ccccc1Oc1nc2nc(-c3ccc(N4CCOCC4)cc3)c(Cl)cc2[nH]1] | 2.22 | 475.15 | A |
| B-129 | 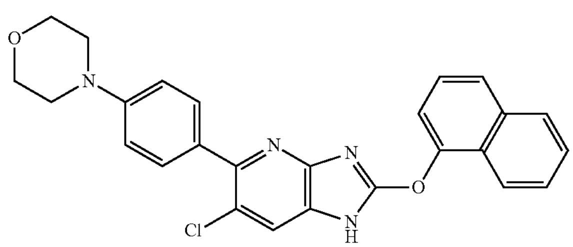 [SMILES: Clc1cc2[nH]c(Oc3cccc4ccccc34)nc2nc1-c1ccc(N2CCOCC2)cc1] | 2.28 | 457.17 | A |

TABLE 22

| No. | Structure | retention time | Mass (M + H) | method |
|---|---|---|---|---|
| B-130 | 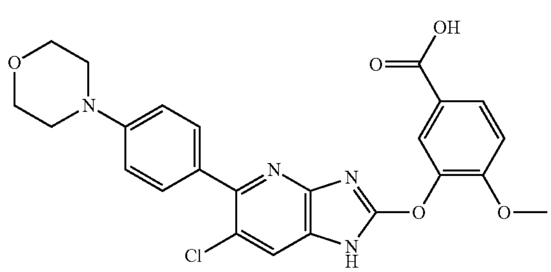 [SMILES: COc1ccc(C(=O)O)cc1Oc1nc2nc(-c3ccc(N4CCOCC4)cc3)c(Cl)cc2[nH]1] | 1.67 | 481.15 | A |

TABLE 22-continued

| No. | Structure | retention time | Mass (M + H) | method |
|---|---|---|---|---|
| B-131 | 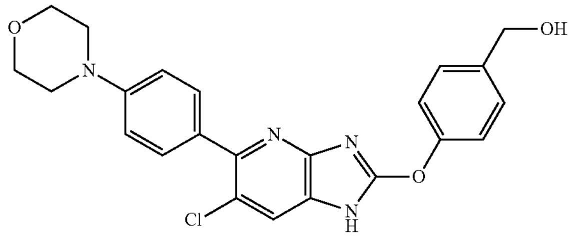 [SMILES: OCc1ccc(Oc2nc3nc(-c4ccc(N5CCOCC5)cc4)c(Cl)cc3[nH]2)cc1] | 1.61 | 437.2 | A |
| B-132 | 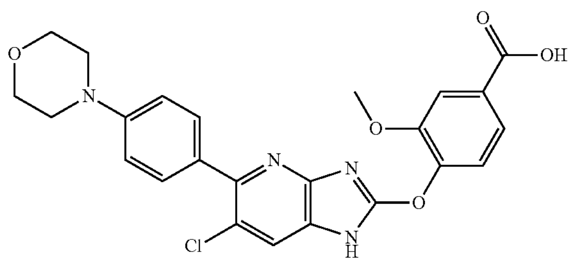 [SMILES: COc1cc(C(=O)O)ccc1Oc1nc2nc(-c3ccc(N4CCOCC4)cc3)c(Cl)cc2[nH]1] | 1.7 | 481.15 | A |
| B-133 | 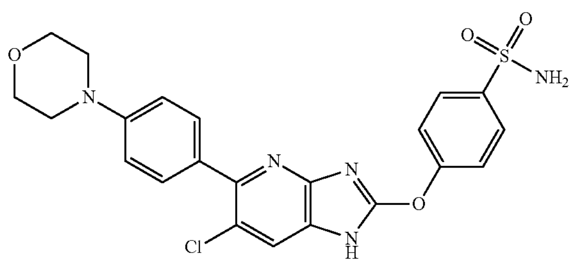 [SMILES: NS(=O)(=O)c1ccc(Oc2nc3nc(-c4ccc(N5CCOCC5)cc4)c(Cl)cc3[nH]2)cc1] | 1.62 | 486.12 | A |
| B-134 | 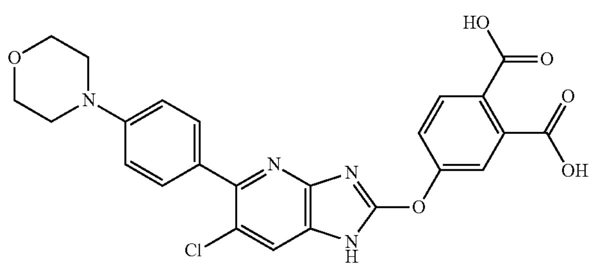 [SMILES: O=C(O)c1ccc(Oc2nc3nc(-c4ccc(N5CCOCC5)cc4)c(Cl)cc3[nH]2)cc1C(=O)O] | 1.54 | 495.13 | A |
| B-135 | 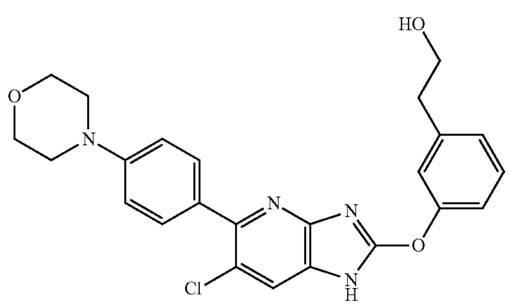 [SMILES: OCCc1cccc(Oc2nc3nc(-c4ccc(N5CCOCC5)cc4)c(Cl)cc3[nH]2)c1] | 1.71 | 451.2 | A |

TABLE 23

| No. | Structure | retention time | Mass (M + H) | method |
|---|---|---|---|---|
| B-136 | 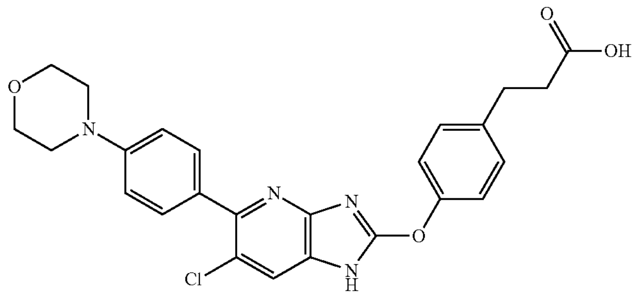 [SMILES: O=C(O)CCc1ccc(Oc2nc3nc(-c4ccc(N5CCOCC5)cc4)c(Cl)cc3[nH]2)cc1] | 1.78 | 479.17 | A |
| B-137 | 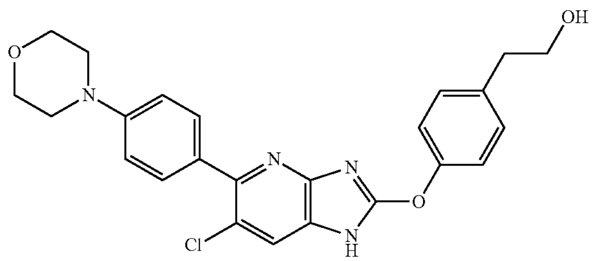 [SMILES: OCCc1ccc(Oc2nc3nc(-c4ccc(N5CCOCC5)cc4)c(Cl)cc3[nH]2)cc1] | 1.69 | 451.2 | A |
| B-138 | 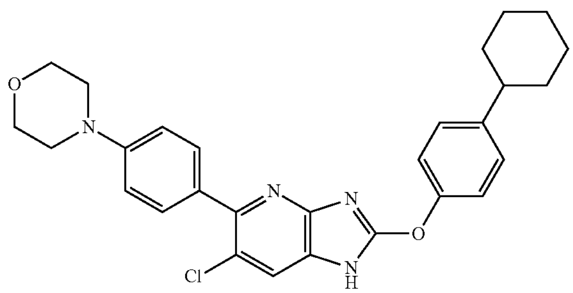 [SMILES: Clc1cc2[nH]c(Oc3ccc(C4CCCCC4)cc3)nc2nc1-c1ccc(N2CCOCC2)cc1] | 2.89 | 489.25 | A |
| B-139 | 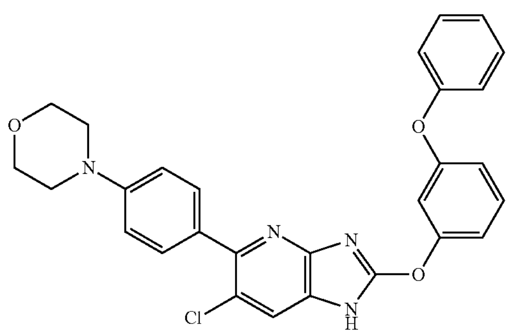 [SMILES: Clc1cc2[nH]c(Oc3cccc(Oc4ccccc4)c3)nc2nc1-c1ccc(N2CCOCC2)cc1] | 2.51 | 461.21 | A |
| B-140 | 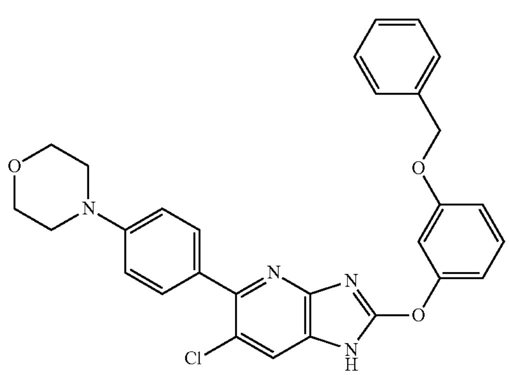 [SMILES: Clc1cc2[nH]c(Oc3cccc(OCc4ccccc4)c3)nc2nc1-c1ccc(N2CCOCC2)cc1] | 2.51 | 513.21 | A |

TABLE 23-continued
| No. | Structure | retention time | Mass (M + H) | method |
|---|---|---|---|---|
| B-141 | 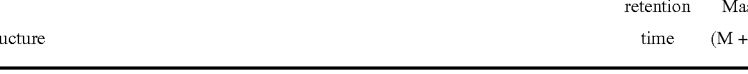 | 1.69 | 476.18 | A |
TABLE 24
| No. | Structure | retention time | Mass (M + H) | method |
|---|---|---|---|---|
| B-142 | 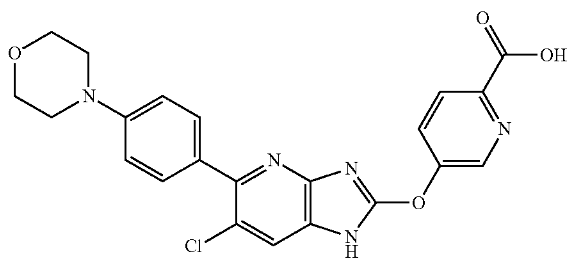 [SMILES: O=C(O)c1ccc(Oc2nc3nc(-c4ccc(N5CCOCC5)cc4)c(Cl)cc3[nH]2)cn1] | 1.5 | 452.15 | A |
| B-143 | 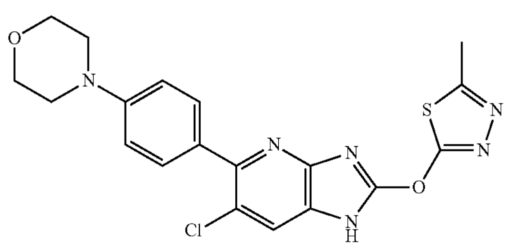 [SMILES: Cc1nnc(Oc2nc3nc(-c4ccc(N5CCOCC5)cc4)c(Cl)cc3[nH]2)s1] | 1.63 | 429.13 | A |
| B-144 | 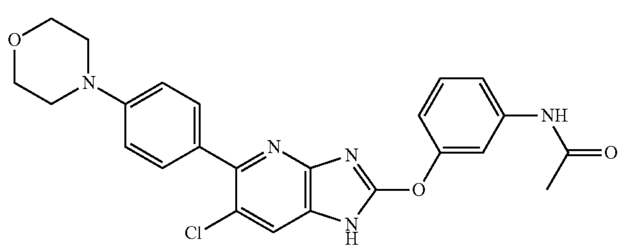 [SMILES: CC(=O)Nc1cccc(Oc2nc3nc(-c4ccc(N5CCOCC5)cc4)c(Cl)cc3[nH]2)c1] | 1.67 | 464.18 | A |
| B-145 | 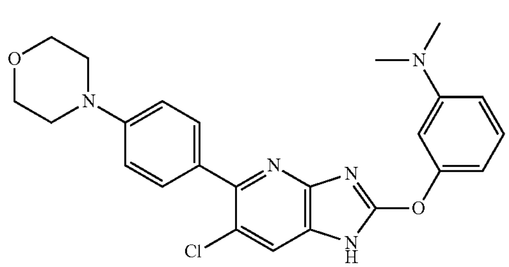 [SMILES: CN(C)c1cccc(Oc2nc3nc(-c4ccc(N5CCOCC5)cc4)c(Cl)cc3[nH]2)c1] | 2.04 | 450.22 | A |

TABLE 24-continued

| No. | Structure | retention time | Mass (M + H) | method |
|---|---|---|---|---|
| B-146 | (morpholine-phenyl-imidazopyridine-Cl, O-phenyl-ethynyl) | 2.15 | 431.18 | A |
| B-147 | (morpholine-phenyl-imidazopyridine-Cl, O-phenyl-O-isopropyl) | 2.3 | 465.21 | A |

TABLE 25

| No. | Structure | NMR(δ) | retention time | Mass (M + H) | method |
|---|---|---|---|---|---|
| B-148 | (morpholine-phenyl-imidazopyridine-Cl, O-phenyl-butyl) | | 2.7 | 463.22 | A |
| B-149 | (biphenyl-thienoimidazole-O-phenyl-methyl-COOH) | (DMSO-d6) δ: 2.53 (s, 3H), 7.35-7.50 (m, 5H), 7.56 (s, 1H), 7.67-7.77 (m, 7H), 12.76 (s, 1H), 13.07 (br s, 1H). | | | |
| B-150 | (Cl-phenyl-thienoimidazole-O-phenyl-methyl-COOH) | (DMSO-d6) δ: 2.51 (s, 3H), 7.32-7.47 (m, 4H), 7.54 (s, 1H), 7.64-7.69 (m, 3H), 12.83 (br s, 1H). | | | |
| B-151 | (Br-phenyl-thienoimidazole-S-CH2-COOH) | (DMSO-d6) δ: 3.58 (s, 2H), 7.57 (s, 1H), 7.64 (d, J = 9.11 Hz, 2H), 7.82 (d, J = 8.11 Hz, 2H). | | | |

TABLE 25-continued

| No. | Structure | NMR(δ) | retention time | Mass (M + H) | method |
|---|---|---|---|---|---|
| B-152 | 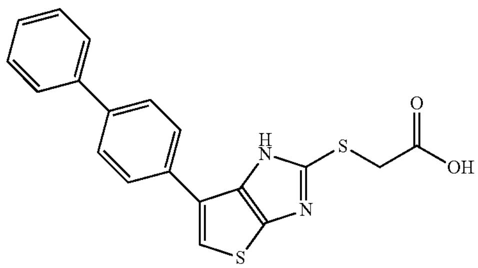 [SMILES: O=C(O)CSc1nc2scc(-c3ccc(-c4ccccc4)cc3)c2[nH]1] | (DMSO-d6) δ: 4.02 (d, J = 6.59 Hz, 2H), 7.39 (t, J = 7.35 Hz, 1H), 7.50 (t, J = 7.60 Hz, 2H), 7.72-8.02 (m, 7H), 12.80-13.21 (m, 2H). | | | |
| B-153 | 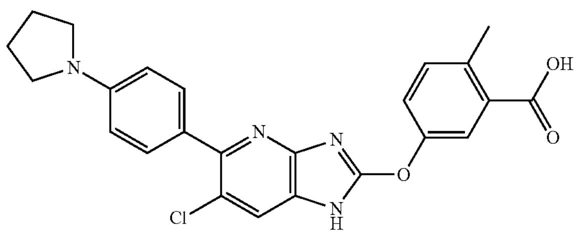 [SMILES: Cc1ccc(Oc2nc3nc(-c4ccc(N5CCCC5)cc4)c(Cl)cc3[nH]2)cc1C(=O)O] | (DMSO-d6) δ: 1.89-2.04 (m, 4H), 2.55 (s. 3H), 3.19-3.44 (m, 4H), 6.58-6.63 (m, 2H), 7.40-7.44 (m, 1H), 7.50-7.56 (m ,3H), 7.82 (s, 1H), 7.91 (s, 1H), 13.09 (s, 1H) | | | |

TABLE 26

| No. | Structure | NMR(δ) | retention time | Mass (M + H) | method |
|---|---|---|---|---|---|
| B-154 | 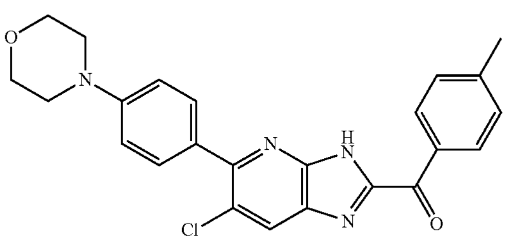 [SMILES: Cc1ccc(C(=O)c2nc3cc(Cl)c(-c4ccc(N5CCOCC5)cc4)nc3[nH]2)cc1] | (DMSO-d$_6$) δ: 2.45 (s, 3H), 3.23 (t, J = 4.82 Hz, 4H), 3.77 (t, J = 4.82 Hz, 4H), 7.06 (d, J = 9.12 Hz, 2H), 7.45 (d, J = 8.11 Hz, 2H), 7.64 (d, J = 9.12 Hz, 2H), 8.48 (br s, 3H), 14.20 (br s, 1H) | | | |
| B-155 | 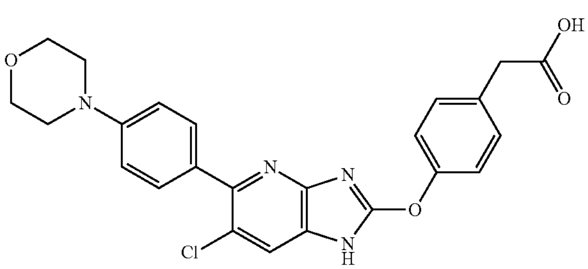 [SMILES: O=C(O)Cc1ccc(Oc2nc3nc(-c4ccc(N5CCOCC5)cc4)c(Cl)cc3[nH]2)cc1] | | 1.69 | 465.2 | A |
| B-156 | 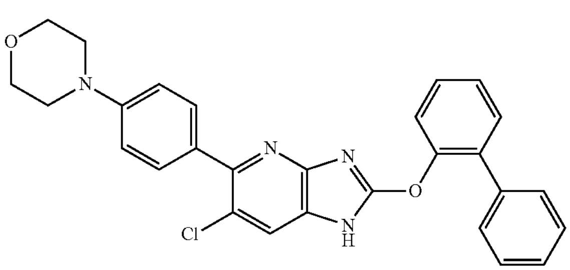 [SMILES: Clc1cc2[nH]c(Oc3ccccc3-c3ccccc3)nc2nc1-c1ccc(N2CCOCC2)cc1] | | 2.34 | 483.2 | A |

TABLE 26-continued

| No. | Structure | NMR(δ) | retention time | Mass (M + H) | method |
|---|---|---|---|---|---|
| B-157 | 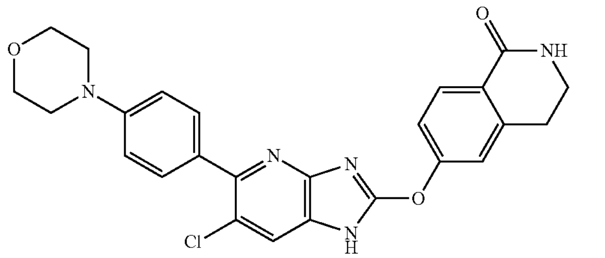 [SMILES: O=C1NCCc2cc(Oc3nc4nc(-c5ccc(N6CCOCC6)cc5)c(Cl)cc4[nH]3)ccc21] | | 1.59 | 476.19 | A |
| B-158 | 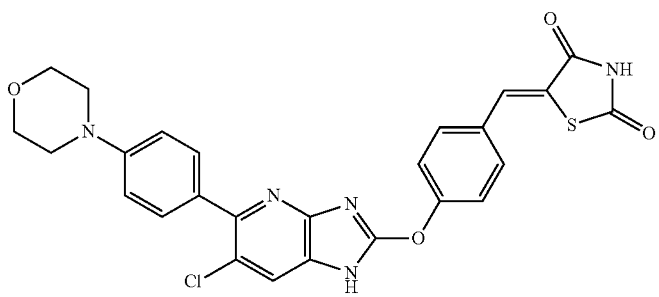 [SMILES: O=C1NC(=O)/C(=C/c2ccc(Oc3nc4nc(-c5ccc(N6CCOCC6)cc5)c(Cl)cc4[nH]3)cc2)S1] | | 1.98 | 534.17 | A |
| B-159 | 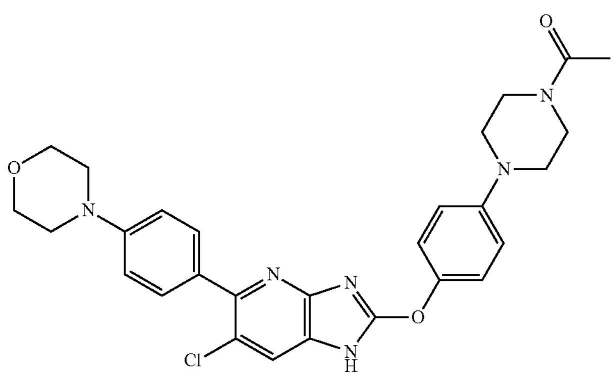 [SMILES: CC(=O)N1CCN(c2ccc(Oc3nc4nc(-c5ccc(N6CCOCC6)cc5)c(Cl)cc4[nH]3)cc2)CC1] | | 1.69 | 533.27 | A |

TABLE 27

| No. | Structure | retention time | Mass (M + H) | method |
|---|---|---|---|---|
| B-160 | 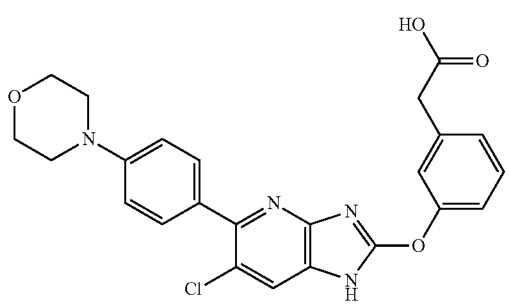 [SMILES: O=C(O)Cc1cccc(Oc2nc3nc(-c4ccc(N5CCOCC5)cc4)c(Cl)cc3[nH]2)c1] | 1.71 | 465.2 | A |

TABLE 27-continued

| No. | Structure | retention time | Mass (M + H) | method |
|---|---|---|---|---|
| B-161 | 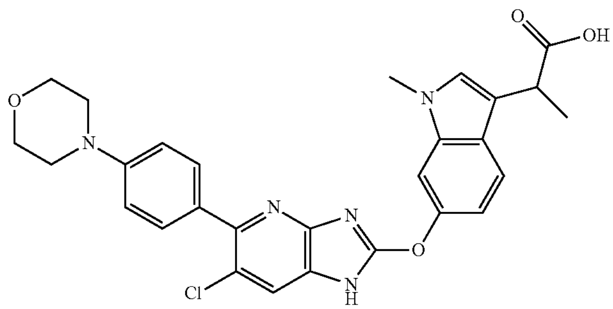 [SMILES: CC(C(=O)O)c1cn(C)c2cc(Oc3nc4nc(-c5ccc(N6CCOCC6)cc5)c(Cl)cc4[nH]3)ccc12] | 1.95 | 532.23 | A |
| B-162 | 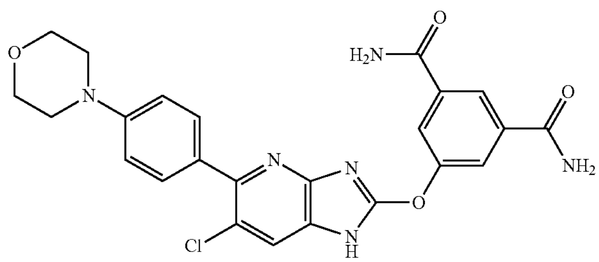 [SMILES: NC(=O)c1cc(Oc2nc3nc(-c4ccc(N5CCOCC5)cc4)c(Cl)cc3[nH]2)cc(C(N)=O)c1] | 1.33 | 493.19 | A |
| B-163 | 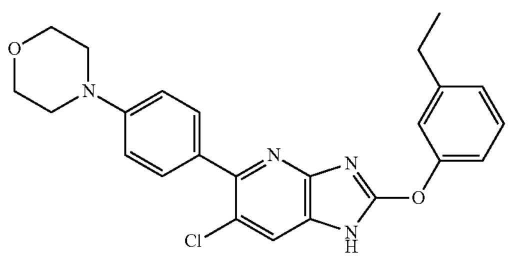 [SMILES: CCc1cccc(Oc2nc3nc(-c4ccc(N5CCOCC5)cc4)c(Cl)cc3[nH]2)c1] | 2.33 | 435.2 | A |
| B-164 | 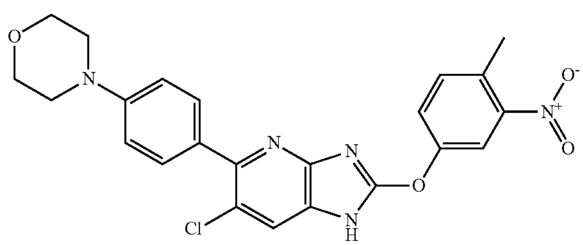 [SMILES: Cc1ccc(Oc2nc3nc(-c4ccc(N5CCOCC5)cc4)c(Cl)cc3[nH]2)cc1[N+](=O)[O-]] | 2.19 | 466.17 | A |
| B-165 | 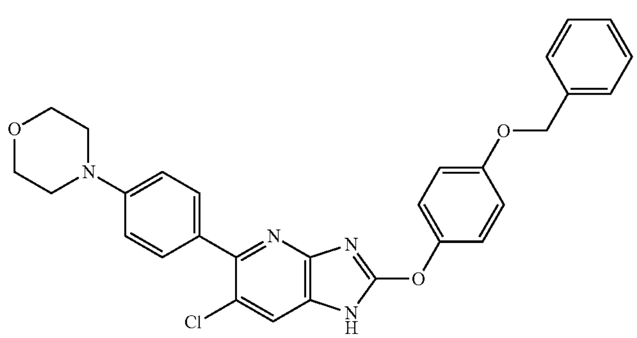 [SMILES: Clc1cc2[nH]c(Oc3ccc(OCc4ccccc4)cc3)nc2nc1-c1ccc(N2CCOCC2)cc1] | 2.48 | 513.22 | A |

TABLE 28

| No. | Structure | retention time | Mass (M + H) | method |
|---|---|---|---|---|
| B-166 | 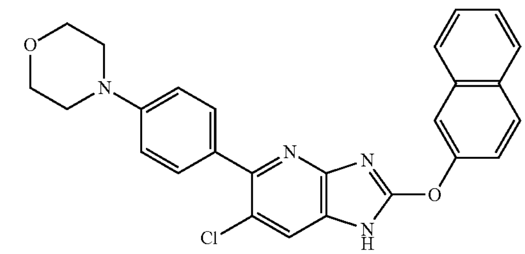 [SMILES: Clc1cc2[nH]c(Oc3ccc4ccccc4c3)nc2nc1-c1ccc(N2CCOCC2)cc1] | 2.34 | 467.17 | A |
| B-167 | 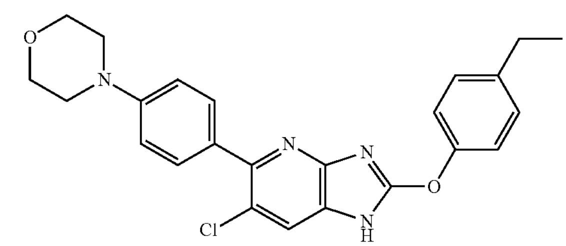 [SMILES: CCc1ccc(Oc2nc3nc(-c4ccc(N5CCOCC5)cc4)c(Cl)cc3[nH]2)cc1] | 2.35 | 435.21 | A |
| B-168 | 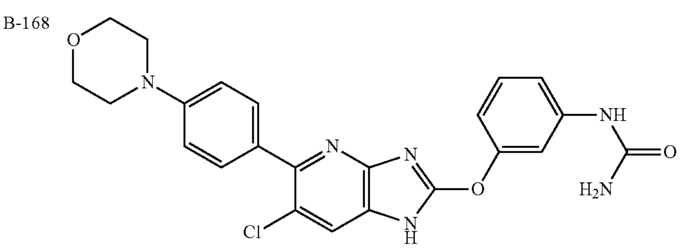 | 1.58 | 465.17 | A |
| B-169 | 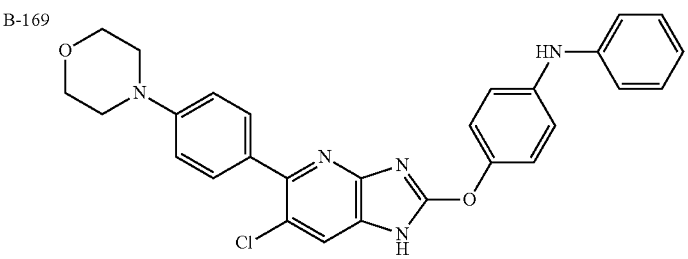 | 2.35 | 498.21 | A |
| B-170 | 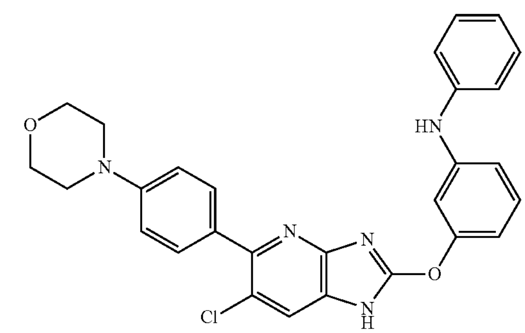 [SMILES: Clc1cc2[nH]c(Oc3cccc(Nc4ccccc4)c3)nc2nc1-c1ccc(N2CCOCC2)cc1] | 2.38 | 498.21 | A |
| B-171 | 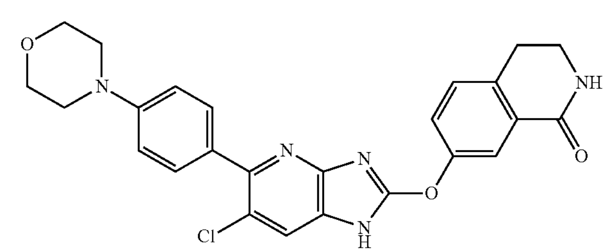 [SMILES: O=C1NCCc2ccc(Oc3nc4nc(-c5ccc(N6CCOCC6)cc5)c(Cl)cc4[nH]3)cc21] | 1.63 | 478.18 | A |

TABLE 29

| No. | Structure | NMR (δ) | retention time | Mass (M + H) | method |
|---|---|---|---|---|---|
| B-172 | 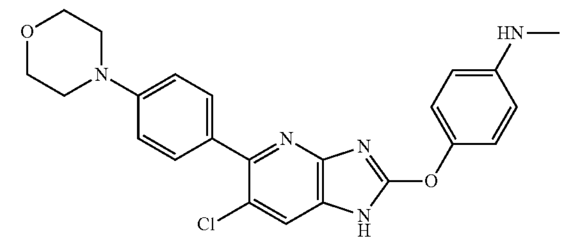 [SMILES: CNc1ccc(Oc2nc3nc(-c4ccc(N5CCOCC5)cc4)c(Cl)cc3[nH]2)cc1] | | 1.51 | 436.19 | A |
| B-173 | 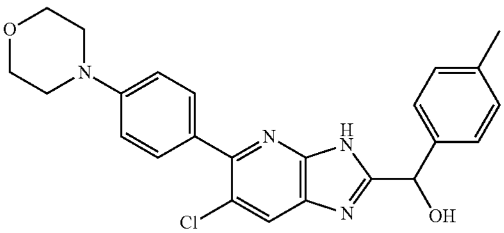 [SMILES: Cc1ccc(C(O)c2nc3cc(Cl)c(-c4ccc(N5CCOCC5)cc4)nc3[nH]2)cc1] | (DMSO-d6) δ: 2.27 (s, 3H), 3.19 (t, J = 4.56 Hz, 4H), 3.76 (t, J = 4.56 Hz, 4H), 5.89 (s, 1H), 6.52 (s, 1H), 7.02 (d, J = 8.62 Hz, 2H), 7.15 (d, J = 8.11 Hz, 2H), 7.38 (d, J = 7.60 Hz, 2H), 7.55 (d, J = 8.62 Hz, 2H), 8.08 (br s, 1H), 13.21 (br s, 1H). | | | |
| B-174 | 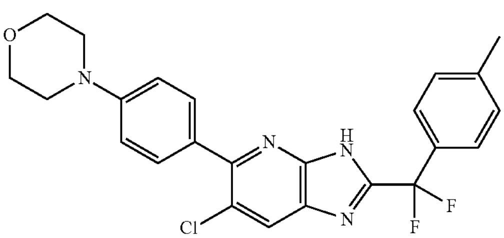 [SMILES: Cc1ccc(C(F)(F)c2nc3cc(Cl)c(-c4ccc(N5CCOCC5)cc4)nc3[nH]2)cc1] | (DMSO-d6) δ: 2.37 (s, 3.0H), 3.21 (t, J = 4.56 Hz, 4.0H), 3.76 (t, J = 4.56 Hz, 4.0H), 7.04 (d, J = 9.12 Hz, 2.0H), 7.36 (d, J = 8.11 Hz, 2.0H), 7.54 (d, J = 8.11 Hz, 2.0H), 7.60 (d, J = 9.12 Hz, 2.0H), 8.35 (s, 1.0H), 14.28 (s, 1.0H). | | | |
| B-175 | 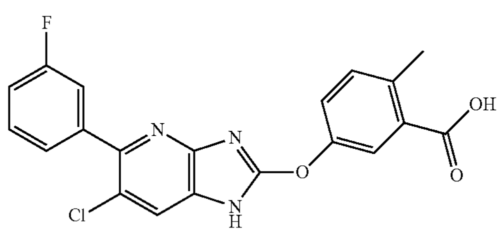 [SMILES: Cc1ccc(Oc2nc3nc(-c4cccc(F)c4)c(Cl)cc3[nH]2)cc1C(=O)O] | | 1.98 | 398.12 | A |
| B-176 | 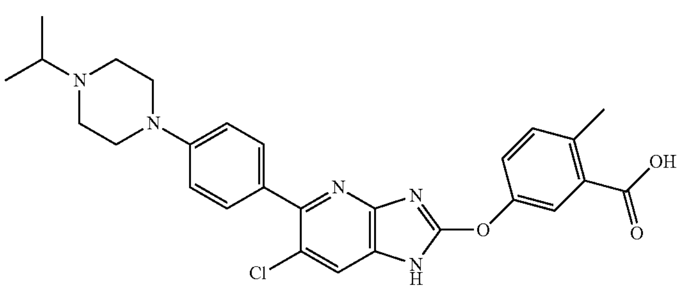 [SMILES: Cc1ccc(Oc2nc3nc(-c4ccc(N5CCN(C(C)C)CC5)cc4)c(Cl)cc3[nH]2)cc1C(=O)O] | | 1.27 | 506.26 | A |
| B-177 | 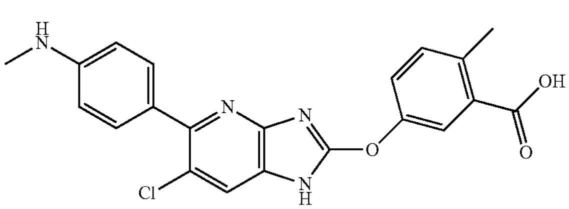 [SMILES: CNc1ccc(-c2nc3nc(Oc4ccc(C)c(C(=O)O)c4)[nH]c3cc2Cl)cc1] | | 1.54 | 409.18 | A |

TABLE 30

| No. | Structure | retention time | Mass (M + H) | method |
|---|---|---|---|---|
| B-178 | 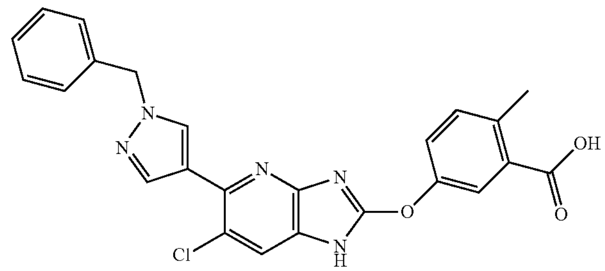 [SMILES: Cc1ccc(Oc2nc3nc(-c4cnn(Cc5ccccc5)c4)c(Cl)cc3[nH]2)cc1C(=O)O] | 1.9 | 460.18 | A |
| B-179 | 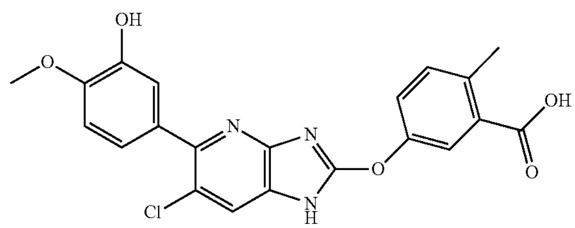 [SMILES: COc1ccc(-c2nc3nc(Oc4ccc(C)c(C(=O)O)c4)[nH]c3cc2Cl)cc1O] | 1.59 | 426.17 | A |
| B-180 | 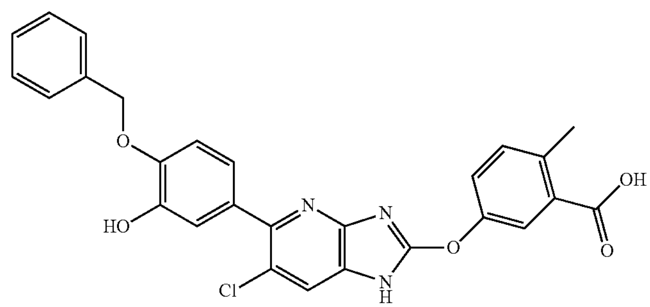 [SMILES: Cc1ccc(Oc2nc3nc(-c4ccc(OCc5ccccc5)c(O)c4)c(Cl)cc3[nH]2)cc1C(=O)O] | 2.06 | 502.17 | A |
| B-181 | 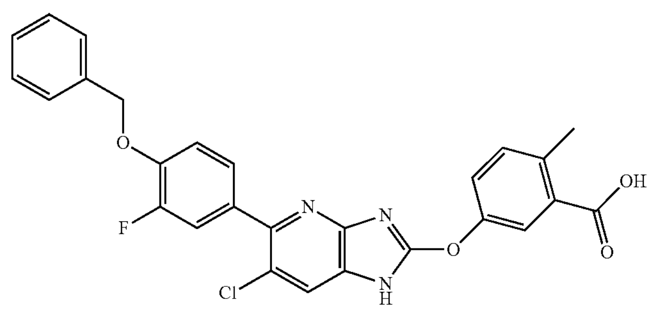 [SMILES: Cc1ccc(Oc2nc3nc(-c4ccc(OCc5ccccc5)c(F)c4)c(Cl)cc3[nH]2)cc1C(=O)O] | 2.39 | 504.17 | A |
| B-182 | 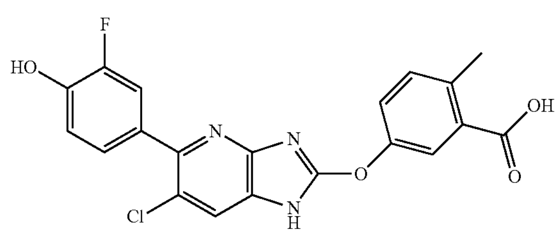 [SMILES: Cc1ccc(Oc2nc3nc(-c4ccc(O)c(F)c4)c(Cl)cc3[nH]2)cc1C(=O)O] | 1.62 | 414.12 | A |
| B-183 | 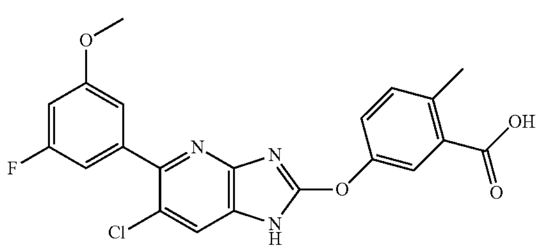 [SMILES: COc1cc(F)cc(-c2nc3nc(Oc4ccc(C)c(C(=O)O)c4)[nH]c3cc2Cl)c1] | 2.03 | 428.14 | A |

TABLE 31

| No. | Structure | retention time | Mass (M + H) | method |
|---|---|---|---|---|
| B-184 | 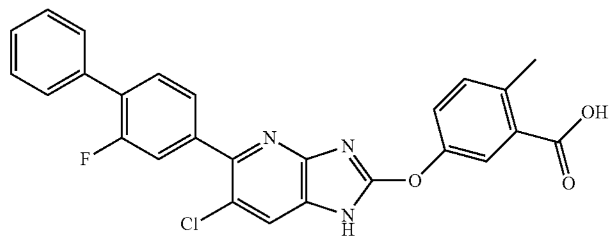 [SMILES: Cc1ccc(Oc2nc3nc(-c4ccc(-c5ccccc5)c(F)c4)c(Cl)cc3[nH]2)cc1C(=O)O] | 2.44 | 474.16 | A |
| B-185 | 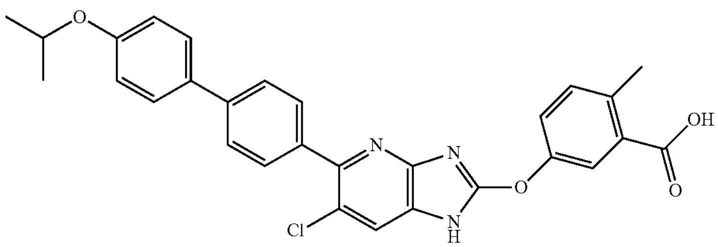 [SMILES: Cc1ccc(Oc2nc3nc(-c4ccc(-c5ccc(OC(C)C)cc5)cc4)c(Cl)cc3[nH]2)cc1C(=O)O] | 2.6 | 514.21 | A |
| B-186 | 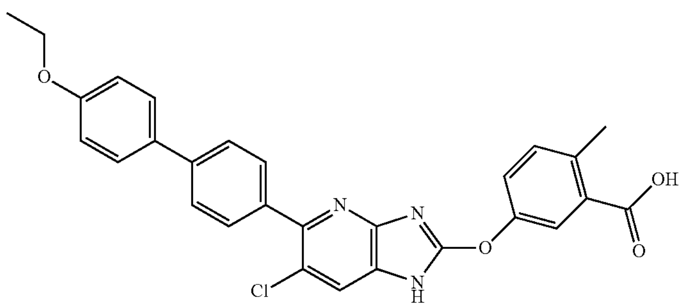 [SMILES: CCOc1ccc(-c2ccc(-c3nc4nc(Oc5ccc(C)c(C(=O)O)c5)[nH]c4cc3Cl)cc2)cc1] | 2.49 | 500.19 | A |
| B-187 | 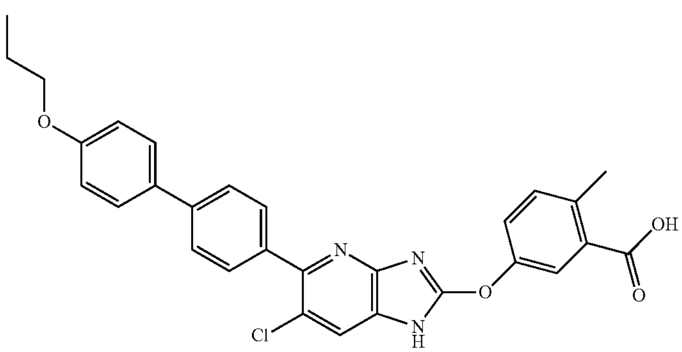 [SMILES: CCCOc1ccc(-c2ccc(-c3nc4nc(Oc5ccc(C)c(C(=O)O)c5)[nH]c4cc3Cl)cc2)cc1] | 2.68 | 514.22 | A |
| B-188 | 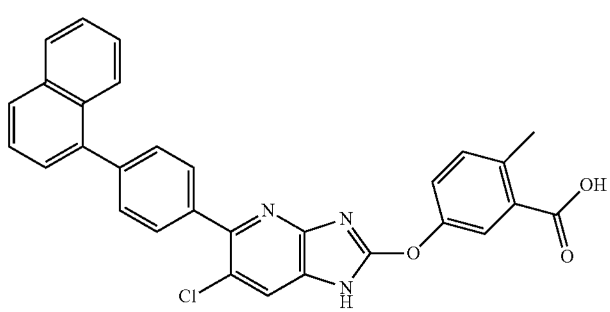 [SMILES: Cc1ccc(Oc2nc3nc(-c4ccc(-c5cccc6ccccc56)cc4)c(Cl)cc3[nH]2)cc1C(=O)O] | 2.67 | 506.19 | A |

TABLE 31-continued
| No. | Structure | retention time | Mass (M + H) | method |
|---|---|---|---|---|
| B-189 | 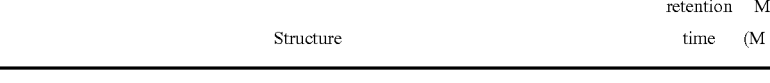 | 1.66 | 457.17 | A |
TABLE 32
| No. | Structure | NMR (δ) |
|---|---|---|
| C-1 | 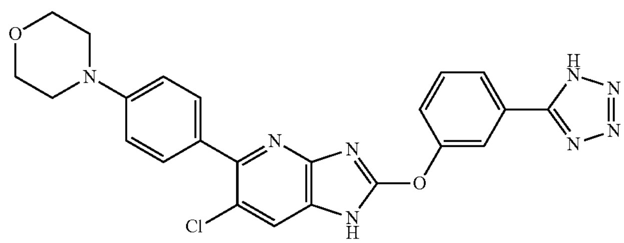 [SMILES: Clc1cc2[nH]c(Oc3cccc(-c4nnn[nH]4)c3)nc2nc1-c1ccc(N2CCOCC2)cc1] | 1H-NMR (DMSO-d6) δ: 3.20 (t, J = 4.82 Hz, 4H), 3.76 (t, J = 4.82 Hz, 4H), 7.02 (d, J = 8.11 Hz, 2H), 7.53-7.77 (m, 4H), 7.95-8.13 (m, 3H), 13.39 (s, 1H). |
| C-2 | 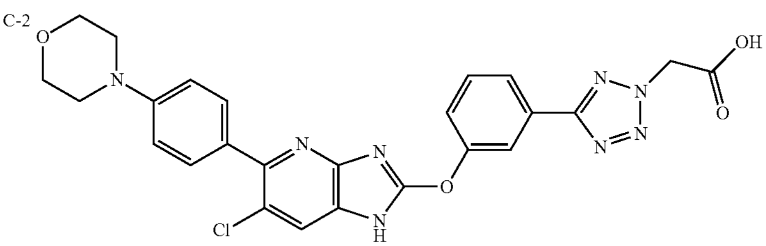 | 1H-NMR (DMSO-d6) δ: 3.19 (t, J = 4.82 Hz, 4H), 3.76 (t, J = 4.82 Hz, 4H), 5.31 (s, 2H), 7.02 (d, J = 8.62 Hz, 2H), 7.58 (d, J = 8.62 Hz, 2H), 7.61 (d, J = 1.52 Hz, 1H), 7.69 (t, J = 8.11 Hz, 1H), 7.95-8.05 (m, 2H), 8.10 (s, 1H). |
| C-3 | 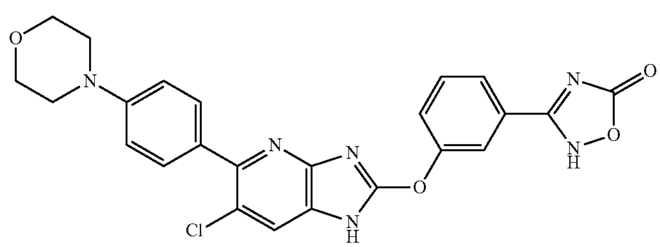 [SMILES: O=c1nc(-c2cccc(Oc3nc4nc(-c5ccc(N6CCOCC6)cc5)c(Cl)cc4[nH]3)c2)[nH]o1] | 1H-NMR (DMSO-d6) δ: 3.20 (t, J = 4.56 Hz, 4H), 3.76 (t, J = 4.56 Hz, 4H), 7.02 (d, J = 8.62 Hz, 2H), 7.57 (d, J = 8.62 Hz, 2H), 7.68-7.79 (m, 3H), 7.87 (s, 1H), 7.97 (s, 1H). |
| C-4 | 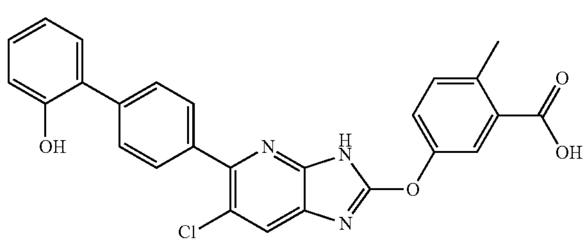 [SMILES: Cc1ccc(Oc2nc3cc(Cl)c(-c4ccc(-c5ccccc5O)cc4)nc3[nH]2)cc1C(=O)O] | (DMSO-d6) δ: 2.56 (s, 3H), 6.91 (dd, J = 7.6, 7.6 Hz, 1H), 6.97 (d, J = 7.60 Hz, 1H), 7.19 (td, J = 7.60, 1.5 Hz, 1H), 7.33 (dd, J = 7.60, 1.5 Hz, 1H), 7.42 (d, J = 8.1 Hz, 1H), 7.54 (dd, J = 8.1, 2.3 Hz, 1H), 7.65 (d, J = 8.4 Hz, 2H), 7.69 (d, J = 8.4 Hz, 2H), 7.83 (d, J = 2.3 Hz, 1H), 8.00 (s, 1H), 9.6 (s, 1H). |

TABLE 32-continued

| No. | Structure | NMR (δ) |
|---|---|---|
| C-5 | 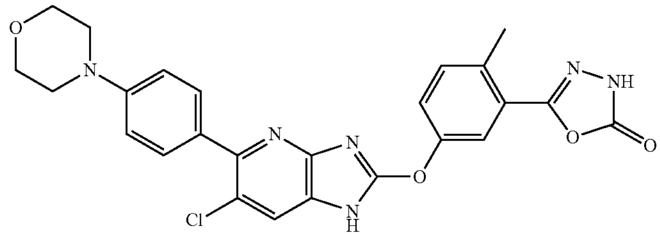 [SMILES: Cc1ccc(Oc2nc3nc(-c4ccc(N5CCOCC5)cc4)c(Cl)cc3[nH]2)cc1-c1n[nH]c(=O)o1] | 1H-NMR (DMSO-d6) δ: 2.57 (s, 3H), 3.19 (t, J = 4.82 Hz, 4H), 3.76 (t, J = 4.82 Hz, 4H), 7.02 (d, J = 8.62 Hz, 2H), 7.48-7.59 (m, 4H), 7.77 (d, J = 2.03 Hz, 1H), 7.94 (s, 1H), 12.71 (s, 1H). |
| C-6 | 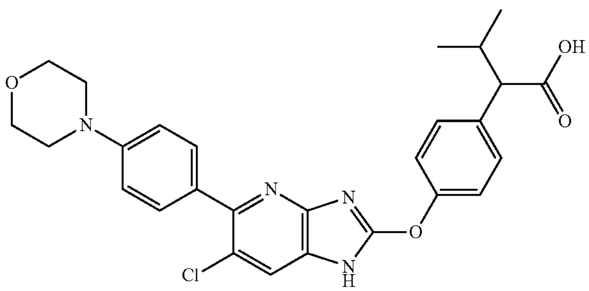 [SMILES: CC(C)C(C(=O)O)c1ccc(Oc2nc3nc(-c4ccc(N5CCOCC5)cc4)c(Cl)cc3[nH]2)cc1] | 1H-NMR (DMSO-d6) δ: 0.69 (d, J = 8.0 Hz, 3H), 1.02 (d, J = 8.0 Hz, 3H), 2.20-2.28 (m, 1H), 3.16-3.20 (m, 4H), 3.75-3.77 (m, 4H), 4.05-4.11 (m, 1H), 7.02 (d, J = 8.6 Hz, 2H), 7.38 (d, J = 8.6 Hz, 2H), 7.42 (d, J = 8.6 Hz, 2H), 7.57 (d, J = 8.6 Hz, 2H), 7.92 (s, 1H) |

TABLE 33

| No. | Structure | NMR (δ) |
|---|---|---|
| C-7 | 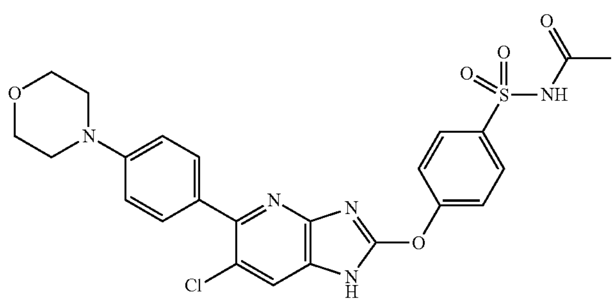 [SMILES: CC(=O)NS(=O)(=O)c1ccc(Oc2nc3nc(-c4ccc(N5CCOCC5)cc4)c(Cl)cc3[nH]2)cc1] | 1H-NMR (DMSO-d6) δ: 1.67 (s, 3H), 3.19 (t, J = 4.82 Hz, 4H), 3.76 (t, J = 4.82 Hz, 4H), 7.02 (d, J = 8.62 Hz, 2H), 7.40 (d, J = 8.62 Hz, 2H), 7.57 (d, J = 8.62 Hz, 2H), 7.82 (d, J = 8.62 Hz, 2H), 7.92 (s, 1H). |
| C-8 | 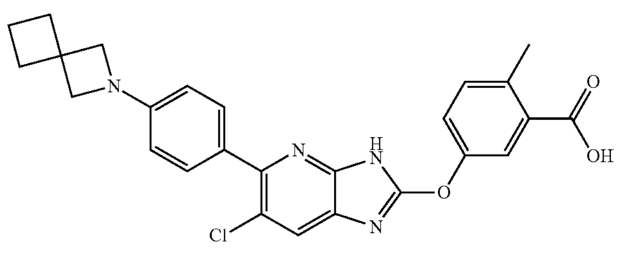 [SMILES: Cc1ccc(Oc2nc3cc(Cl)c(-c4ccc(N5CC6(CCC6)C5)cc4)nc3[nH]2)cc1C(=O)O] | (DMSO-d6) δ: 1.84 (tt, J = 7.4, 7.4 Hz, 2H), 2.19 (t, J = 7.4 Hz, 4H), 2.55 (s, 3H), 3.84 (s, 4H), 6.44-6.48 (m, 2H), 7.41-7.52 (m, 4H), 7.80-7.92 (m, 2H). |
| C-9 | 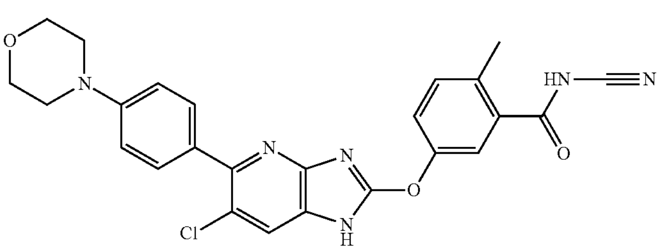 [SMILES: Cc1ccc(Oc2nc3nc(-c4ccc(N5CCOCC5)cc4)c(Cl)cc3[nH]2)cc1C(=O)NC#N] | 1H-NMR (DMSO-d6) δ: 2.46 (s, 3H), 3.19 (t, J = 4.31 Hz, 4H), 3.76 (t, J = 4.31 Hz, 4H), 7.02 (d, J = 8.62 Hz, 2H), 7.18-7.25 (m, 2H), 7.53-7.60 (m, 3H), 7.91 (s, 1H). |

TABLE 33-continued

| No. | Structure | NMR (δ) |
|---|---|---|
| C-10 | 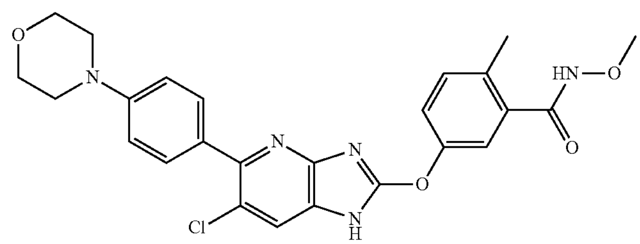 [SMILES: CONC(=O)c1cc(Oc2nc3nc(-c4ccc(N5CCOCC5)cc4)c(Cl)cc3[nH]2)ccc1C] | 1H-NMR (DMSO-d6) δ: 2.37 (s, 3H), 3.19 (t, J = 4.82 Hz, 4H), 3.72 (s, 3H), 3.76 (t, J = 4.82 Hz, 4H), 7.02 (d, J = 8.62 Hz, 2H), 7.36-7.48 (m, 3H), 7.57 (d, J = 8.62 Hz, 2H), 7.93 (s, 1H), 11.54 (s, 1H), 13.23 (s, 1H). |
| C-11 | 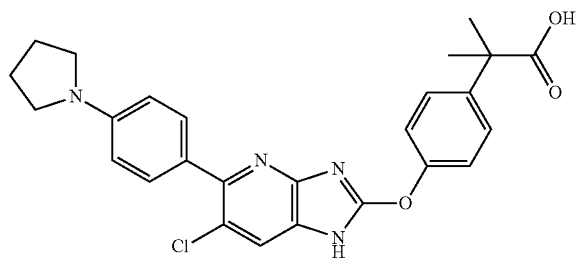 [SMILES: CC(C)(C(=O)O)c1ccc(Oc2nc3nc(-c4ccc(N5CCCC5)cc4)c(Cl)cc3[nH]2)cc1] | 1H-NMR (DMSO-d6) δ: 1.51 (s, 6H), 1.98-2.00 (m, 4H), 3.27-3.21 (m, 4H), 6.60 (d, J = 8.6 Hz, 2H), 7.36 (d, J = 8.6 Hz, 2H), 7.44 (d, J = 8.6 Hz, 2H), 7.52 (d, J = 8.6 Hz, 2H), 7.84 (s, 1H) |
| C-12 | 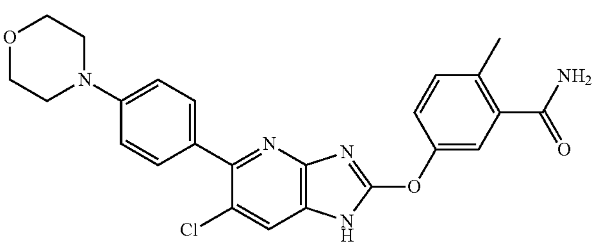 [SMILES: Cc1ccc(Oc2nc3nc(-c4ccc(N5CCOCC5)cc4)c(Cl)cc3[nH]2)cc1C(N)=O] | 1H-NMR (DMSO-d6) δ: 2.39 (s, 3H), 3.19 (t, J = 4.82 Hz, 4H), 3.76 (t, J = 4.82 Hz, 4H), 7.01 (d, J = 8.62 Hz, 2H), 7.30-7.48 (m, 4H), 7.57 (d, J = 8.62 Hz, 2H), 7.79 (s, 1H), 7.89 (s, 1H). |

TABLE 34

| No. | Structure | NMR (δ) |
|---|---|---|
| C-13 | 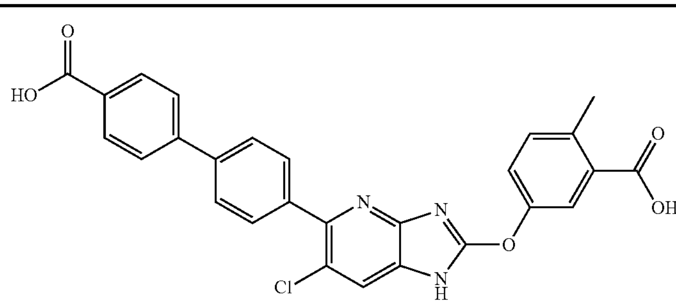 | (DMSO-d6) δ: 2.55 (s, 3H), 7.40 (d, J = 8.1 Hz, 1H), 7.51 (d, J = 8.1 Hz, 1H), 7.78-7.81 (m, 3H), 7.85 (d, J = 8.6 Hz, 2H), 7.88 (d, J = 8.1 Hz, 2H), 7.97 (s, 1H), 8.05 (d, J = 8.11 Hz, 2H). |
| C-14 | 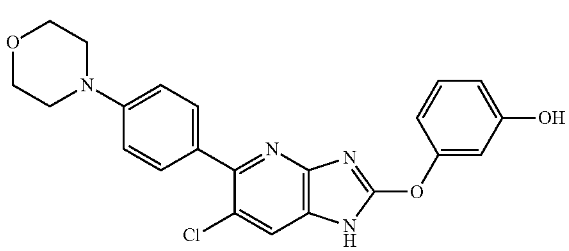 [SMILES: Oc1cccc(Oc2nc3nc(-c4ccc(N5CCOCC5)cc4)c(Cl)cc3[nH]2)c1] | 1H-NMR (DMSO-d6) δ: 3.19 (t, J = 4.82 Hz, 4H), 3.76 (t, J = 4.82 Hz, 4H), 6.71 (m, 1H), 6.79-6.84 (m, 2H), 7.02 (d, J = 8.62 Hz, 2H), 7.26 (m, 1H), 7.57 (d, J = 8.62 Hz, 2H), 7.92 (s, 1H), 9.80 (s, 1H). |

TABLE 34-continued

| No. | Structure | NMR (δ) |
|---|---|---|
| C-15 | 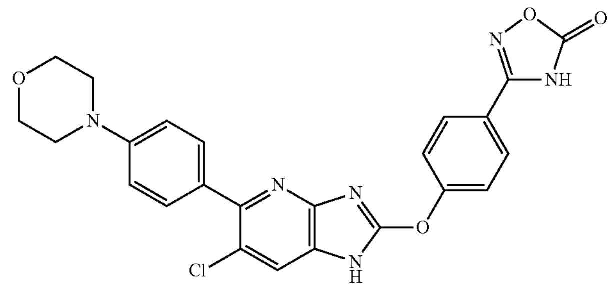 [SMILES: O=c1[nH]c(-c2ccc(Oc3nc4nc(-c5ccc(N6CCOCC6)cc5)c(Cl)cc4[nH]3)cc2)no1] | 1H-NMR (DMSO-d6) δ: 3.20 (t, J = 4.82 Hz, 4H), 3.76 (t, J = 4.82 Hz, 4H), 7.02 (d, J = 9.12 Hz, 2H), 7.48 (d, J = 9.12 Hz, 2H), 7.58 (d, J = 8.62 Hz, 2H), 7.88 (d, J = 8.62 Hz, 2H), 7.95 (s, 1H). |
| C-16 | 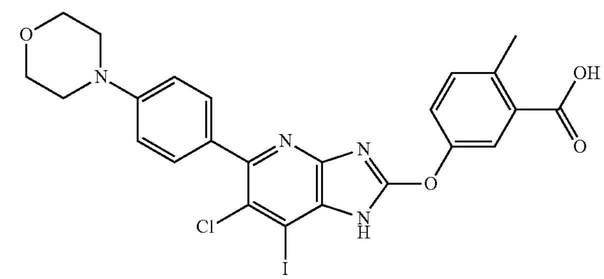 [SMILES: Cc1ccc(Oc2nc3nc(-c4ccc(N5CCOCC5)cc4)c(Cl)c(I)c3[nH]2)cc1C(=O)O] | 1H-NMR (DMSO-d6) δ: 2.55 (s, 3H), 3.19 (t, J = 4.82 Hz, 4H), 3.76 (t, J = 4.82 Hz, 4H), 7.00 (d, J = 9.12 Hz, 2H), 7.39-7.55 (m, 4H), 7.80 (d, J = 3.04 Hz, 1H). |
| C-17 | 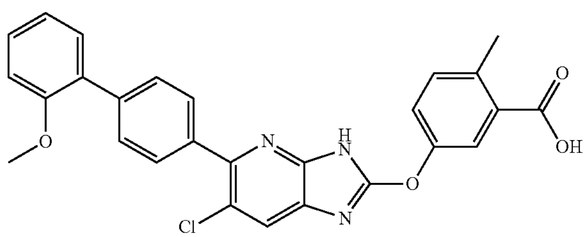 [SMILES: COc1ccccc1-c1ccc(-c2nc3[nH]c(Oc4ccc(C)c(C(=O)O)c4)nc3cc2Cl)cc1] | (DMSO-d$_6$) δ: 2.56 (s, 3H), 3.80 (s, 3H), 7.07 (dd, J = 7.4, 7.4 Hz, 1H), 7.15 (d, J = 8.6 Hz, 1H), 7.36-7.40 (m, 2H), 7.43 (d, J = 8.5 Hz, 1H), 7.55 (dd, J = 8.5, 2.6 Hz, 1H), 7.58 (d, J = 8.1 Hz, 2H), 7.69 (d, J = 8.1 Hz, 2H), 7.84 (d, J = 2.6 Hz, 1H), 8.01 (s, 1H). |
| C-18 | 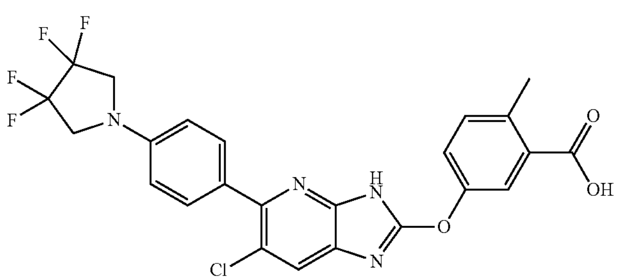 [SMILES: Cc1ccc(Oc2nc3cc(Cl)c(-c4ccc(N5CC(F)(F)C(F)(F)C5)cc4)nc3[nH]2)cc1C(=O)O] | (DMSO-d$_6$) δ: 2.54 (s, 3H), 4.06-4.13 (m, 4H), 6.80 (d, J = 8.6 Hz, 2H), 7.42 (d, J = 8.6 Hz, 1H), 7.52 (dd, J = 8.6, 2.5 Hz, 1H), 7.59 (d, J = 8.6 Hz, 2H), 7.82 (d, J = 2.53 Hz, 1H), 7.94 (s, 1H). |

TABLE 35

| No. | Structure | NMR (δ) |
|---|---|---|
| C-19 | 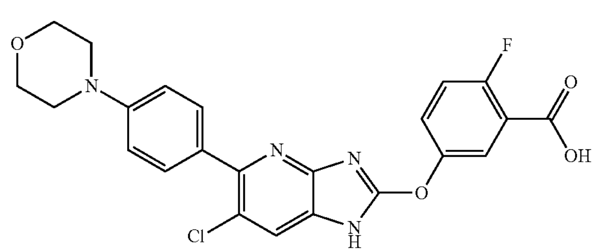 [SMILES: O=C(O)c1cc(Oc2nc3nc(-c4ccc(N5CCOCC5)cc4)c(Cl)cc3[nH]2)ccc1F] | (DMSO-d6) δ: 3.19 (dd, J = 5.2, 4.4 Hz, 4H), 3.76 (dd, J = 5.2, 4.4 Hz, 4H), 7.01 (d, J = 9.2 Hz, 2H), 7.22-7.27 (m, 1H), 7.44-7.46 (m, 1H), 7.57 (d, J = 9.2 Hz, 2H), 7.65-7.66 (m, 1H), 7.91 (s, 1H). |

TABLE 35-continued

| No. | Structure | NMR (δ) |
|---|---|---|
| C-20 | 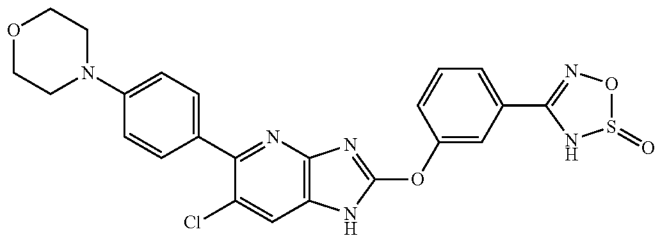 [SMILES: O=S1NC(c2cccc(Oc3nc4nc(-c5ccc(N6CCOCC6)cc5)c(Cl)cc4[nH]3)c2)=NO1] | 1H-NMR (DMSO-d6) δ: 3.20 (t, J = 4.82 Hz, 4H), 3.76 (t, J = 7.82 Hz, 4H), 7.02 (d, J = 8.62 Hz, 2H), 7.58 (d, J = 8.62 Hz, 2H), 7.69-7.83 (m, 3H), 7.93 (s, 1H), 7.98 (s, 1H). |
| C-21 | 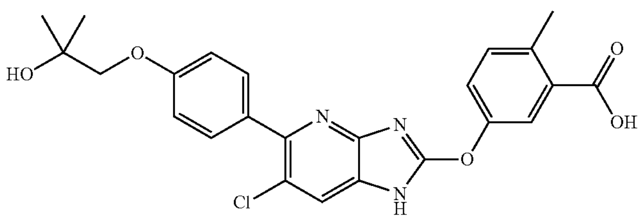 [SMILES: Cc1ccc(Oc2nc3nc(-c4ccc(OCC(C)(C)O)cc4)c(Cl)cc3[nH]2)cc1C(=O)O] | (DMSO-d6) δ: 1.23 (s, 6H), 2.54 (s, 3H), 3.77 (s, 2H), 7.02 (d, J = 8.6 Hz, 2H), 7.41 (d, J = 8.6 Hz, 1H), 7.52 (d, J = 8.6 Hz, 1H), 7.59 (d, J = 8.6 Hz, 2H), 7.81 (s, 1H), 7.94 (s, 1H). |
| C-22 | 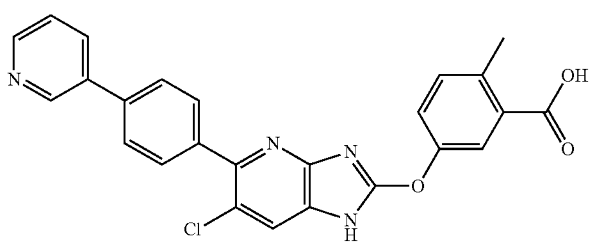 [SMILES: Cc1ccc(Oc2nc3nc(-c4ccc(-c5cccnc5)cc4)c(Cl)cc3[nH]2)cc1C(=O)O] | 1H-NMR (DMSO-d6) δ: 2.56 (s, 3H), 7.44 (d, J = 8.6 Hz, 1H), 7.54-7.59 (m, 2H), 7.80 (d, J = 8.6 Hz, 2H), 7.84-7.88 (m, 3H), 8.03 (s, 1H), 8.21-8.23 (m, 1H), 8.63 (s, 1H), 9.01 (s, 1H) |
| C-23 | 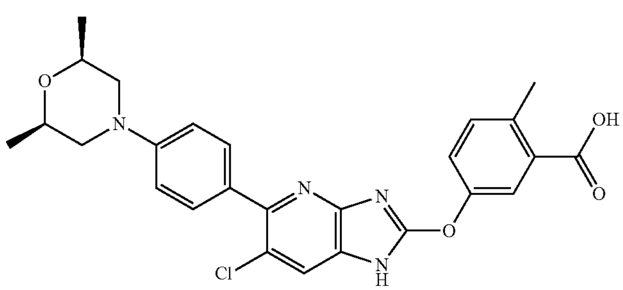 [SMILES: Cc1ccc(Oc2nc3nc(-c4ccc(N5C[C@@H](C)O[C@@H](C)C5)cc4)c(Cl)cc3[nH]2)cc1C(=O)O] | 1H-NMR (DMSO-d6) δ: 1.17 (s, 3H), 1.18 (s, 3H), 2.29-2.34 (m, 2H), 2.54 (s, 3H), 3.67-3.70 (m, 4H), 7.02 (d, J = 8.6 Hz, 2H), 7.39 (d, J = 8.6 Hz, 1H), 7.49 (d, J = 8.6 Hz, 1H), 7.56 (d, J = 8.6 Hz, 2H), 7.79 (s, 1H), 7.90 (s, 1H) |
| C-24 | 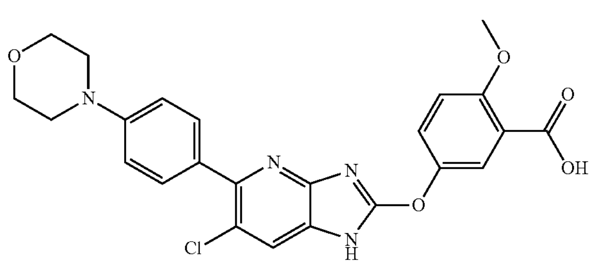 | (DMSO-d6) δ: 3.19 (dd, J = 5.2, 4.4 Hz, 4H), 3.76 (dd, J = 5.2, 4.4 Hz, 4H), 3.86 (s, 3H), 7.02 (d, J = 8.8 Hz, 2H), 7.22 (d, J = 8.8 Hz, 2H), 7.56-7.58 (m, 3H), 7.67-7.68 (m, 1H), 7.93-7.94 (m, 1H). |

TABLE 36

| No. | Structure | NMR (δ) | retention time | Mass (M + H) | method |
|---|---|---|---|---|---|
| C-25 | 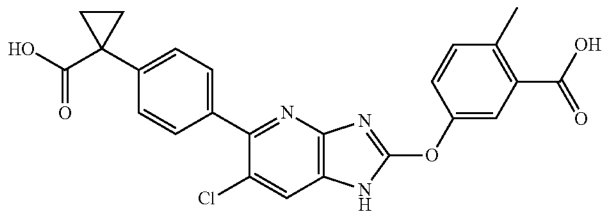 [SMILES: Cc1ccc(Oc2nc3nc(-c4ccc(C5(C(=O)O)CC5)cc4)c(Cl)cc3[nH]2)cc1C(=O)O] | 1H-NMR (DMSO-d6) δ: 1.19-1.23 (m, 2H), 1.47-1.50 (m, 2H), 2.55 (s, 3H), 7.40-7.42 (m, 1H), 7.42 (d, J = 8.6 Hz, 2H), 7.52 (dd, J = 4.0, 8.6 Hz, 1H), 7.58 (d, J = 8.6 Hz, 2H), 7.81 (d, J = 4.0 Hz, 1H), 7.97 (s, 1H), | | | |
| C-26 | 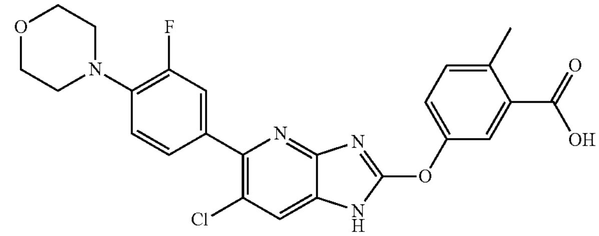 [SMILES: Cc1ccc(Oc2nc3nc(-c4ccc(N5CCOCC5)c(F)c4)c(Cl)cc3[nH]2)cc1C(=O)O] | (DMSO-d6) δ: 2.55 (s, 3H), 3.09 (dd, J = 4.4, 4.4 Hz, 4H), 3.77 (dd, J = 4.4, 4.4 Hz, 4H), 7.12 (m, 1H), 7.41-7.48 (m, 3H), 7.53 (dd, J = 8.1, 2.5 Hz, 1H), 7.83 (d, J = 2.5 Hz, 1H), 7.97 (s, 1H). | | | |
| C-27 | 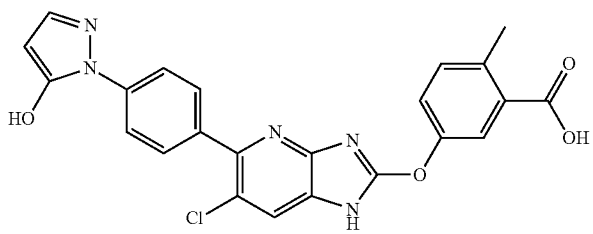 [SMILES: Cc1ccc(Oc2nc3nc(-c4ccc(-n5nccc5O)cc4)c(Cl)cc3[nH]2)cc1C(=O)O] | (DMSO-d6) δ: 2.56 (s, 3H), 5.57 (d, J = 2.0 Hz, 1H), 7.43 (d, J = 8.6 Hz, 2H), 7.55 (dd, J = 8.6, 2.8 Hz, 1H), 7.74 (d, J = 8.6 Hz, 2H), 7.86 (m, 3H), 8.01 (s, 1H). | | | |
| C-28 | 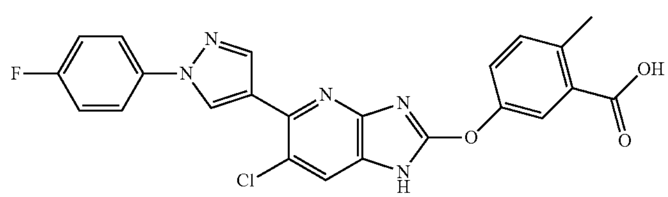 [SMILES: Cc1ccc(Oc2nc3nc(-c4cnn(-c5ccc(F)cc5)c4)c(Cl)cc3[nH]2)cc1C(=O)O] | | 2.09 | 464.15 | A |
| C-29 | 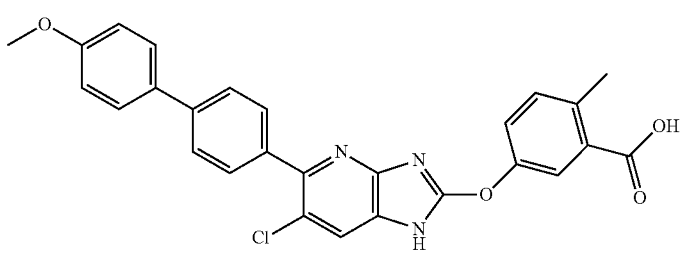 [SMILES: COc1ccc(-c2ccc(-c3nc4nc(Oc5ccc(C)c(C(=O)O)c5)[nH]c4cc3Cl)cc2)cc1] | | 2.33 | 486.18 | A |
| C-30 | 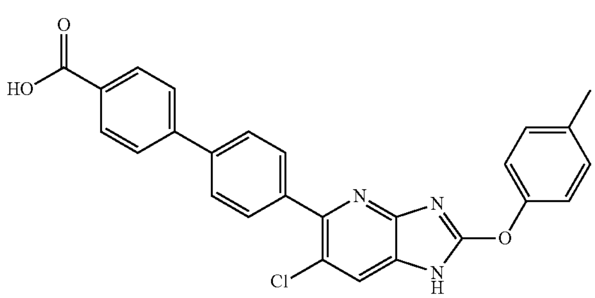 [SMILES: Cc1ccc(Oc2nc3nc(-c4ccc(-c5ccc(C(=O)O)cc5)cc4)c(Cl)cc3[nH]2)cc1] | (DMSO-d6) δ: 2.35 (s, 3H), 7.30 (m, 4H), 7.79 (d, J = 8.1 Hz, 2H), 7.85 (d, J = 8.1 Hz, 2H), 7.88 (d, J = 8.1 Hz, 2H), 7.98 (s, 1H), 8.05 (d, J = 8.1 Hz, 2H). | | | |

TABLE 37

| No. | Structure | NMR (δ) |
| --- | --- | --- |
| C-31 | 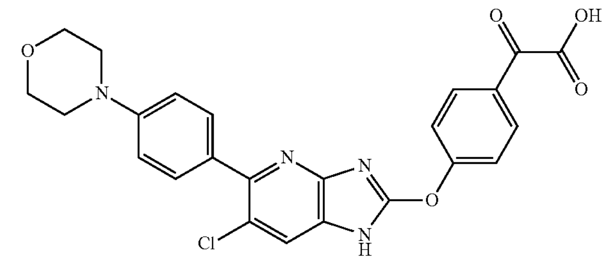 [SMILES: O=C(O)C(=O)c1ccc(Oc2nc3nc(-c4ccc(N5CCOCC5)cc4)c(Cl)cc3[nH]2)cc1] | 1H-NMR (DMSO-d6) δ: 3.19-3.21 (m, 4H), 3.75-3.78 (m, 4H), 7.03 (d, J = 8.6 Hz, 2H), 7.58 (d, J = 8.6 Hz, 2H), 7.71 (d, J = 8.6 Hz, 2H), 8.01 (s, 1H), 8.09 (d, J = 8.6 Hz, 2H) |
| C-32 | 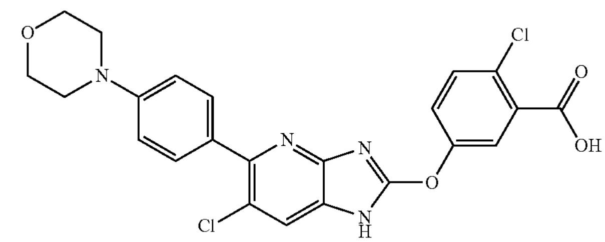 | (DMSO-d6) δ: 3.20 (dd, J = 5.2, 4.4 Hz, 4H), 3.77 (dd, J = 5.2, 4.4 Hz, 4H), 7.02 (d, J = 8.8 Hz, 2H), 7.57 (d, J = 8.8 Hz, 2H), 7.66-7.69 (m, 2H), 7.89 (d, J = 2.0 Hz, 1H), 7.97 (s, 1H). |
| C-33 | 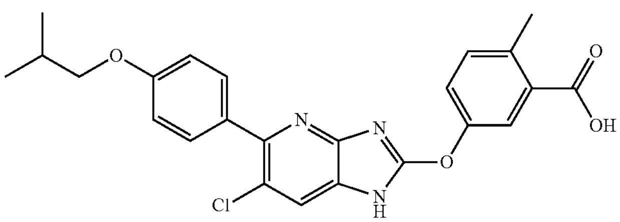 [SMILES: Cc1ccc(Oc2nc3nc(-c4ccc(OCC(C)C)cc4)c(Cl)cc3[nH]2)cc1C(=O)O] | (DMSO-d6) δ: 1.01 (d, J = 8.8 Hz, 6H), 2.05 (septt, J = 6.6, 6.6 Hz, 1H), 2.55 (s, 3H), 3.81 (d, J = 6.6 Hz, 2H), 7.02 (d, J = 8.6 Hz, 2H), 7.42 (d, J = 8.6 Hz, 1H), 7.53 (dd, J = 8.6, 2.5 Hz, 1H), 7.59 (d, J = 8.6 Hz, 2H), 7.82 (d, J = 2.5 Hz, 1H), 7.95 (s, 1H). |
| C-34 | 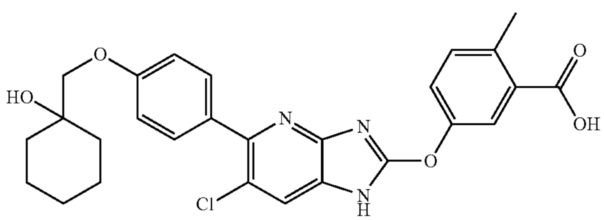 [SMILES: Cc1ccc(Oc2nc3nc(-c4ccc(OCC5(O)CCCCC5)cc4)c(Cl)cc3[nH]2)cc1C(=O)O] | (DMSO-d6) δ: 1.42-1.65 (m, 10H), 2.55 (s, 3H), 3.78 (s, 2H), 4.41 (s, 1H), 7.03 (d, J = 8.6 Hz, 2H), 7.42 (d, J = 8.6 Hz, 1H), 7.53 (dd, J = 8.6, 2.5 Hz, 1H), 7.59 (d, J = 8.6 Hz, 2H), 7.83 (d, J = 2.5 Hz, 1H), 7.96 (s, 1H). |
| C-35 | 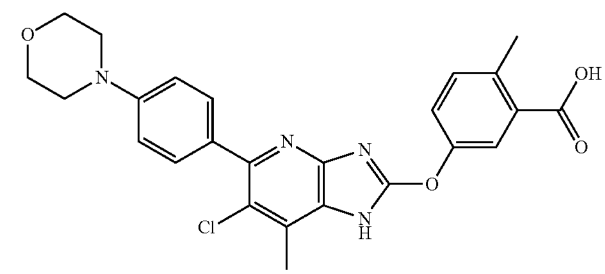 [SMILES: Cc1ccc(Oc2nc3nc(-c4ccc(N5CCOCC5)cc4)c(Cl)c(C)c3[nH]2)cc1C(=O)O] | 1H-NMR (DMSO-d6) δ: 2.49 (s, 3H), 2.53 (s, 3H), 3.18 (t, J = 4.82 Hz, 4H), 3.76 (t, J = 4.82 Hz, 4H), 7.00 (d, J = 9.12 Hz, 2H), 7.37 (d, J = 8.62 Hz, 1H), 7.46 (dd, J = 8.62, 2.03 Hz, 1H), 7.51 (d, J = 9.12 Hz, 2H), 7.75 (d, J = 2.03 Hz, 1H). |
| C-36 | 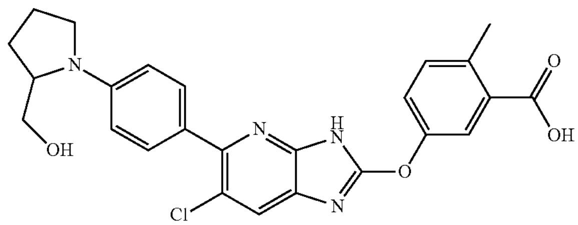 [SMILES: Cc1ccc(Oc2nc3cc(Cl)c(-c4ccc(N5CCCC5CO)cc4)nc3[nH]2)cc1C(=O)O] | (DMSO-d6) δ: 1.89-2.04 (m, 4H), 2.55 (s, 3H), 3.49-3.51 (m, 2H), 3.67-3.76 (m, 3H), 6.67 (d, J = 8.6 Hz, 2H), 7.42 (d, J = 8.6 Hz, 1H), 7.53 (m, 3H), 7.82 (brs, 1H), 7.91 (s, 1H). |

TABLE 38

| No. | Structure | NMR (δ) | retention time | Mass (M + H) | method |
|---|---|---|---|---|---|
| C-37 | 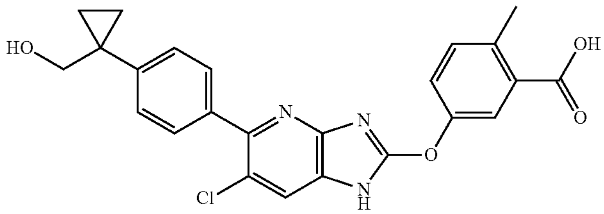 [SMILES: Cc1ccc(Oc2nc3nc(-c4ccc(C5(CO)CC5)cc4)c(Cl)cc3[nH]2)cc1C(=O)O] | 1H-NMR (DMSO-d6) δ: 0.79-0.81 (m, 2H), 0.87-0.90 (m, 2H), 2.55 (s, 3H), 3.65 (s, 2H), 7.37-7.42 (m, 3H), 7.50-7.57 (m, 3H), 7.81 (d, J = 4.0 Hz, 1H), 7.96 (s, 1H) | | | |
| C-38 | 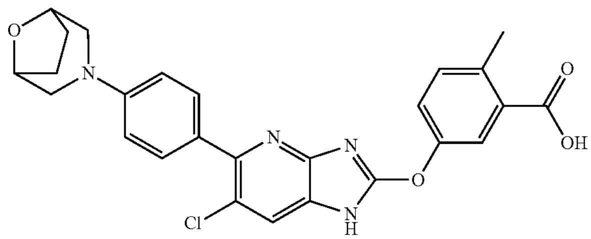 [SMILES: Cc1ccc(Oc2nc3nc(-c4ccc(N5CC6CCC(C5)O6)cc4)c(Cl)cc3[nH]2)cc1C(=O)O] | (DMSO-d6) δ: 1.85 (s, 4H), 2.56 (s, 3H), 2.87 (dd, J = 11.0, 2.3 Hz, 2H), 3.48 (d, J = 11.0 Hz, 2H), 4.45 (brs, 2H), 6.91 (d, J = 8.6 Hz, 2H), 7.42 (d, J = 8.6 Hz, 1H), 7.51-7.55 (m, 3H), 7.82 (d, J = 2.3 Hz, 1H), 7.92 (s, 1H). | | | |
| C-39 | 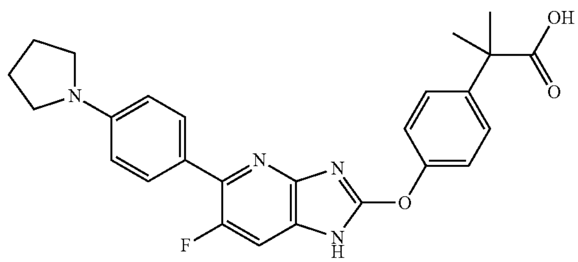 [SMILES: CC(C)(C(=O)O)c1ccc(Oc2nc3nc(-c4ccc(N5CCCC5)cc4)c(F)cc3[nH]2)cc1] | 1H-NMR (DMSO-d6) δ: 1.51 (s, 6H), 1.98 (t, J = 4.39 Hz, 4H), 3.29 (t, J = 4.39 Hz, 4H), 6.63 (d, J = 9.12 Hz, 2H), 7.37 (d, J = 8.62 Hz, 2H), 7.44 (d, J = 8.62 Hz, 2H), 7.71 (d, J = 12.17 Hz, 1H), 7.76 (d, J = 9.12 Hz, 2H), 12.43 (s, 1H), 13.09 (s, 1H). | | | |
| C-40 | 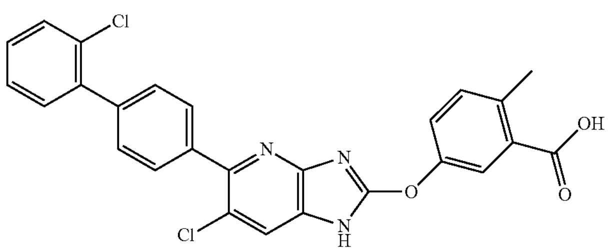 | | 2.52 | 490.05 | A |
| C-41 | 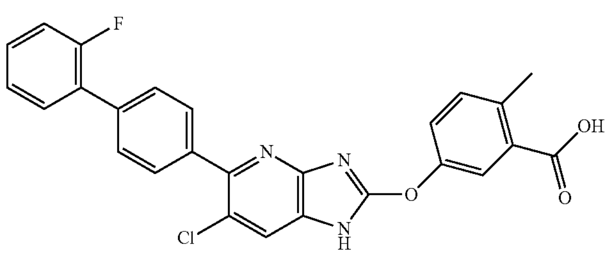 [SMILES: Cc1ccc(Oc2nc3nc(-c4ccc(-c5ccccc5Cl)cc4)c(Cl)cc3[nH]2)cc1C(=O)O] | | 2.41 | 474.08 | A |
| C-42 | 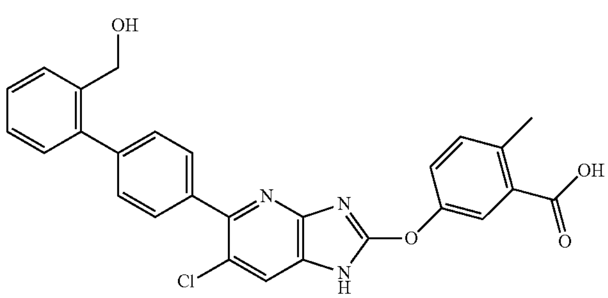 [SMILES: Cc1ccc(Oc2nc3nc(-c4ccc(-c5ccccc5CO)cc4)c(Cl)cc3[nH]2)cc1C(=O)O] | | 2.02 | 486.10 | A |

TABLE 39

| No | Structure | retention time | Mass (M + 1) | method |
|---|---|---|---|---|
| C-43 | 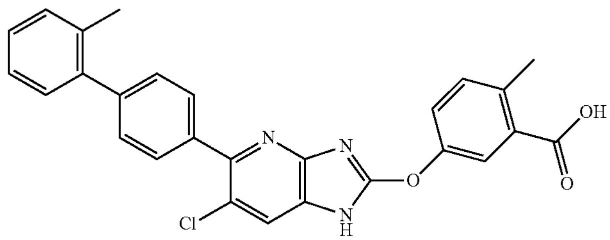 [SMILES: Cc1ccc(Oc2nc3nc(-c4ccc(-c5ccccc5C)cc4)c(Cl)cc3[nH]2)cc1C(=O)O] | 2.55 | 470.11 | A |
| C-44 | 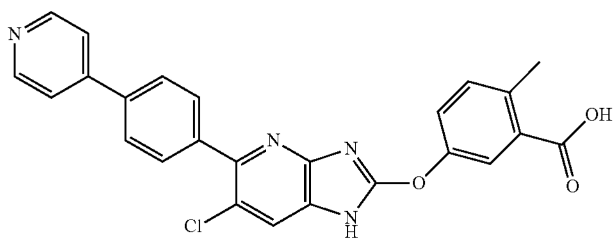 [SMILES: Cc1ccc(Oc2nc3nc(-c4ccc(-c5ccncc5)cc4)c(Cl)cc3[nH]2)cc1C(=O)O] | 1.37 | 457.09 | A |
| C-45 | 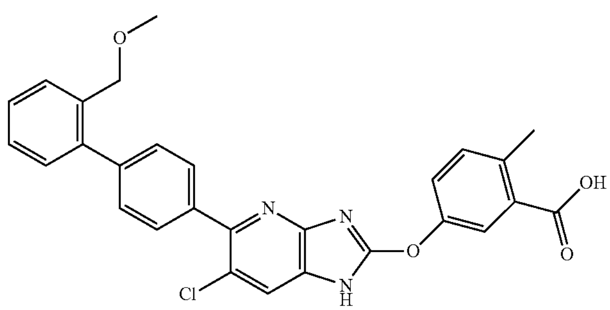 [SMILES: COCc1ccccc1-c1ccc(-c2nc3nc(Oc4ccc(C)c(C(=O)O)c4)[nH]c3cc2Cl)cc1] | 2.38 | 500.12 | A |
| C-46 | 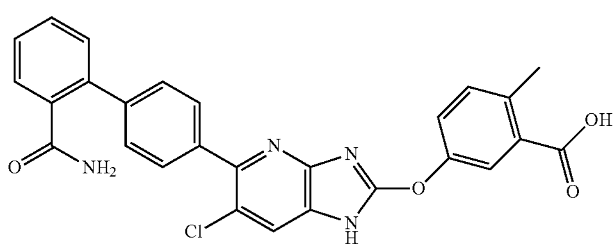 [SMILES: Cc1ccc(Oc2nc3nc(-c4ccc(-c5ccccc5C(N)=O)cc4)c(Cl)cc3[nH]2)cc1C(=O)O] | 1.75 | 499.10 | A |
| C-47 | 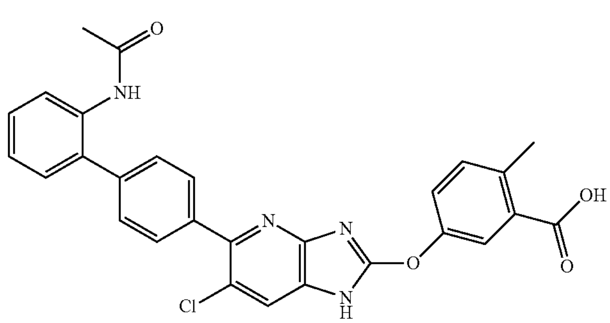 [SMILES: CC(=O)Nc1ccccc1-c1ccc(-c2nc3nc(Oc4ccc(C)c(C(=O)O)c4)[nH]c3cc2Cl)cc1] | 1.89 | 513.12 | A |

TABLE 39-continued

| No | Structure | retention time | Mass (M + 1) | method |
|---|---|---|---|---|
| C-48 | 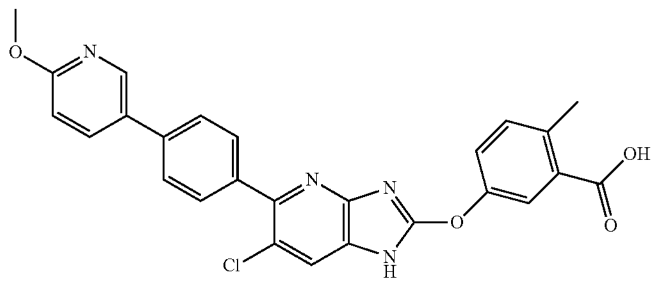 [SMILES: COc1ccc(-c2ccc(-c3nc4nc(Oc5ccc(C)c(C(=O)O)c5)[nH]c4cc3Cl)cc2)cn1] | 2.2 | 487.10 | A |

TABLE 40

| No. | Structure | retention time | Mass (M + H) | method |
|---|---|---|---|---|
| C-49 | 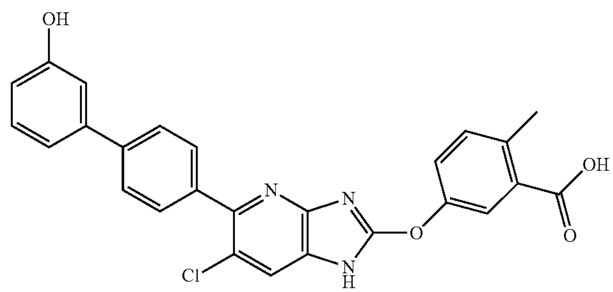 [SMILES: Cc1ccc(Oc2nc3nc(-c4ccc(-c5cccc(O)c5)cc4)c(Cl)cc3[nH]2)cc1C(=O)O] | 2.01 | 472.09 | A |
| C-50 | 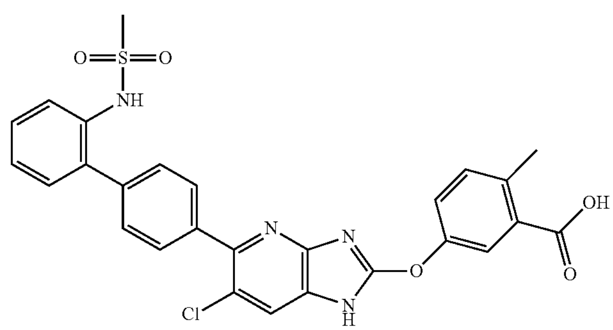 [SMILES: Cc1ccc(Oc2nc3nc(-c4ccc(-c5ccccc5NS(C)(=O)=O)cc4)c(Cl)cc3[nH]2)cc1C(=O)O] | 2.03 | 549.08 | A |
| C-51 | 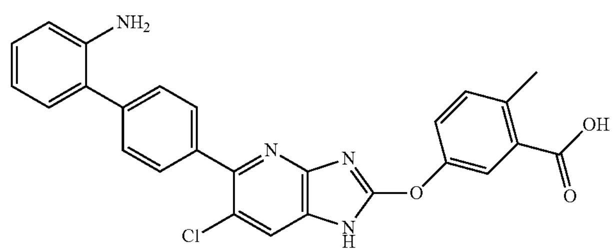 [SMILES: Cc1ccc(Oc2nc3nc(-c4ccc(-c5ccccc5N)cc4)c(Cl)cc3[nH]2)cc1C(=O)O] | 2.02 | 471.10 | A |
| C-52 | 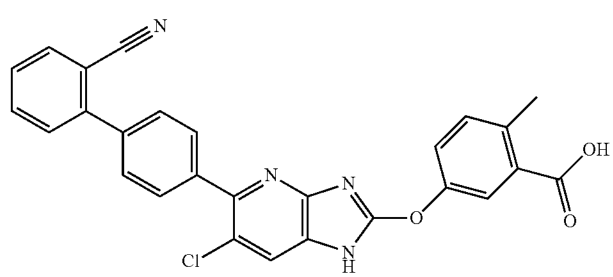 [SMILES: Cc1ccc(Oc2nc3nc(-c4ccc(-c5ccccc5C#N)cc4)c(Cl)cc3[nH]2)cc1C(=O)O] | 2.22 | 481.09 | A |

TABLE 40-continued

| No. | Structure | retention time | Mass (M + H) | method |
|---|---|---|---|---|
| C-53 | 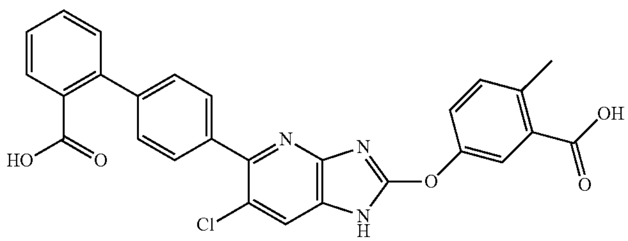 [SMILES: Cc1ccc(Oc2nc3nc(-c4ccc(-c5ccccc5C(=O)O)cc4)c(Cl)cc3[nH]2)cc1C(=O)O] | 2 | 500.08 | A |
| C-54 | 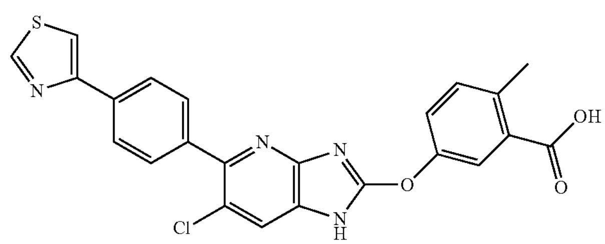 [SMILES: Cc1ccc(Oc2nc3nc(-c4ccc(-c5cscn5)cc4)c(Cl)cc3[nH]2)cc1C(=O)O] | 1.97 | 463.05 | A |

TABLE 41

| No. | Structure | retention time | Mass (M + H) | method |
|---|---|---|---|---|
| C-55 | 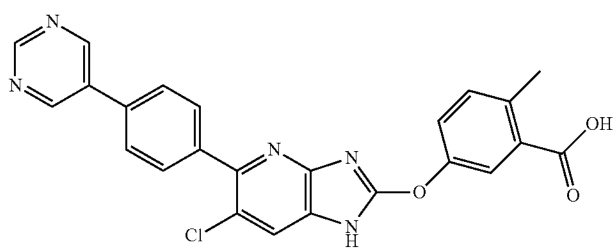 [SMILES: Cc1ccc(Oc2nc3nc(-c4ccc(-c5cncnc5)cc4)c(Cl)cc3[nH]2)cc1C(=O)O] | 1.7 | 458.08 | A |
| C-56 | 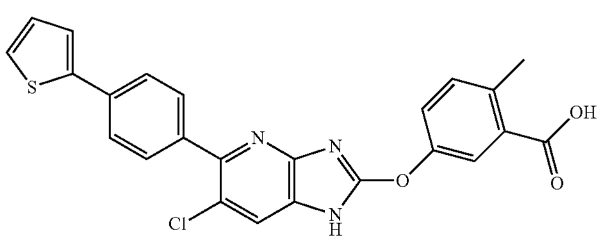 [SMILES: Cc1ccc(Oc2nc3nc(-c4ccc(-c5cccs5)cc4)c(Cl)cc3[nH]2)cc1C(=O)O] | 2.38 | 462.05 | A |
| C-57 | 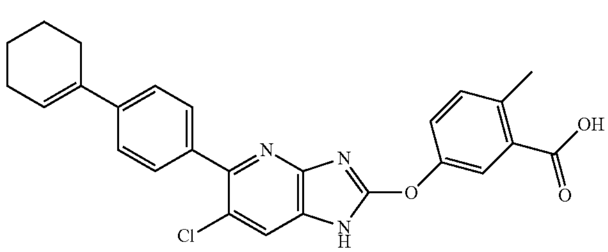 [SMILES: Cc1ccc(Oc2nc3nc(-c4ccc(C5=CCCCC5)cc4)c(Cl)cc3[nH]2)cc1C(=O)O] | 1.35 | 461.12 | A |

TABLE 41-continued

| No. | Structure | retention time | Mass (M + H) | method |
|---|---|---|---|---|
| C-58 | 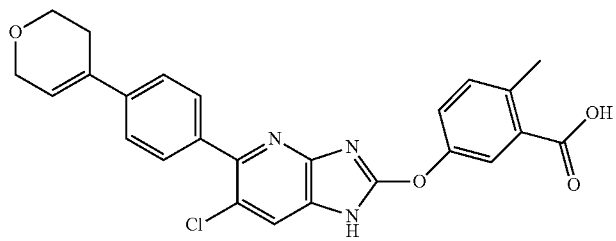 [SMILES: Cc1ccc(Oc2nc3nc(-c4ccc(C5=CCOCC5)cc4)c(Cl)cc3[nH]2)cc1C(=O)O] | 2.03 | 462.10 | A |
| C-59 | 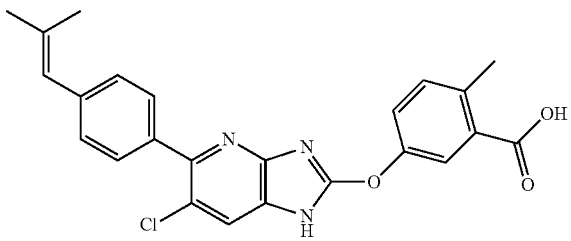 [SMILES: CC(C)=Cc1ccc(-c2nc3nc(Oc4ccc(C)c(C(=O)O)c4)[nH]c3cc2Cl)cc1] | 2.47 | 434.11 | A |
| C-60 | 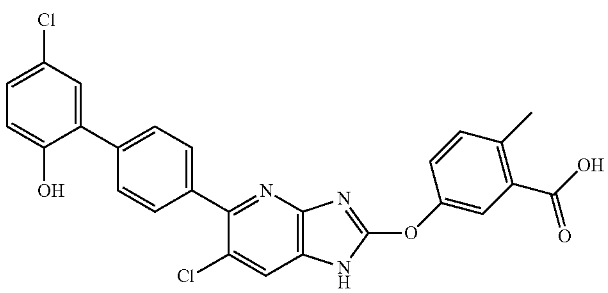 [SMILES: Cc1ccc(Oc2nc3nc(-c4ccc(-c5cc(Cl)ccc5O)cc4)c(Cl)cc3[nH]2)cc1C(=O)O] | 2.27 | 506.05 | A |

TABLE 42

| No. | Structure | NMR (δ) | retention time | Mass (M + H) | method |
|---|---|---|---|---|---|
| C-61 | 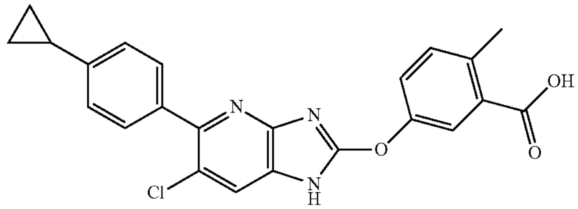 [SMILES: Cc1ccc(Oc2nc3nc(-c4ccc(C5CC5)cc4)c(Cl)cc3[nH]2)cc1C(=O)O] | | 2.25 | 420.09 | A |
| C-62 | 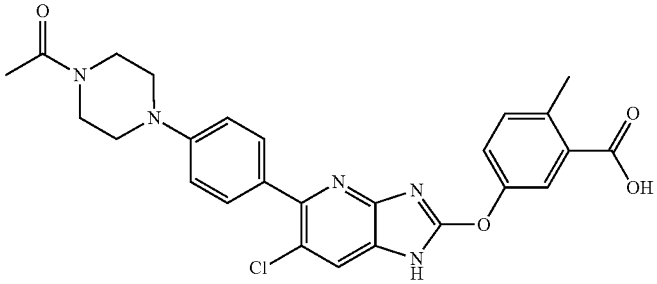 [SMILES: CC(=O)N1CCN(c2ccc(-c3nc4nc(Oc5ccc(C)c(C(=O)O)c5)[nH]c4cc3Cl)cc2)CC1] | | 1.64 | 506.12 | A |

TABLE 42-continued

| No. | Structure | NMR (δ) | retention time | Mass (M + H) | method |
|---|---|---|---|---|---|
| C-63 | 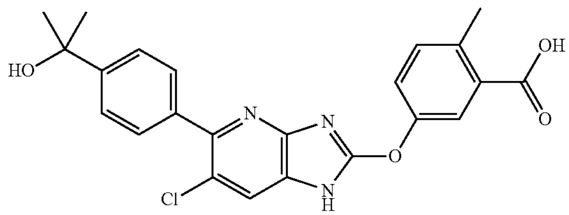 [SMILES: Cc1ccc(Oc2nc3nc(-c4ccc(C(C)(C)O)cc4)c(Cl)cc3[nH]2)cc1C(=O)O] | 1H-NMR (DMSO-d6) δ: 1.48 (s, 6H), 2.56 (s, 3H), 7.43 (d, J = 8.6 Hz, 1H), 7.54-7.60 (m, 5H), 7.84 (s, 1H), 7.98 (s, 1H) | | | |
| C-64 | 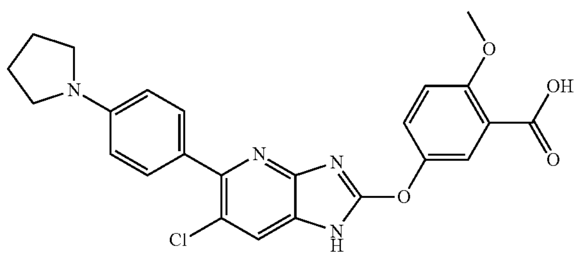 [SMILES: COc1ccc(Oc2nc3nc(-c4ccc(N5CCCC5)cc4)c(Cl)cc3[nH]2)cc1C(=O)O] | (DMSO-d6) δ: 1.98 (dd, J = 6.3, 6.3 Hz, 4H), 3.29 (dd, J = 6.3, 6.3 Hz, 4H), 3.86 (s, 3H), 6.60 (d, J = 8.6 Hz, 2H), 7.22 (d, J = 9.1 Hz, 1H), 7.53 (d, J = 8.6 Hz, 2H), 7.57 (dd, J = 9.1, 3.0 Hz, 1H), 7.66 (d, J = 3.0 Hz, 1H), 7.89 (s, 1H). | | | |
| C-65 | 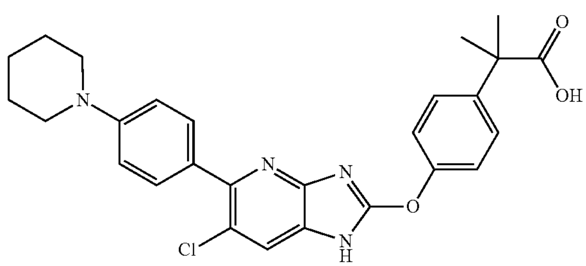 [SMILES: CC(C)(C(=O)O)c1ccc(Oc2nc3nc(-c4ccc(N5CCCCC5)cc4)c(Cl)cc3[nH]2)cc1] | (DMSO-d6) δ: 1.52 (s, 6H), 1.57-1.63 (m, 6H), 3.22-3.25 (m, 4H), 6.99 (d, J = 8.4 Hz, 2H), 7.38 (d, J = 8.8 Hz, 2H), 7.45 (d, J = 8.4 Hz, 2H), 7.54 (d, J = 8.8 Hz, 2H), 7.91 (s, 1H). | | | |
| C-66 | 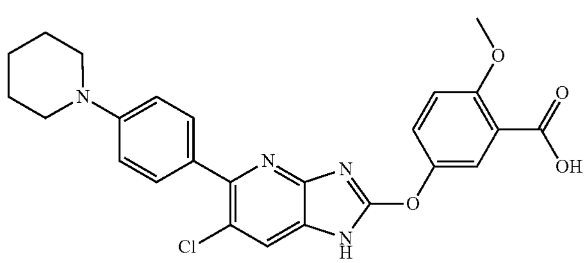 [SMILES: COc1ccc(Oc2nc3nc(-c4ccc(N5CCCCC5)cc4)c(Cl)cc3[nH]2)cc1C(=O)O] | (DMSO-d6) δ: 1.57-1.63 (m, 6H), 3.22-3.25 (m, 4H), 3.86 (s, 3H), 6.99 (d, J = 8.0 Hz, 2H), 7.23 (d, J = 9.2 Hz, 1H), 7.53-7.57 (m, 3H), 7.67 (s, 1H), 7.92 (s, 1H). | | | |

TABLE 43

| No. | Structure | NMR(δ) |
|---|---|---|
| C-67 | 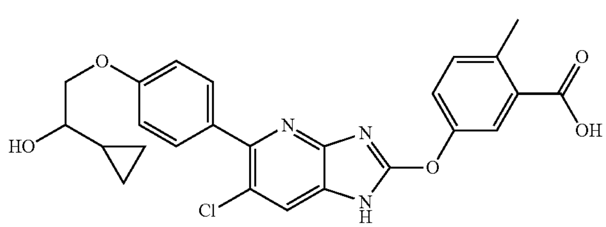 [SMILES: Cc1ccc(Oc2nc3nc(-c4ccc(OCC(O)C5CC5)cc4)c(Cl)cc3[nH]2)cc1C(=O)O] | (DMSO-d6) δ: 0.30-0.34 (m, 2H), 0.39-0.44 (m, 2H), 2.55 (s, 3H), 3.94-4.05 (m, 2H), 4.90-4.92 (m, 1H), 7.03 (d, J = 8.6 Hz, 2H), 7.42 (d, J = 8.6 Hz, 1H), 7.53 (dd, J = 8.6, 2.5 Hz, 1H), 7.59 (d, J = 8.6 Hz, 2H), 7.82 (d, J = 2.5 Hz, 1H), 7.95 (s, 1H). |

TABLE 43-continued

| No. | Structure | NMR(δ) |
|---|---|---|
| C-68 | 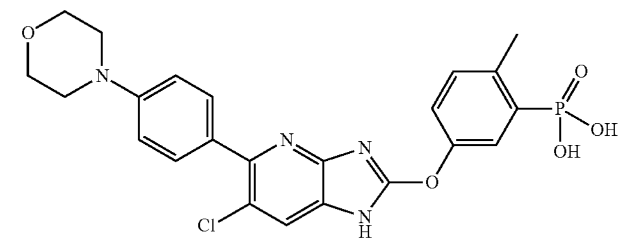 [SMILES: Cc1ccc(Oc2nc3nc(-c4ccc(N5CCOCC5)cc4)c(Cl)cc3[nH]2)cc1P(=O)(O)O] | (DMSO-d6) δ: 2.56 (s, 3H), 3.19 (dd, J = 5.2, 4.4 Hz, 4H), 3.76 (dd, J = 5.2, 4.4 Hz, 4H), 7.02 (d, J = 8.6 Hz, 2H), 7.36-7.39 (m, 1H), 7.45-7.48 (m, 1H), 7.57 (d, J = 8.6 Hz, 2H), 7.67-7.71 (m, 1H), 7.92 (s, 1H). |
| C-69 | 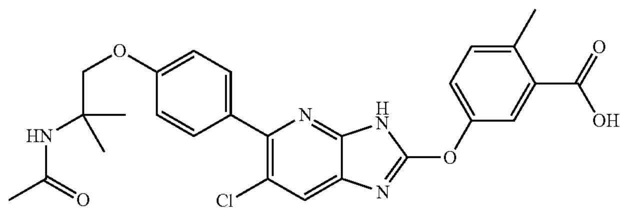 [SMILES: CC(=O)NC(C)(C)COc1ccc(-c2nc3[nH]c(Oc4ccc(C)c(C(=O)O)c4)nc3cc2Cl)cc1] | (DMSO-d6) δ: 1.35 (s, 6H), 1.79 (s, 3H), 2.56 (s, 3H), 4.11 (s, 2H), 7.01 (d, J = 8.6 Hz, 2H), 7.42 (d, J = 8.1 Hz, 1H), 7.54 (dd, J = 8.1, 2.5 Hz, 1H), 7.59 (d, J = 8.6 Hz, 2H), 7.62 (s, 1H), 7.83 (d, J = 2.5 Hz, 1H), 7.96 (s, 1H). |
| C-70 | 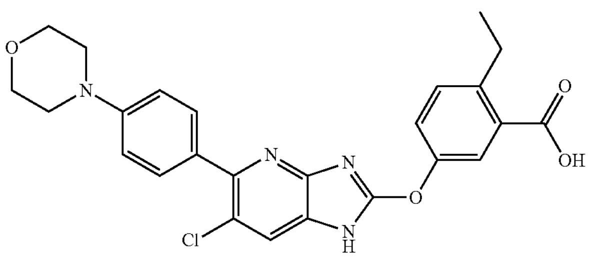 | (DMSO-d6) δ: 1.20 (t, J = 7.9 Hz, 3H), 2.96 (q, J = 7.9 Hz, 2H), 3.19 (dd, J = 5.2, 4.4 Hz, 4H), 3.76 (t, J = 5.2, 4.4 Hz, 4H), 7.02 (d, J = 9.1 Hz, 2H), 7.44 (d, J = 8.1 Hz, 1H), 7.54-7.58 (m, 3H), 7.78 (d, J = 2.5 Hz, 1H), 7.94 (s, 1H). |
| C-71 | 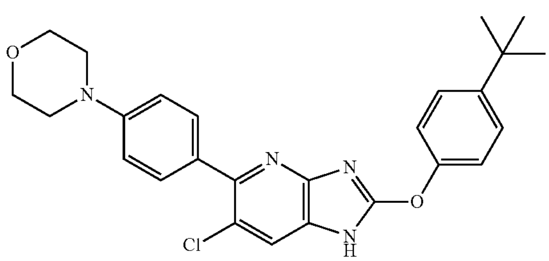 [SMILES: CC(C)(C)c1ccc(Oc2nc3nc(-c4ccc(N5CCOCC5)cc4)c(Cl)cc3[nH]2)cc1] | 1H-NMR (DMSO-d6) δ: 1.32(s, 9H), 3.18-3.20 (m, 4H), 3.75-3.77 (m, 4H), 7.02 (d, J = 8.6 Hz, 2H), 7.32 (d, J = 8.6 Hz, 2H), 7.49 (d, J = 8.6 Hz, 2H), 7.56 (d, J = 8.6 Hz, 2H), 7.89 (s, 1H) |
| C-72 | 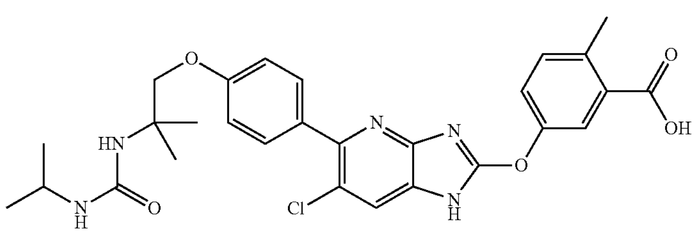 [SMILES: Cc1ccc(Oc2nc3nc(-c4ccc(OCC(C)(C)NC(=O)NC(C)C)cc4)c(Cl)cc3[nH]2)cc1C(=O)O] | (DMSO-d6) δ: 0.99 (d, J = 6.1 Hz, 6H), 1.33 (s, 6H), 2.54 (s, 3H), 3.62 (sept, J = 6.1 Hz, 1H), 4.06 (s, 2H), 5.66-5.68 (m, 2H), 7.02 (d, J = 8.6 Hz, 2H), 7.40 (d, J = 8.6 Hz, 1H), 7.50 (dd, J = 8.6, 2.5 Hz, 1H), 7.58 (d, J = 8.6 Hz, 2H), 7.79 (d, J = 2.5 Hz, 1H), 7.93 (s, 1H). |

TABLE 44

| No. | Structure | NMR(δ) | retention time | Mass (M + H) | method |
|---|---|---|---|---|---|
| C-73 | 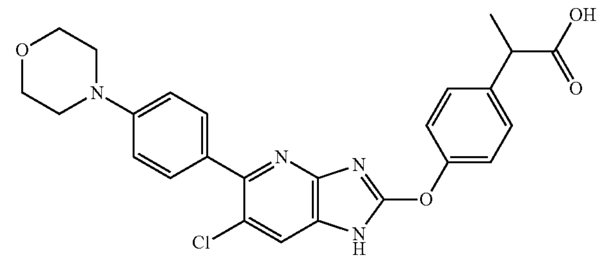 [SMILES: CC(C(=O)O)c1ccc(Oc2nc3nc(-c4ccc(N5CCOCC5)cc4)c(Cl)cc3[nH]2)cc1] | 1H-NMR (DMSO-d6) δ: 1.40 (d, J = 8.6 Hz, 3H), 3.18-3.20 (m, 4H), 3.72-3.78 (m, 5H), 7.02 (d, J = 8.6 Hz, 2H), 7.36-7.41 (m, 4H), 7.56 (d, J = 8.6 Hz, 2H), 7.92 (s, 1H) | | | |
| C-74 | 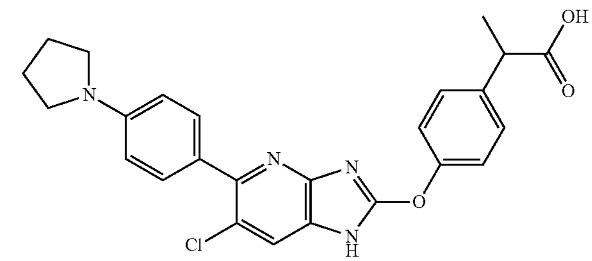 [SMILES: CC(C(=O)O)c1ccc(Oc2nc3nc(-c4ccc(N5CCCC5)cc4)c(Cl)cc3[nH]2)cc1] | 1H-NMR (DMSO-d6) δ: 1.40 (d, J = 8.6 Hz, 3H), 1.96-1.99 (m, 4H), 3.26-3.30 (m, 4H), 3.75 (q, J = 8.6 Hz, 1H), 6.60 (d, J = 8.6 Hz, 2H), 7.35-7.42 (m, 4H), 7.53 (d, J = 8.6 Hz, 2H), 7.88 (s, 1H) | | | |
| C-75 | 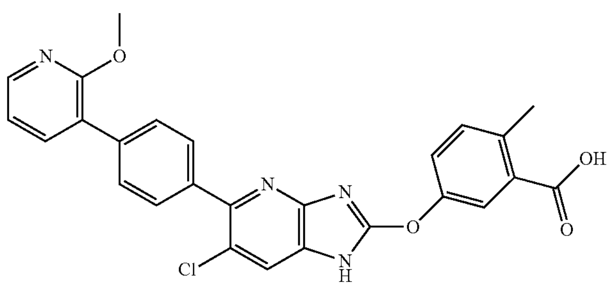 [SMILES: COc1ncccc1-c1ccc(-c2nc3nc(Oc4ccc(C)c(C(=O)O)c4)[nH]c3cc2Cl)cc1] | | 2.18 | 487.11 | A |
| C-76 | 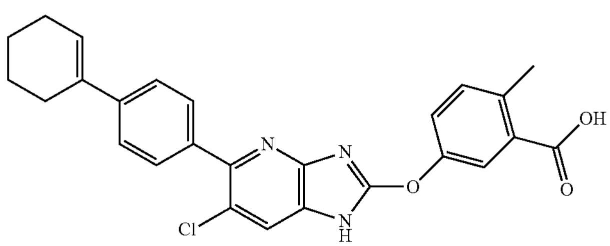 [SMILES: Cc1ccc(Oc2nc3nc(-c4ccc(C5=CCCCC5)cc4)c(Cl)cc3[nH]2)cc1C(=O)O] | | 2.68 | 460.14 | A |
| C-77 | 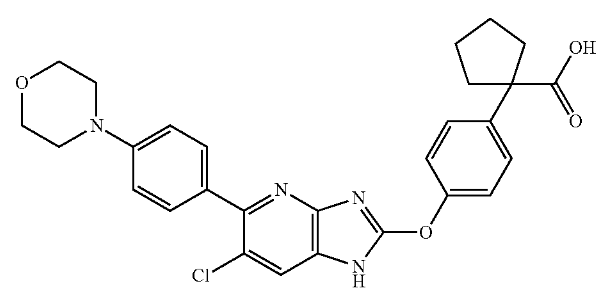 [SMILES: O=C(O)C1(c2ccc(Oc3nc4nc(-c5ccc(N6CCOCC6)cc5)c(Cl)cc4[nH]3)cc2)CCCC1] | 1H-NMR (DMSO-d6) δ: 1.61-1.75 (m, 4H), 1.78-1.88 (m, 2H), 2.53-2.58 (m, 2H), 3.17-3.20 (m, 4H), 3.75-3.77 (m, 4H), 7.02 (d, J = 8.6 Hz, 2H), 7.36 (d, J = 8.6 Hz, 2H), 7.44 (d, J = 8.6 Hz, 2H), 7.56 (d, J = 8.6 Hz, 2H), 7.90 (s, 1H) | | | |
| C-78 | 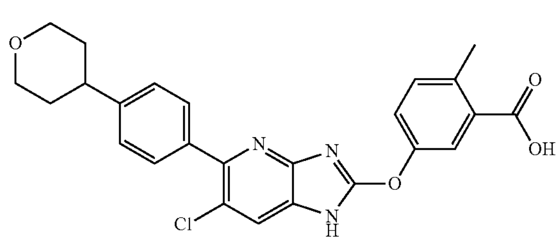 [SMILES: Cc1ccc(Oc2nc3nc(-c4ccc(C5CCOCC5)cc4)c(Cl)cc3[nH]2)cc1C(=O)O] | (DMSO-d6) δ: 1.68-1.77 (m, 4H), 2.55 (s, 3H), 2.81-2.87 (m, 1H), 3.43-3.49 (m, 2H), 3.95-3.99 (m, 2H), 7.36 (d, J = 8.1 Hz, 2H), 7.40 (d, J = 8.1 Hz, 1H), 7.51 (dd, J = 8.1, 2.5 Hz, 1H), 7.59 (d, J = 8.1 Hz, 2H), 7.80 (d, J = 2.5 Hz, 1H), 7.95 (s, 1H). | | | |

TABLE 45

| No. | Structure | retention time | Mass (M + H) | method |
|---|---|---|---|---|
| C-79 | 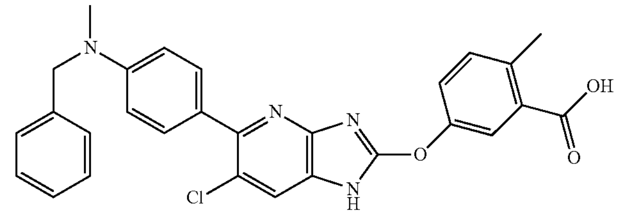 [SMILES: Cc1ccc(Oc2nc3nc(-c4ccc(N(C)Cc5ccccc5)cc4)c(Cl)cc3[nH]2)cc1C(=O)O] | 2.44 | 499.12 | A |
| C-80 | 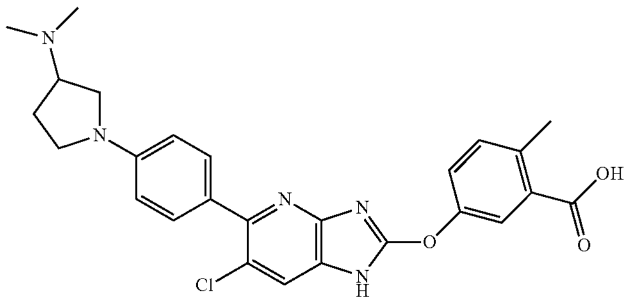 [SMILES: Cc1ccc(Oc2nc3nc(-c4ccc(N5CCC(N(C)C)C5)cc4)c(Cl)cc3[nH]2)cc1C(=O)O] | 1.37 | 492.16 | A |
| C-81 | 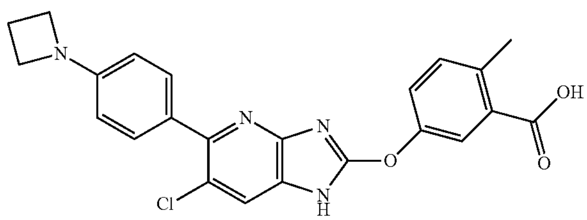 [SMILES: Cc1ccc(Oc2nc3nc(-c4ccc(N5CCC5)cc4)c(Cl)cc3[nH]2)cc1C(=O)O] | 1.97 | 435.09 | A |
| C-82 | 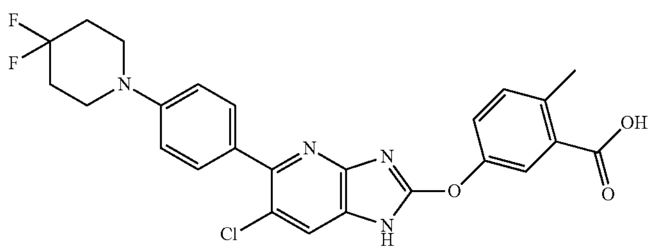 [SMILES: Cc1ccc(Oc2nc3nc(-c4ccc(N5CCC(F)(F)CC5)cc4)c(Cl)cc3[nH]2)cc1C(=O)O] | 2.23 | 499.11 | A |
| C-83 | 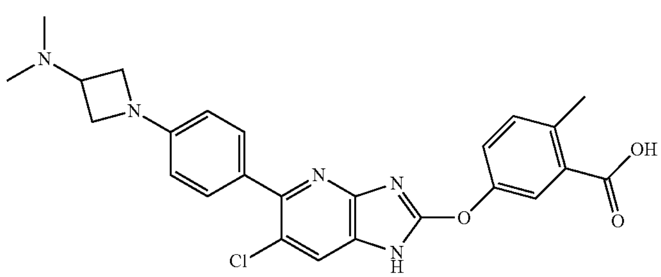 [SMILES: Cc1ccc(Oc2nc3nc(-c4ccc(N5CC(N(C)C)C5)cc4)c(Cl)cc3[nH]2)cc1C(=O)O] | 1.31 | 478.16 | A |
| C-84 | 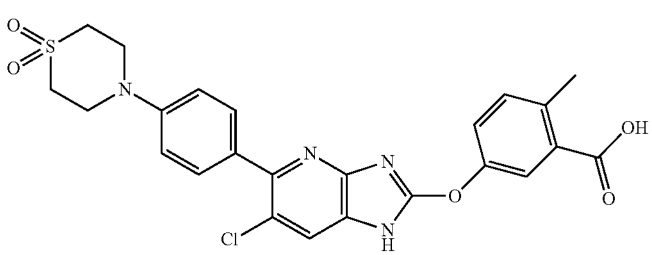 [SMILES: Cc1ccc(Oc2nc3nc(-c4ccc(N5CCS(=O)(=O)CC5)cc4)c(Cl)cc3[nH]2)cc1C(=O)O] | 1.7 | 513.07 | A |

TABLE 46

| No. | Structure | NMR(δ) | retention time | Mass (M + H) | method |
|---|---|---|---|---|---|
| C-85 | 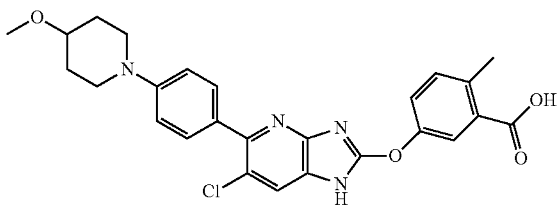 [SMILES: COC1CCN(c2ccc(-c3nc4nc(Oc5ccc(C)c(C(=O)O)c5)[nH]c4cc3Cl)cc2)CC1] | | 1.65 | 493.15 | A |
| C-86 | 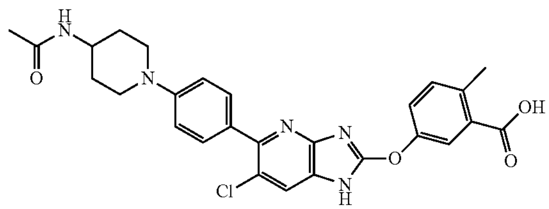 [SMILES: CC(=O)NC1CCN(c2ccc(-c3nc4nc(Oc5ccc(C)c(C(=O)O)c5)[nH]c4cc3Cl)cc2)CC1] | (DMSO-d6) δ: 1.42-1.51 (m, 2H), 1.79-1.83 (m, 5H), 2.55 (s, 3H), 2.85-2.91 (m, 1H), 3.73-3.78 (m, 4H), 7.01 (d, J = 8.1 Hz, 2H), 7.42 (d, J = 8.1 Hz, 1H), 7.51-7.55 (m, 3H), 7.81-7.85 (m, 2H), 7.93 (d, J = 8.1 Hz, 1H). | | | |
| C-87 | 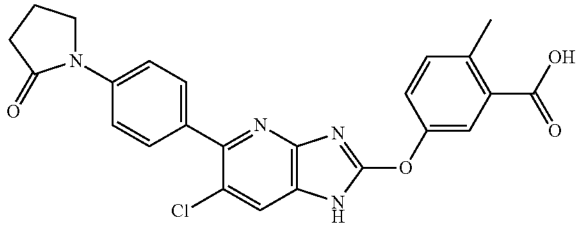 [SMILES: Cc1ccc(Oc2nc3nc(-c4ccc(N5CCCC5=O)cc4)c(Cl)cc3[nH]2)cc1C(=O)O] | 1H-NMR (DMSO-d6) δ: 2.06-2.13 (m, 2H), 2.56 (s, 3H), 3.41-4.52 (m, 2H), 3.90 (t, J = 8.6 Hz, 2H), 7.43 (d, J = 8.6 Hz, 1H), 7.54 (dd, J = 4.0, 8.6 Hz, 1H), 7.67 (d, J = 8.6 Hz, 2H), 7.77 (d, J = 8.6 Hz, 2H), 7.83 (d, J = 4.0 Hz, 1H), 7.98 (s, 1H) | | | |
| C-88 | 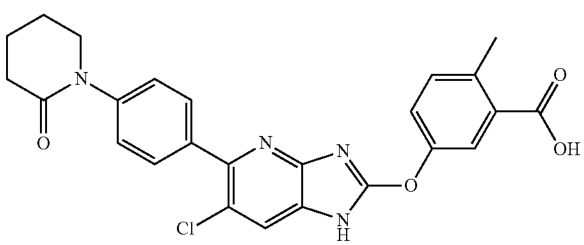 [SMILES: Cc1ccc(Oc2nc3nc(-c4ccc(N5CCCCC5=O)cc4)c(Cl)cc3[nH]2)cc1C(=O)O] | (DMSO-d6) δ: 1.85-1.91 (m, 4H), 2.43 (dd, J = 6.1, 6.1 Hz, 2H), 2.56 (s, 3H), 3.67 (dd, J = 5.6, 5.6 Hz, 2H), 7.37-7.44 (m, 3H), 7.54 (d, J = 8.6 Hz, 1H), 7.67 (d, J = 8.6 Hz, 2H), 7.83 (brs, 1H), 8.01 (s, 1H). | | | |
| C-89 | 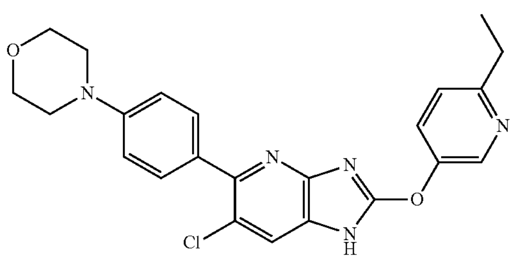 [SMILES: CCc1ccc(Oc2nc3nc(-c4ccc(N5CCOCC5)cc4)c(Cl)cc3[nH]2)cn1] | 1H-NMR (DMSO-d6) δ: 1.26 (t, J = 8.6 Hz, 3H), 2.81 (q, J = 8.6 Hz, 2H), 3.18-3.20 (m, 4H), 3.75-3.77 (m, 4H), 7.02 (d, J = 8.6 Hz, 2H), 7.41 (d, J = 8.6 Hz, 1H), 7.57 (d, J = 8.6 Hz, 2H), 7.86 (dd, J = 4.0, 8.6 Hz, 1H), 7.94 (s, 1H) | | | |
| C-90 | 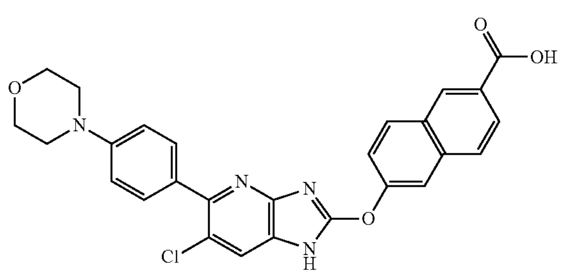 [SMILES: O=C(O)c1ccc2cc(Oc3nc4nc(-c5ccc(N6CCOCC6)cc5)c(Cl)cc4[nH]3)ccc2c1] | 1H-NMR (DMSO-d6) δ: 3.18-3.21 (m, 4H), 3.75-3.78 (m, 4H), 7.03 (d, J = 8.6 Hz, 2H), 7.58 (d, J = 8.6 Hz, 2H), 7.70 (dd, J = 4.0, 8.6 Hz, 1H), 7.96 (s, 1H), 8.04 (s, 2H), 8.08 (s, 1H), 8.26 (d, J = 8.6 Hz, 1H), 8.68 (s, 1H) | | | |

TABLE 47

| No. | Structure | NMR(δ) | retention time | Mass (M + H) | method |
|---|---|---|---|---|---|
| C-91 | 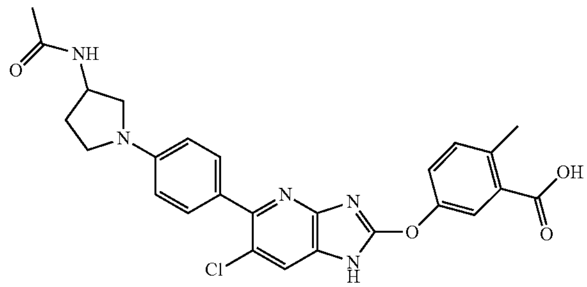 [SMILES: CC(=O)NC1CCN(c2ccc(-c3nc4nc(Oc5ccc(C)c(C(=O)O)c5)[nH]c4cc3Cl)cc2)C1] | | 1.68 | 506.12 | A |
| C-92 | 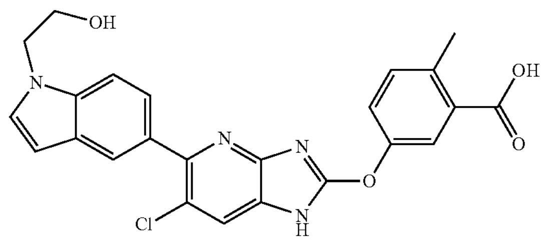 [SMILES: Cc1ccc(Oc2nc3nc(-c4ccc5c(ccn5CCO)c4)c(Cl)cc3[nH]2)cc1C(=O)O] | 1H-NMR (DMSO-d6) δ: 2.51 (s, 3H), 3.75 (t, J = 5.5 Hz, 2H), 4.25 (t, J = 5.5 Hz, 2H), 6.48 (d, J = 3.0 Hz, 1H), 7.25-7.34 (m, 2H), 7.39-7.42 (m, 2H), 7.52 (d, J = 8.6 Hz, 1H), 7.63 (s, 1H), 7.80 (s, 1H), 7.83(s, 1H). | | | |
| C-93 | 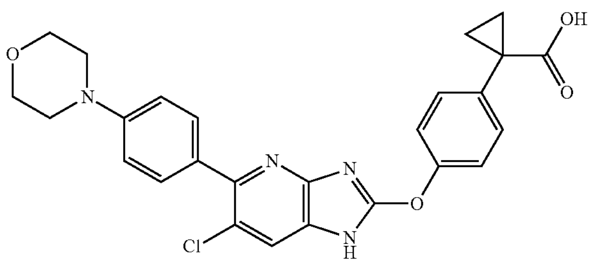 [SMILES: O=C(O)C1(c2ccc(Oc3nc4nc(-c5ccc(N6CCOCC6)cc5)c(Cl)cc4[nH]3)cc2)CC1] | 1H-NMR (DMSO-d6) δ: 1.17-1.20 (m, 2H), 1.47-1.49 (m, 2H), 3.17-3.20 (m, 4H), 3.75-3.78 (m, 4H), 7.02 (d, J = 8.6 Hz, 2H), 7.34 (d, J = 8.6 Hz, 2H), 7.43 (d, J = 8.6 Hz, 2H), 7.57 (d, J = 8.6 Hz, 2H), 7.93 (s, 1H) | | | |
| C-94 | 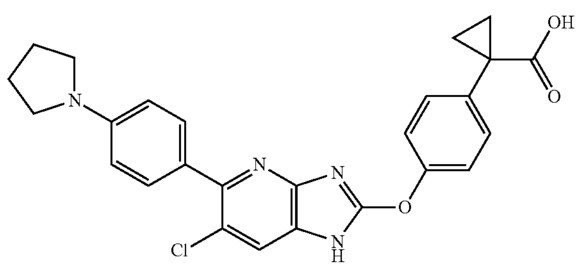 [SMILES: O=C(O)C1(c2ccc(Oc3nc4nc(-c5ccc(N6CCCC6)cc5)c(Cl)cc4[nH]3)cc2)CC1] | 1H-NMR (DMSO-d6) δ: 1.17-1.19 (m, 2H), 1.46-1.50 (m, 2H), 1.97-2.00 (m, 4H), 3.27-3.29 (m, 4H), 6.60 (d, J = 8.6 Hz, 2H), 7.33 (d, J = 8.6 Hz, 2H), 7.42 (d, J = 8.6 Hz, 2H), 7.53 (d, J = 8.6 Hz, 2H), 7.88 (s, 1H) | | | |
| C-95 | 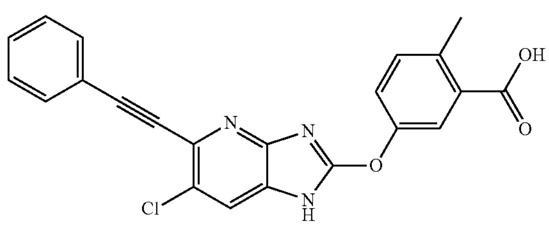 [SMILES: Cc1ccc(Oc2nc3nc(C#Cc4ccccc4)c(Cl)cc3[nH]2)cc1C(=O)O] | (DMSO-d6) δ: 2.56 (s, 3H), 7.42-7.48 (m, 4H), 7.54 (dd, J = 8.1, 2.5 Hz, 1H), 7.62 (dd, J = 6.6, 3.0 Hz, 2H), 7.84 (d, J = 3.0 Hz, 1H), 8.02 (s, 1H). | | | |
| C-96 | 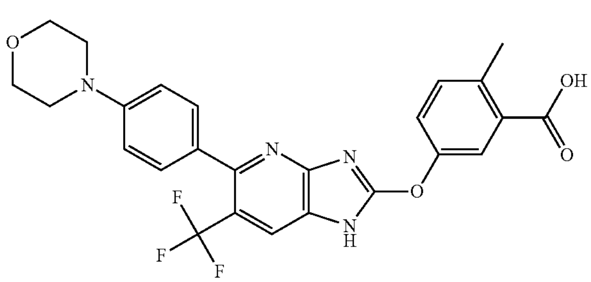 [SMILES: Cc1ccc(Oc2nc3nc(-c4ccc(N5CCOCC5)cc4)c(C(F)(F)F)cc3[nH]2)cc1C(=O)O] | 1H-NMR (DMSO-d6) δ: 2.56 (s, 3H), 3.19 (t, J = 4.82 Hz, 4H), 3.76 (t, J = 4.82 Hz, 4H), 7.01 (d, J = 8.62 Hz, 2H), 7.34 (d, J = 8.62 Hz, 2H), 7.44 (d, J = 8.62 Hz, 1H), 7.56 (dd, J = 8.62, 2.03 Hz, 1H), 7.85 (d, J = 2.03 Hz, 1H), 8.16 (br s, 1H), 13.13 (br s, 1H), 13.54 (br s, 1H). | | | |

TABLE 48

| No. | Structure | NMR(δ) | retention time | Mass (M + H) | method |
|---|---|---|---|---|---|
| C-97 | 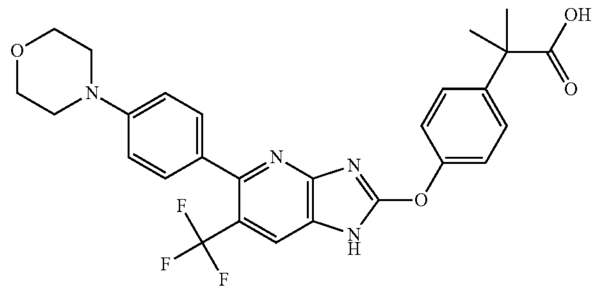 [SMILES: CC(C)(C(=O)O)c1ccc(Oc2nc3nc(-c4ccc(N5CCOCC5)cc4)c(C(F)(F)F)cc3[nH]2)cc1] | 1H-NMR (DMSO-d6) δ: 1.52 (s, 6H), 3.19 (t, J = 4.82 Hz, 4H), 3.76 (t, J = 4.82 Hz, 4H), 7.01 (d, J = 8.62 Hz, 2H), 7.34 (d, J = 8.62 Hz, 2H), 7.40 (d, J = 8.62 Hz, 2H), 7.46 (d, J = 8.62 Hz, 2H), 8.17 (br s, 1H), 12.45 (br s, 1H), 13.51 (br s, 1H). | | | |
| C-98 | 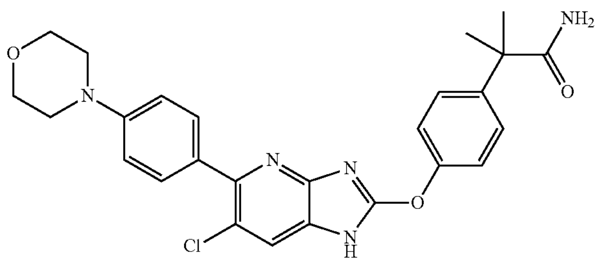 [SMILES: CC(C)(C(N)=O)c1ccc(Oc2nc3nc(-c4ccc(N5CCOCC5)cc4)c(Cl)cc3[nH]2)cc1] | (DMSO-d6) δ: 1.47 (s, 6H), 3.19 (dd, J = 5.2, 4.4 Hz, 4H), 3.76 (dd, J = 5.2, 4.4.8 Hz, 4H), 6.95 (s, 1H), 6.99 (s, 1H), 7.02 (d, J = 8.4 Hz, 2H), 7.36 (d, J = 9.1 Hz, 2H), 7.43 (d, J = 9.1 Hz, 2H), 7.56 (d, J = 8.4 Hz, 2H), 7.91 (s, 1H). | | | |
| C-99 | 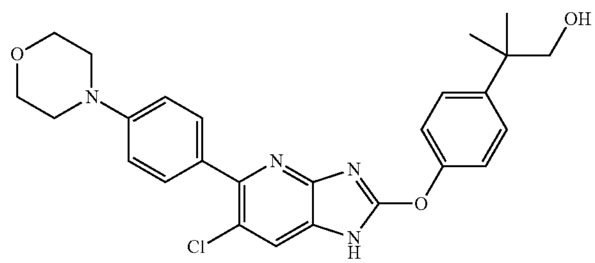 [SMILES: CC(C)(CO)c1ccc(Oc2nc3nc(-c4ccc(N5CCOCC5)cc4)c(Cl)cc3[nH]2)cc1] | (DMSO-d6) δ: 3.19 (dd, J = 5.2, 4.4 Hz, 4H), 3.76 (dd, J = 5.2, 4.4 Hz, 4H), 7.01 (d, J = 9.2 Hz, 2H), 7.22-7.27 (m, 1H), 7.44-7.46 (m, 1H), 7.57 (d, J = 9.2 Hz, 2H), 7.65-7.66 (m, 1H), 7.91 (s, 1H). | | | |
| C-100 | 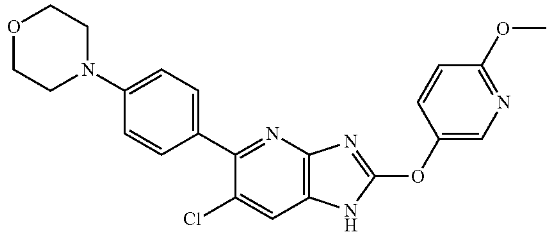 [SMILES: COc1ccc(Oc2nc3nc(-c4ccc(N5CCOCC5)cc4)c(Cl)cc3[nH]2)cn1] | 1H-NMR (DMSO-d6) δ: 3.18-3.21 (m, 4H), 3.75-3.78 (m, 4H), 3.89 (s, 3H), 6.96 (d, J = 8.6 Hz, 1H), 7.02 (d, J = 8.6 Hz, 2H), 7.57 (d, J = 8.6 Hz, 2H), 7.88 (dd, J = 4.0, 8.6 Hz, 1H), 7.93 (s, 1H), 8.30 (d, J = 4.0 Hz, 1H) | | | |
| C-101 | 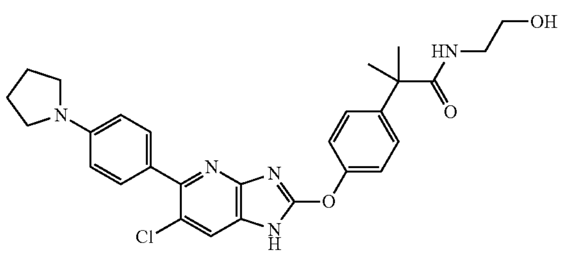 [SMILES: CC(C)(C(=O)NCCO)c1ccc(Oc2nc3nc(-c4ccc(N5CCCC5)cc4)c(Cl)cc3[nH]2)cc1] | | 2.08 | 520.19 | A |
| C-102 | 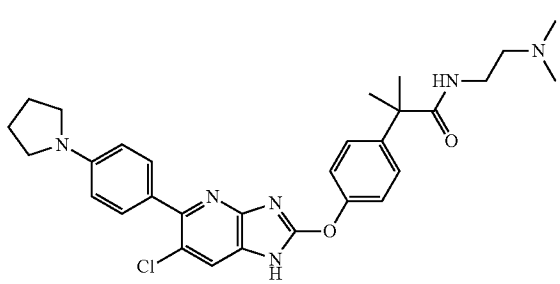 [SMILES: CN(C)CCNC(=O)C(C)(C)c1ccc(Oc2nc3nc(-c4ccc(N5CCCC5)cc4)c(Cl)cc3[nH]2)cc1] | | 1.84 | 547.23 | A |

TABLE 49

| No. | Structure | NMR(δ) | retention time | Mass (M + H) | method |
|---|---|---|---|---|---|
| C-103 | 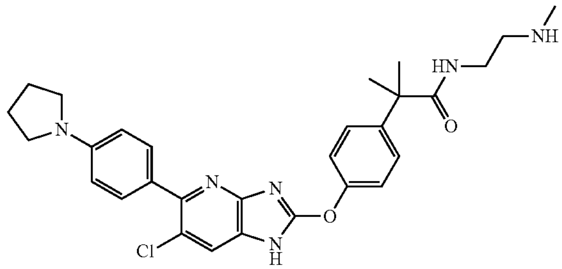 [SMILES: CNCCNC(=O)C(C)(C)c1ccc(Oc2nc3nc(-c4ccc(N5CCCC5)cc4)c(Cl)cc3[nH]2)cc1] | | 1.82 | 533.21 | A |
| C-104 | 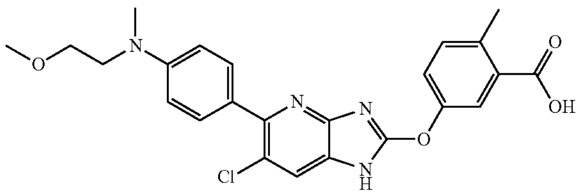 [SMILES: COCCN(C)c1ccc(-c2nc3nc(Oc4ccc(C)c(C(=O)O)c4)[nH]c3cc2Cl)cc1] | (DMSO-d6) δ: 2.55 (s, 3H), 2.98 (s, 3H), 3.27 (s, 3H), 3.52-3.56 (m, 4H), 6.77 (d, J = 8.6 Hz, 2H), 7.42 (d, J = 8.6 Hz, 1H), 7.51-7.54 (m, 3H), 7.82 (s, 1H), 7.91 (s, 1H). | | | |
| C-105 | 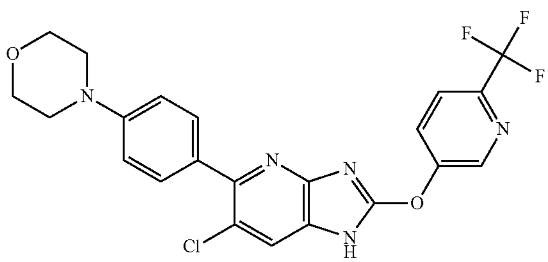 [SMILES: FC(F)(F)c1ccc(Oc2nc3nc(-c4ccc(N5CCOCC5)cc4)c(Cl)cc3[nH]2)cn1] | 1H-NMR (DMSO-d6) δ: 3.19-3.21 (m, 4H), 3.76-3.78 (m, 4H), 7.03 (d, J = 8.0 Hz, 2H), 7.58 (d, J = 8.6 Hz, 2H), 8.01 (s, 1H), 8.12 (d, J = 8.6 Hz, 1H), 8.33 (d, J = 4.0, 8.6 Hz, 1H), 8.97 (d, J = 4.0 Hz, 1H) | | | |
| C-106 | 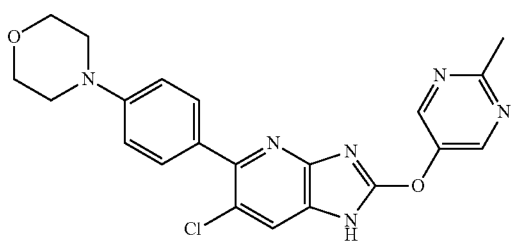 [SMILES: Cc1ncc(Oc2nc3nc(-c4ccc(N5CCOCC5)cc4)c(Cl)cc3[nH]2)cn1] | 1H-NMR (DMSO-d6) δ: 2.69 (s, 3H), 3.19-3.21 (m, 4H), 3.75-3.78 (m, 4H), 7.03 (d, J = 8.6 Hz, 2H), 7.58 (d, J = 8.6 Hz, 2H), 7.99 (s, 1H), 8.93 (s, 2H), 13.51 (s, 1H) | | | |
| C-107 | 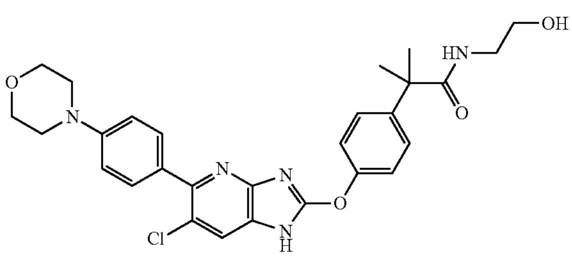 [SMILES: CC(C)(C(=O)NCCO)c1ccc(Oc2nc3nc(-c4ccc(N5CCOCC5)cc4)c(Cl)cc3[nH]2)cc1] | | 1.66 | 536.18 | A |
| C-108 | 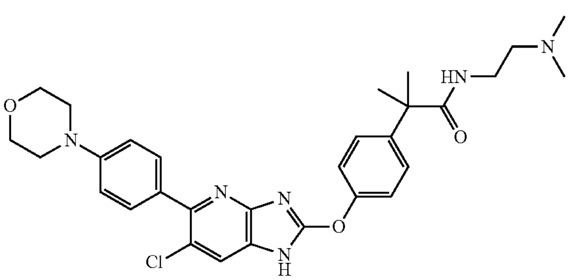 [SMILES: CN(C)CCNC(=O)C(C)(C)c1ccc(Oc2nc3nc(-c4ccc(N5CCOCC5)cc4)c(Cl)cc3[nH]2)cc1] | | 1.43 | 563.21 | A |

TABLE 50

| No. | Structure | NMR(δ) | retention time | Mass (M + H) | method |
|---|---|---|---|---|---|
| C-109 | 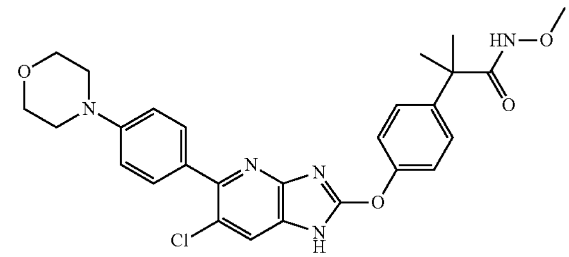 [SMILES: CONC(=O)C(C)(C)c1ccc(Oc2nc3nc(-c4ccc(N5CCOCC5)cc4)c(Cl)cc3[nH]2)cc1] | | 1.76 | 522.17 | A |
| C-110 | 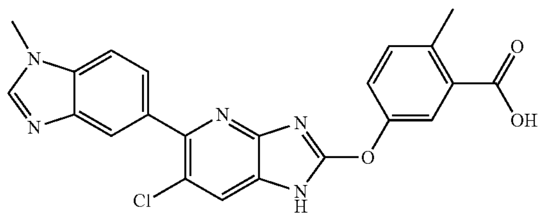 [SMILES: Cc1ccc(Oc2nc3nc(-c4ccc5c(c4)ncn5C)c(Cl)cc3[nH]2)cc1C(=O)O] | (DMSO-d6) δ: 2.56 (s, 3H), 3.89 (s, 3H), 7.43 (d, J = 8.6 Hz, 1H), 7.53-7.56 (d, 2H), 7.65 (d, J = 8.6 Hz, 1H), 7.84 (s, 1H), 7.88 (s, 1H), 7.99 (s, 1H), 8.25 (s, 1H). | | | |
| C-111 | 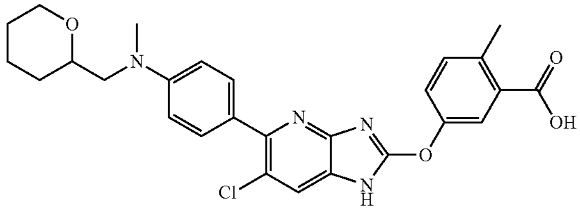 [SMILES: Cc1ccc(Oc2nc3nc(-c4ccc(N(C)CC5CCCCO5)cc4)c(Cl)cc3[nH]2)cc1C(=O)O] | (DMSO-d6) δ: 1.23-1.26 (m, 2H), 1.43-1.47 (m, 2H), 1.60-1.65 (m, 1H), 1.75-1.81 (m, 1H), 2.55 (s, 3H), 2.98 (s, 3H), 3.46-3.58 (m, 4H), 3.86-3.89 (m, 1H), 6.74 (d, J = 8.1 Hz, 2H), 7.42 (d, J = 8.1 Hz, 1H), 7.51-7.54 (m, 3H), 7.82 (s, 1H), 7.92 (s, 1H). | | | |
| C-112 | 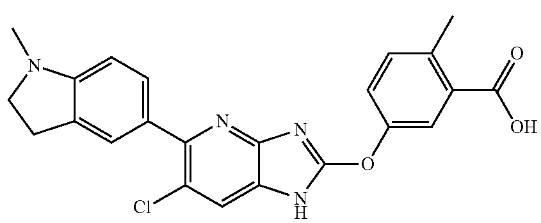 [SMILES: Cc1ccc(Oc2nc3nc(-c4ccc5c(c4)CCN5C)c(Cl)cc3[nH]2)cc1C(=O)O] | (DMSO-d6) δ: 2.55 (s, 3H), 2.76 (s, 3H), 2.92-2.98 (m, 2H), 3.32-3.38 (m, 2H), 6.56 (d, J = 8.1 Hz, 1H), 7.31-7.38 (m, 2H), 7.42 (d, J = 8.1 Hz, 1H), 7.52 (m, 1H), 7.80-7.93 (m, 2H). | | | |
| C-113 | 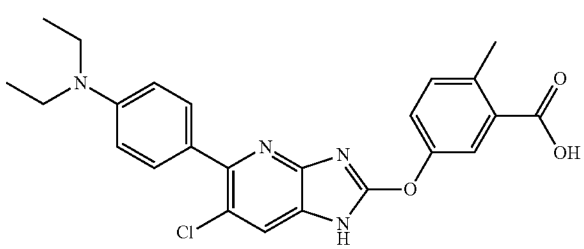 [SMILES: CCN(CC)c1ccc(-c2nc3nc(Oc4ccc(C)c(C(=O)O)c4)[nH]c3cc2Cl)cc1] | (DMSO-d6) δ: 1.12 (t, J = 6.8 Hz, 6H), 2.55 (s, 3H), 3.42 (q, J = 6.8 Hz, 4H), 6.70-6.95 (brs, 2H), 7.42 (d, J = 8.1 Hz, 1H), 7.51-7.60 (m, 3H), 7.83 (d, J = 2.5 Hz, 1H), 7.93 (s, 1H). | | | |
| C-114 | 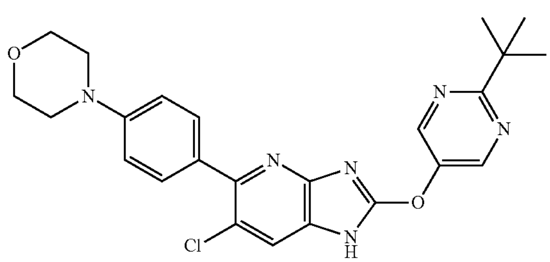 [SMILES: CC(C)(C)c1ncc(Oc2nc3nc(-c4ccc(N5CCOCC5)cc4)c(Cl)cc3[nH]2)cn1] | | 2.31 | 465.22 | A |

TABLE 51
| No. | Structure | NMR(δ) | retention time | Mass (M + H) | method |
|---|---|---|---|---|---|
| C-115 | 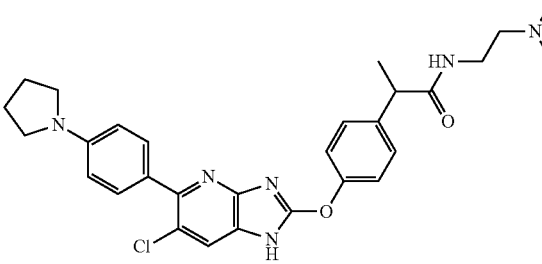 | | 1.8 | 533.23 | A |
| C-116 | 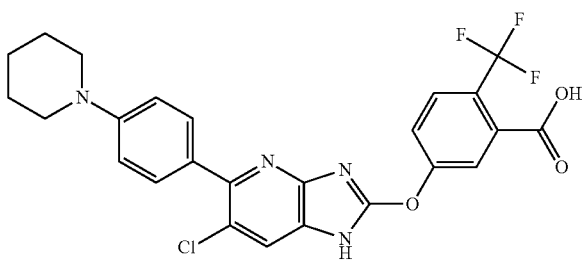 [SMILES: O=C(O)c1cc(Oc2nc3nc(-c4ccc(N5CCCCC5)cc4)c(Cl)cc3[nH]2)ccc1C(F)(F)F] | | 1.63 | 517.13 | A |
| C-117 | 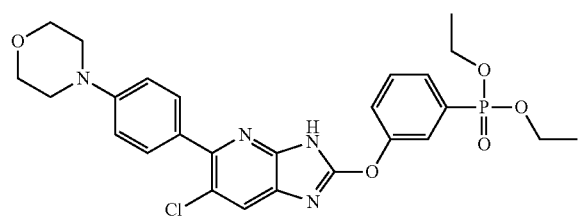 [SMILES: CCOP(=O)(OCC)c1cccc(Oc2nc3cc(Cl)c(-c4ccc(N5CCOCC5)cc4)nc3[nH]2)c1] | (CDCl3) δ: 1.30-1.38 (6H, m), 3.07 (4H, t, J = 4.56 Hz), 3.79 (4H, t, J = 4.82 Hz), 4.11-4.24 (4H, m), 6.92 (2H, d, J = 8.62 Hz), 7.50-7.54 (2H, m), 7.69-7.75 (4H, m), 7.85 (1H, s). | | | |
| C-118 | 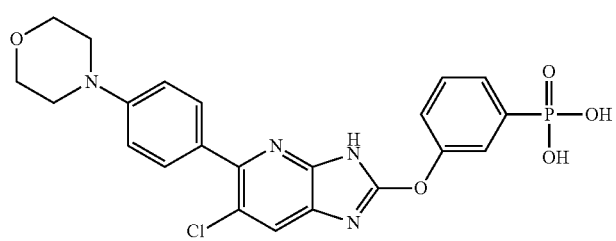 [SMILES: O=P(O)(O)c1cccc(Oc2nc3cc(Cl)c(-c4ccc(N5CCOCC5)cc4)nc3[nH]2)c1] | (DMSO-d6) δ: 3.18 (4H, t, J = 4.82 Hz), 3.76 (4H, t, J = 4.56 Hz), 7.00 (2H, d, J = 9.12 Hz), 7.36-7.38 (2H, m), 7.55-7.57 (4H, m), 7.89 (1H, s). | | | |
| C-119 | 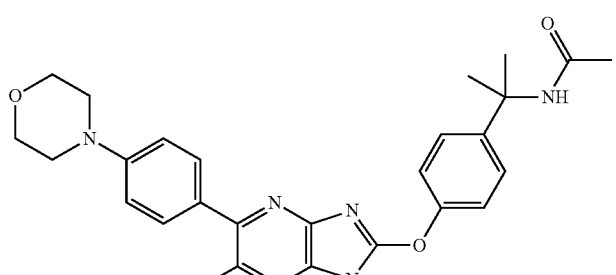 | (DMSO-d6) δ: 1.57 (s, 6H), 1.84 (s, 3H), 3.19 (t, J = 4.8 Hz, 4H), 3.76 (t, J = 4.6 Hz, 4H), 7.02 (d, J = 9.1 Hz, 2H), 7.31 (d, J = 8.6 Hz, 2H), 7.40 (d, J = 8.6 Hz, 2H), 7.57 (d, J = 8.6 Hz, 2H), 7.92 (s, 1H), 8.09 (s, 1H), 13.18 (s, 1H). | | | |
| C-120 | 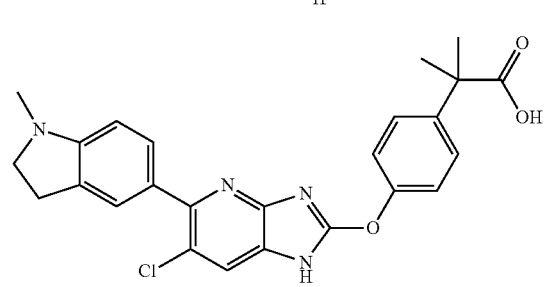 | (DMSO-d6) δ: 1.52 (s, 6H), 2.76 (s, 3H), 2.94 (dd, J = 8.1, 8.1 Hz, 2H), 3.34 (dd, J = 8.1, 8.1 Hz, 2H), 6.55 (d, J = 8.6 Hz, 1H), 7.33-7.39 (m, 4H), 7.45 (d, J = 8.6 Hz, 2H), 7.88 (s, 1H). | | | |

TABLE 52

| No. | Structure | NMR(δ) | retention time | Mass (M + H) | method |
|---|---|---|---|---|---|
| C-121 | 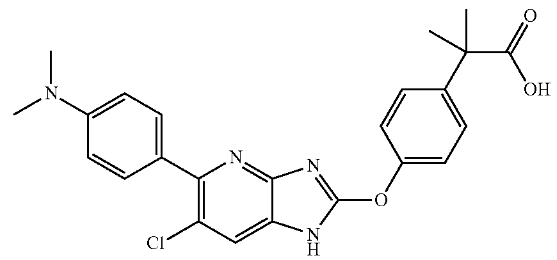 [SMILES: CN(C)c1ccc(-c2nc3nc(Oc4ccc(C(C)(C)C(=O)O)cc4)[nH]c3cc2Cl)cc1] | (DMSO-d6) δ: 1.51 (s, 6H), 2.96 (s, 6H), 6.78 (d, J = 8.6 Hz, 2H), 7.37 (d, J = 8.6 Hz, 2H), 7.45 (d, J = 8.6 Hz, 2H), 7.54 (d, J = 8.6 Hz, 2H), 7.88 (s, 1H). | | | |
| C-122 | 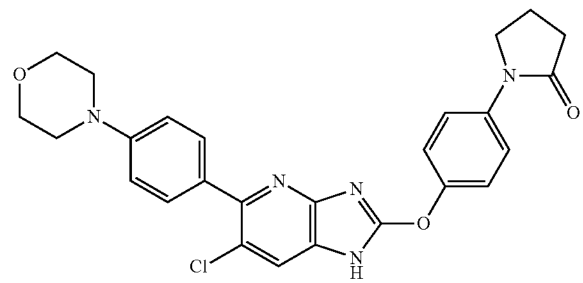 [SMILES: O=C1CCCN1c1ccc(Oc2nc3nc(-c4ccc(N5CCOCC5)cc4)c(Cl)cc3[nH]2)cc1] | | 1.77 | 490.24 | A |
| C-123 | 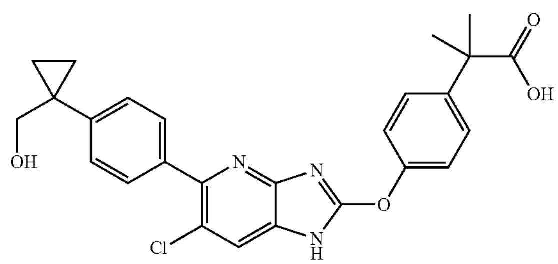 [SMILES: CC(C)(C(=O)O)c1ccc(Oc2nc3nc(-c4ccc(C5(CO)CC5)cc4)c(Cl)cc3[nH]2)cc1] | (DMSO-d6) δ: 0.78-0.84 (m, 2H), 0.86-0.91 (m, 2H), 1.52 (s, 6H), 3.59 (d, J = 5.8 Hz, 2H), 4.71 (t, J = 5.8 Hz, 1H), 7.35-7.41 (m, 4H), 7.45 (d, J = 8.6 Hz, 2H), 7.55 (d, J = 8.6 Hz, 2H), 7.95 (s, 1H). | | | |
| C-124 | 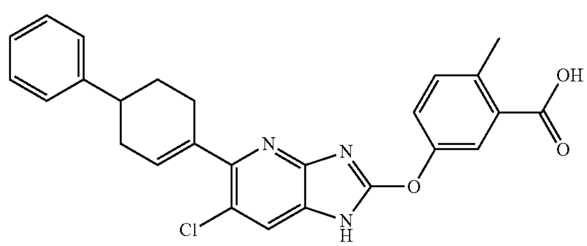 [SMILES: Cc1ccc(Oc2nc3nc(C4=CCC(c5ccccc5)CC4)c(Cl)cc3[nH]2)cc1C(=O)O] | (DMSO-d6) δ: 1.83-1.94 (m, 1H), 1.96-2.03 (m, 1H), 2.28-2.35 (m, 1H), 2.43-2.55 (m, 3H), 2.55 (s, 3H), 2.88-2.93 (m, 1H), 6.00-6.05 (m, 1H), 7.18-7.24 (m, 1H), 7.30-7.35 (m, 4H), 7.40 (d, J = 8.1 Hz, 1H), 7.50 (dd, J = 8.6, 2.5 Hz, 1H), 7.80 (d, J = 2.5 Hz, 1H), 7.87 (s, 1H). | | | |
| C-125 | 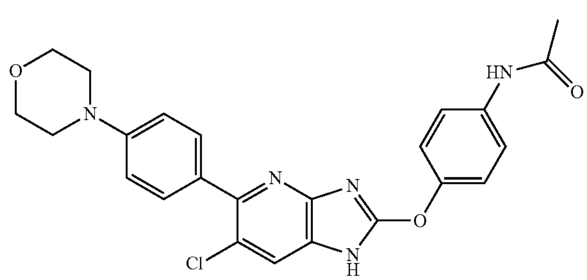 [SMILES: CC(=O)Nc1ccc(Oc2nc3nc(-c4ccc(N5CCOCC5)cc4)c(Cl)cc3[nH]2)cc1] | | 1.61 | 464.18 | A |

TABLE 52-continued

| No. | Structure | NMR(δ) | retention time | Mass (M + H) | method |
|---|---|---|---|---|---|
| C-126 | 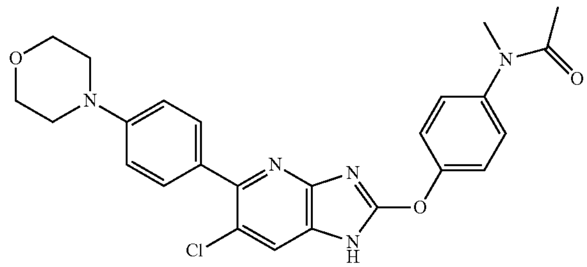 [SMILES: CC(=O)N(C)c1ccc(Oc2nc3nc(-c4ccc(N5CCOCC5)cc4)c(Cl)cc3[nH]2)cc1] | | 1.69 | 478.19 | A |

TABLE 53

| No. | Structure | retention time | Mass (M + H) | method |
|---|---|---|---|---|
| C-127 | 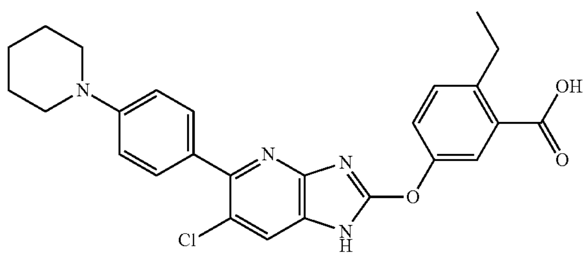 [SMILES: CCc1ccc(Oc2nc3nc(-c4ccc(N5CCCCC5)cc4)c(Cl)cc3[nH]2)cc1C(=O)O] | 1.68 | 477.22 | A |
| C-128 | 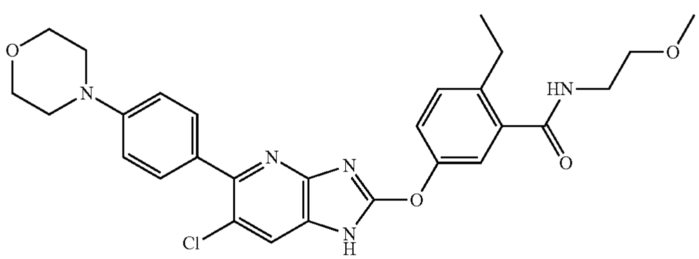 [SMILES: CCc1ccc(Oc2nc3nc(-c4ccc(N5CCOCC5)cc4)c(Cl)cc3[nH]2)cc1C(=O)NCCOC] | 1.85 | 536.26 | A |
| C-129 | 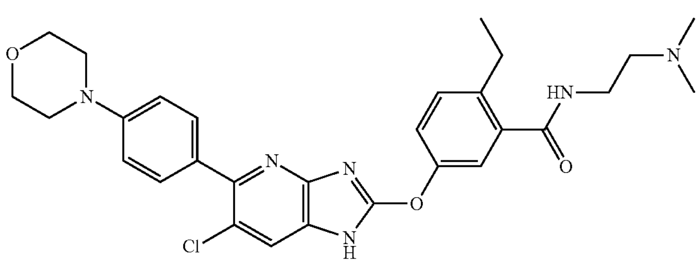 [SMILES: CCc1ccc(Oc2nc3nc(-c4ccc(N5CCOCC5)cc4)c(Cl)cc3[nH]2)cc1C(=O)NCCN(C)C] | 1.48 | 549.28 | A |
| C-130 | 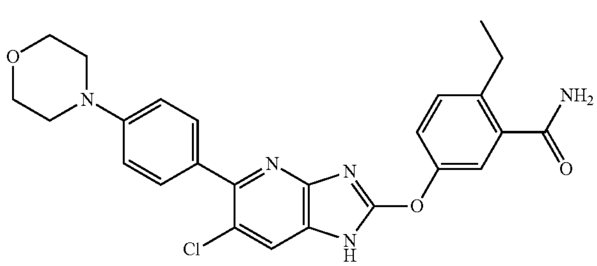 [SMILES: CCc1ccc(Oc2nc3nc(-c4ccc(N5CCOCC5)cc4)c(Cl)cc3[nH]2)cc1C(N)=O] | 1.72 | 478.21 | A |

TABLE 53-continued

| No. | Structure | retention time | Mass (M + H) | method |
|---|---|---|---|---|
| C-131 | 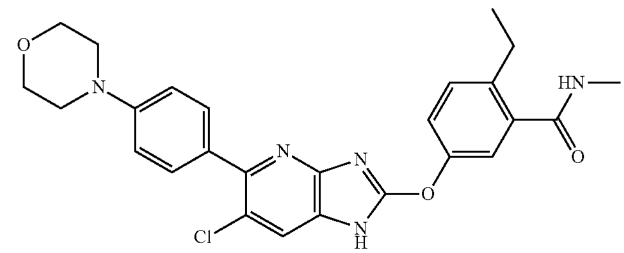 [SMILES: CCc1ccc(Oc2nc3nc(-c4ccc(N5CCOCC5)cc4)c(Cl)cc3[nH]2)cc1C(=O)NC] | 1.79 | 492.21 | A |
| C-132 | 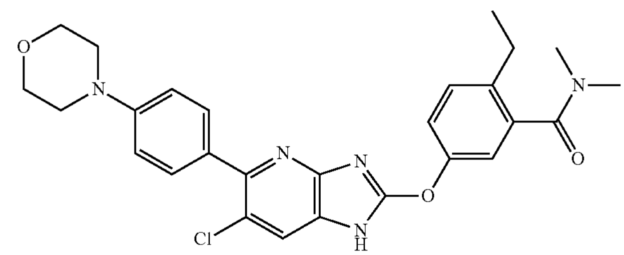 [SMILES: CCc1ccc(Oc2nc3nc(-c4ccc(N5CCOCC5)cc4)c(Cl)cc3[nH]2)cc1C(=O)N(C)C] | 1.89 | 506.24 | A |

TABLE 54

| No. | Structure | NMR(δ) | retention time | Mass (M + H) | method |
|---|---|---|---|---|---|
| C-133 | 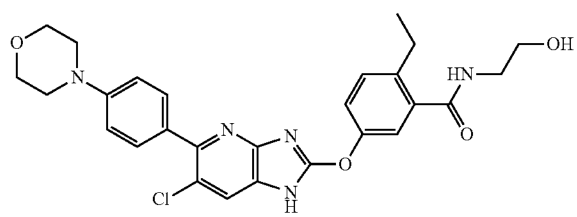 [SMILES: CCc1ccc(Oc2nc3nc(-c4ccc(N5CCOCC5)cc4)c(Cl)cc3[nH]2)cc1C(=O)NCCO] | | 1.65 | 522.22 | A |
| C-134 | 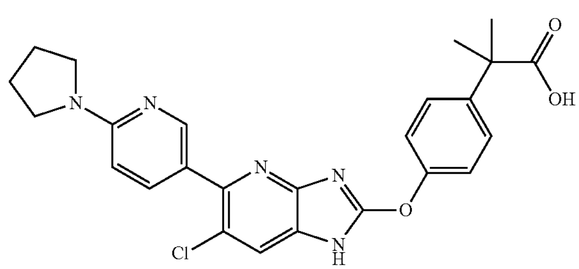 [SMILES: CC(C)(C(=O)O)c1ccc(Oc2nc3nc(-c4ccc(N5CCCC5)nc4)c(Cl)cc3[nH]2)cc1] | (DMSO-d6) δ: 1.51 (s, 6H), 1.94-1.99 (m, 4H), 3.41-3.47 (m, 4H), 6.52 (d, J = 8.6 Hz, 1H), 7.37 (d, J = 8.6 Hz, 2H), 7.45 (d, J = 8.6 Hz, 2H), 7.80 (dd, J = 8.6, 2.1 Hz, 1H), 7.92 (s, 1H), 8.39 (d, J = 2.1 Hz, 1H). | | | |
| C-135 | 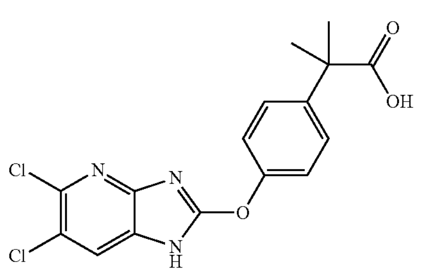 [SMILES: CC(C)(C(=O)O)c1ccc(Oc2nc3nc(Cl)c(Cl)cc3[nH]2)cc1] | (DMSO-d6) δ: 1.51 (s, 6H), 7.37 (d, J = 8.6 Hz, 2H), 7.45 (d, J = 8.6 Hz, 2H), 8.09 (s, 1H). | | | |

TABLE 54-continued

| No. | Structure | NMR(δ) | retention time | Mass (M + H) | method |
|---|---|---|---|---|---|
| C-136 | 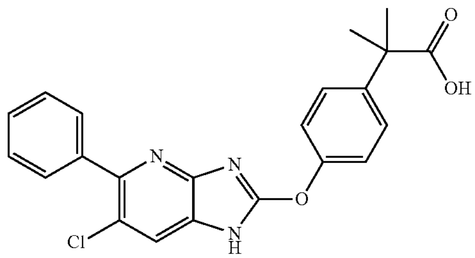 [SMILES: CC(C)(C(=O)O)c1ccc(Oc2nc3nc(-c4ccccc4)c(Cl)cc3[nH]2)cc1] | 1H-NMR (DMSO-d6) δ: 1.52 (s, 6H), 7.40-7.47 (m, 7H), 7.63 (d, J = 8.6 Hz, 2H), 7.96 (s, 1H). | | | |
| C-137 | 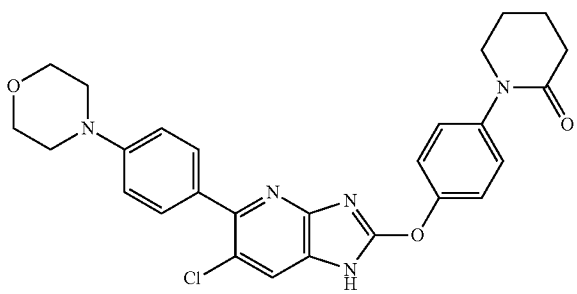 [SMILES: O=C1CCCCN1c1ccc(Oc2nc3nc(-c4ccc(N5CCOCC5)cc4)c(Cl)cc3[nH]2)cc1] | | 1.75 | 504.27 | A |
| C-138 | 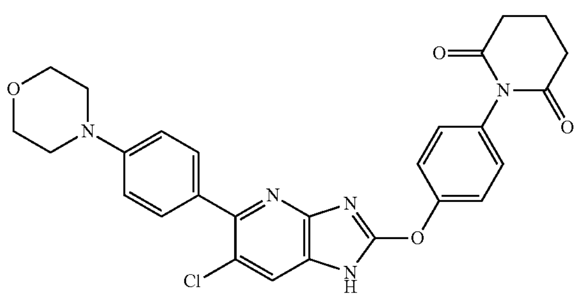 [SMILES: O=C1CCCC(=O)N1c1ccc(Oc2nc3nc(-c4ccc(N5CCOCC5)cc4)c(Cl)cc3[nH]2)cc1] | | 1.74 | 518.21 | A |

TABLE 55

| No. | Structure | NMR(δ) | retention time | Mass (M + H) | method |
|---|---|---|---|---|---|
| C-139 | 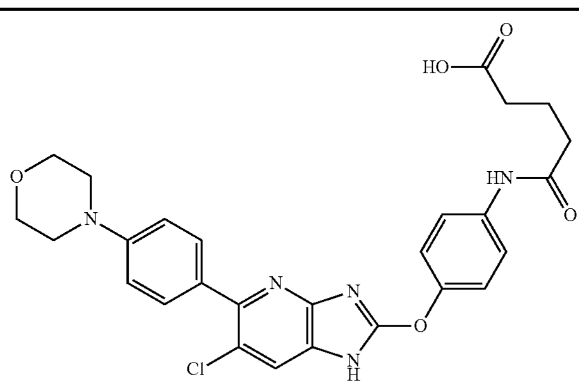 | | 1.61 | 536.23 | A |

TABLE 55-continued

| No. | Structure | NMR(δ) | retention time | Mass (M + H) | method |
|---|---|---|---|---|---|
| C-140 | 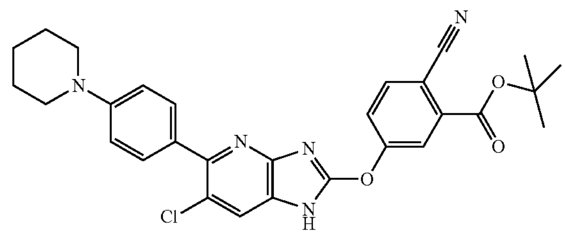 [SMILES: CC(C)(C)OC(=O)c1cc(Oc2nc3nc(-c4ccc(N5CCCCC5)cc4)c(Cl)cc3[nH]2)ccc1C#N] | | 2.24 | 530.27 | A |
| C-141 | 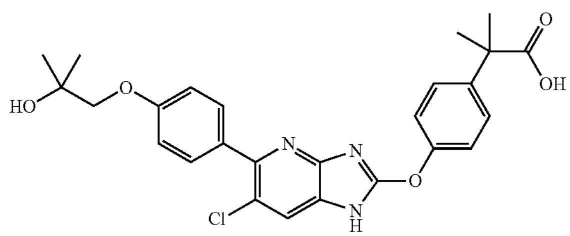 [SMILES: CC(C)(O)COc1ccc(-c2nc3nc(Oc4ccc(C(C)(C)C(=O)O)cc4)[nH]c3cc2Cl)cc1] | (DMSO-d6) δ: 1.23 (s, 6H), 1.50 (s, 6H), 3.77 (s, 3H), 4.64 (s, 1H), 7.00 (d, J = 8.6 Hz, 2H), 7.31 (d, J = 8.6 Hz, 2H), 7.41 (d, J = 8.6 Hz, 2H), 7.57 (d, J = 8.6 Hz, 2H), 7.76 (s, 1H). | | | |
| C-142 | 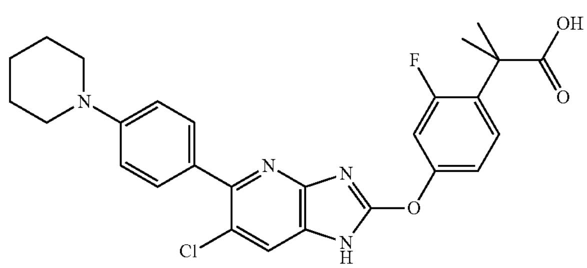 [SMILES: CC(C)(C(=O)O)c1ccc(Oc2nc3nc(-c4ccc(N5CCCCC5)cc4)c(Cl)cc3[nH]2)cc1F] | 1H-NMR (DMSO-d6) δ: 1.50 (s, 6H), 1.54-1.68 (m, 6H), 3.23-3.26 (m, 4H), 7.00 (d, J = 8.6 Hz, 2H), 7.26-7.28 (m, 1H), 7.38-7.42 (m, 1H), 7.50 (t, J = 8.6 Hz, 1H), 7.55 (d, J = 8.6 Hz, 2H), 7.96 (s, 1H) | | | |
| C-143 | 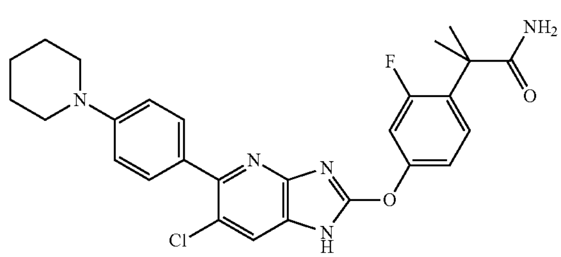 [SMILES: CC(C)(C(N)=O)c1ccc(Oc2nc3nc(-c4ccc(N5CCCCC5)cc4)c(Cl)cc3[nH]2)cc1F] | 1H-NMR (DMSO-d6) δ: 1.47 (s, 6H), 1.54-1.68 (m, 6H), 3.22-3.27 (m, 4H), 6.89 (bs, 2H), 6.99 (d, J = 8.6 Hz, 2H), 7.24-7.26 (m, 1H), 7.34-7.37 (m, 1H), 7.47 (t, J = 8.6 Hz, 1H), 7.54 (d, J = 8.6 Hz, 2H), 7.94 (s, 1H) | | | |
| C-144 | 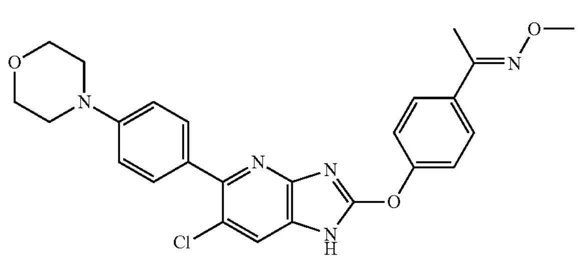 [SMILES: CO/N=C(\C)c1ccc(Oc2nc3nc(-c4ccc(N5CCOCC5)cc4)c(Cl)cc3[nH]2)cc1] | 1H-NMR (DMSO-d6) δ: 2.21 (s, 3H), 3.18-3.22 (m, 4H), 3.75-3.79 (m, 4H), 3.93 (s, 3H), 7.02 (d, J = 8.6 Hz, 2H), 7.47 (d, J = 8.6 Hz, 2H), 7.57 (d, J = 8.6 Hz, 2H), 7.77 (d, J = 8.6 Hz, 2H), 7.92 (s, 1H) | | | |

TABLE 56

| No. | Structure | NMR(δ) |
|---|---|---|
| C-145 | 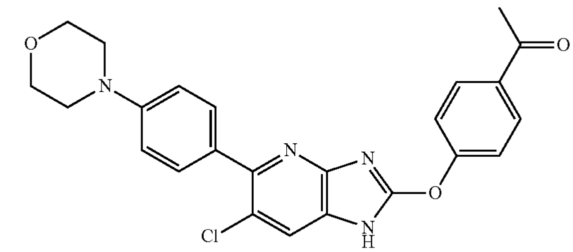 [SMILES: CC(=O)c1ccc(Oc2nc3nc(-c4ccc(N5CCOCC5)cc4)c(Cl)cc3[nH]2)cc1] | 1H-NMR (DMSO-d6) δ: 2.61 (s, 3H), 3.18-3.21 (m, 4H), 3.75-3.78 (m, 4H), 7.02 (d, J = 8.6 Hz, 2H), 7.57 (d, J = 8.6 Hz, 2H), 7.58 (d, J = 8.6 Hz, 2H), 7.94 (s, 1H), 8.08 (d, J = 8.6 Hz, 2H) |
| C-146 | 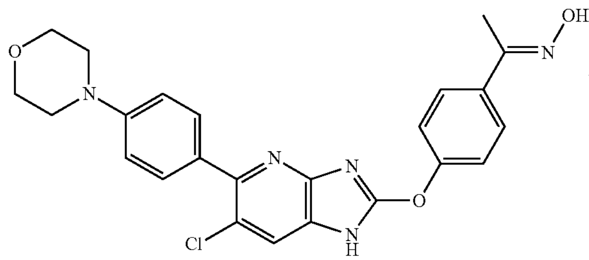 [SMILES: C/C(=N\O)c1ccc(Oc2nc3nc(-c4ccc(N5CCOCC5)cc4)c(Cl)cc3[nH]2)cc1] | 1H-NMR (DMSO-d6) δ: 2.19 (s, 3H), 3.18-3.20 (m, 4H), 3.75-3.78 (m, 4H), 7.02 (d, J = 8.6 Hz, 2H), 7.44 (d, J = 8.6 Hz, 2H), 7.57 (d, J = 8.6 Hz, 2H), 7.75 (s, J = 8.6 Hz, 2H), 7.90 (s, 1H) |
| C-147 | 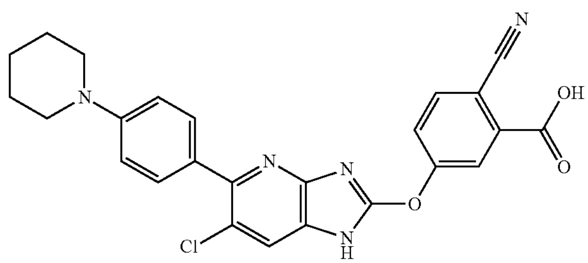 [SMILES: N#Cc1ccc(Oc2nc3nc(-c4ccc(N5CCCCC5)cc4)c(Cl)cc3[nH]2)cc1C(=O)O] | 1H-NMR (DMSO-d6) δ: 1.57-1.64 (m, 6H), 3.22-3.24 (m, 4H), 6.98 (d, J = 8.6 Hz, 2H), 7.54 (d, J = 8.6 Hz, 2H), 7.81 (dd, J = 4.0, 8.6 Hz, 1H), 7.88 (s, 1H), 7.91 (d, J = 8.6 Hz, 1H), 7.94 (d, J = 4.0 Hz, 1H), 11.4 (bs, 1H) |

TABLE 57

| No. | Structure | NMR(δ) |
|---|---|---|
| D-3 | 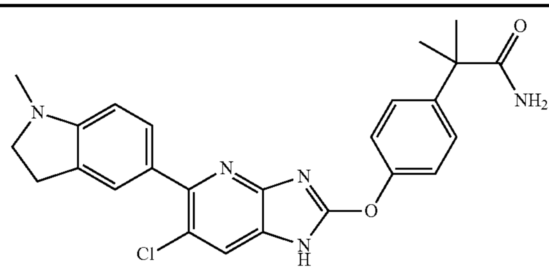 | 1H-NMR (DMSO-d6) δ: 1.47 (s, 6H), 2.76 (s, 3H), 2.94 (dd, J = 8.1, 8.1 Hz, 2H), 3.31-3.33 (m, 2H), 6.55 (d, J = 8.6 Hz, 1H), 6.92 (brs, 1H), 6.97 (brs, 1H), 7.32-7.37 (m, 4H), 7.43 (d, J = 8.6 Hz, 2H), 7.87 (s, 1H). |
| D-4 | 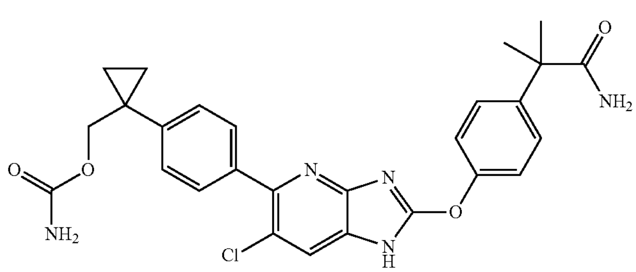 [SMILES: CC(C)(C(N)=O)c1ccc(Oc2nc3nc(-c4ccc(C5(COC(N)=O)CC5)cc4)c(Cl)cc3[nH]2)cc1] | $^1$H-NMR (DMSO-d$_6$) δ: 0.93-0.96 (m, 2H), 0.98-1.02 (m, 2H), 1.47 (s, 6H), 4.14 (s, 2H), 6.45 (brs, 2H), 6.92 (s, 1H), 6.96 (s, 1H), 7.34 (d, J = 8.6 Hz, 2H), 7.36 (d, J = 8.6 Hz, 2H), 7.42 (d, J = 8.6 Hz, 2H), 7.56 (d, J = 8.6 Hz, 2H), 7.90 (s, 1H). |

TABLE 57-continued

| No. | Structure | NMR(δ) |
|---|---|---|
| D-5 | 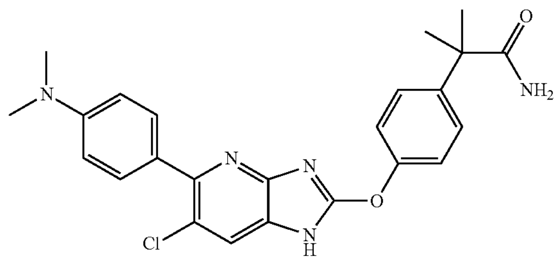 [SMILES: CN(C)c1ccc(-c2nc3nc(Oc4ccc(C(C)(C)C(N)=O)cc4)[nH]c3cc2Cl)cc1] | ¹H-NMR (DMSO-d₆) δ: 1.47 (s, 6H), 2.96 (s, 6H), 6.78 (d, J = 8.6 Hz, 2H), 6.92 (s, 1H), 6.96 (s, 1H), 7.34 (d, J = 8.6 Hz, 2H), 7.42 (d, J = 8.6 Hz, 2H), 7.54 (d, J = 8.6 Hz, 2H), 7.85 (s, 1H). |
| D-6 | 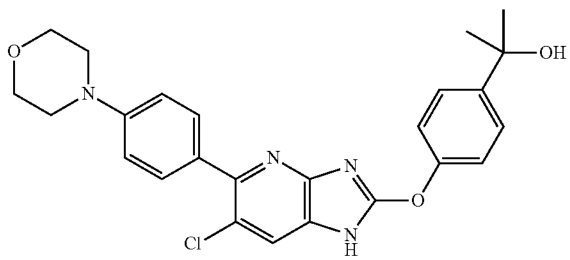 [SMILES: CC(C)(O)c1ccc(Oc2nc3nc(-c4ccc(N5CCOCC5)cc4)c(Cl)cc3[nH]2)cc1] | 1H-NMR (DMSO-d6) δ: 1.46(s, 6H), 3.18-3.20 (m, 4H), 3.75-3.78 (m, 4H), 5.08 (s, 1H), 7.02 (d, J = 8.6 Hz, 2H), 7.32 (d, J = 8.6 Hz, 2H), 7.55 (d, J = 8.6 Hz, 2H), 7.56 (d, J = 8.6 Hz, 2H), 7.89 (s, 1H) |
| D-7 | 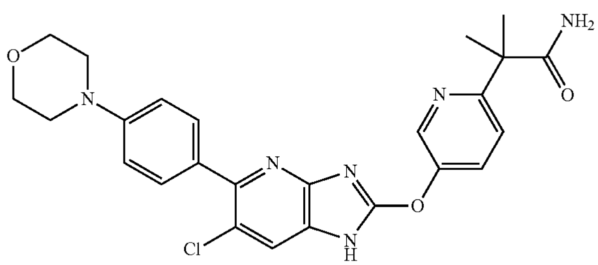 [SMILES: CC(C)(C(N)=O)c1ccc(Oc2nc3nc(-c4ccc(N5CCOCC5)cc4)c(Cl)cc3[nH]2)cn1] | 1H-NMR (DMSO-d6) δ: 1.52 (s, 6H), 3.19 (t, J = 4.82 Hz, 4H), 3.76 (t, J = 4.82 Hz, 4H), 6.93-7.05 (m, 4H), 7.50 (d, J = 8.62 Hz, 1H), 7.57 (d, J = 8.62 Hz, 2H), 7.90 (dd, J = 8.62, 3.04 Hz, 1H), 7.95 (s, 1H), 8.63 (d, J = 3.04 Hz, 1H), 13.26 (s, 1H). |

TABLE 58

| No. | Structure | NMR(δ) |
|---|---|---|
| D-8 | 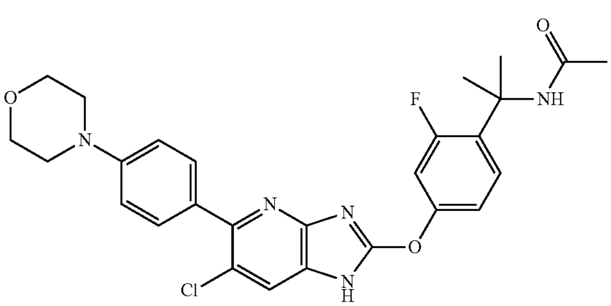 [SMILES: CC(=O)NC(C)(C)c1ccc(Oc2nc3nc(-c4ccc(N5CCOCC5)cc4)c(Cl)cc3[nH]2)cc1F] | 1H-NMR (DMSO-d6) δ: 1.62(s, 6H), 1.83 (s, 3H), 3.18-3.21 (m, 4H), 3.75-3.78 (m, 4H), 7.02 (d, J = 8.6 Hz, 2H), 7.18 (dd, J = 4.0, 8.6 Hz, 1H), 7.29-7.40 (m, 2H), 7.57 (d, J = 8.6 Hz, 2H), 7.95 (s, 1H), 8.17 (s, 1H) |
| D-9 | 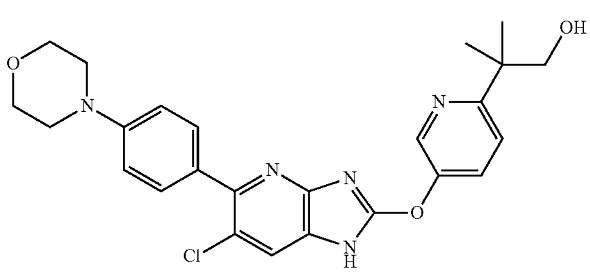 [SMILES: CC(C)(CO)c1ccc(Oc2nc3nc(-c4ccc(N5CCOCC5)cc4)c(Cl)cc3[nH]2)cn1] | 1H-NMR (DMSO-d6) δ: 1.29 (s, 6H), 3.19 (t, J = 4.56 Hz, 4H), 3.58 (d, J = 5.07 Hz, 2H), 3.76 (t, J = 4.56 Hz, 4H), 4.69 (t, J = 5.07 Hz, 1H), 7.02 (d, J = 8.62 Hz, 2H), 7.53 (d, J = 8.62 Hz, 1H), 7.57 (d, J = 8.62 Hz, 2H), 7.85 (dd, J = 8.62, 3.04 Hz, 1H), 7.94 (s, 1H), 8.62 (d, J = 3.04 Hz, 1H), 13.26 (s, 1H). |

TABLE 58-continued

| No. | Structure | NMR(δ) |
|---|---|---|
| D-10 | 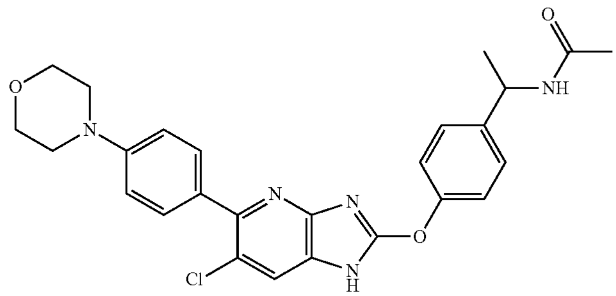 [SMILES: CC(=O)NC(C)c1ccc(Oc2nc3nc(-c4ccc(N5CCOCC5)cc4)c(Cl)cc3[nH]2)cc1] | 1H-NMR (DMSO-d6) δ: 1.37 (d, J = 8.6 Hz, 3H), 1.85 (s, 3H), 3.18-3.20 (m, 4H), 3.75-3.77 (m, 4H), 4.94 (t, J = 8.6 Hz, 1H), 7.02 (d, J = 8.6 Hz, 2H), 7.35 (d, J = 8.6 Hz, 2H), 7.40 (d, J = 8.6 Hz, 2H), 7.56 (d, J = 8.6 Hz, 2H), 7.90 (s, 1H), 8.32 (d, J = 8.6 Hz, 1H) |
| D-11 | 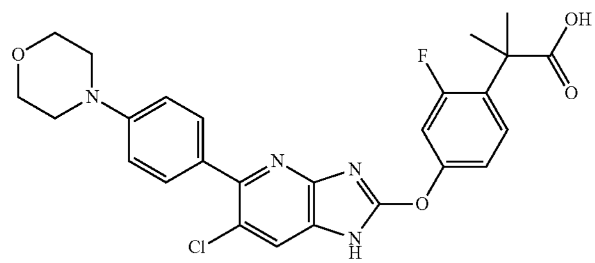 [SMILES: CC(C)(C(=O)O)c1ccc(Oc2nc3nc(-c4ccc(N5CCOCC5)cc4)c(Cl)cc3[nH]2)cc1F] | 1H-NMR (DMSO-d6) δ: 1.50(s, 6H), 3.18-3.20 (m 4H), 3.75-3.78 (m, 4H), 7.01 (d, J = 8.6 Hz, 2H), 7.20-7.23 (m, 1H), 7.32-7.35 (m, 1H), 7.47 (t, J = 8.6 Hz, 1H), 7.56 (d, J = 8.6 Hz, 2H), 7.84 (s, 1H) |
| D-12 | 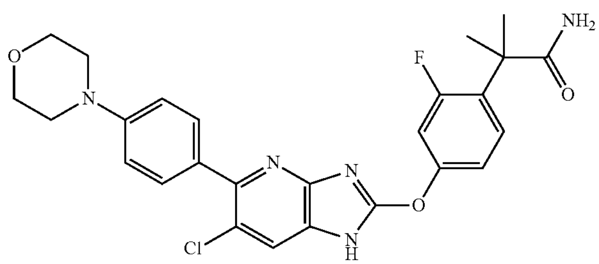 | 1H-NMR (DMSO-d6) δ: 1.47(s, 6H), 3.18-3.21 (m 4H), 3.75-3.78 (m, 4H), 6.88 (bs, 2H), 7.02 (d, J = 8.6 Hz, 2H), 7.23-7.26 (m, 1H), 7.33-7.37 (m, 1H), 7.47 (t. J = 8.6 Hz, 1H), 7.57 (d, J = 8.6 Hz, 2H), 7.94 (s, 1H) |

TABLE 59

| No. | Structure | NMR(δ) | retention time | Mass (M + H) | method |
|---|---|---|---|---|---|
| D-13 | 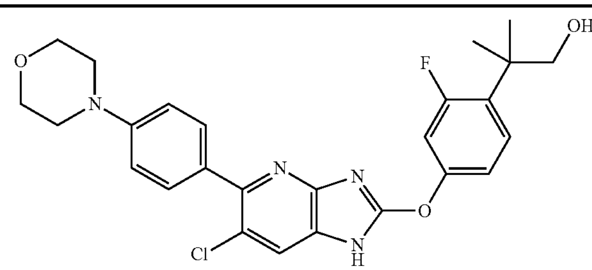 | 1H-NMR (DMSO-d6) δ: 1.30 (s, 6H), 3.18-3.20 (m 4H), 3.58 (s, 2H), 3.75-3.78 (m, 4H), 6.88 (bs, 2H), 4.78 (bs, 1H), 7.02 (d, J = 8.6 Hz, 2H), 7.18-7.20 (m, 1H), 7.29-7.33 (m, 1H), 7.43 (t, J = 8.6 Hz, 1H), 7.57 (d, J = 8.6 Hz, 2H), 7.92 (s, 1H) | | | |
| D-14 | 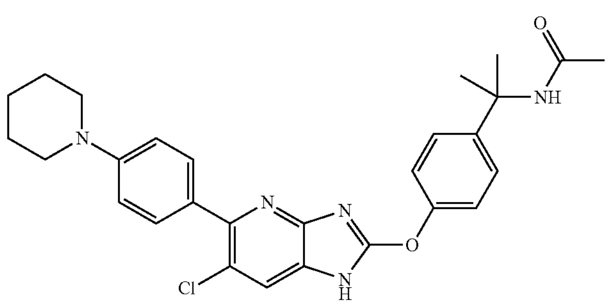 [SMILES: CC(=O)NC(C)(C)c1ccc(Oc2nc3nc(-c4ccc(N5CCCCC5)cc4)c(Cl)cc3[nH]2)cc1] | 1H-NMR (DMSO-d6) δ: 1.57 (s, 3H), 1.61-1.66 (m, 4H), 1.84 (s, 3H), 3.23 (t, J = 5.1 Hz, 4H), 6.99 (d, J = 8.6 Hz, 2H), 7.30 (d, J = 8.6 Hz, 2H), 7.39 (d, J = 8.6 Hz, 2H), 7.54 (d, J = 8.6 Hz, 2H), 7.90 (s, 1H), 8.09 (s, 1H), 13.10 (br s, 1H). | 1.55 | 504.2 | B |

TABLE 59-continued

| No. | Structure | NMR(δ) | retention time | Mass (M + H) | method |
|---|---|---|---|---|---|
| D-15 | 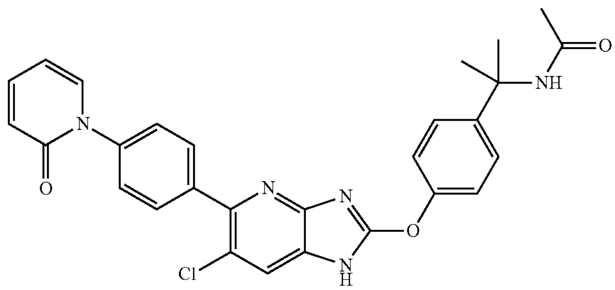 [SMILES: CC(=O)NC(C)(C)c1ccc(Oc2nc3nc(-c4ccc(-n5ccccc5=O)cc4)c(Cl)cc3[nH]2)cc1] | 1H-NMR(DMSO-d6) δ: 1.57 (s, 6H), 1.85 (s, 3H), 6.35 (t, J = 6.08 Hz, 3H), 6.52 (d, J = 9.12 Hz, 1H), 7.32 (d, J = 8.62 Hz, 2H), 7.41 (d, J = 8.62 Hz, 2H), 7.52-7.54 (m, 3H), 7.73-7.79 (m, 3H), 8.01 (s, 0.5H), 8.10 (d, J = 3.55 Hz, 1H), 8.31 (s, 1H), 13.40 (brs, 0.5H). | 1.62 | 514.45 | B |
| D-16 | 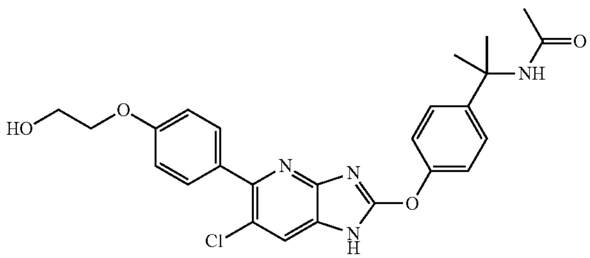 [SMILES: CC(=O)NC(C)(C)c1ccc(Oc2nc3nc(-c4ccc(OCCO)cc4)c(Cl)cc3[nH]2)cc1] | 1H-NMR (DMSO-d6) δ: 1.57 (s, 6H), 1.85 (s, 3H), 3.75 (q, J = 5.24 Hz, 2H), 4.05 (t, J = 5.07 Hz, 2H), 4.88 (t, J = 5.58 Hz, 1H), 7.03 (d, J = 9.12 Hz, 2H), 7.31 (d, J = 8.62 Hz, 2H), 7.40 (d, J = 8.62 Hz, 2H), 7.59 (d, J = 8.62 Hz, 2H), 7.94 (s, 1H), 8.09 (s, 1H), 13.2 (brs, 1H). | 1.59 | 481.15 | B |
| D-17 | 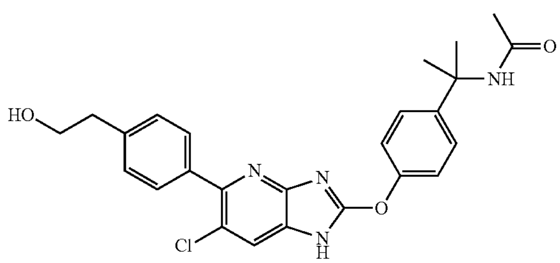 [SMILES: CC(=O)NC(C)(C)c1ccc(Oc2nc3nc(-c4ccc(CCO)cc4)c(Cl)cc3[nH]2)cc1] | 1H-NMR (DMSO-d6) δ: 1.57 (s, 6H), 1.85 (s, 3H), 2.79 (t, J = 6.84 Hz, 2H), 3.66 (s, 2H), 4.68 (s, 1H), 7.30-7.31 (m, 4H), 7.40 (d, J = 8.62 Hz, 2H), 7.55 (d, J = 8.11 Hz, 2H), 7.93 (s, 1H), 8.09 (s, 1H), 13.20 (brs, 1H). | 1.62 | 465.2 | B |

TABLE 60

| No. | Structure | NMR(δ) | retention time | Mass (M + H) | method |
|---|---|---|---|---|---|
| D-18 | 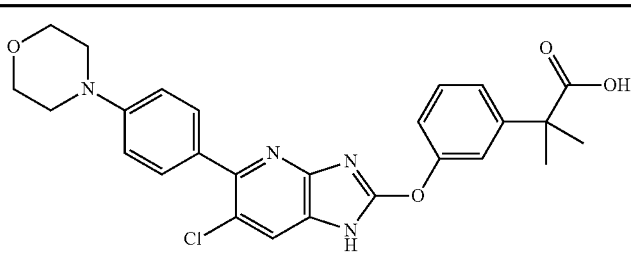 | 1H-NMR (DMSO-d6) δ: 1.50 (s, 6H), 3.17-3.19 (m, 4H), 3.75-3.78 (m, 4H), 7.02 (d, J = 8.6 Hz, 2H), 7.29-7.34 (m, 3H), 7.45 (t, J = 8.6 Hz, 1H), 7.57 (d, J = 8.6 Hz, 2H), 7.93 (s, 1H), 13.3 (s, 1H) | | | |
| D-19 | 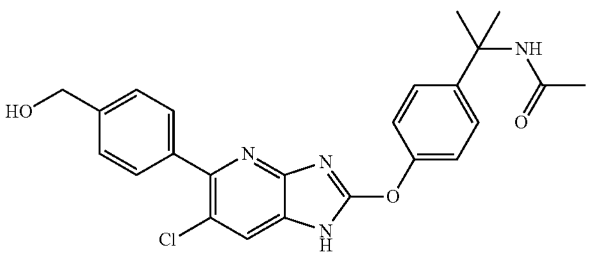 [SMILES: CC(=O)NC(C)(C)c1ccc(Oc2nc3nc(-c4ccc(CO)cc4)c(Cl)cc3[nH]2)cc1] | 1H-NMR (DMSO-d6) δ: 1.57 (s, 6H), 1.84 (s, 3H), 4.57 (d, J = 5.6 Hz, 2H), 5.24 (t, J = 5.6 Hz, 1H), 7.30 (d, J = 8.6 Hz, 2H), 7.39 (d, J = 6.6 Hz, 2H), 7.41 (d, J = 6.1 Hz, 2H), 7.59 (d, J = 8.1 Hz, 2H), 7.91 (s, 1H), 8.08 (s, 1H). | 1.52 | 451.25 | B |

TABLE 60-continued

| No. | Structure | NMR(δ) | retention time | Mass (M + H) | method |
|---|---|---|---|---|---|
| D-20 | 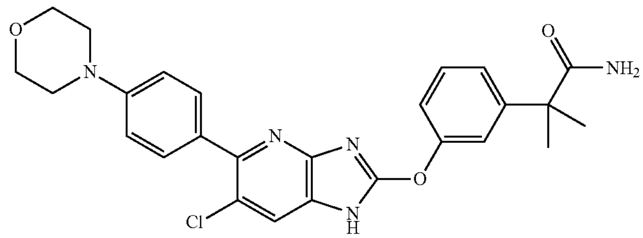 [SMILES: CC(C)(C(N)=O)c1cccc(Oc2nc3nc(-c4ccc(N5CCOCC5)cc4)c(Cl)cc3[nH]2)c1] | 1H-NMR (DMSO-d6) δ: 1.46 (s, 6H), 3.16-3.19 (m, 4H), 3.73-3.79 (m, 4H), 6.94-7.04 (m, 4H), 7.28-7.35 (m, 3H), 7.44 (t, J = 8.6 Hz, 1H), 7.58 (d, J = 8.6 Hz, 2H), 7.93 (s, 1H), 13.23 (s, 1H) | | | |
| D-21 | 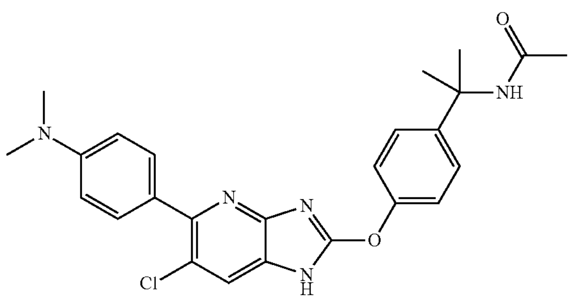 [SMILES: CC(=O)NC(C)(C)c1ccc(Oc2nc3nc(-c4ccc(N(C)C)cc4)c(Cl)cc3[nH]2)cc1] | 1H-NMR (DMSO-d6) δ: 1.57 (s, 6H), 1.84 (s, 3H), 2.97 (s, 6H), 6.79 (d, J = 8.6 Hz, 2H), 7.30 (d, J = 8.6 Hz, 2H), 7.39 (d, J = 8.6 Hz, 2H), 7.55 (d, J = 7.6 Hz, 2H), 7.91 (s, 1H), 8.09 (s, 1H), 13.17 (s, 1H). | 1.76 | 464.5 | B |
| D-22 | 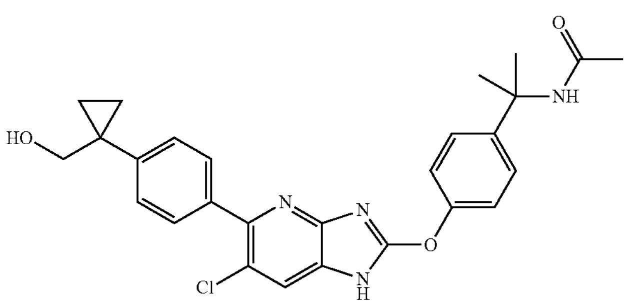 [SMILES: CC(=O)NC(C)(C)c1ccc(Oc2nc3nc(-c4ccc(C5(CO)CC5)cc4)c(Cl)cc3[nH]2)cc1] | 1H-NMR (DMSO-d6) δ: 0.78-0.81 (m, 2H), 0.86-0.89 (m, 2H), 1.57 (s, 6H), 1.84 (s, 3H), 3.59 (d, J = 5.6 Hz, 2H), 4.72 (t, J = 5.6 Hz, 1H), 7.30 (d, J = 8.6 Hz, 2H), 7.38 (d, J = 8.6 Hz, 2H), 7.39 (d, J = 8.6 Hz, 2H), 7.55 (d, J = 8.6 Hz, 2H), 7.92 (s, 1H), 8.09 (s, 1H). | | | |

TABLE 61

| No. | Structure | NMR(δ) | retention time | Mass (M + H) | method |
|---|---|---|---|---|---|
| D-23 | 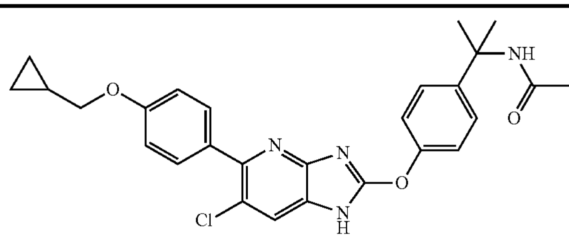 | 1H-NMR (DMSO-d6) δ: 0.35 (d, J = 5.1 Hz, 2H), 0.59 (d, J = 7.6 Hz, 2H), 1.22-1.29 (m, 1H), 1.57 (s, 6H), 1.84 (s, 3H), 3.88 (d, J = 6.6 Hz, 2H), 7.01 (d, J = 8.6 Hz, 2H), 7.31 (d, J = 8.6 Hz, 2H), 7.40 (d, J = 9.1 Hz, 2H), 7.58 (d, J = 8.1 Hz, 2H), 7.94 (s, 1H), 8.09 (s, 1H). | 2.17 | 491.25 | B |
| D-24 | 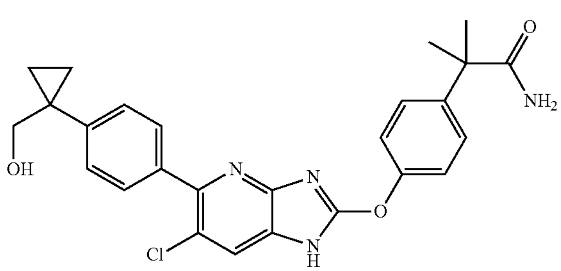 [SMILES: CC(C)(C(N)=O)c1ccc(Oc2nc3nc(-c4ccc(C5(CO)CC5)cc4)c(Cl)cc3[nH]2)cc1] | 1H-NMR (DMSO-d6) δ: 0.78-0.81 (m, 2H), 0.87-0.90 (m, 2H), 1.47 (s, 6H), 3.59 (d, J = 5.3 Hz, 2H), 4.73 (t, J = 5.3 Hz, 1H), 6.91 (s, 1H), 6.96 (s, 1H), 7.32 (d, J = 8.6 Hz, 2H), 7.37 (d, J = 8.6 Hz, 2H), 7.41 (d, J = 8.6 Hz, 2H), 7.55 (d, J = 8.6 Hz, 2H), 7.85 (s, 1H). | | | |

TABLE 61-continued

| No. | Structure | NMR(δ) | retention time | Mass (M + H) | method |
|---|---|---|---|---|---|
| D-25 | 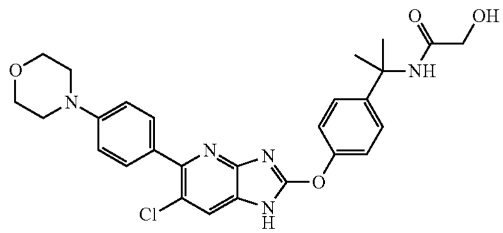 [SMILES: CC(C)(NC(=O)CO)c1ccc(Oc2nc3nc(-c4ccc(N5CCOCC5)cc4)c(Cl)cc3[nH]2)cc1] | 1H-NMR (DMSO-d6) δ: 1.64 (s, 6H), 3.19 (dd, J = 5.2, 4.4 Hz, 4H), 3.7 (dd, J = 5.2, 4.4 Hz, 4H), 3.80 (s, 2H), 7.02 (d, J = 8.6 Hz, 2H), 7.33 (d, J = 9.1 Hz, 2H), 7.44 (d, J = 9.1 Hz, 2H), 7.57 (d, J = 8.6 Hz, 2H), 7.62 (s, 1H), 7.92 (s, 1H). | | | |
| D-26 | 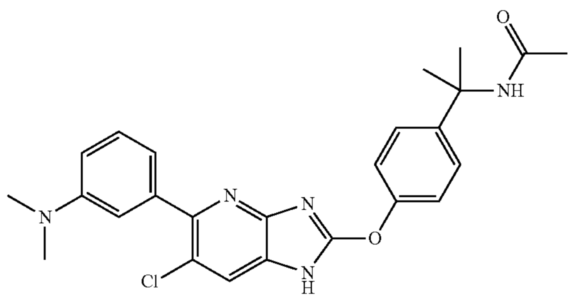 [SMILES: CC(=O)NC(C)(C)c1ccc(Oc2nc3nc(-c4cccc(N(C)C)c4)c(Cl)cc3[nH]2)cc1] | 1H-NMR (DMSO-d6) δ: 1.57 (s, 6H), 1.84 (s, 3H), 2.93 (s, 6H), 6.78 (dd, J = 8.1, 2.0 Hz, 1H), 6.88-6.93 (m, 2H), 7.26 (t, J = 7.9 Hz, 1H), 7.30 (d, J = 8.6 Hz, 2H), 7.39 (d, J = 8.6 Hz, 2H), 7.92 (s, 1H), 8.09 (s, 1H), 13.15 (br s, 1H). | 1.59 | 464.4 | B |
| D-27 | 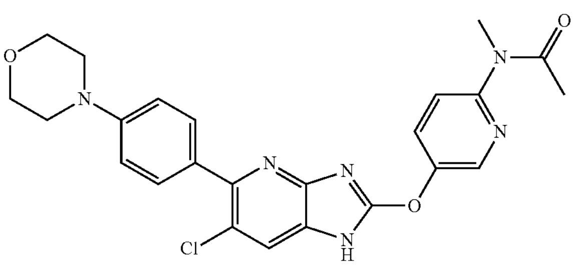 [SMILES: CC(=O)N(C)c1ccc(Oc2nc3nc(-c4ccc(N5CCOCC5)cc4)c(Cl)cc3[nH]2)cn1] | $^1$H-NMR (DMSO-d$_6$) δ: 2.08 (s, 3H), 3.19 (dd, J = 4.8, 4.8 Hz, 4H), 3.32 (s, 3H), 3.76 (dd, J = 4.8, 4.8 Hz, 4H), 7.02 (d, J = 8.6 Hz, 2H), 7.57 (d, J = 8.6 Hz, 2H), 7.67 (d, J = 8.6 Hz, 1H), 7.98 (s, 1H), 8.05 (dd, J = 8.6, 2.9 Hz, 1H), 8.61 (d, J = 2.9 Hz, 1H). | | | |

TABLE 62

| No. | Structure | NMR(δ) | retention time | Mass (M + H) | method |
|---|---|---|---|---|---|
| D-28 | 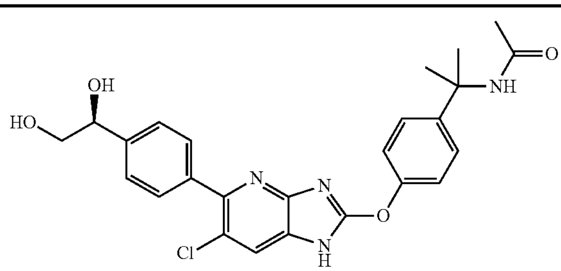 | | 1.38 | 481.3 | B |
| D-29 | 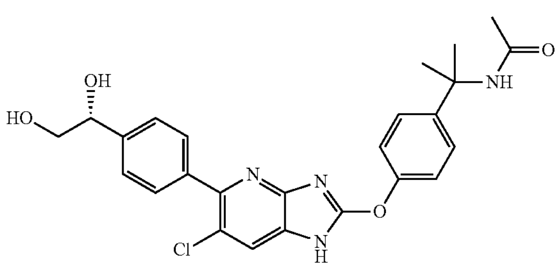 [SMILES: CC(=O)NC(C)(C)c1ccc(Oc2nc3nc(-c4ccc([C@@H](O)CO)cc4)c(Cl)cc3[nH]2)cc1] | | 1.38 | 481.15 | B |

TABLE 62-continued

| No. | Structure | NMR(δ) | retention time | Mass (M + H) | method |
|---|---|---|---|---|---|
| D-30 | 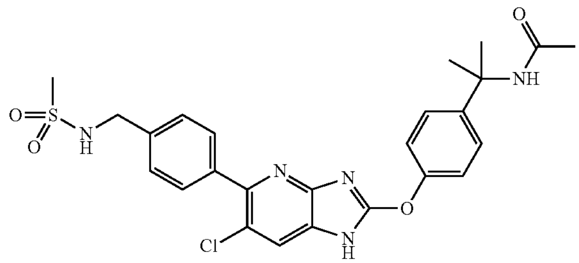 [SMILES: CC(=O)NC(C)(C)c1ccc(Oc2nc3nc(-c4ccc(CNS(C)(=O)=O)cc4)c(Cl)cc3[nH]2)cc1] | 1H-NMR (DMSO-d6) δ: 1.57 (s. 6H), 1.85 (s, 3H), 2.90-3.07 (m, 3H), 4.23-4.61 (m, 2H), 7.31 (d, J = 8.6 Hz, 2H), 7.40 (d, J = 9.1 Hz, 2H), 7.45 (d, J = 7.6 Hz, 2H), 7.64 (t, J = 8.1 Hz, 2H), 7.97 (s, 1H), 8.11 (s, 1H), 13.24 (br s, 1H). | 1.61 | 528.2 | B |
| D-31 | 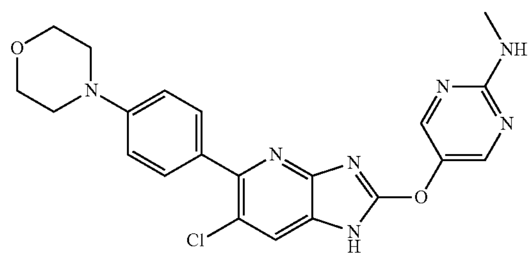 [SMILES: CNc1ncc(Oc2nc3nc(-c4ccc(N5CCOCC5)cc4)c(Cl)cc3[nH]2)cn1] | $^1$H-NMR (DMSO-d$_6$) δ: 2.83 (d, J = 4.6 Hz, 3H), 3.19 (dd, J = 4.8, 4.8 Hz, 4H), 3.76 (dd, J = 4.8, 4.6 Hz, 4H), 7.02 (d, J = 8.6 Hz, 2H), 7.29 (q, J = 4.6 Hz, 1H), 7.56 (d, J = 8.6 Hz, 2H), 7.91 (s, 1H), 8.44 (s, 2H). | | | |
| D-32 | 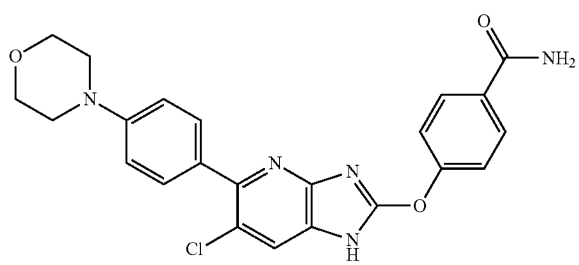 [SMILES: NC(=O)c1ccc(Oc2nc3nc(-c4ccc(N5CCOCC5)cc4)c(Cl)cc3[nH]2)cc1] | | 1.5 | 450.27 | A |

TABLE 63

| No. | Structure | NMR(δ) | retention time | Mass (M + H) | method |
|---|---|---|---|---|---|
| D-33 | 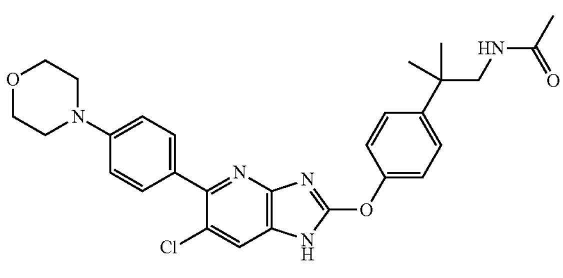 [SMILES: CC(=O)NCC(C)(C)c1ccc(Oc2nc3nc(-c4ccc(N5CCOCC5)cc4)c(Cl)cc3[nH]2)cc1] | 1H-NMR (DMSO-d6) δ: 1.26 (s, 6H), 1.81 (s, 3H), 3.19 (d, J = 4.0 Hz, 2H), 3.29-3.36 (m, 4H), 3.75-3.79 (m, 4H), 7.02 (d, J = 8.6 Hz, 2H), 7.35 (d, J = 8.6 Hz, 2H), 7.47 (d, J = 8.6 Hz, 2H), 7.57 (d, J = 8.6 Hz, 2H), 7.69 (t, J = 4.0 Hz, 1H), 7.91 (s, 1H) | | | |
| D-34 | 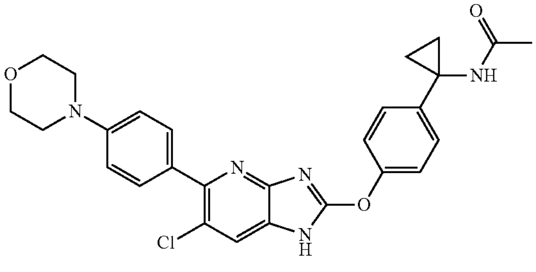 [SMILES: CC(=O)NC1(c2ccc(Oc3nc4nc(-c5ccc(N6CCOCC6)cc5)c(Cl)cc4[nH]3)cc2)CC1] | $^1$H-NMR (DMSO-d$_6$) δ: 1.13-1.18 (m, 4H), 1.84 (s, 3H), 3.19 (dd, J = 4.8, 4.8 Hz, 4H), 3.76 (dd, J = 4.8, 4.8 Hz, 4H), 7.02 (d, J = 8.6 Hz, 2H), 7.23 (d, J = 8.6 Hz, 2H), 7.30 (d, J = 8.6 Hz, 2H), 7.56 (d, J = 8.6 Hz, 2H), 7.90 (s, 1H), 8.62 (s, 1H). | | | |

TABLE 63-continued

| No. | Structure | NMR(δ) | retention time | Mass (M + H) | method |
|---|---|---|---|---|---|
| D-35 | 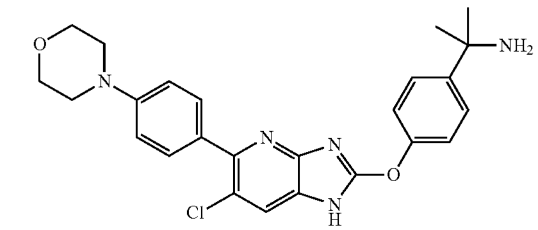 [SMILES: CC(C)(N)c1ccc(Oc2nc3nc(-c4ccc(N5CCOCC5)cc4)c(Cl)cc3[nH]2)cc1] | (1H-NMR (DMSO-d6) δ: 1.60 (s, 6H), 3.19 (dd, J = 5.2, 4.4 Hz, 4H), 3.76 (dd, J = 5.2, 4.4 Hz, 4H), 7.01 (d, J = 9.1 Hz, 2H), 7.43 (d, J = 8.6 Hz, 2H), 7.56 (d, J = 8.6 Hz, 2H), 7.62 (d, J = 9.1 Hz, 2H), 7.83 (s, 1H) | | | |
| D-36 | 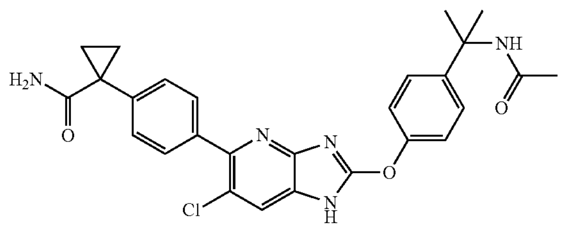 [SMILES: CC(=O)NC(C)(C)c1ccc(Oc2nc3nc(-c4ccc(C5(C(N)=O)CC5)cc4)c(Cl)cc3[nH]2)cc1] | 1H-NMR (DMSO-d6) δ: 1.03 (m, 2H), 1.36 (m, 2H), 1.57 (s, 6H), 1.84 (s, 3H), 6.27 (s, 1H), 7.07 (s, 1H), 7.29 (d, J = 8.6 Hz, 2H), 7.39 (d, J = 8.6 Hz, 2H), 7.43 (d, J = 8.1 Hz, 2H), 7.64 (d, J = 8.1 Hz, 2H), 7.91 (s, 1H), 8.09 (s, 1H). | 1.61 | 504.25 | B |
| D-37 | 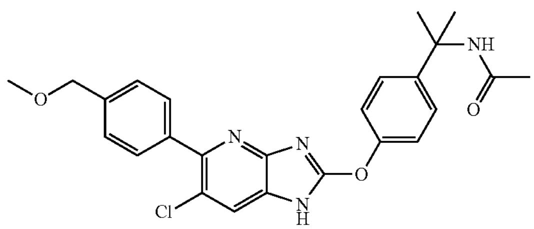 [SMILES: COCc1ccc(-c2nc3nc(Oc4ccc(C(C)(C)NC(C)=O)cc4)[nH]c3cc2Cl)cc1] | 1H-NMR (DMSO-d6) δ: 1.57 (s, 6H), 1.85 (s, 3H), 3.34 (s, 3H), 4.48 (s, 2H), 7.31 (d, J = 8.6 Hz, 2H), 7.39 (d, J = 6.1 Hz, 2H), 7.41 (d, J = 6.1 Hz, 2H), 7.62 (d, J = 8.1 Hz, 2H), 7.96 (s, 1H), 8.10 (s, 1H). | 1.87 | 465.2 | B |

TABLE 64

| No. | Structure | NMR(δ) | retention time | Mass (M + H) | method |
|---|---|---|---|---|---|
| D-38 | 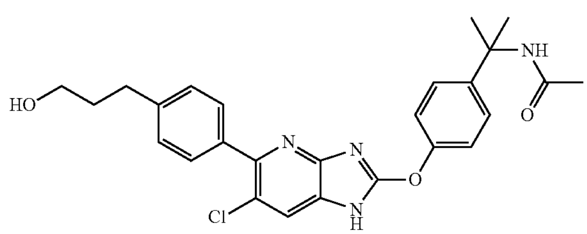 [SMILES: CC(=O)NC(C)(C)c1ccc(Oc2nc3nc(-c4ccc(CCCO)cc4)c(Cl)cc3[nH]2)cc1] | 1H-NMR (DMSO-d6) δ: 1.57 (s, 6H), 1.77 (m, 2H), 1.84 (s, 3H), 2.67 (t, J = 7.9 Hz, 2H), 3.45 (m, 2H), 4.49 (t, J = 5.1 Hz, 1H), 7.29 (m, 4H), 7.39 (d, J = 8.6 Hz, 2H), 7.55 (d, J = 8.1 Hz, 2H), 7.92 (s, 1H), 8.09 (s, 1H). | 1.68 | 479.2 | B |
| D-39 | 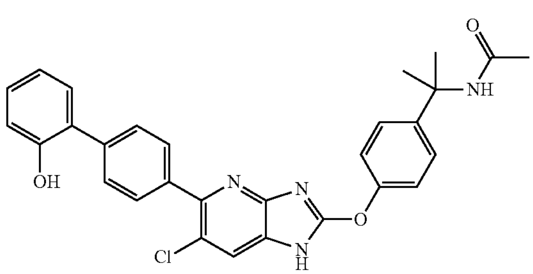 [SMILES: CC(=O)NC(C)(C)c1ccc(Oc2nc3nc(-c4ccc(-c5ccccc5O)cc4)c(Cl)cc3[nH]2)cc1] | 1H-NMR (DMSO-d6) δ: 1.57 (s, 6H), 1.85 (s, 3H), 6.91 (t, J = 7.4 Hz, 1H), 6.97 (d, J = 7.6 Hz, 1H), 7.19 (td, J = 7.6, 1.4 Hz, 1H), 7.30 (d, J = 9.1 Hz, 2H), 7.33 (d, J = 8.1 Hz, 1H), 7.39 (d, J = 8.6 Hz, 2H), 7.64 (d, J = 8.1 Hz, 2H), 7.68 (d, J = 8.6 Hz, 2H), 7.93 (s, 1H), 8.09 (s, 1H), 9.60 (s, 1H), 13.25 (br s, 1H). | 2.04 | 513.2 | B |

TABLE 64-continued

| No. | Structure | NMR(δ) | retention time | Mass (M + H) | method |
|---|---|---|---|---|---|
| D-40 | 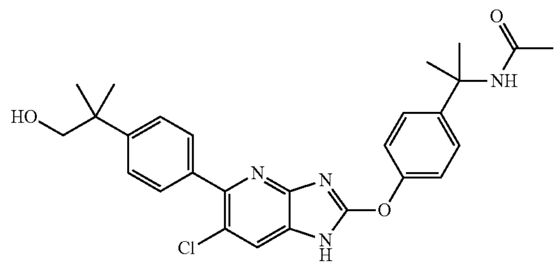 [SMILES: CC(=O)NC(C)(C)c1ccc(Oc2nc3nc(-c4ccc(C(C)(C)CO)cc4)c(Cl)cc3[nH]2)cc1] | 1H-NMR (DMSO-d6) δ: 1.27 (s, 6H), 1.57 (s, 6H), 1.84 (s, 3H), 3.47 (d, J = 5.6 Hz, 2H), 4.72 (t, J = 5.3 Hz, 1H), 7.31 (d, J = 8.6 Hz, 2H), 7.40 (d, J = 9.1 Hz, 2H), 7.46 (d, J = 8.6 Hz, 2H), 7.58 (d, J = 8.6 Hz, 2H), 7.95 (s, 1H), 8.10 (s, 1H), 13.18 (s, 1H). | 1.85 | 493.4 | B |
| D-41 | 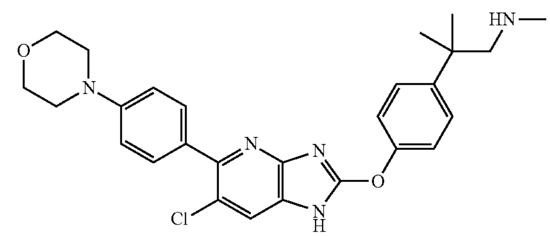 [SMILES: CNCC(C)(C)c1ccc(Oc2nc3nc(-c4ccc(N5CCOCC5)cc4)c(Cl)cc3[nH]2)cc1] | 1H-NMR (DMSO-d6) δ: 1.35(s, 6H), 2.39 (s, 3H), 2.73 (s, 2H), 3.17-3.19 (m, 4H), 3.75-3.77 (m, 4H), 7.00 (d, J = 8.6 Hz, 2H), 7.30 (d, J = 8.6 Hz, 2H), 7.44 (d, J = 8.6 Hz, 2H), 7.55 (d, J = 8.6 Hz, 2H), 7.78 (s, 1H) | | | |
| D-42 | 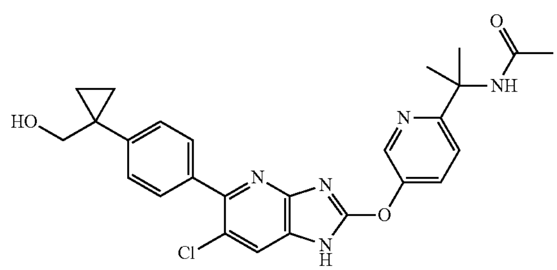 [SMILES: CC(=O)NC(C)(C)c1ccc(Oc2nc3nc(-c4ccc(C5(CO)CC5)cc4)c(Cl)cc3[nH]2)cn1] | 1H-NMR (DMSO-d6) δ: 0.78-0.90 (m, 4H), 1.58 (s, 6H), 1.86 (s, 3H), 3.59 (d, J = 5.58 Hz, 2H), 4.72 (t, J = 5.58 Hz, 1H), 7.39 (d, J = 8.11 Hz, 2H), 7.47 (d, J = 9.12 Hz, 1H), 7.56 (d, J = 8.11 Hz, 2H), 7.84 (dd, J = 9.12, 3.04 Hz, 1H), 8.00 (s, 1H), 8.20 (s, 1H), 8.58 (d, J = 3.04 Hz, 1H), 13.39 (s, 1H). | | | |

TABLE 65

| No. | Structure | NMR(δ) | retention time | Mass (M + H) | method |
|---|---|---|---|---|---|
| D-43 | 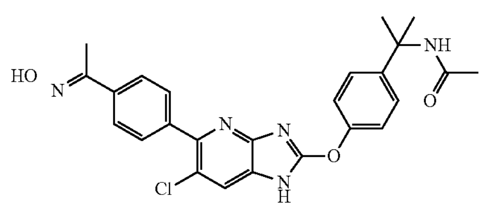 | 1H-NMR (DMSO-d6) δ: 1.57 (s, 6H), 1.85 (s, 3H), 2.20 (s, 3H), 7.31 (d, J = 9.1 Hz, 2H), 7.40 (d, J = 8.6 Hz, 2H), 7.67 (d, J = 8.1 Hz, 2H), 7.75 (d, J = 8.1 Hz, 2H), 7.97 (s, 1H), 8.10 (s, 1H), 11.29 (s, 1H). | 1.73 | 478.2 | B |
| D-44 | 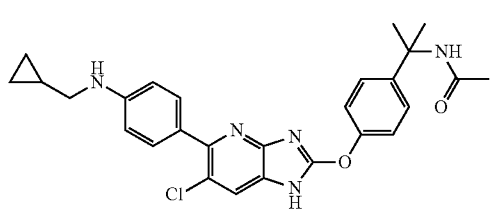 [SMILES: CC(=O)NC(C)(C)c1ccc(Oc2nc3nc(-c4ccc(NCC5CC5)cc4)c(Cl)cc3[nH]2)cc1] | 1H-NMR (DMSO-d6) δ: 0.22-0.25 (m, 2H), 0.47-0.51 (m, 2H), 1.05-1.10 (m, 1H), 1.56 (s, 6H), 1.84 (s, 3H), 2.95 (t, J = 6.1 Hz, 2H), 5.91 (s, 1H), 6.64 (d, J = 8.6 Hz, 2H), 7.28 (d, J = 9.1 Hz, 2H), 7.38 (d, J = 8.6 Hz, 2H), 7.43 (d, J = 8.6 Hz, 2H), 7.83 (s, 1H), 8.09 (s, 1H). | 1.84 | 490.3 | B |

TABLE 65-continued

| No. | Structure | NMR(δ) | retention time | Mass (M + H) | method |
|---|---|---|---|---|---|
| D-45 | 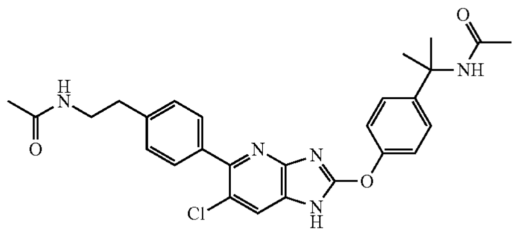 [SMILES: CC(=O)NCCc1ccc(-c2nc3nc(Oc4ccc(C(C)(C)NC(C)=O)cc4)[nH]c3cc2Cl)cc1] | 1H-NMR (DMSO-d6) δ: 1.57 (s, 6H), 1.81 (s, 3H), 1.91 (s, 3H), 2.77 (t, J = 4.0 Hz, 2H), 3.32 (dd, J = 4.0, 4.0 Hz, 2H), 7.30-7.32 (m, 4H), 7.40 (d, J = 8.6 Hz, 2H), 7.58 (d, J = 8.6 Hz, 2H), 7.95 (s, 1H), 7.99 (t, J = 4.0 Hz, 1H), 8.13 (s, 1H) | | | |
| D-46 | 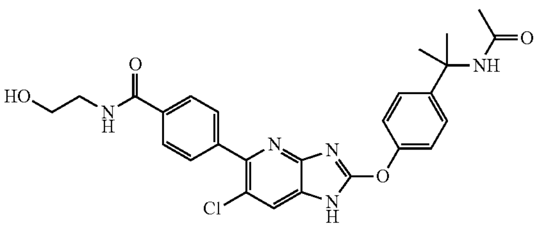 [SMILES: CC(=O)NC(C)(C)c1ccc(Oc2nc3nc(-c4ccc(C(=O)NCCO)cc4)c(Cl)cc3[nH]2)cc1] | 1H-NMR (DMSO-d6) δ: 1.57 (s, 6H), 1.85 (s, 3H), 3.33-3.53 (m, 4H), 4.74 (s, 1H), 7.30 (d, J = 8.62 Hz, 2H), 7.39 (d, J = 8.62 Hz, 2H), 7.72 (d, J = 8.11 Hz, 2H), 7.93-7.95 (m, 3H), 8.10 (s, 1H), 8.51 (t, J = 8.11 Hz, 1H). | 1.39 | 508.2 | B |
| D-47 | 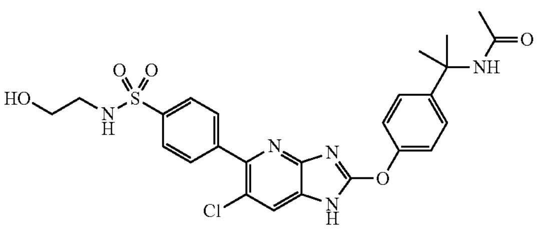 [SMILES: CC(=O)NC(C)(C)c1ccc(Oc2nc3nc(-c4ccc(S(=O)(=O)NCCO)cc4)c(Cl)cc3[nH]2)cc1] | 1H-NMR (DMSO-d6) δ: 1.57 (s, 6H), 1.85 (s, 3H), 2.86 (q, J = 6.25 Hz, 2H), 3.30 (m, 2H), 7.31 (d, J = 8.62 Hz, 2H), 7.39 (d, J = 9.12 Hz, 2H), 7.69 (t, J = 5.83 Hz, 1H), 7.87 (dd, J = 13.94, 8.36 Hz. 4H), 7.98 (s, 1H), 8.10 (s, 1H), 8.16 (s, 1H). | 1.51 | 544.35 | B |

TABLE 66

| No. | Structure | NMR(δ) | retention time | Mass (M + H) | method |
|---|---|---|---|---|---|
| D-48 | 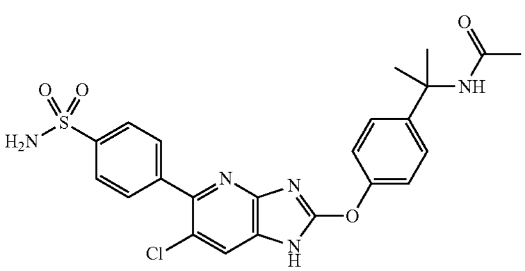 [SMILES: CC(=O)NC(C)(C)c1ccc(Oc2nc3nc(-c4ccc(S(N)(=O)=O)cc4)c(Cl)cc3[nH]2)cc1] | 1H-NMR (DMSO-d6) δ: 1.57 (s, 6H), 1.85 (s, 3H), 7.32 (d, J = 8.6 Hz, 2H), 7.40 (d, J = 8.6 Hz, 2H), 7.45 (bs, 2H), 7.83 (d, J = 8.6 Hz, 2H), 7.92 (d, J = 8.6 Hz, 2H), 8.03 (s, 1H), 8.11 (s, 1H) | | | |
| D-49 | 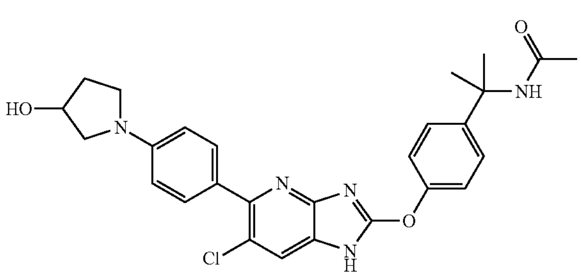 [SMILES: CC(=O)NC(C)(C)c1ccc(Oc2nc3nc(-c4ccc(N5CCC(O)C5)cc4)c(Cl)cc3[nH]2)cc1] | 1H-NMR (DMSO-d6) δ: 1.57 (s, 6H), 1.85 (s, 3H), 1.88-1.96 (m, 1H), 2.02-2.11 (m, 1H), 3.14 (d, J = 10.1 Hz, 1H), 3.39 (q, J = 8.3 Hz, 2H), 3.46 (dd, J = 9.9, 4.8 Hz, 1H), 4.42 (s, 1H), 4.98 (d, J = 3.5 Hz, 1H), 6.58 (d, J = 8.6 Hz, 2H), 7.30 (d, J = 8.6 Hz, 2H), 7.39 (d, J = 9.1 Hz, 2H), 7.53 (d, J = 8.6 Hz, 2H), 7.88 (s, 1H), 8.10 (s, 1H), 13.07 (s, 1H). | 1.71 | 506.2 | B |

TABLE 66-continued

| No. | Structure | NMR(δ) | retention time | Mass (M + H) | method |
|---|---|---|---|---|---|
| D-50 | 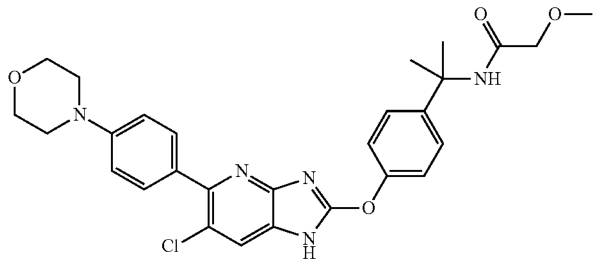 [SMILES: COCC(=O)NC(C)(C)c1ccc(Oc2nc3nc(-c4ccc(N5CCOCC5)cc4)c(Cl)cc3[nH]2)cc1] | 1H-NMR (DMSO-d6) δ: 1.62 (s, 6H), 3.19 (dd, J = 5.2, 4.4 Hz, 4H), 3.33 (s, 3H), 3.76 (dd, J = 5.2, 4.4 Hz, 4H), 3.80 (s, 2H), 7.02 (d, J = 9.1 Hz, 2H), 7.33 (d, J = 8.6 Hz, 2H), 7.43 (d, J = 8.6 Hz, 2H), 7.57 (d, J = 9.1 Hz, 2H), 7.73 (s, 1H), 7.92 (s, 1H). | | | |
| D-51 | 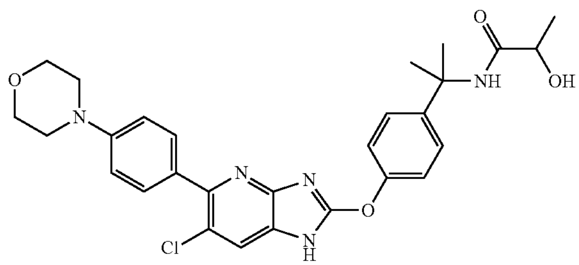 [SMILES: CC(O)C(=O)NC(C)(C)c1ccc(Oc2nc3nc(-c4ccc(N5CCOCC5)cc4)c(Cl)cc3[nH]2)cc1] | 1H-NMR (DMSO-d6) δ: 1.22 (d, J = 6.6 Hz, 3H), 1.62 (s, 6H), 3.19 (dd, J = 5.2, 4.4 Hz, 4H), 3.76 (dd, J = 5.2, 4.4 Hz, 4H), 3.93-3.99 (m, 1H), 5.49 (d, J = 5.1 Hz, 1H), 7.02 (d, J = 8.6 Hz, 2H), 7.33 (d, J = 8.6 Hz, 2H), 7.43 (d, J = 8.6 Hz, 2H), 7.56 (d, J = 8.6 Hz, 2H), 7.61 (s, 1H), 7.92 (s, 1H). | | | |
| D-52 | 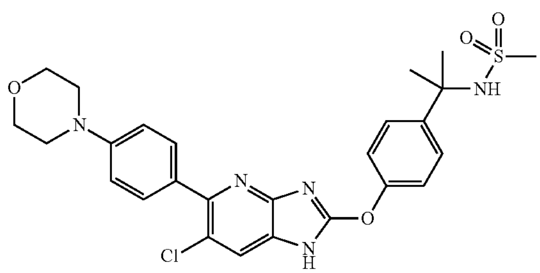 [SMILES: CC(C)(NS(C)(=O)=O)c1ccc(Oc2nc3nc(-c4ccc(N5CCOCC5)cc4)c(Cl)cc3[nH]2)cc1] | 1H-NMR (DMSO-d6) δ: 1.55 (s, 6H), 3.20 (brs, 4H), 3.75 (brs, 4H), 3.90 (s, 3H), 7.02 (d, J = 8.6 Hz, 2H), 7.53-7.58 (m, 5H), 7.69 (d, J = 8.6 Hz, 2H), 8.10 (s, 1H). | | | |

TABLE 67

| No. | Structure | NMR(δ) | retention time | Mass (M + H) | method |
|---|---|---|---|---|---|
| D-53 | 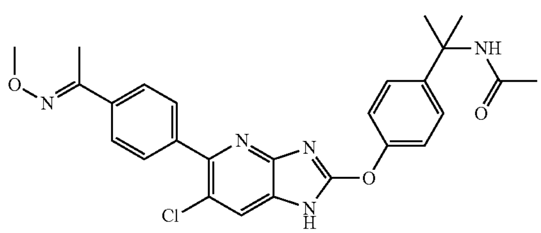 [SMILES: CO/N=C(\C)c1ccc(-c2nc3nc(Oc4ccc(C(C)(C)NC(C)=O)cc4)[nH]c3cc2Cl)cc1] | 1H-NMR (DMSO-d6) δ: 1.57 (s, 6H), 1.85 (s, 3H), 2.23 (s, 3H), 3.95 (s, 3H), 7.30 (t, J = 4.1 Hz, 2H), 7.39 (d, J = 9.1 Hz, 2H), 7.69 (d, J = 8.6 Hz, 2H), 7.76 (d, J = 8.1 Hz, 2H), 7.94 (s, 1H), 8.10 (s, 1H). | 2.14 | 492.25 | B |
| D-54 | 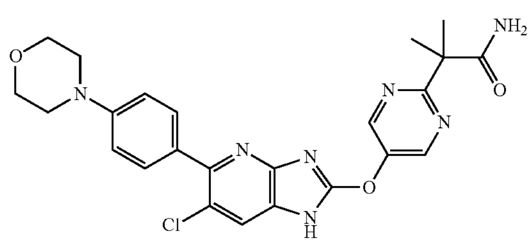 [SMILES: CC(C)(C(N)=O)c1ncc(Oc2nc3nc(-c4ccc(N5CCOCC5)cc4)c(Cl)cc3[nH]2)cn1] | 1H-NMR (DMSO-d6) δ: 1.56 (s, 6H), 3.20 (t, J = 4.56 Hz, 4H), 3.76 (t, J = 4.58 Hz, 4H), 6.94-7.05 (m, 4H), 7.57 (d, J = 8.62 Hz, 2H), 8.00 (s, 1H), 9.00 (s, 2H), 13.43 (s, 1H). | | | |

TABLE 67-continued

| No. | Structure | NMR(δ) | retention time | Mass (M + H) | method |
|---|---|---|---|---|---|
| D-55 | 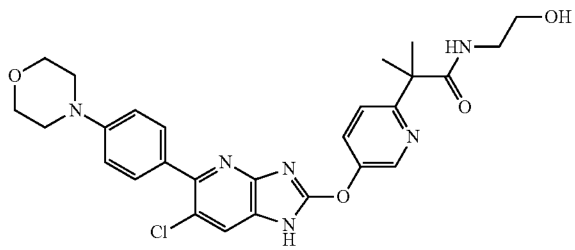 [SMILES: CC(C)(C(=O)NCCO)c1ccc(Oc2nc3nc(-c4ccc(N5CCOCC5)cc4)c(Cl)cc3[nH]2)cn1] | 1H-NMR (DMSO-d6) δ: 1.52 (s, 6H), 3.12-3.21 (m, 6H), 3.36-3.41 (m, 2H), 3.75-3.78 (m, 4H), 4.61 (t, J = 4.0 Hz, 1H), 7.02 (d, J = 8.6 Hz, 2H), 7.44 (t, J = 4.0 Hz, 1H), 7.48 (d, J = 8.6 Hz, 1H), 7.57 (d, J = 8.6 Hz, 2H), 7.90 (dd, J = 4.0 Hz, 8.6 Hz, 1H), 7.95 (s, 1H), 8.63 (d, J = 4.0 Hz, 1H) | | | |
| D-56 | 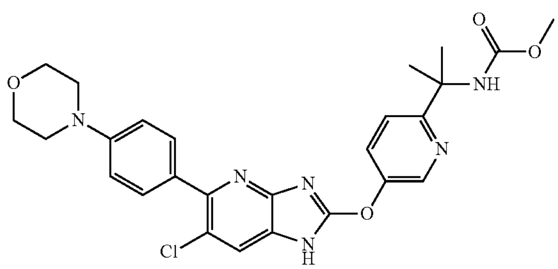 [SMILES: COC(=O)NC(C)(C)c1ccc(Oc2nc3nc(-c4ccc(N5CCOCC5)cc4)c(Cl)cc3[nH]2)cn1] | 1H-NMR (DMSO-d6) δ: 1.64 (s, 6H), 3.19 (dd, J = 5.2, 4.4 Hz, 4H), 3.47 (s, 3H), 3.76 (dd, J = 5.2, 4.4 Hz, 4H), 7.02 (d, J = 8.6 Hz, 2H), 7.33 (d, J = 8.6 Hz, 2H), 7.42 (d, J = 8.6 Hz, 2H), 7.57 (d, J = 8.6 Hz, 2H), 7.61 (s, 1H), 7.92 (s, 1H). | | | |
| D-57 | 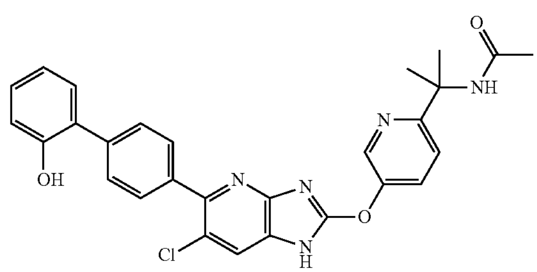 [SMILES: CC(=O)NC(C)(C)c1ccc(Oc2nc3nc(-c4ccc(-c5ccccc5O)cc4)c(Cl)cc3[nH]2)cn1] | 1H-NMR (DMSO-d6) δ: 1.58 (s, 6H), 1.87 (s, 3H), 6.88-6.99 (m, 2H), 7.19 (t, J = 7.60 Hz, 1H), 7.33 (d, J = 6.59 Hz, 1H), 7.48 (d, J = 8.62 Hz, 1H), 7.67 (dd, J = 14.19, 8.62 Hz, 4H), 7.86 (dd, J = 8.62, 3.04 Hz, 1H), 8.04 (s, 1H), 8.20 (s, 1H), 8.60 (d, J = 3.04 Hz, 1H), 9.61 (s, 1H), 13.46 (s, 1H). | | | |

TABLE 68

| No. | Structure | NMR(δ) | retention time | Mass (M + H) | method |
|---|---|---|---|---|---|
| D-58 | 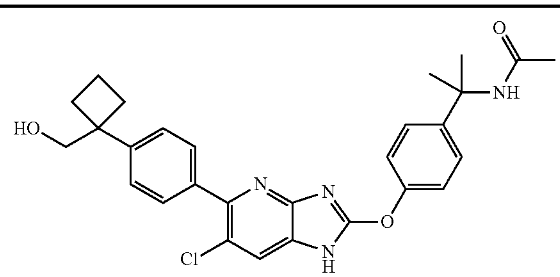 | 1H-NMR (DMSO-d6) δ: 1.57 (s, 6H), 1.80-1.85 (m, 4H), 1.98-2.02 (m, 1H), 2.19-2.28 (m, 4H), 3.56 (s, 2H), 7.21 (d, J = 8.1 Hz, 2H), 7.31 (d, J = 8.6 Hz, 2H), 7.40 (d, J = 8.6 Hz, 2H), 7.58 (d, J = 8.1 Hz, 2H), 7.96 (s, 1H), 8.11 (s, 1H). | | | |
| D-59 | 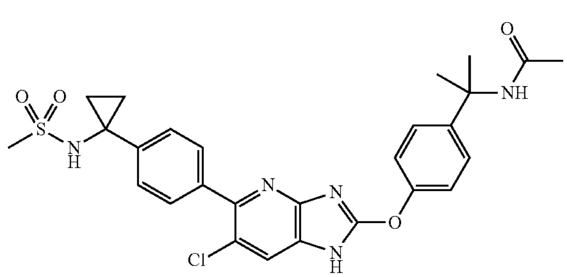 [SMILES: CC(=O)NC(C)(C)c1ccc(Oc2nc3nc(-c4ccc(C5(NS(C)(=O)=O)CC5)cc4)c(Cl)cc3[nH]2)cc1] | 1H-NMR (DMSO-d6) δ: 1.18-1.21(m, 2H), 1.33-1.36 (m, 2H), 1.57 (s, 6H), 1.85 (s, 3H), 2.63 (s, 3H), 7.31 (d, J = 8.6 Hz, 2H), 7.40 (d, J = 8.6 Hz, 2H), 7.47 (d, J = 8.6 Hz, 2H), 7.60 (d, J = 8.6 Hz, 2H), 7.97 (s, 1H), 8.11 (s, 1H), 8.27 (s, 1H) | | | |

TABLE 68-continued

| No. | Structure | NMR(δ) | retention time | Mass (M + H) | method |
|---|---|---|---|---|---|
| D-60 | 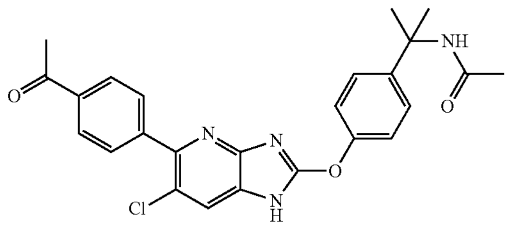 [SMILES: CC(=O)NC(C)(C)c1ccc(Oc2nc3nc(-c4ccc(C(C)=O)cc4)c(Cl)cc3[nH]2)cc1] | 1H-NMR (DMSO-d6) δ: 1.57 (s, 6H), 1.85 (s, 3H), 2.64 (s, 3H), 7.31 (d, J = 8.6 Hz, 2H), 7.40 (d, J = 8.6 Hz, 2H), 7.80 (d, J = 8.1 Hz, 2H), 7.98 (s, 1H), 8.06 (d, J = 8.1 Hz, 2H), 8.10 (s, 1H). | 1.82 | 463.1 | B |
| D-61 | 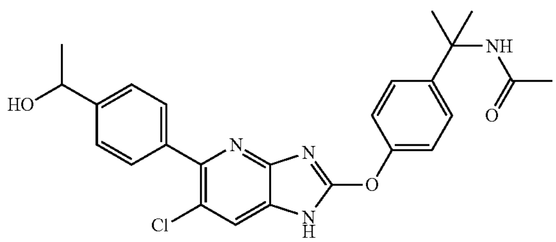 [SMILES: CC(=O)NC(C)(C)c1ccc(Oc2nc3nc(-c4ccc(C(C)O)cc4)c(Cl)cc3[nH]2)cc1] | 1H-NMR (DMSO-d6) δ: 1.37 (d, J = 6.6 Hz, 3H), 1.57 (s, 6H), 1.84 (s, 3H), 4.75-4.81 (m, 1H), 5.22 (d, J = 4.1 Hz, 1H), 7.30 (d, J = 8.6 Hz, 2H), 7.39 (d, J = 8.6 Hz, 2H), 7.43 (d, J = 8.1 Hz, 2H), 7.59 (d, J = 8.1 Hz, 2H), 7.92 (s, 1H), 8.10 (s, 1H). | 1.63 | 465.2 | B |
| D-62 | 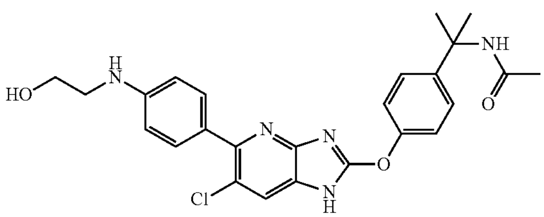 [SMILES: CC(=O)NC(C)(C)c1ccc(Oc2nc3nc(-c4ccc(NCCO)cc4)c(Cl)cc3[nH]2)cc1] | 1H-NMR (DMSO-d6) δ: 1.57 (s, 6H), 1.84 (s, 3H), 3.13-3.17 (m, 2H), 3.56-3.60 (m, 2H), 4.71 (t, J = 5.3 Hz, 1H), 5.83 (s, 1H), 6.65 (d, J = 8.1 Hz, 2H), 7.30 (d, J = 8.6 Hz, 2H), 7.42 (m, 4H), 7.89 (s, 1H), 8.10 (s, 1H). | 1.42 | 480.25 | B |

TABLE 69

| No. | Structure | NMR(δ) | retention time | Mass (M + H) | method |
|---|---|---|---|---|---|
| D-63 | 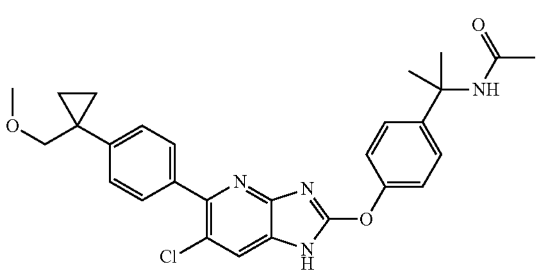 [SMILES: COCC1(c2ccc(-c3nc4nc(Oc5ccc(C(C)(C)NC(C)=O)cc5)[nH]c4cc3Cl)cc2)CC1] | 1H-NMR (DMSO-d6) δ: 0.89 (s, 4H), 1.57 (s, 6H), 1.84 (s, 3H), 3.26 (s, 3H), 3.53 (d, J = 11.7 Hz, 2H), 7.21-7.62 (m, 8H), 7.79 (s, 1H), 8.07 (s, 1H). | 2.12 | 505.2 | B |
| D-64 | 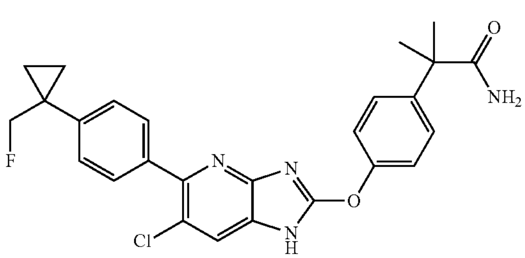 [SMILES: CC(C)(C(N)=O)c1ccc(Oc2nc3nc(-c4ccc(C5(CF)CC5)cc4)c(Cl)cc3[nH]2)cc1] | 1H-NMR (DMSO-d6) δ: 1.47 (s, 6H), 1.74 (dd, J = 18.8, 9.1 Hz, 1H), 2.57-2.67 (m, 5H), 6.94 (s, 1H), 6.98 (s, 1H), 7.36 (d, J = 8.6 Hz, 2H), 7.43 (d, J = 8.6 Hz, 2H), 7.59 (d, J = 8.1 Hz, 2H), 7.70 (d, J = 8.1 Hz, 2H), 7.96 (s, 1H). | | | |

TABLE 69-continued

| No. | Structure | NMR(δ) | retention time | Mass (M + H) | method |
|---|---|---|---|---|---|
| D-65 | 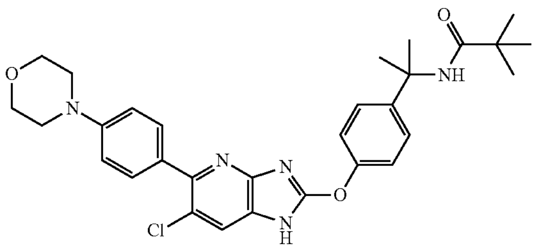 [SMILES: CC(C)(C)C(=O)NC(C)(C)c1ccc(Oc2nc3nc(-c4ccc(N5CCOCC5)cc4)c(Cl)cc3[nH]2)cc1] | | 2.19 | 548.42 | A |
| D-66 | 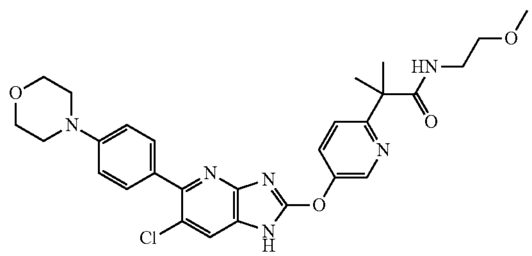 [SMILES: COCCNC(=O)C(C)(C)c1ccc(Oc2nc3nc(-c4ccc(N5CCOCC5)cc4)c(Cl)cc3[nH]2)cn1] | | 1.71 | 551.39 | A |
| D-67 | 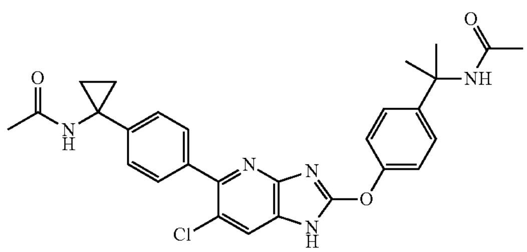 [SMILES: CC(=O)NC(C)(C)c1ccc(Oc2nc3nc(-c4ccc(C5(NC(C)=O)CC5)cc4)c(Cl)cc3[nH]2)cc1] | 1H-NMR (DMSO-d6) δ: 1.15-1.19 (m, 2H), 1.21-1.27 (m, 2H), 1.57 (s, 6H), 1.84 (s, 3H), 1.88 (s, 3H), 7.20 (d, J = 8.6 Hz, 2H), 7.31 (d, J = 8.6 Hz, 2H), 7.40 (d, J = 8.6 Hz, 2H), 7.54 (d, J = 8.6 Hz, 2H), 7.95 (s, 1H), 8.10 (s, 1H), 8.61 (s, 1H) | | | |

TABLE 70

| No. | Structure | NMR(δ) | retention time | Mass (M + H) | method |
|---|---|---|---|---|---|
| D-68 | 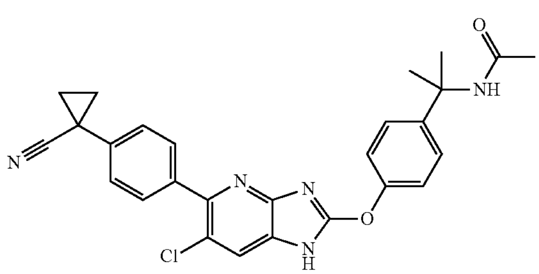 [SMILES: CC(=O)NC(C)(C)c1ccc(Oc2nc3nc(-c4ccc(C5(C#N)CC5)cc4)c(Cl)cc3[nH]2)cc1] | 1H-NMR (DMSO-d6) δ: 1.57 (s, 6H), 1.60 (t, J = 3.8 Hz, 2H), 1.80 (t, J = 3.5 Hz, 2H), 1.84 (s, 3H), 7.31 (d, J = 8.6 Hz, 2H), 7.40 (d, J = 8.6 Hz, 2H), 7.43 (d, J = 8.1 Hz, 2H), 7.67 (d, J = 8.1 Hz, 2H), 7.97 (s, 1H), 8.10 (s, 1H), 13.23 (br s, 1H). | 1.96 | 486.1 | B |
| D-69 | 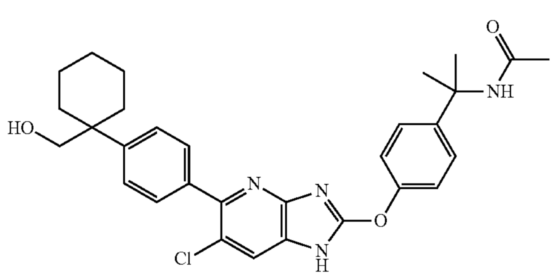 [SMILES: CC(=O)NC(C)(C)c1ccc(Oc2nc3nc(-c4ccc(C5(CO)CCCCC5)cc4)c(Cl)cc3[nH]2)cc1] | 1H-NMR (DMSO-d6) δ: 1.25-1.31 (m, 4H), 1.45-1.59 (m, 2H), 1.57 (s, 6H), 1.63-1.68 (m, 2H), 1.85 (s, 3H), 2.05-2.12 (m, 2H), 3.33 (s, 2H), 7.32 (d, J = 8.6 Hz, 2H), 7.40 (d, J = 8.6 Hz, 2H), 7.45 (d, J = 8.6 Hz, 2H), 7.62 (d, J = 8.6 Hz, 2H), 7.96 (s, 1H), 8.10 (s, 1H) | | | |

TABLE 70-continued

| No. | Structure | NMR(δ) | retention time | Mass (M + H) | method |
|---|---|---|---|---|---|
| D-70 | 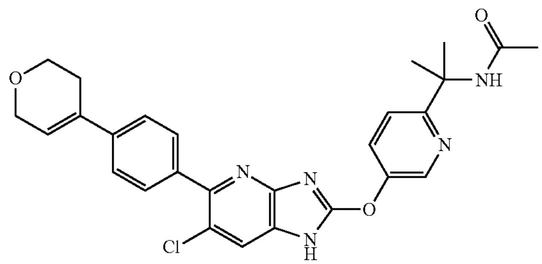 [SMILES: CC(=O)NC(C)(C)c1ccc(Oc2nc3nc(-c4ccc(C5=CCOCC5)cc4)c(Cl)cc3[nH]2)cn1] | 1H-NMR (DMSO-d6) δ: 1.58 (s, 6H), 1.86 (s, 3H), 2.44-2.55 (m, 2H), 3.85 (t, J = 5.3 Hz, 2H), 4.24-4.27 (m, 2H), 6.37 (s, 1H), 7.47 (d, J = 8.6 Hz, 1H), 7.56 (d, J = 8.6 Hz, 2H), 7.65 (d, J = 8.6 Hz, 2H), 7.85 (dd, J = 3.0 Hz, 8.6 Hz, 1H), 8.02 (s, 1H), 8.20 (s, 1H), 8.59 (d, J = 3.0 Hz, 1H) | | | |
| D-71 | 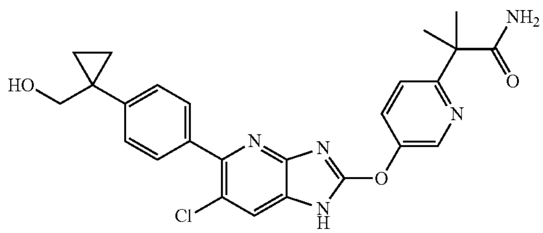 [SMILES: CC(C)(C(N)=O)c1ccc(Oc2nc3nc(-c4ccc(C5(CO)CC5)cc4)c(Cl)cc3[nH]2)cn1] | 1H-NMR (DMSO-d$_6$) δ: 0.80-0.83 (m, 2H), 0.84-0.90 (m, 2H), 1.51 (s, 6H), 3.59 (d, J = 5.7 Hz, 2H), 4.72 (t, J = 5.7 Hz, 1H), 6.97 (d, J = 8.1 Hz, 1H), 7.01 (s, 1H), 7.38 (d, J = 8.6 Hz, 2H), 7.50 (d, J = 8.6 Hz, 1H), 7.55 (d, J = 8.1 Hz, 2H), 7.89 (dd, J = 8.6, 2.5 Hz, 1H), 7.95 (s, 1H), 8.62 (d, J = 2.5 Hz, 1H). | | | |
| D-72 | 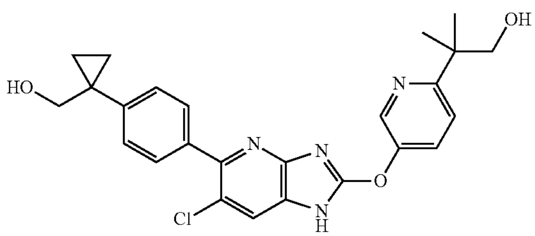 [SMILES: CC(C)(CO)c1ccc(Oc2nc3nc(-c4ccc(C5(CO)CC5)cc4)c(Cl)cc3[nH]2)cn1] | 1H-NMR (DMSO-d6) δ: 0.78-0.91 (m, 4H), 1.29 (s, 6H), 3.58 (t, J = 5.58 Hz, 4H), 4.71 (q, J = 5.58 Hz, 2H), 7.39 (d, J = 8.11 Hz, 2H), 7.55 (t, J = 8.62 Hz, 3H), 7.85 (dd, J = 8.62, 2.53 Hz, 1H), 7.98 (s, 1H), 8.62 (d, J = 2.53 Hz, 1H), 13.30 (s, 1H). | | | |

TABLE 71

| No. | Structure | NMR(δ) | retention time | Mass (M + H) | method |
|---|---|---|---|---|---|
| D-73 | 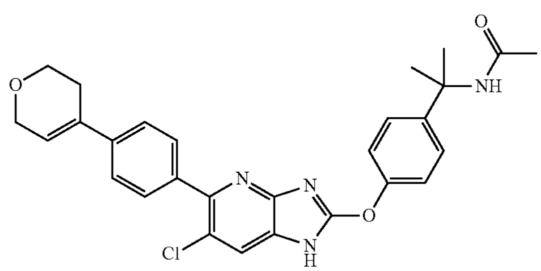 [SMILES: CC(=O)NC(C)(C)c1ccc(Oc2nc3nc(-c4ccc(C5=CCOCC5)cc4)c(Cl)cc3[nH]2)cc1] | 1H-NMR (DMSO-d6) δ: 1.57 (s, 6H), 1.85 (s, 3H), 2.50 (s, 2H), 3.85 (t, J = 5.3 Hz, 2H), 4.26 (d, J = 2.5 Hz, 2H), 6.36 (s, 1H), 7.31 (d, J = 8 Hz, 2H), 7.40 (d, J = 8.6 Hz, 2H), 7.56 (d, J = 8.6 Hz, 2H), 7.65 (d, J = 8.6 Hz, 2H), 7.97 (s, 1H), 8.11 (s, 1H). | | | |
| D-74 | 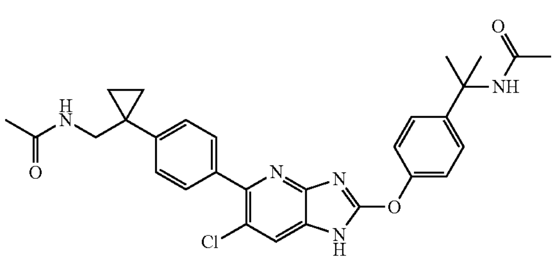 [SMILES: CC(=O)NCC1(c2ccc(-c3nc4nc(Oc5ccc(C(C)(C)NC(C)=O)cc5)[nH]c4cc3Cl)cc2)CC1] | 1H-NMR (DMSO-d6) δ: 0.82-0.88 (m, 2H), 0.93 (m, 2H), 1.57 (s, 6H), 1.79 (s, 3H), 1.84 (s, 3H), 3.37 (t, J = 5.6 Hz, 2H), 7.30 (d, J = 8.6 Hz, 2H), 7.34 (d, J = 8.6 Hz, 2H), 7.39 (d, J = 8.6 Hz, 2H), 7.57 (d, J = 8.1 Hz, 2H), 7.89 (t, J = 5.6 Hz, 1H), 7.94 (s, 1H), 8.10 (s, 1H). | 1.72 | 532.45 | B |

TABLE 71-continued

| No. | Structure | NMR(δ) | retention time | Mass (M + H) | method |
|---|---|---|---|---|---|
| D-75 | 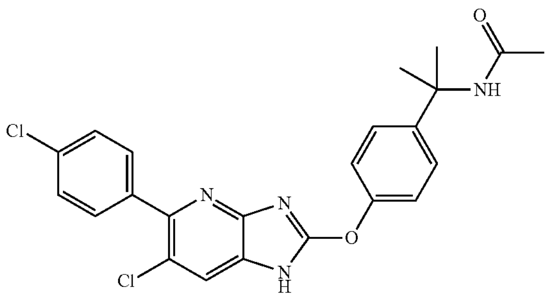 [SMILES: CC(=O)NC(C)(C)c1ccc(Oc2nc3nc(-c4ccc(Cl)cc4)c(Cl)cc3[nH]2)cc1] | | 2.1 | 455.25 | A |
| D-76 | 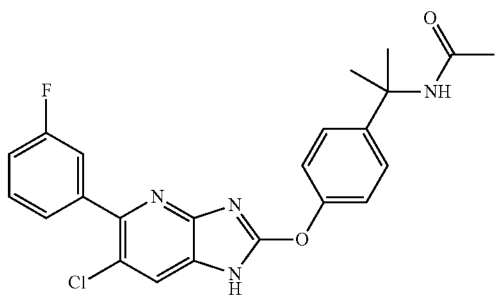 | | 1.93 | 439.3 | A |
| D-77 | 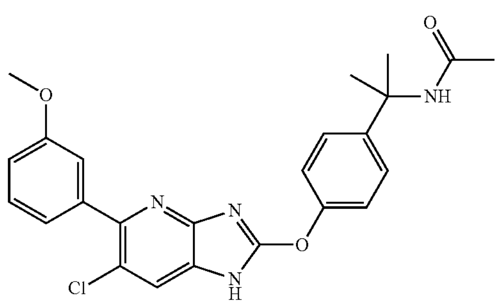 [SMILES: COc1cccc(-c2nc3nc(Oc4ccc(C(C)(C)NC(C)=O)cc4)[nH]c3cc2Cl)c1] | | 1.86 | 451.33 | A |

TABLE 72

| No. | Structure | retention time | Mass (M + H) | method |
|---|---|---|---|---|
| D-78 | 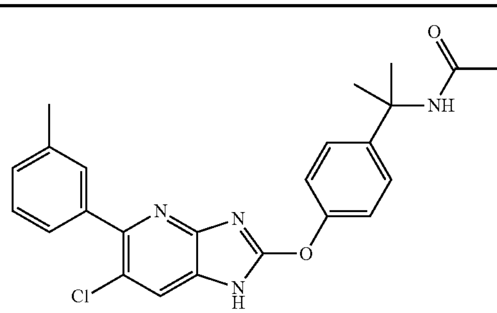 | 2 | 435.34 | A |

TABLE 72-continued

| No. | Structure | retention time | Mass (M + H) | method |
|---|---|---|---|---|
| D-79 | 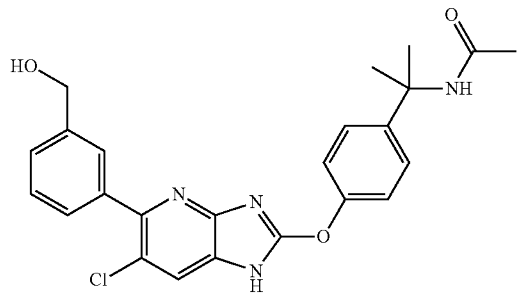 [SMILES: CC(=O)NC(C)(C)c1ccc(Oc2nc3nc(-c4cccc(CO)c4)c(Cl)cc3[nH]2)cc1] | 1.52 | 451.29 | A |
| D-80 | 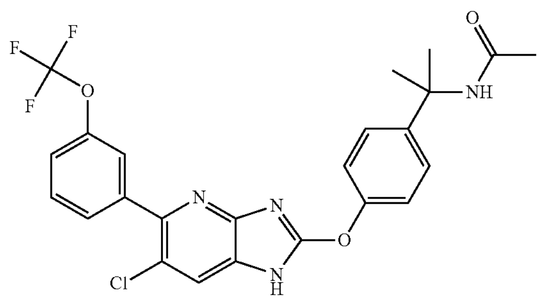 [SMILES: CC(=O)NC(C)(C)c1ccc(Oc2nc3nc(-c4cccc(OC(F)(F)F)c4)c(Cl)cc3[nH]2)cc1] | 2.22 | 505.29 | A |
| D-81 | 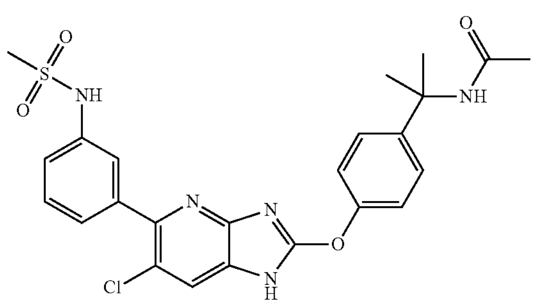 [SMILES: CC(=O)NC(C)(C)c1ccc(Oc2nc3nc(-c4cccc(NS(C)(=O)=O)c4)c(Cl)cc3[nH]2)cc1] | 1.58 | 514.29 | A |
| D-82 | 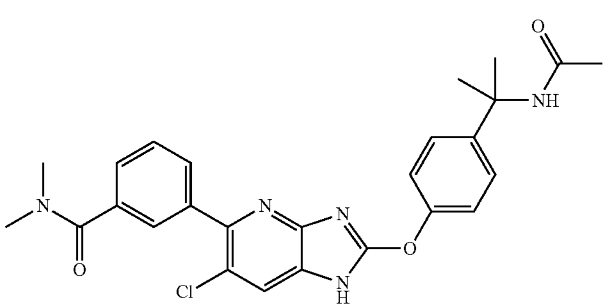 [SMILES: CC(=O)NC(C)(C)c1ccc(Oc2nc3nc(-c4cccc(C(=O)N(C)C)c4)c(Cl)cc3[nH]2)cc1] | 1.55 | 492.33 | A |

TABLE 73

| No. | Structure | retention time | Mass (M + H) | method |
|---|---|---|---|---|
| D-83 | 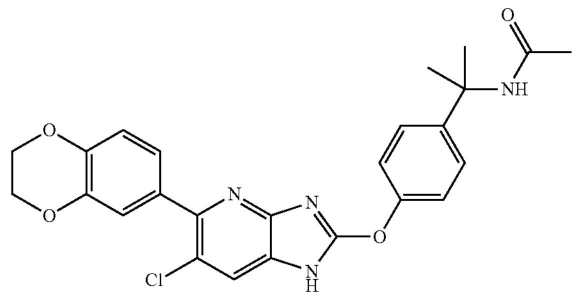 [SMILES: CC(=O)NC(C)(C)c1ccc(Oc2nc3nc(-c4ccc5c(c4)OCCO5)c(Cl)cc3[nH]2)cc1] | 1.81 | 479.3 | A |
| D-84 | 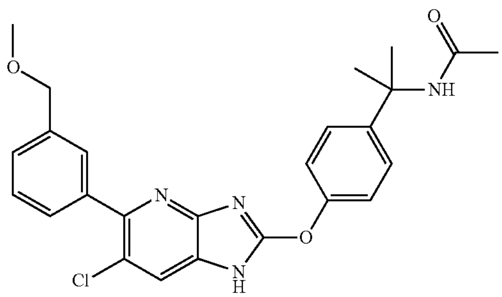 [SMILES: COCc1cccc(-c2nc3nc(Oc4ccc(C(C)(C)NC(C)=O)cc4)[nH]c3cc2Cl)c1] | 1.83 | 465.33 | A |
| D-85 | 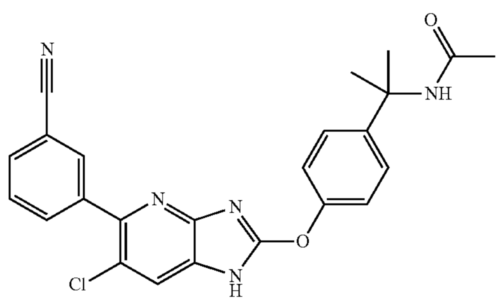 [SMILES: CC(=O)NC(C)(C)c1ccc(Oc2nc3nc(-c4cccc(C#N)c4)c(Cl)cc3[nH]2)cc1] | 1.8 | 446.29 | A |
| D-86 | 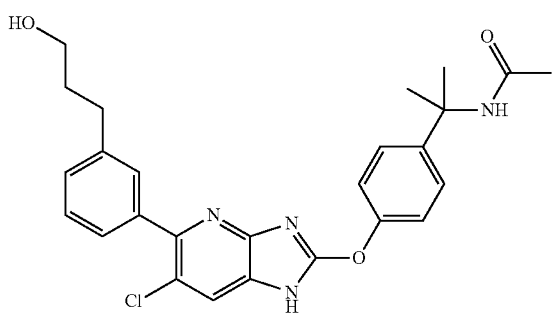 [SMILES: CC(=O)NC(C)(C)c1ccc(Oc2nc3nc(-c4cccc(CCCO)c4)c(Cl)cc3[nH]2)cc1] | 1.66 | 479.33 | A |
| D-87 | 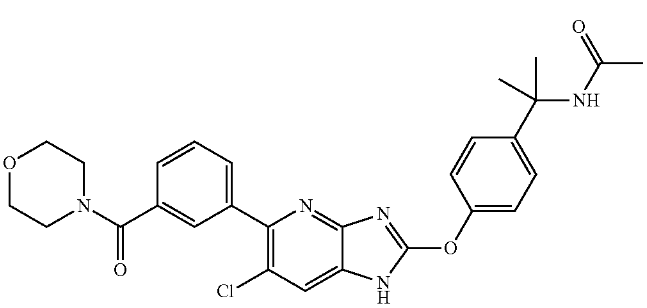 [SMILES: CC(=O)NC(C)(C)c1ccc(Oc2nc3nc(-c4cccc(C(=O)N5CCOCC5)c4)c(Cl)cc3[nH]2)cc1] | 1.52 | 534.38 | A |

TABLE 74

| No. | Structure | retention time | Mass (M + H) | method |
|---|---|---|---|---|
| D-88 | 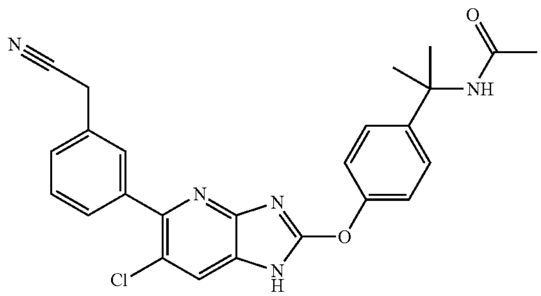 [SMILES: CC(=O)NC(C)(C)c1ccc(Oc2nc3nc(-c4cccc(CC#N)c4)c(Cl)cc3[nH]2)cc1] | 1.75 | 460.33 | A |
| D-89 | 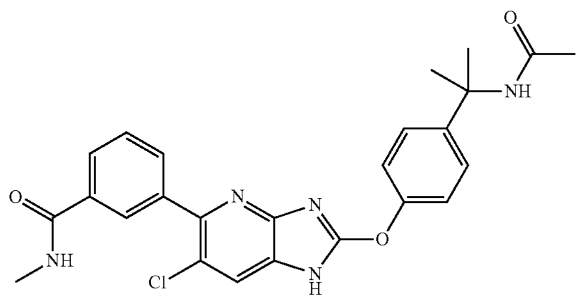 [SMILES: CNC(=O)c1cccc(-c2nc3nc(Oc4ccc(C(C)(C)NC(C)=O)cc4)[nH]c3cc2Cl)c1] | 1.46 | 478.33 | A |
| D-90 | 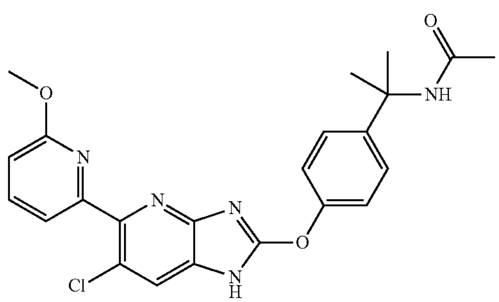 [SMILES: COc1cccc(-c2nc3nc(Oc4ccc(C(C)(C)NC(C)=O)cc4)[nH]c3cc2Cl)n1] | 1.74 | 452.3 | A |
| D-91 | 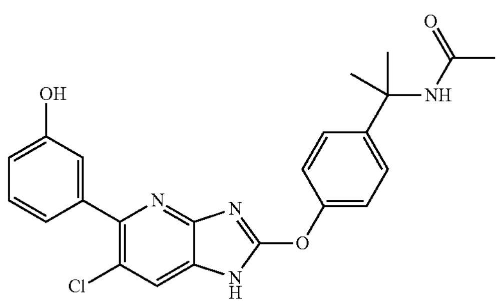 | 1.56 | 437.29 | A |
| D-92 | 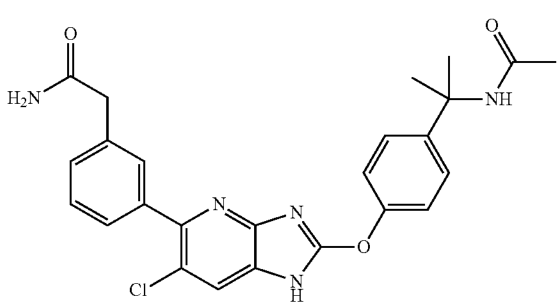 [SMILES: CC(=O)NC(C)(C)c1ccc(Oc2nc3nc(-c4cccc(CC(N)=O)c4)c(Cl)cc3[nH]2)cc1] | 1.42 | 478.33 | A |

TABLE 75

| No. | Structure | retention time | Mass (M + H) | method |
|---|---|---|---|---|
| D-93 | 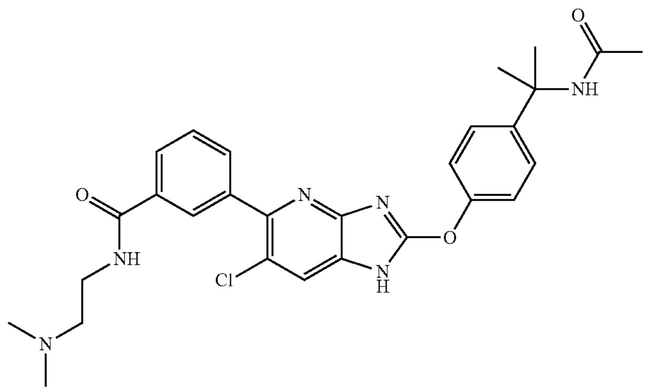 [SMILES: CC(=O)NC(C)(C)c1ccc(Oc2nc3nc(-c4cccc(C(=O)NCCN(C)C)c4)c(Cl)cc3[nH]2)cc1] | 1.23 | 535.39 | A |
| D-94 | 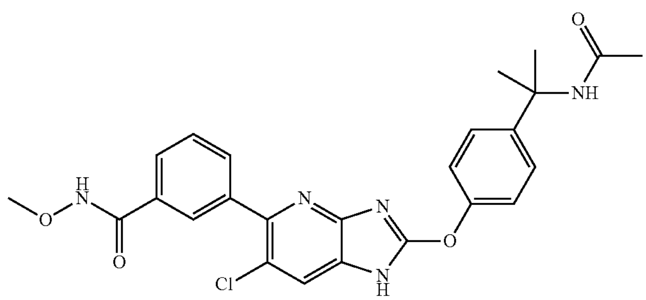 [SMILES: CONC(=O)c1cccc(-c2nc3nc(Oc4ccc(C(C)(C)NC(C)=O)cc4)[nH]c3cc2Cl)c1] | 1.45 | 494.31 | A |
| D-95 | 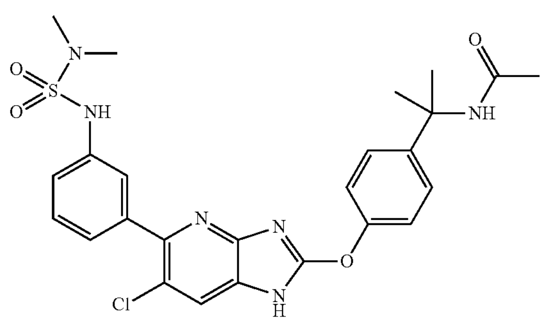 [SMILES: CC(=O)NC(C)(C)c1ccc(Oc2nc3nc(-c4cccc(NS(=O)(=O)N(C)C)c4)c(Cl)cc3[nH]2)cc1] | 1.72 | 543.34 | A |
| D-96 | 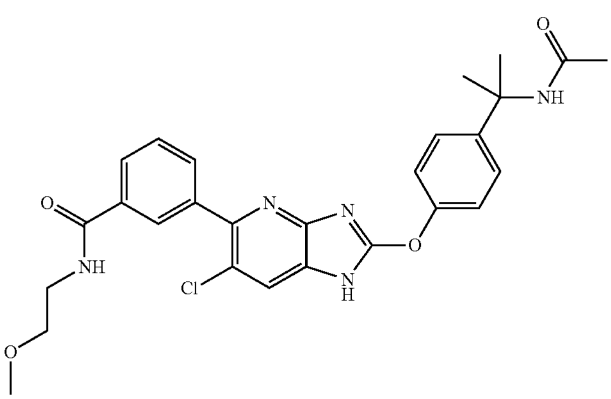 [SMILES: COCCNC(=O)c1cccc(-c2nc3nc(Oc4ccc(C(C)(C)NC(C)=O)cc4)[nH]c3cc2Cl)c1] | 1.52 | 522.35 | A |

TABLE 75-continued

| No. | Structure | retention time | Mass (M + H) | method |
|---|---|---|---|---|
| D-97 | 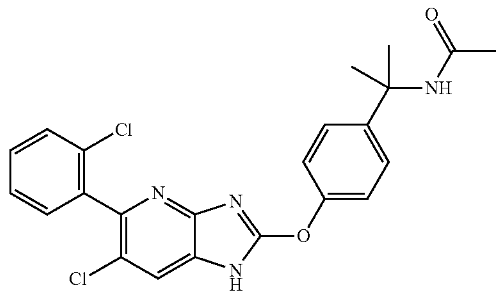 [SMILES: CC(=O)NC(C)(C)c1ccc(Oc2nc3nc(-c4ccccc4Cl)c(Cl)cc3[nH]2)cc1] | 1.91 | 455.25 | A |

TABLE 76

| No. | Structure | NMR(δ) | retention time | Mass (M + H) | method |
|---|---|---|---|---|---|
| D-98 | 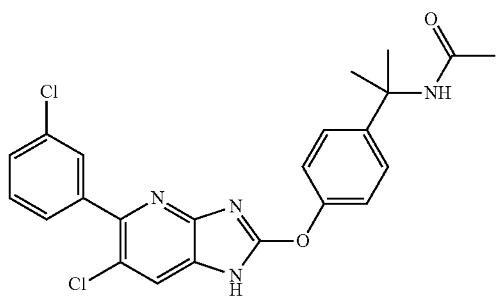 [SMILES: CC(=O)NC(C)(C)c1ccc(Oc2nc3nc(-c4cccc(Cl)c4)c(Cl)cc3[nH]2)cc1] | | 2.09 | 455.25 | A |
| D-99 | 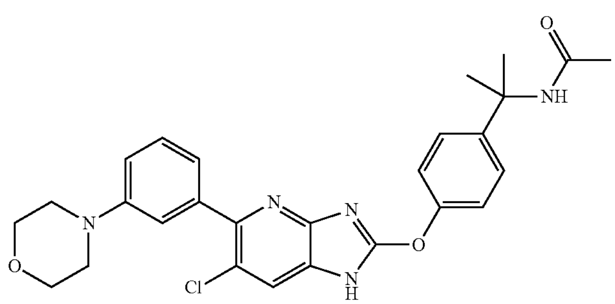 [SMILES: CC(=O)NC(C)(C)c1ccc(Oc2nc3nc(-c4cccc(N5CCOCC5)c4)c(Cl)cc3[nH]2)cc1] | | 1.74 | 506.37 | A |
| D-100 | 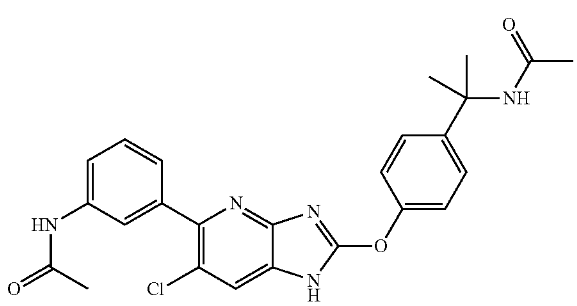 [SMILES: CC(=O)Nc1cccc(-c2nc3nc(Oc4ccc(C(C)(C)NC(C)=O)cc4)[nH]c3cc2Cl)c1] | | 1.51 | 478.33 | A |

TABLE 76-continued

| No. | Structure | NMR(δ) | retention time | Mass (M + H) | method |
|---|---|---|---|---|---|
| D-101 | 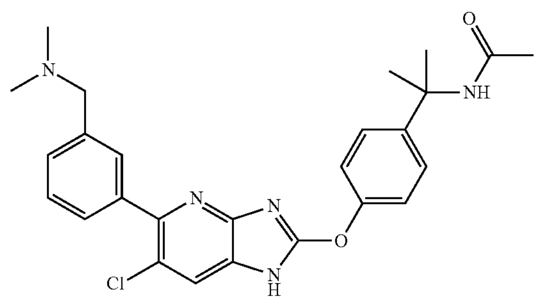 [SMILES: CC(=O)NC(C)(C)c1ccc(Oc2nc3nc(-c4cccc(CN(C)C)c4)c(Cl)cc3[nH]2)cc1] | | 1.23 | 478.36 | A |
| D-102 | 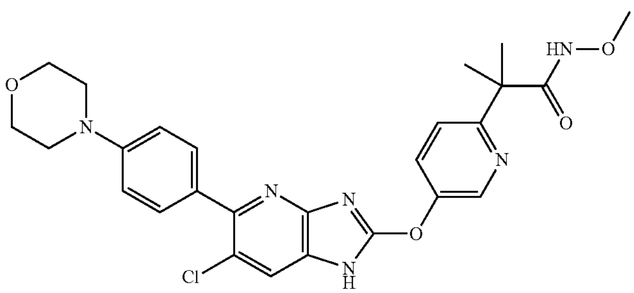 [SMILES: CONC(=O)C(C)(C)c1ccc(Oc2nc3nc(-c4ccc(N5CCOCC5)cc4)c(Cl)cc3[nH]2)cn1] | 1H-NMR (DMSO-d6) δ: 1.51 (s, 6H), 3.18-3.21 (m, 4H), 3.57 (s, 3H), 3.75-3.78 (m, 4H), 7.-2 (d, J = 8.6 Hz, 2H), 7.49 (d, J = 8.6 Hz, 1H), 7.57 (d, J = 8.6 Hz, 2H), 7.92 (dd, J = 3.0 Hz, 8.6 Hz, 1H), 7.95 (s, 1H), 8.63 (d, J = 3.0 Hz, 1H) | | | |

TABLE 77

| No. | Structure | NMR(δ) | retention time | Mass (M + H) | method |
|---|---|---|---|---|---|
| D-103 | 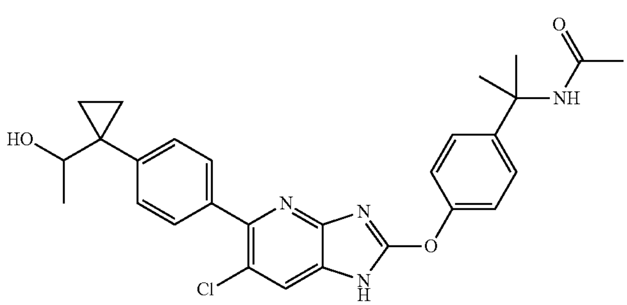 [SMILES: CC(=O)NC(C)(C)c1ccc(Oc2nc3nc(-c4ccc(C5(C(C)O)CC5)cc4)c(Cl)cc3[nH]2)cc1] | 1H-NMR (DMSO-d6) δ: 0.66-0.68 (m, 2H), 0.84-0.86 (m, 2H), 0.99 (d, J = 6.1 Hz, 2H), 1.57 (s, 6H), 1.84 (s, 3H), 4.66 (q, J = 6.1 Hz, 1H), 7.30 (d, J = 8.6 Hz, 2H), 7.39 (d, J = 8.6 Hz, 2H), 7.41 (d, J = 8.6 Hz, 2H), 7.55 (d, J = 8.6 Hz, 2H), 7.92 (s, 1H), 8.10 (s, 1H). | | | |
| D-104 | 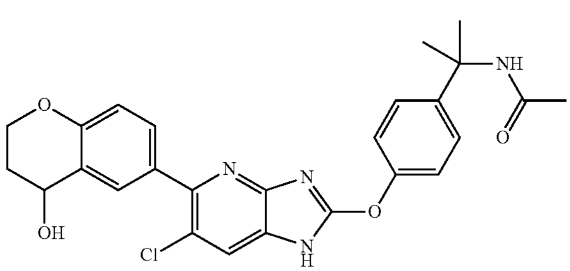 [SMILES: CC(=O)NC(C)(C)c1ccc(Oc2nc3nc(-c4ccc5c(c4)C(O)CCO5)c(Cl)cc3[nH]2)cc1] | 1H-NMR (DMSO-d6) δ: 1.57 (s, 6H), 1.85 (s, 3H), 1.92 (m, 1H), 2.05 (m, 1H), 4.23-4.25 (m, 2H), 4.68 (q, J = 5.07 Hz, 1H), 5.45 (d, J = 5.58 Hz, 1H), 6.83 (d, J = 8 62 Hz, 1H), 7.31 (d, J = 9.12 Hz, 2H), 7.40 (d, J = 9.12 Hz, 2H), 7.47 (dd, J = 10.65, 5.32 Hz, 1H), 7.64 (d, J = 10.00 Hz, 1H), 7.93 (s, 1H), 8.10 (s, 1H), 13.2 (brs, 1H). | 1.68 | 493.15 | B |

TABLE 77-continued

| No. | Structure | NMR(δ) | retention time | Mass (M + H) | method |
|---|---|---|---|---|---|
| D-105 | 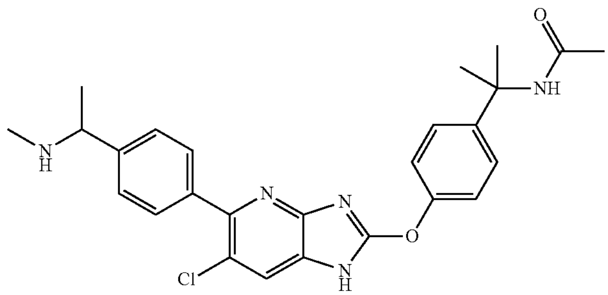 [SMILES: CNC(C)c1ccc(-c2nc3nc(Oc4ccc(C(C)(C)NC(C)=O)cc4)[nH]c3cc2Cl)cc1] | 1H-NMR (DMSO-d6) δ: 1.24 (s, 1H), 1.34 (d, J = 6.6 Hz, 3H), 1.57 (s, 6H), 1.84 (s, 3H), 2.23 (s, 3H), 3.77 (q, J = 6.4 Hz, 1H), 7.27 (d, J = 8.6 Hz, 2H), 7.37 (d, J = 8.6 Hz, 2H), 7.42 (d, J = 8.1 Hz, 2H), 7.62 (d, J = 8.1 Hz, 2H), 7.85 (s, 1H), 8.08 (s, 1H). | 1.19 | 478.3 | B |
| D-106 | 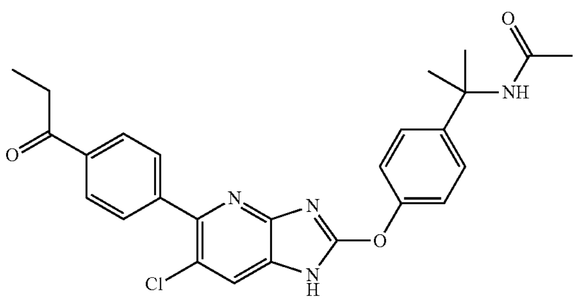 [SMILES: CCC(=O)c1ccc(-c2nc3nc(Oc4ccc(C(C)(C)NC(C)=O)cc4)[nH]c3cc2Cl)cc1] | 1H-NMR (DMSO-d6) δ: 1.12 (t, J = 7.1 Hz, 3H), 1.57 (s, 6H), 1.85 (s, 3H), 3.11 (q, J = 7.1 Hz, 2H), 7.31 (d, J = 8.6 Hz, 2H), 7.39 (d, J = 9.1 Hz, 2H), 7.79 (d, J = 8.6 Hz, 2H), 7.97 (s, 1H), 8.06 (d, J = 8.1 Hz, 2H), 8.09 (s, 1H). | 1.96 | 477.25 | B |
| D-107 | 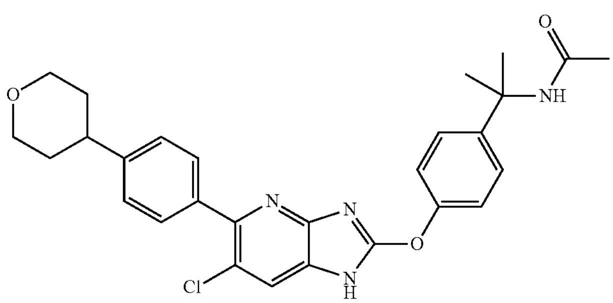 [SMILES: CC(=O)NC(C)(C)c1ccc(Oc2nc3nc(-c4ccc(C5CCOCC5)cc4)c(Cl)cc3[nH]2)cc1] | 1H-NMR (DMSO-d6) δ: 1.57 (s, 6H), 1.70-1.76 (m, 4H), 1.85 (s, 3H), 2.81-2.87 (m, 1H), 3.43-3.47 (m, 2H), 3.96-3.99 (m, 2H), 7.30-7.41 (m, 4H), 7.57-7.63 (m, 4H), 7.95 (s, 1H), 8.10 (s, 1H). | | | |

TABLE 78

| No. | Structure | NMR(δ) | retention time | Mass (M + H) | method |
|---|---|---|---|---|---|
| D-108 | 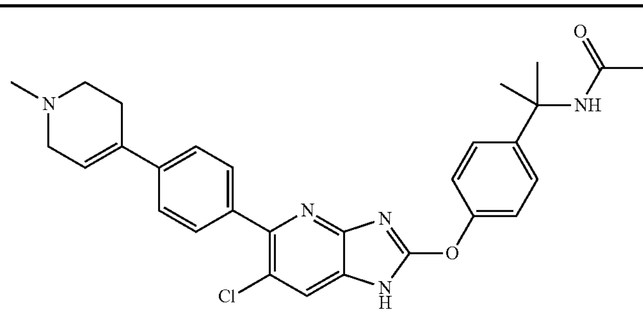 | 1H-NMR (DMSO-d6) δ: 1.57 (s, 6H), 1.85 (s, 3H), 2.32 (s, 3H), 2.55 (brs, 2H), 2.61-2.64 (m, 2H), 3.08 (brs, 2H), 6.26 (s, 1H), 7.31 (d, J = 8.6 Hz, 2H), 7.39 (d, J = 8.6 Hz, 2H), 7.53 (d, J = 8.6 Hz, 2H), 7.63 (d, J = 8.6 Hz, 2H), 7.94 (s, 1H), 8.10 (s, 1H). | | | |

TABLE 78-continued

| No. | Structure | NMR(δ) | retention time | Mass (M + H) | method |
|---|---|---|---|---|---|
| D-109 | 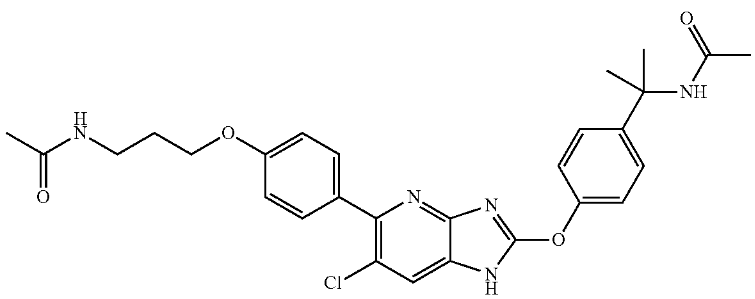 [SMILES: CC(=O)NCCCOc1ccc(-c2nc3nc(Oc4ccc(C(C)(C)NC(C)=O)cc4)[nH]c3cc2Cl)cc1] | 1H-NMR (DMSO-d6) δ: 1.57 (s, 6H), 1.82 (d, J = 6.1 Hz, 3H), 1.82-1.91 (m, 5H), 3.20-3.22 (m, 2H), 4.02-4.06 (m, 2H), 7.02 (d, J = 8.6 Hz, 2H), 7.31 (d, J = 8.6 Hz, 2H), 7.40 (d, J = 8.6 Hz, 2H), 7.59 (d, J = 8.6 Hz, 2H), 7.91-7.95 (m, 2H), 8.11 (s, 1H). | | | |
| D-110 | 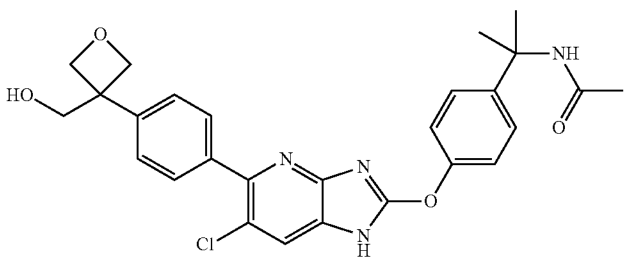 [SMILES: CC(=O)NC(C)(C)c1ccc(Oc2nc3nc(-c4ccc(C5(CO)COC5)cc4)c(Cl)cc3[nH]2)cc1] | 1H-NMR (DMSO-d6) δ: 1.57 (s, 6H), 1.85 (s, 3H), 3.76 (d, J = 5.07 Hz, 2H), 4.75-4.77 (m, 4H), 5.20 (t, J = 10.00 Hz, 1H), 7.25 (d, J = 8.11 Hz, 2H), 7.31 (d, J = 8.62 Hz, 2H), 7.40 (d, J = 9.12 Hz, 2H), 7.63 (d, J = 8.11 Hz, 2H), 7.97 (s, 1H), 8.11 (s, 1H), 13.25 (brs, 1H). | 1.5 | 507.25 | B |
| D-111 | 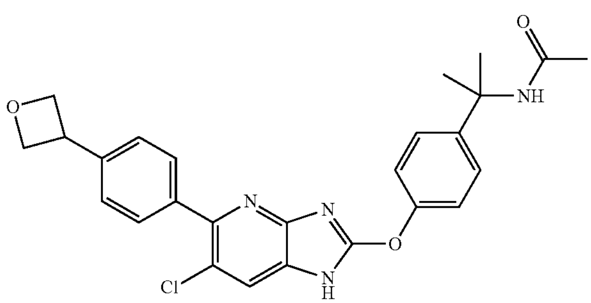 [SMILES: CC(=O)NC(C)(C)c1ccc(Oc2nc3nc(-c4ccc(C5COC5)cc4)c(Cl)cc3[nH]2)cc1] | 1H-NMR (DMSO-d6) δ: 1.57 (s, 6H), 1.85 (s, 3H), 4.29-4.36 (m, 1H), 4.68 (t, J = 6.3 Hz, 2H), 4.98 (dd, J = 8.4, 5.8 Hz, 2H), 7.30 (d, J = 8.6 Hz, 2H), 7.39 (d, J = 8.6 Hz, 2H), 7.50 (d, J = 8.1 Hz, 2H), 7.65 (d, J = 8.1 Hz, 2H), 7.94 (s, 1H), 8.09 (s, 1H). | 1.75 | 477.25 | B |
| D-112 | 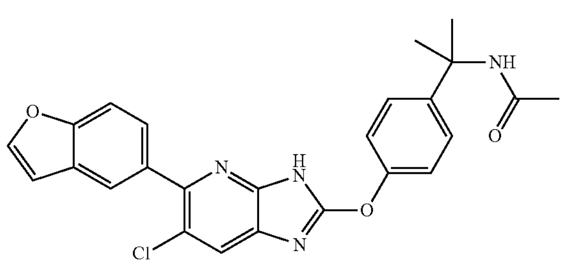 [SMILES: CC(=O)NC(C)(C)c1ccc(Oc2nc3cc(Cl)c(-c4ccc5occc5c4)nc3[nH]2)cc1] | 1H-NMR (DMSO-d6) δ: 1.57 (s, 6H), 1.85 (s, 3H), 7.03 (d, J = 10.00 Hz, 1H), 7.27 (d, J = 8.62 Hz, 2H), 7.37 (d, J = 8.62 Hz, 2H), 7.56 (dd, J = 8.62, 4.31 Hz, 1H), 7.66 (d, J = 8.62 Hz, 1H), 7.84 (s, 1H), 7.89 (d, J = 10.00 Hz, 1H), 8.04 (d, J = 2.03 Hz, 1H), 8.08 (s, 1H). | 2 | 461.3 | B |

TABLE 79

| No. | Structure | NMR(δ) | retention time | Mass (M + H) | method |
|---|---|---|---|---|---|
| D-113 | 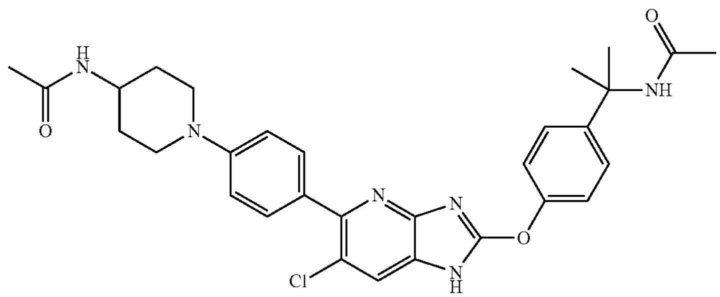 [SMILES: CC(=O)NC1CCN(c2ccc(-c3nc4nc(Oc5ccc(C(C)(C)NC(C)=O)cc5)[nH]c4cc3Cl)cc2)CC1] | 1H-NMR (DMSO-d6) δ: 1.46-1.48 (m, 2H), 1.57 (s, 6H), 1.80-1.84 (m, 8H), 2.86-2.89 (m, 2H), 3.74-3.77 (m, 3H), 7.00 (d, J = 8.6 Hz, 2H), 7.29 (d, J = 8.6 Hz, 2H), 7.39 (d, J = 8.6 Hz, 2H), 7.54 (d, J = 8.6 Hz, 2H), 7.83 (d, J = 7.1 Hz, 1H), 7.87 (s, 1H), 8.09 (s, 1H). | | | |
| D-114 | 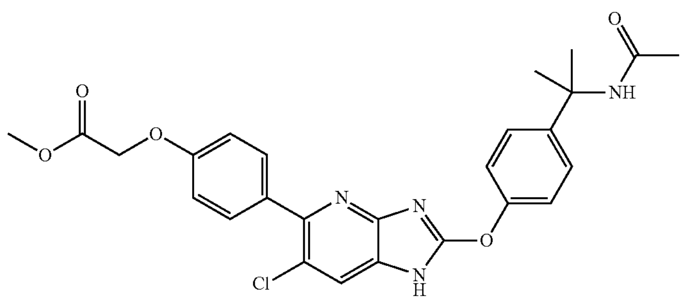 [SMILES: COC(=O)COc1ccc(-c2nc3nc(Oc4ccc(C(C)(C)NC(C)=O)cc4)[nH]c3cc2Cl)cc1] | 1H-NMR (DMSO-d6) δ: 1.57 (s, 6H), 1.85 (s, 3H), 3.73 (s, 3H), 4.87 (s, 2H), 7.02 (d, J = 8.6 Hz, 2H), 7.31 (d, J = 9.1 Hz, 2H), 7.40 (d, J = 8.6 Hz, 2H), 7.59 (d, J = 8.6 Hz, 2H), 7.94 (s, 1H), 8.10 (s, 1H), 13.18 (br s, 1H). | 1.85 | 509.2 | B |
| D-115 | 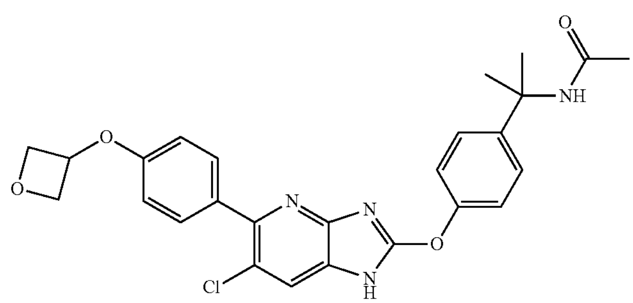 [SMILES: CC(=O)NC(C)(C)c1ccc(Oc2nc3nc(-c4ccc(OC5COC5)cc4)c(Cl)cc3[nH]2)cc1] | 1H-NMR (DMSO-d6) δ: 1.57 (s, 6H), 1.84 (s, 3H), 4.59 (t, J = 6.1 Hz, 2H), 4.96 (t, J = 6.8 Hz, 2H), 5.32-5.38 (m, 1H), 6.88 (d, J = 9.1 Hz, 2H), 7.30 (d, J = 8.6 Hz, 2H), 7.39 (d, J = 9.1 Hz, 2H), 7.59 (d, J = 8.6 Hz, 2H), 7.93 (s, 1H), 8.10 (s, 1H), 13.11 (br s, 1H). | 1.8 | 493.2 | B |
| D-116 | 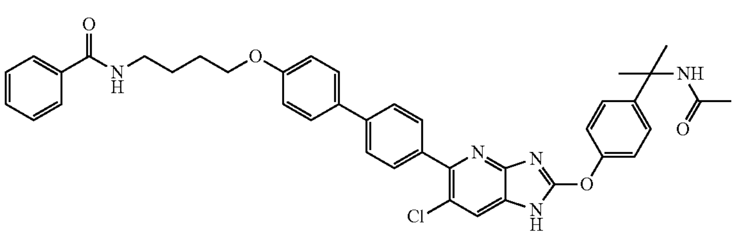 [SMILES: CC(=O)NC(C)(C)c1ccc(Oc2nc3nc(-c4ccc(-c5ccc(OCCCCNC(=O)c6ccccc6)cc5)cc4)c(Cl)cc3[nH]2)cc1] | 1H NMR (300 MHz, DMSO-d6) δ 1.57 (s, 6H), 1.71 (m, 2H), 1.80 (m, 2H), 1.85 (s, 3H), 3.32 (m, 2H), 4.07 (t, J = 6.3 Hz, 2H), 7.04 (d, J = 8.5 Hz, 2H), 7.29-7.51 (m, 7H), 7.67 (d, J = 8.7 Hz, 2H), 7.71 (s, 4H), 7.84 (m, 2H), 7.96 (s, 1H), 8.10 (s, 1H), 8.50 (m, 1H), 13.21 (brs, 1H) | | | |
| D-117 | 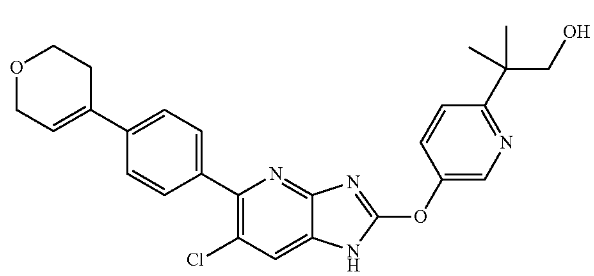 [SMILES: CC(C)(CO)c1ccc(Oc2nc3nc(-c4ccc(C5=CCOCC5)cc4)c(Cl)cc3[nH]2)cn1] | 1H-NMR (DMSO-d6) δ: 2.53-2.55 (m, 2H), 3.58 (s, 3H), 3.85 (t, J = 5.6 Hz, 2H), 4.26 (d, J = 2.5 Hz, 2H), 4.71 (br s, 1H), 6.36 (br s, 1H), 7.51-7.55 (m, 3H), 7.63 (d, J = 8.6 Hz, 2H), 7.85 (dd, J = 8.6, 2.6 Hz, 1H), 7.96 (s, 1H), 8.62 (d, J = 2.6 Hz, 1H). | | | |

TABLE 80

| No. | Structure | NMR(δ) | retention time | Mass (M + H) | method |
|---|---|---|---|---|---|
| D-118 | 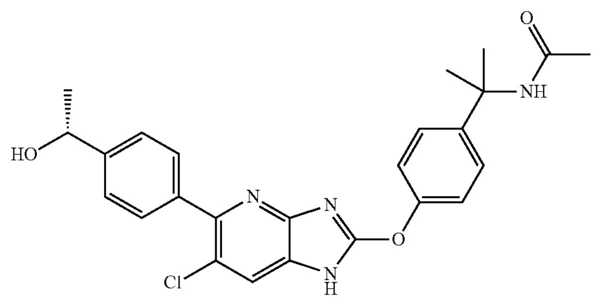 [SMILES: CC(=O)NC(C)(C)c1ccc(Oc2nc3nc(-c4ccc([C@@H](C)O)cc4)c(Cl)cc3[nH]2)cc1] | 1H-NMR (DMSO-d6) δ: 1.37 (d, J = 6.6 Hz, 3H), 1.57 (s, 6H), 1.84 (s, 3H), 4.75-4.81 (m, 1H), 5.22 (d, J = 4.1 Hz, 1H), 7.30 (d, J = 8.6 Hz, 2H), 7.39 (d, J = 8.6 Hz, 2H), 7.43 (d, J = 8.1 Hz, 2H), 7.59 (d, J = 8.1 Hz, 2H), 7.92 (s, 1H), 8.10 (s, 1H). | 1.63 | 465.2 | B |
| D-119 | 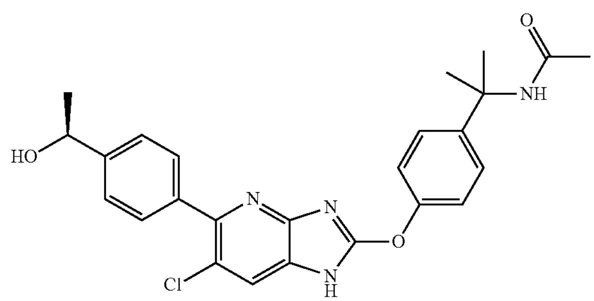 [SMILES: CC(=O)NC(C)(C)c1ccc(Oc2nc3nc(-c4ccc([C@H](C)O)cc4)c(Cl)cc3[nH]2)cc1] | 1H-NMR (DMSO-d6) δ: 1.37 (d, J = 6.6 Hz, 3H), 1.57 (s, 6H), 1.84 (s, 3H), 4.75-4.81 (m, 1H), 5.22 (d, J = 4.1 Hz, 1H), 7.30 (d, J = 8.6 Hz, 2H), 7.39 (d, J = 8.6 Hz, 2H), 7.43 (d, J = 8.1 Hz, 2H), 7.59 (d, J = 8.1 Hz, 2H), 7.92 (s, 1H), 8.10 (s, 1H). | 1.62 | 465.2 | B |
| D-120 | 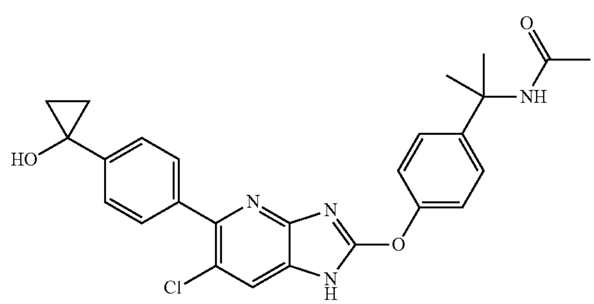 [SMILES: CC(=O)NC(C)(C)c1ccc(Oc2nc3nc(-c4ccc(C5(O)CC5)cc4)c(Cl)cc3[nH]2)cc1] | 1H-NMR (DMSO-d6) δ: 1.00-1.02 (m, 2H), 1.14-1.16 (m, 2H), 1.57 (s, 6H), 1.84 (s, 3H), 5.99 (s, 1H), 7.30-7.32 (m, 4H), 7.39 (d, J = 8.6 Hz, 2H), 7.57 (d, J = 8.6 Hz, 2H), 7.92 (s, 1H), 8.10 (s, 1H). | 1.73 | 477.15 | B |
| D-121 | 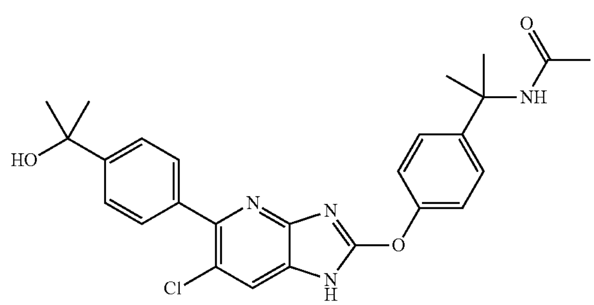 [SMILES: CC(=O)NC(C)(C)c1ccc(Oc2nc3nc(-c4ccc(C(C)(C)O)cc4)c(Cl)cc3[nH]2)cc1] | 1H-NMR (DMSO-d6) δ: 1.47 (s, 6H), 1.57 (s, 6H), 1.84 (s, 3H), 5.07 (s, 1H), 7.30 (d, J = 8.6 Hz, 2H), 7.39 (d, J = 8.6 Hz, 2H), 7.55-7.58 (m, 4H), 7.92 (s, 1H), 8.09 (s, 1H). | 1.72 | 479.25 | B |
| D-122 | 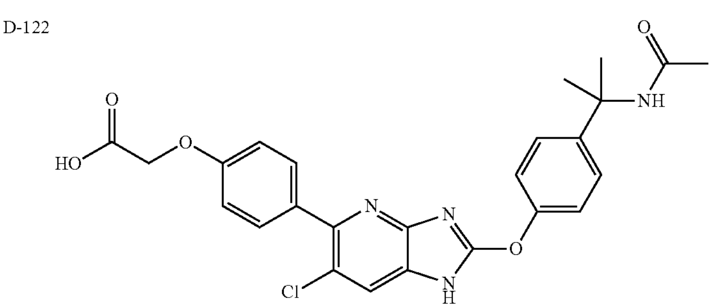 | 1H-NMR (DMSO-d6) δ: 1.57 (s, 6H), 1.85 (s, 3H), 4.74 (s, 2H), 7.00 (d, J = 8.1 Hz, 2H), 7.31 (d, J = 8.6 Hz, 2H), 7.40 (d, J = 8.6 Hz, 2H), 7.59 (d, J = 8.1 Hz, 2H), 7.95 (s, 1H), 8.10 (s, 1H), 13.05 (br s, 1H), 13.26 (br s, 1H). | 1.59 | 495.1 | B |

TABLE 81

| No. | Structure | NMR(δ) | retention time | Mass (M + H) | method |
|---|---|---|---|---|---|
| D-123 | 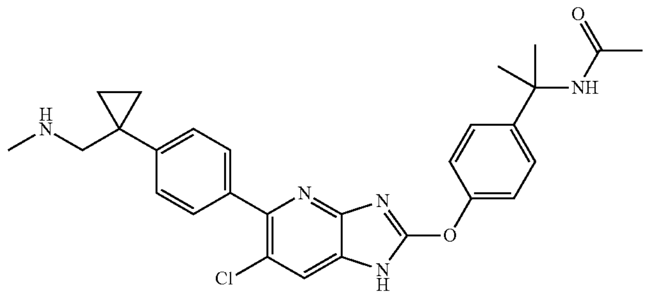 [SMILES: CNCC1(c2ccc(-c3nc4nc(Oc5ccc(C(C)(C)NC(C)=O)cc5)[nH]c4cc3Cl)cc2)CC1] | 1H-NMR (DMSO-d6) δ: 0.87 (d, J = 9.1 Hz, 4H), 1.56 (s, 6H), 1.84 (s, 3H), 2.34 (s, 3H), 2.86 (s, 2H), 7.23 (d, J = 8.6 Hz, 2H), 7.35 (d, J = 9.1 Hz, 2H), 7.38 (d, J = 8.6 Hz, 2H), 7.57 (d, J = 8.1 Hz, 2H), 7.74 (s, 1H), 8.07 (s, 1H). | 1.23 | 504.3 | B |
| D-124 | 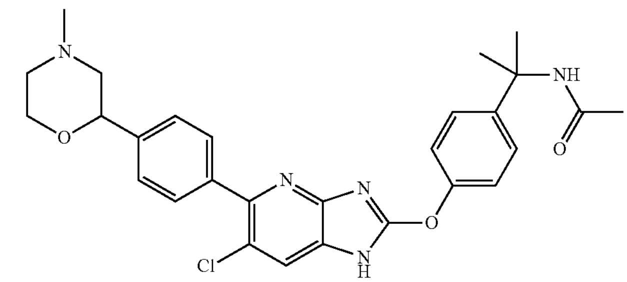 [SMILES: CC(=O)NC(C)(C)c1ccc(Oc2nc3nc(-c4ccc(C5CN(C)CCO5)cc4)c(Cl)cc3[nH]2)cc1] | 1H-NMR (DMSO-d6) δ: 1.57 (s, 6H), 1.85 (s, 3H), 1.91 (t, J = 10.65 Hz, 1H), 2.09 (td, J = 3.04, 1.52 Hz, 1H), 2.23 (s, 3H), 2.71 (d, J = 11.15 Hz, 1H), 2.91 (d, J = 11.66 Hz, 1H), 3.70 (t, J = 10.14 Hz, 1H), 3.96 (d, J = 13.18 Hz, 1H), 4.55 (d, J = 8.62 Hz, 1H), 7.31 (d, J = 8.62 Hz, 2H), 7.40 (d, J = 8.62 Hz, 2H), 7.44 (d, J = 8.11 Hz, 2H), 7.61 (d, J = 8.11 Hz, 2H), 7.96 (s, 1H), 8.10 (s, 1H). | 1.19 | 520.35 (M+) | B |
| D-125 | 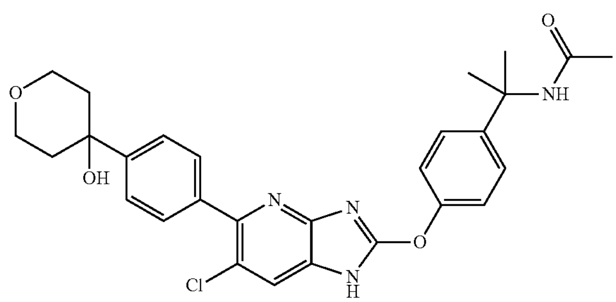 [SMILES: CC(=O)NC(C)(C)c1ccc(Oc2nc3nc(-c4ccc(C5(O)CCOCC5)cc4)c(Cl)cc3[nH]2)cc1] | 1H-NMR (DMSO-d6) δ: 1.57 (s, 6H), 1.61 (s, 2H), 1.85 (s, 3H), 2.02-2.05 (m, 2H), 3.72-3.84 (m, 4H), 5.11 (s, 1H), 7.31 (d, J = 8.6 Hz, 2H), 7.40 (d, J = 8.6 Hz, 2H), 7.58 (d, J = 8.6 Hz, 2H), 7.62 (d, J = 8.6 Hz, 2H), 7.96 (s, 1H), 8.10 (s, 1H). | | | |
| D-126 | 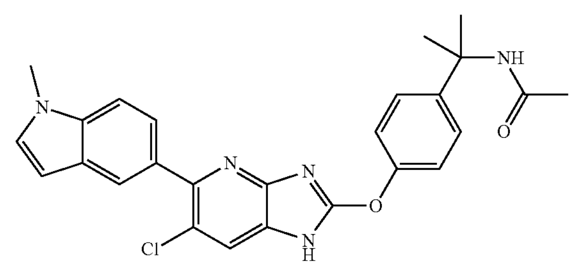 [SMILES: CC(=O)NC(C)(C)c1ccc(Oc2nc3nc(-c4ccc5c(ccn5C)c4)c(Cl)cc3[nH]2)cc1] | 1H-NMR (DMSO-d6) δ: 1.57 (s, 6H), 1.85 (s, 3H), 3.84 (s, 3H), 6.50 (d, J = 2.53 Hz, 1H), 7.32 (d, J = 8.62 Hz, 2H), 7.38-7.44 (m, 4H), 7.50 (d, J = 8.62 Hz, 1H), 7.82 (s, 1H), 7.94 (s, 1H), 8.11 (s, 1H), 8.31 (s, 1H). | 1.94 | 474.25 | B |
| D-127 | 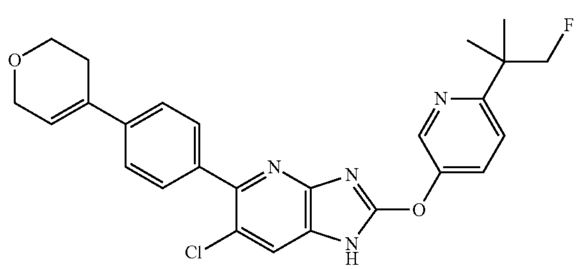 [SMILES: CC(C)(CF)c1ccc(Oc2nc3nc(-c4ccc(C5=CCOCC5)cc4)c(Cl)cc3[nH]2)cn1] | 1H-NMR (CDCl3) δ: 1.42 (d, J = 2.03 Hz, 6H), 2.30-2.36 (brs, 2H), 3.87 (t, J = 5.32 Hz, 2H), 4.29 (d, J = 2.53 Hz, 2H), 4.59 (d, J = 47.65 Hz, 2H), 6.07 (s, 1H), 7.43 (d, J = 8.62 Hz, 1H), 7.46 (d, J = 8.11 Hz, 2H), 7.57 (dd, J = 8.62, 2.54 Hz, 1H), 7.70 (d, J = 8.11 Hz, 2.), 7.91 (s, 1H), 8.41 (d, J = 2.54 Hz, 1H), 12.60 (s, 1H). | | | |

TABLE 82
| No. | Structure | NMR(δ) | retention time | Mass (M + H) | method |
|---|---|---|---|---|---|
| D-128 | 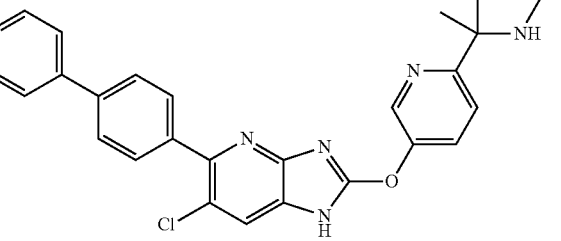 | 1H-NMR (DMSO-d6) δ: 1.58 (s, 6H), 1.87 (s, 3H), 7.48 (d, J = 8.6 Hz, 1H), 7.79-7.87 (m, 5H), 7.93 (d, J = 8.1 Hz, 2H), 8.04 (s, 1H), 8.20 (s, 1H), 8.59 (d, J = 2.5 Hz, 1H), 8.67 (d, J = 6.1 Hz, 2H). | 1.15 | 499.25 | B |
| D-129 | 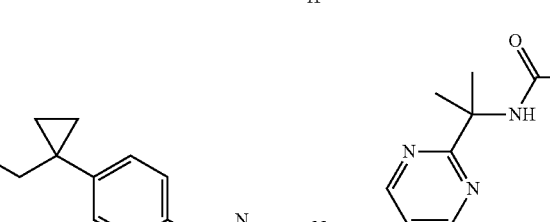 | 1H-NMR (DMSO-d6) δ: 0.78-0.91 (m, 4H), 1.60 (s, 6H), 1.80 (s, 3H), 3.59 (d, J = 5.58 Hz, 2H), 4.72 (t, J = 5.58 Hz, 1H), 7.39 (d, J = 8.11 Hz, 2H), 7.56 (d, J = 8.11 Hz, 2H), 8.05 (s, 1H), 8.26 (s, 1H), 8.95 (s, 2H), 13.53 (s, 1H). | | | |
| D-130 | 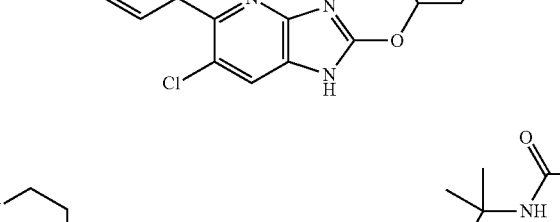 | 1H-NMR(DMSO-d6) δ: 1.57 (s, 6H), 1.85 (s, 3H), 2.74 (br s, 2H), 3.37 (br s, 3H), 3.80 (br s, 2H), 6.31 (s, 1H), 7.32 (d, J = 8.6 Hz, 2H), 7.40 (d, J = 8.6 Hz, 2H), 7.59 (d, J = 8.6 Hz, 2H), 7.68 (d, J = 8.6 Hz, 2H), 7.99 (s, 1H), 8.11 (s, 1H). | 1.21 | 502.5 | B |
| D-131 | 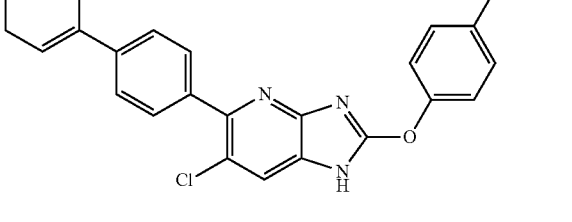 | 1H-NMR (DMSO-d6) δ: 1.58 (s, 6H), 1.75-1.77 (m, 1H), 1.86 (s, 3H), 2.09-2.12 (m, 1H), 2.26-2.29 (m, 1H), 2.55-2.58 (m, 3H), 6.17 (s, 1H), 7.44-7.48 (m, 3H), 7.62 (d, J = 8.1 Hz, 2H), 7.77-7.79 (m, 2H), 8.21 (s, 1H), 8.51 (s, 1H). | 1.19 | 517.35 | B |
| D-132 | 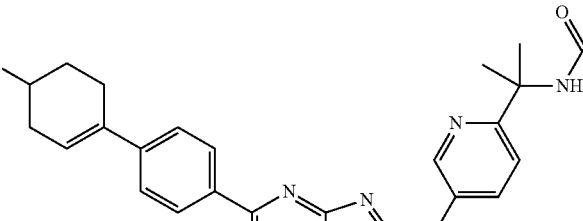 | 1H-NMR (DMSO-d6) δ: 1.61 (s, 6H), 1.81 (s, 3H), 6.91 (dd, J = 7.60, 7.60 Hz, 1H), 6.97 (d, J = 8.11 Hz, 1H), 7.19 (dd, J = 7.60, 8.11 Hz, 1H), 7.33 (d, J = 7.60 Hz, 1H), 7.63-7.72 (m, 4H), 8.08 (s, 1H), 8.26 (s, 1H), 8.96 (s, 2H), 9.61 (s, 1H), 13.59 (s, 1H). | | | |

TABLE 83

| No. | Structure | NMR(δ) | retention time | Mass (M + H) | method |
|---|---|---|---|---|---|
| D-133 | 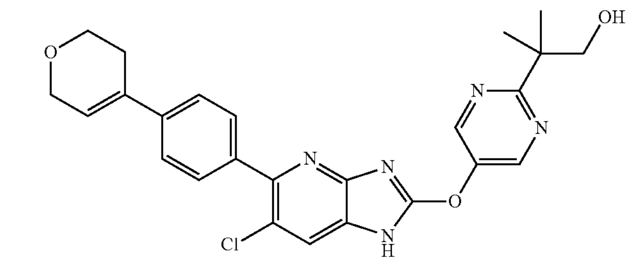 [SMILES: CC(C)(CO)c1ncc(Oc2nc3nc(-c4ccc(C5=CCOCC5)cc4)c(Cl)cc3[nH]2)cn1] | 1H-NMR (DMSO-d6) δ: 1.33 (s, 6H), 2.50 (s, 2H), 3.69 (d, J = 5.6 Hz, 2H), 3.85 (t, J = 5.3 Hz, 2H), 4.257-4.264 (m, 2H), 4.65 (t, J = 5.6 Hz, 1H), 6.37 (s, 1H), 7.56 (d, J = 8.1 Hz, 2H), 7.65 (d, J = 8.1 Hz, 2H), 8.05 (s, 1H), 8.98 (s, 2H). | | | |
| D-134 | 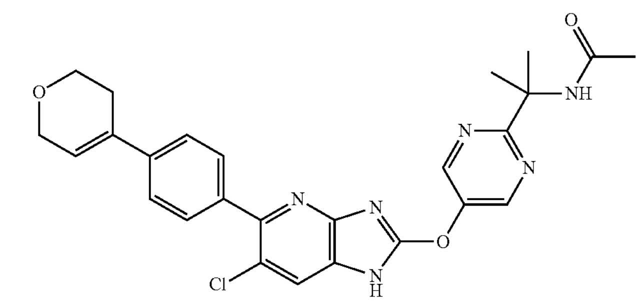 [SMILES: CC(=O)NC(C)(C)c1ncc(Oc2nc3nc(-c4ccc(C5=CCOCC5)cc4)c(Cl)cc3[nH]2)cn1] | 1H-NMR (CDCl3) δ: 1.82 (s, 6H), 2.07 (s, 3H), 2.40-2.50 (br s, 2H), 3.92 (t, J = 5.32 Hz, 2H), 4.33 (d, J = 2.53 Hz, 2H), 6.17 (s, 1H), 7.20 (s, 1H), 7.51 (d, J = 8.11 Hz, 2H), 7.72 (d, J = 8.11 Hz, 2H), 7.94 (s, 1H), 8.72 (s, 2H). | | | |
| D-135 | 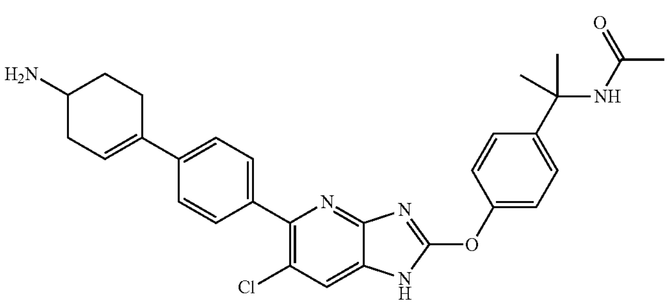 [SMILES: CC(=O)NC(C)(C)c1ccc(Oc2nc3nc(-c4ccc(C5=CCC(N)CC5)cc4)c(Cl)cc3[nH]2)cc1] | 1H-NMR (DMSO-d6) δ: 1.54 (s, 1H), 1.57 (s, 6H), 1.73-1.80 (m, 1H), 1.85 (s, 3H), 2.10-2.33 (m, 2H), 2.60 (s, 2H), 6.19 (s, 1H), 7.31 (d, J = 8.6 Hz, 2H), 7.40 (d, J = 8.6 Hz, 3H), 7.53 (d, J = 8.1 Hz, 3H), 7.63 (d, J = 8.1 Hz, 3H), 7.91 (d, J = 4.1 Hz, 2H), 7.98 (s, 1H), 8.11 (s, 1H), 13.28 (br s, 1H). | 1.27 | 516.9 | B |
| D-136 | 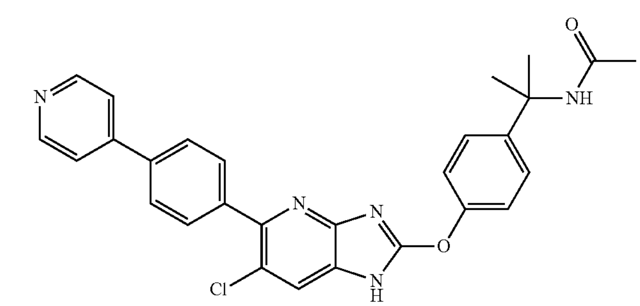 [SMILES: CC(=O)NC(C)(C)c1ccc(Oc2nc3nc(-c4ccc(-c5ccncc5)cc4)c(Cl)cc3[nH]2)cc1] | 1H-NMR (DMSO-d6) δ: 1.57 (s, 6H), 1.85 (s, 3H), 7.33 (d, J = 8.6 Hz, 2H), 7.41 (d, J = 8.6 Hz, 2H), 7.85 (d, J = 8.6 Hz, 2H), 7.98-8.06 (m, 5H), 8.11 (s, 1H), 8.79 (d, J = 5.6 Hz, 2H). | 1.29 | 498.2 | B |
| D-137 | 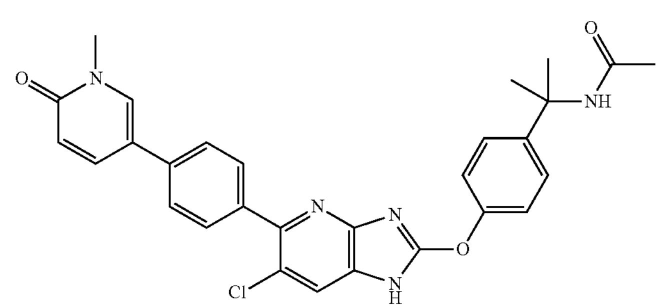 [SMILES: CC(=O)NC(C)(C)c1ccc(Oc2nc3nc(-c4ccc(-c5ccc(=O)n(C)c5)cc4)c(Cl)cc3[nH]2)cc1] | 1H-NMR (DMSO-d6) δ: 1.57 (s, 6H), 1.84 (s, 3H), 3.53 (s, 3H), 6.51 (d, J = 9.1 Hz, 1H), 7.24 (d, J = 9.1 Hz, 2H), 7.36 (d, J = 9.1 Hz, 2H), 7.65 (d, J = 8.6 Hz, 2H), 7.70 (d, J = 8.6 Hz, 2H), 7.77 (s, 1H), 7.90 (dd, J = 2.5, 9.1 Hz, 1H), 8.07 (s, 1H), 8.22 (d, J = 2.5 Hz, 1H), | 1.62 | 528.25 | B |

TABLE 84

| No. | Structure | NMR(δ) | retention time | Mass (M + H) | method |
|---|---|---|---|---|---|
| D-138 | 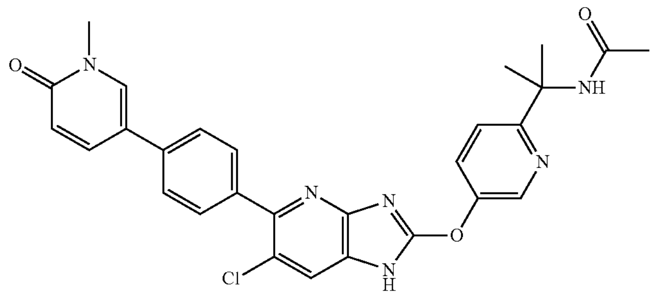 [SMILES: CC(=O)NC(C)(C)c1ccc(Oc2nc3nc(-c4ccc(-c5ccc(=O)n(C)c5)cc4)c(Cl)cc3[nH]2)cn1] | 1H-NMR (DMSO-d6) δ: 1.58 (s, 6H), 1.86 (s, 3H), 3.53 (s, 3H), 6.51 (d, J = 9.1 Hz, 1H), 7.41 (d, J = 9.1 Hz, 1H), 7.64 (d, J = 8.1 Hz, 2H), 7.65 (s, 1H), 7.69-7.73 (m, 3H), 7.90 (dd, J = 2.5, 9.1 Hz, 1H), 8.15 (s, 1H), 8.22 (d, J = 2.5 Hz, 1H), 8.46 (d, J = 2.5 Hz, 1H) | 1.46 | 529.25 | B |
| D-139 | 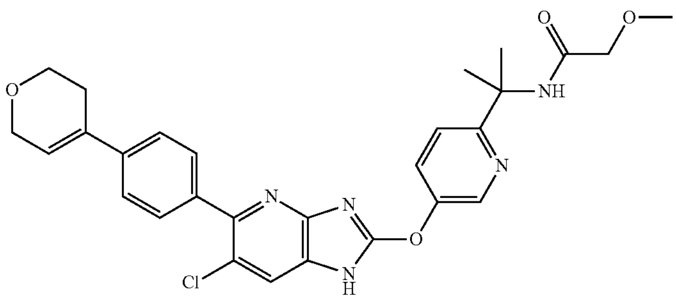 [SMILES: COCC(=O)NC(C)(C)c1ccc(Oc2nc3nc(-c4ccc(C5=CCOCC5)cc4)c(Cl)cc3[nH]2)cn1] | 1H-NMR (DMSO-d6) δ: 1.66 (s, 6H), 2.50 (s, 2H), 3.36 (s, 3H), 3.83 (s, 2H), 3.85 (t, J = 5.3 Hz, 2H), 4.257-4.264 (m, 2H), 6.37 (s, 1H), 7.55-7.66 (m, 5H), 7.93 (dd, J = 8.6, 2.5 Hz, 1H), 8.02 (s, 1H), 8.19 (s, 1H), 8.64 (d, J = 2.5 Hz, 1H). | | | |
| D-140 | 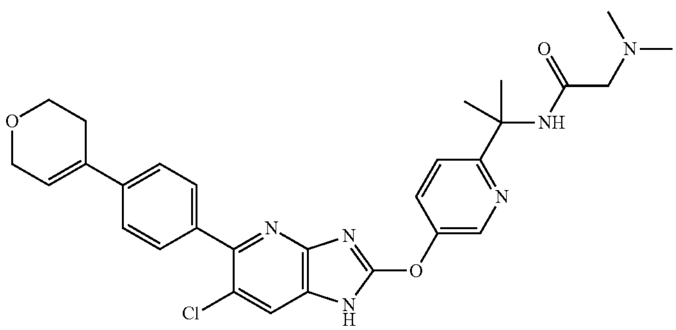 [SMILES: CN(C)CC(=O)NC(C)(C)c1ccc(Oc2nc3nc(-c4ccc(C5=CCOCC5)cc4)c(Cl)cc3[nH]2)cn1] | | 1.47 | 547.25 | B |
| D-141 | 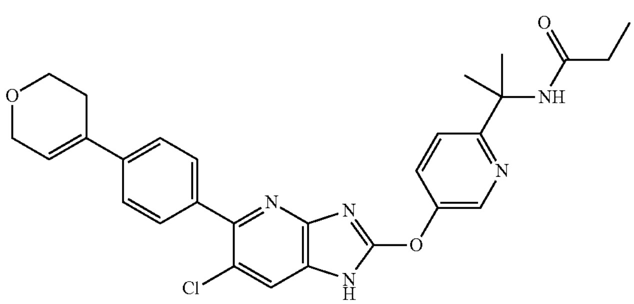 [SMILES: CCC(=O)NC(C)(C)c1ccc(Oc2nc3nc(-c4ccc(C5=CCOCC5)cc4)c(Cl)cc3[nH]2)cn1] | 1H-NMR (DMSO-d6) δ: 0.99 (t, J = 7.6 Hz, 3H), 1.58 (s, 6H), 2.16 (q, J = 7.6 Hz, 2H), 2.50 (s, 2H), 3.85 (t, J = 5.3 Hz, 2H), 4.257-4.263 (m, 2H), 6.37 (s, 1H), 7.46 (d, J = 8.6 Hz, 1H), 7.56 (d, J = 8.1 Hz, 2H), 7.65 (d, J = 8.1 Hz, 2H), 7.85 (dd, J = 8.6, 2.5 Hz, 1H), 8.02 (s, 1H), 8.11 (s, 1H), 8.59 (d, J = 2.5 Hz, 1H). | | | |
| D-142 | 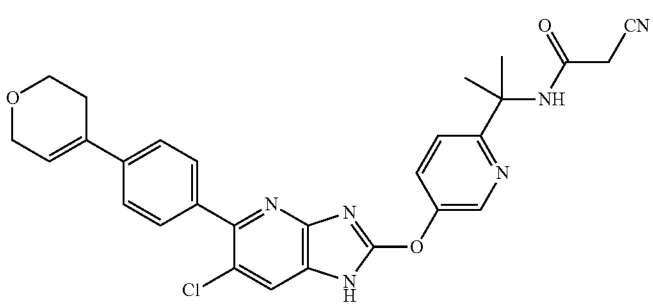 [SMILES: CC(C)(NC(=O)CC#N)c1ccc(Oc2nc3nc(-c4ccc(C5=CCOCC5)cc4)c(Cl)cc3[nH]2)cn1] | 1H-NMR (DMSO-d6) δ: 1.61 (s, 6H), 2.50-2.53 (m, 2H), 3.72 (s, 2H), 3.85 (t, J = 5.3 Hz, 2H), 4.26 (d, J = 2.5 Hz, 2H), 6.37 (s, 1H), 7.54 (d, J = 8.8 Hz, 1H), 7.56 (d, J = 8.1 Hz, 2H), 7.65 (d, J = 8.1 Hz, 2H), 7.90 (dd, J = 2.8, 8.8 Hz, 1H), 8.03 (s, 1H), 8.62 (d, J = 2.8 Hz, 1H), 8.63 (s, 1H) | | | |

TABLE 85

| No. | Structure | NMR(δ) | retention time | Mass (M + H) | method |
|---|---|---|---|---|---|
| D-143 | 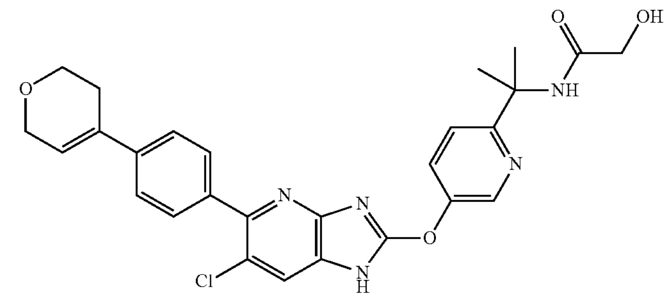 | | 1.78 | 520.45 | B |
| D-144 | 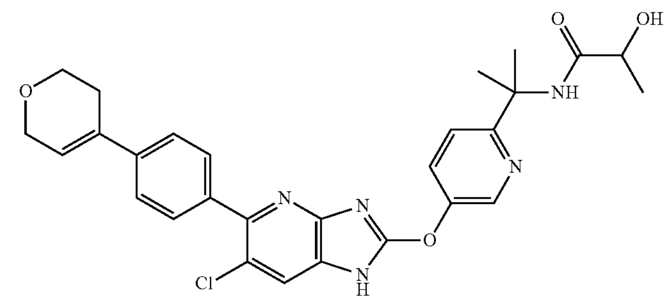 [SMILES: CC(O)C(=O)NC(C)(C)c1ccc(Oc2nc3nc(-c4ccc(C5=CCOCC5)cc4)c(Cl)cc3[nH]2)cn1] | 1H-NMR (DMSO-d6) δ: 1.24 (d, J = 6.6 Hz, 3H), 1.66 (s, 6H), 2.50 (s, 2H), 3.85 (t, J = 5.6 Hz, 2H), 3.98 (qd, J = 6.6, 5.1 Hz, 1H), 4.257-4.263 (m, 2H), 5.62 (d, J = 5.1 Hz, 1H), 6.36 (s, 1H), 7.55-7.66 (m, 5H), 7.94 (dd, J = 8.6, 2.5 Hz, 1H), 8.00 (s, 1H), 8.25 (s, 1H), 8.64 (d, J = 2.5 Hz, 1H). | | | |
| D-145 | 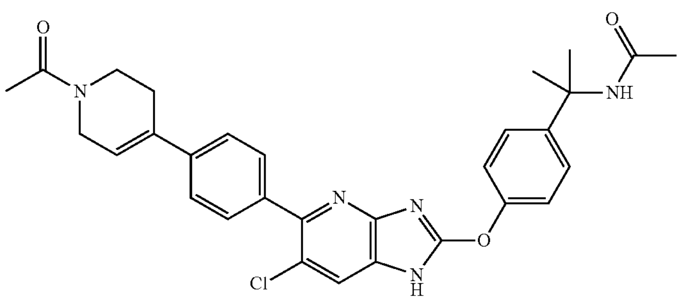 [SMILES: CC(=O)NC(C)(C)c1ccc(Oc2nc3nc(-c4ccc(C5=CCN(C(C)=O)CC5)cc4)c(Cl)cc3[nH]2)cc1] | | 1.78 | 544.3 | B |
| D-146 | 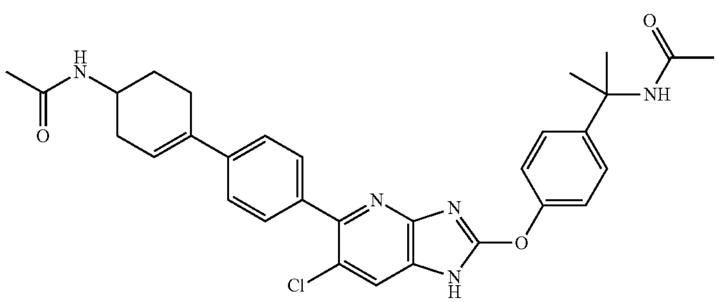 [SMILES: CC(=O)NC1CC=C(c2ccc(-c3nc4nc(Oc5ccc(C(C)(C)NC(C)=O)cc5)[nH]c4cc3Cl)cc2)CC1] | | 1.8 | 558.2 | B |
| D-147 | 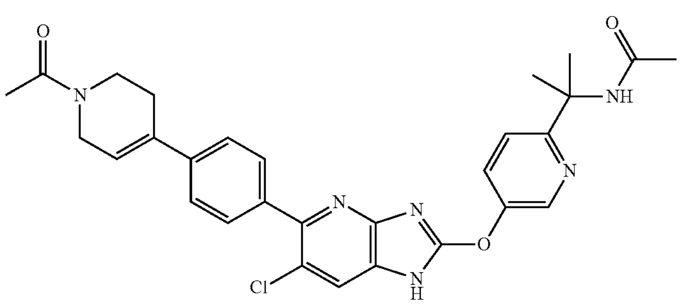 | 1H-NMR (DMSO-d6) δ: 1.58 (s, 6H), 1.75-1.77 (m, 1H), 1.86 (s, 3H), 2.05-2.09 (m, 3H), 2.61 (s, 1H), 3.60-3.69 (m, 2H), 4.13-4.18 (m, 2H), 6.28 (s, 1H), 7.46 (d, J = 8.6 Hz, 1H), 7.56-7.68 (m, 4H), 7.83-7.84 (m, 1H), 7.96-7.98 (m, 1H), 8.19 (s, 1H), 8.57 (s, 1H). | 1.6 | 545.25 | B |

TABLE 86

| No. | Structure | NMR(δ) | retention time | Mass (M + H) | method |
|---|---|---|---|---|---|
| D-148 | 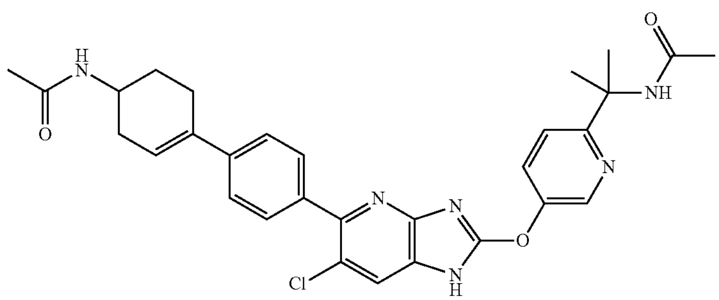 [SMILES: CC(=O)NC1CC=C(c2ccc(-c3nc4nc(Oc5ccc(C(C)(C)NC(C)=O)nc5)[nH]c4cc3Cl)cc2)CC1] | 1H-NMR (DMSO-d6) δ: 1.58 (s, 6H), 1.63-1.65 (m, 1H), 1.83 (s, 3H), 1.86 (s, 3H), 1.92-1.94 (m, 1H), 2.06-2.11 (m, 1H), 2.53-2.55 (m, 3H), 3.86 (s, 1H), 6.19 (s, 1H), 7.47 (d, J = 8.6 Hz, 1H), 7.52 (d, J = 8.6 Hz, 2H), 7.62 (d, J = 8.6 Hz, 2H), 7.83-7.85 (m, 2H), 7.99 (s, 1H), 8.20 (s, 1H), 8.58 (d, J = 3.0 Hz, 1H), 13.32 (br s, 1H). | 1.63 | 559.25 | B |
| D-149 | 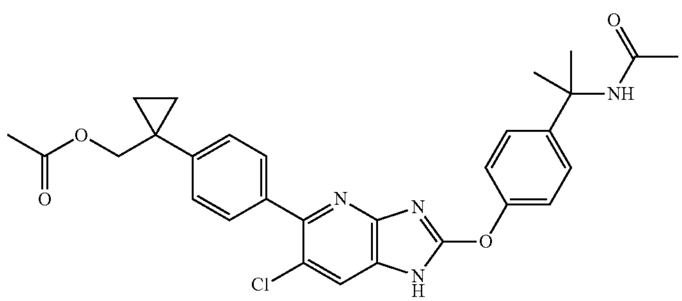 [SMILES: CC(=O)NC(C)(C)c1ccc(Oc2nc3nc(-c4ccc(C5(COC(C)=O)CC5)cc4)c(Cl)cc3[nH]2)cc1] | 1H-NMR (DMSO-d6) δ: 0.95-1.04 (m, 4H), 1.57 (s, 6H), 1.85 (s, 3H), 2.00 (s, 3H), 4.22 (s, 2H), 7.28-7.43 (m, 6H), 7.58 (d, J = 8.62 Hz, 2H), 7.96 (s, 1H), 8.10 (s, 1H), 13.19 (s, 1H). | | | |
| D-150 | 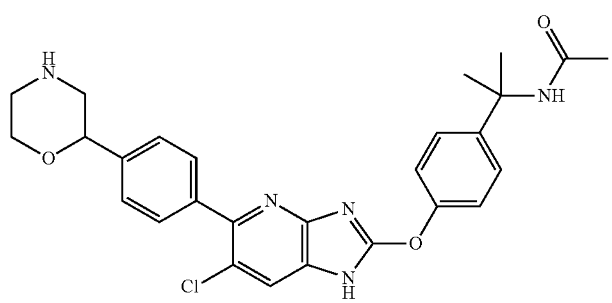 [SMILES: CC(=O)NC(C)(C)c1ccc(Oc2nc3nc(-c4ccc(C5CNCCO5)cc4)c(Cl)cc3[nH]2)cc1] | | 1.16 | 506.95 | B |
| D-151 | 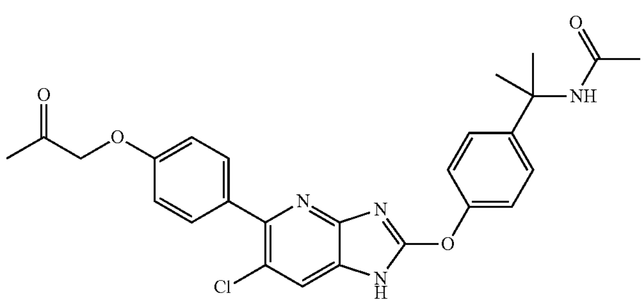 [SMILES: CC(=O)COc1ccc(-c2nc3nc(Oc4ccc(C(C)(C)NC(C)=O)cc4)[nH]c3cc2Cl)cc1] | 1H-NMR (DMSO-d6) δ: 1.57 (s, 6H), 1.84 (s, 3H), 2.19 (s, 3H), 4.88 (s, 2H), 6.98 (d, J = 8.6 Hz, 2H), 7.28 (d, J = 8.6 Hz, 2H), 7.38 (d, J = 8.6 Hz, 2H), 7.57 (d, J = 8.6 Hz, 2H), 7.86 (s, 1H), 8.09 (s, 1H). | 1.77 | 493.1 | B |

TABLE 86-continued

| No. | Structure | NMR(δ) | retention time | Mass (M + H) | method |
|---|---|---|---|---|---|
| D-152 | 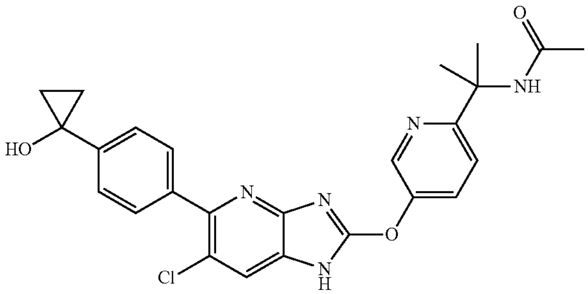 [SMILES: CC(=O)NC(C)(C)c1ccc(Oc2nc3nc(-c4ccc(C5(O)CC5)cc4)c(Cl)cc3[nH]2)cn1] | 1H-NMR (DMSO-d6) δ: 0.99-1.03 (m, 2H), 1.13-1.17 (m, 2H), 1.58 (s, 8H), 1.86 (s, 4H), 6.00 (s, 1H), 7.33 (d, J = 8.6 Hz, 2H), 7.47 (d, J = 8.6 Hz, 1H), 7.57 (d, J = 8.1 Hz, 2H), 7.85 (dd, J = 8.6, 2.5 Hz, 1H), 7.99 (s, 1H), 8.20 (s, 1H), 8.58 (d, J = 2.5 Hz, 1H), 13.36 (br s, 1H). | 1.55 | 478.2 | B |

TABLE 87

| No. | Structure | NMR(δ) | retention time | Mass (M + H) | method |
|---|---|---|---|---|---|
| D-153 | 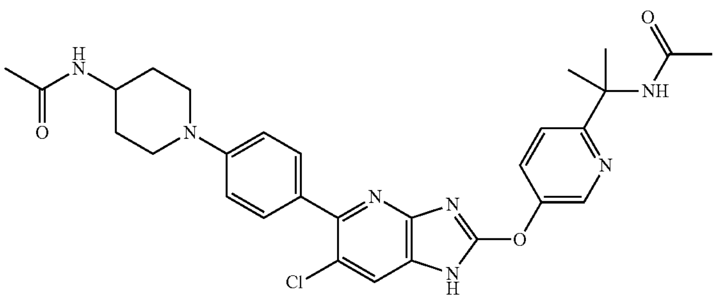 [SMILES: CC(=O)NC1CCN(c2ccc(-c3nc4nc(Oc5ccc(C(C)(C)NC(C)=O)nc5)[nH]c4cc3Cl)cc2)CC1] | 1H-NMR (DMSO-d6) δ: 1.42-1.53 (m, 2H), 1.58 (s, 6H), 1.78-1.88 (m, 8H), 2.88 (t, J = 11.15 Hz, 2H), 3.71-3.80 (m, 3H), 7.01 (d, J = 8.62 Hz, 2H), 7.46 (d, J = 8.62 Hz, 1H), 7.54 (d, J = 8.62 Hz, 2H), 7.82 (dd, J = 8.62, 2.28 Hz, 2H), 7.90 (s, 1H), 8.19 (s, 1H), 8.56 (d, J = 2.28 Hz, 1H). | | | |
| D-154 | 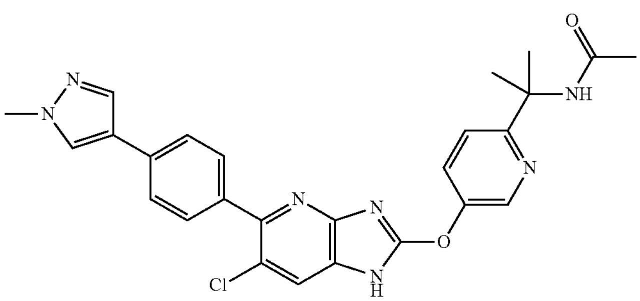 [SMILES: CC(=O)NC(C)(C)c1ccc(Oc2nc3nc(-c4ccc(-c5cnn(C)c5)cc4)c(Cl)cc3[nH]2)cn1] | 1H-NMR (CDCl3) δ: 1.75 (s, 6H), 2.04 (s, 3H), 3.93 (s, 3H), 7.38 (d, J = 8.62 Hz, 1H), 7.45 (s, 1H), 7.52-7.54 (m, 2H), 7.61 (dd, J = 11.15, 5.58 Hz, 1H), 7.68 (s, 1H), 7.72 (d, J = 8.11 Hz, 2H), 7.92 (s, 1H), 8.43 (d, J = 2.53 Hz, 1H), 13.0 (brs, 1H). | 1.59 | 502.35 | B |
| D-155 | 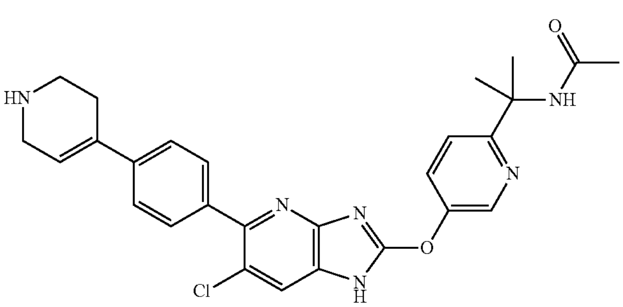 [SMILES: CC(=O)NC(C)(C)c1ccc(Oc2nc3nc(-c4ccc(C5=CCNCC5)cc4)c(Cl)cc3[nH]2)cn1] | | 1.14 | 503.35 | B |

As a compound of the present invention, a compound shown below can be also synthesized in accordance with the above Example.
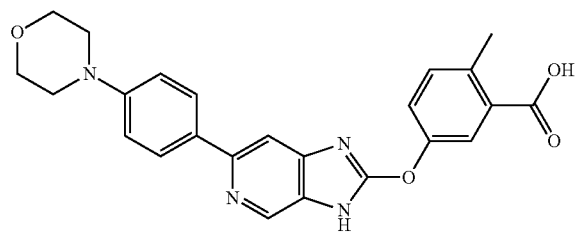
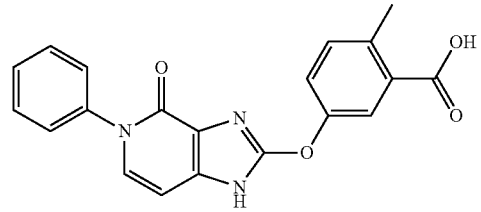
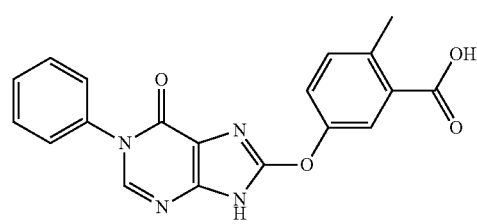
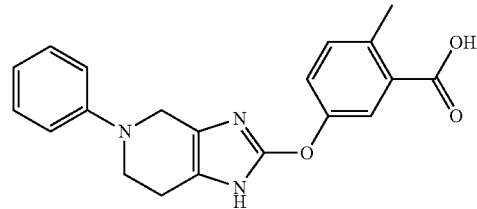
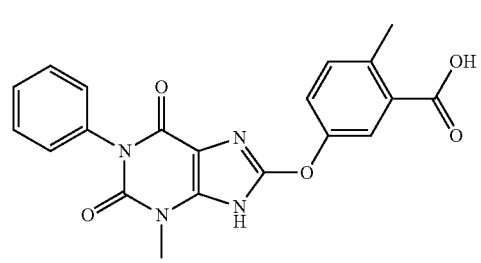
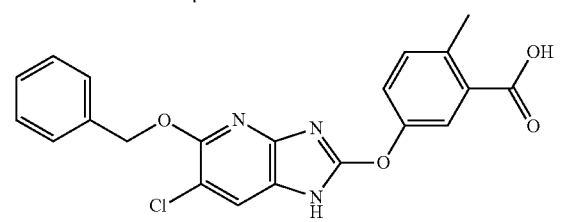
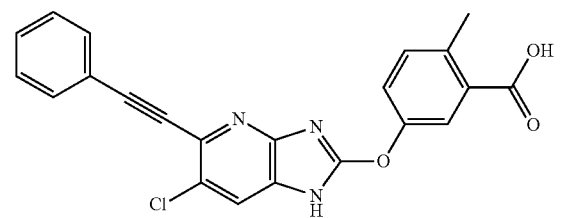
-continued
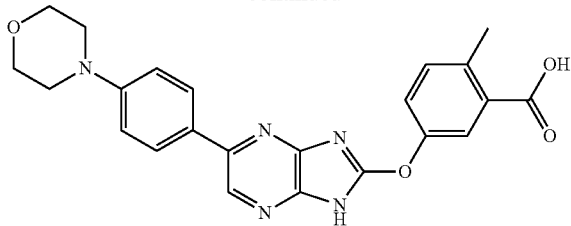
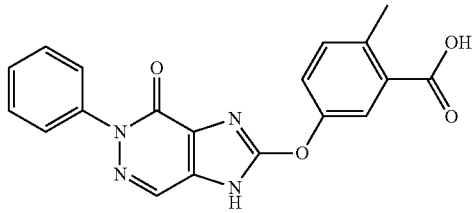
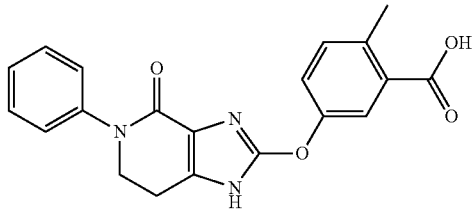
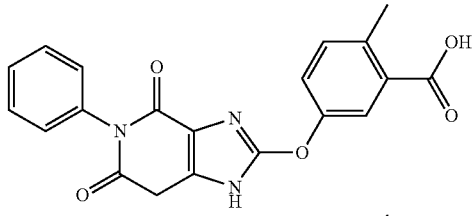
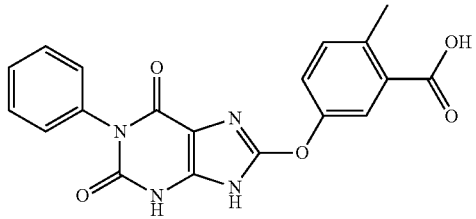
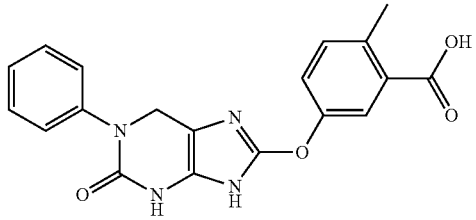
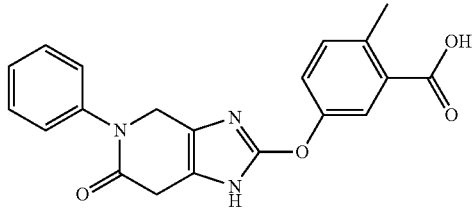
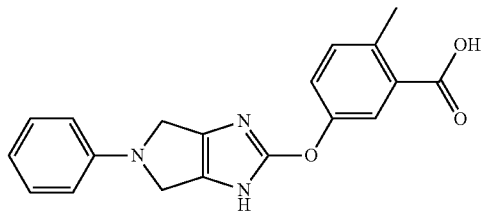

-continued
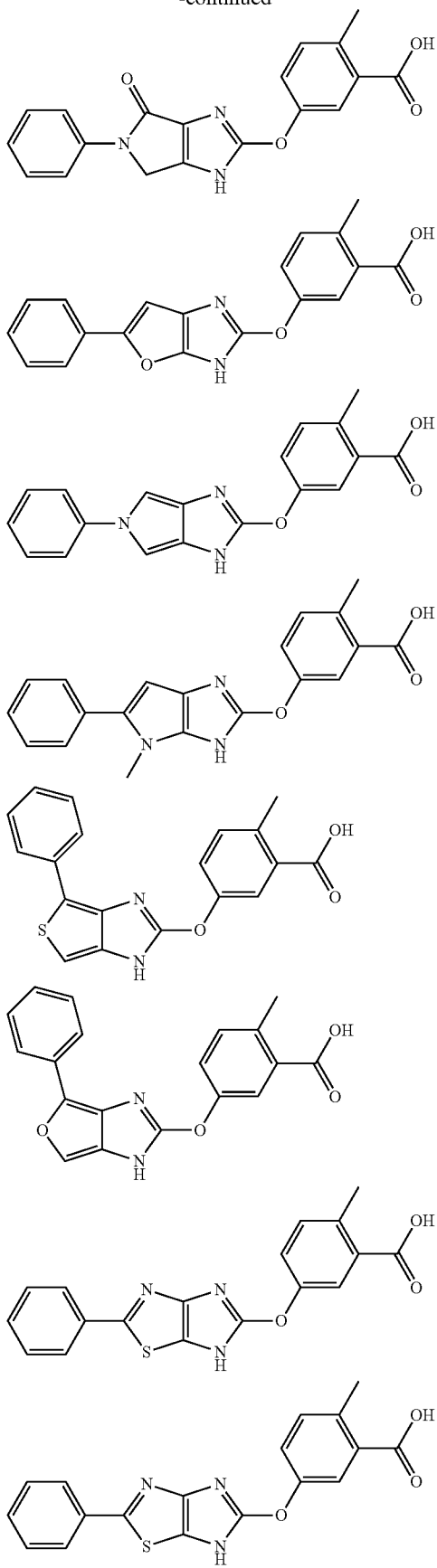
-continued
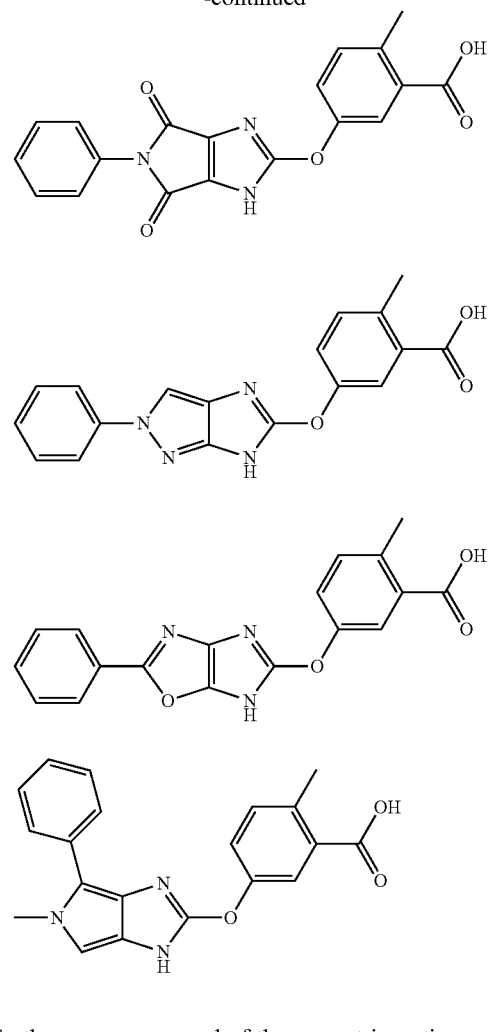
Further, as a compound of the present invention, a compound shown below can be also synthesized.
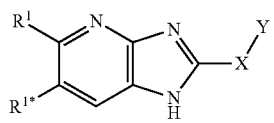
Wherein, X is —O— or —S—.
Wherein, R¹ includes substituents shown below.
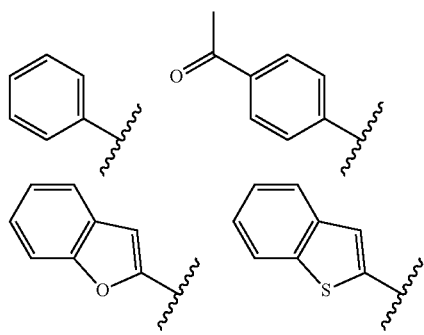

-continued
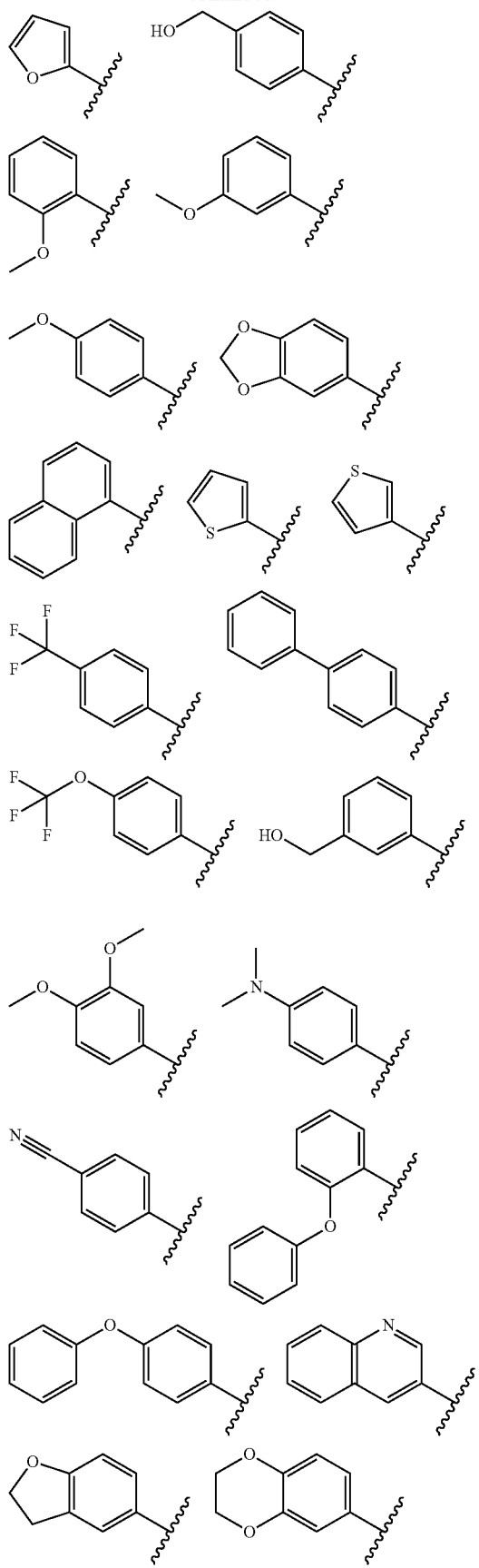
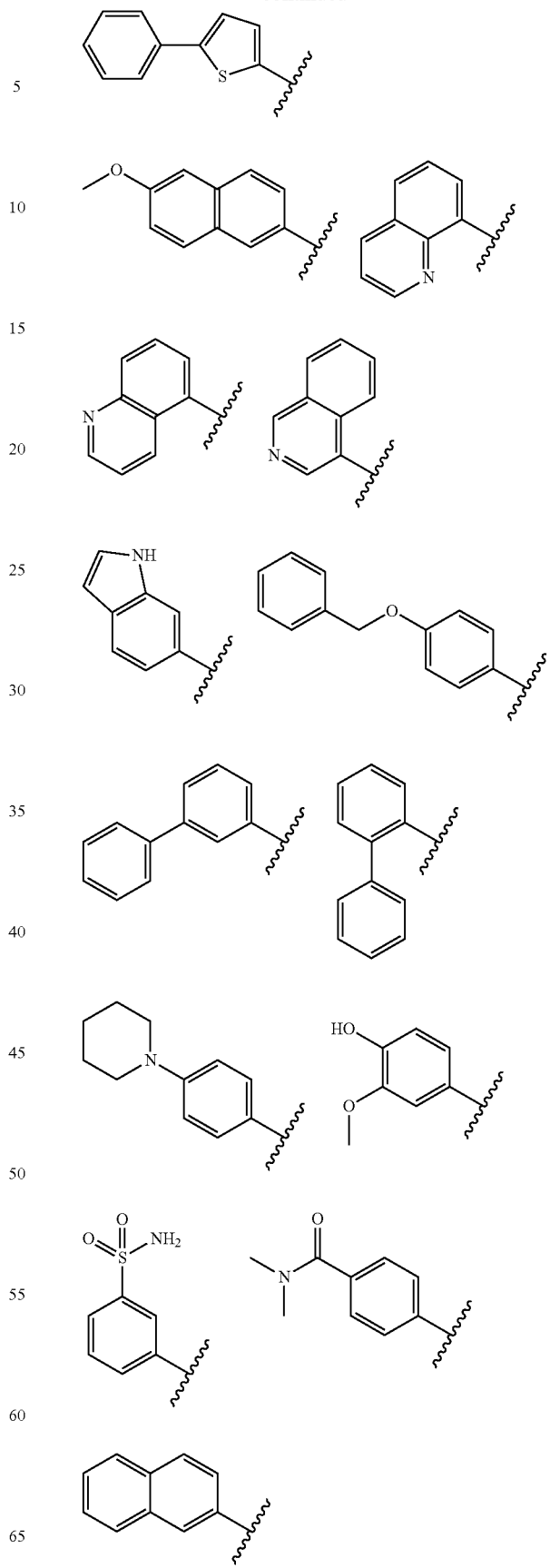

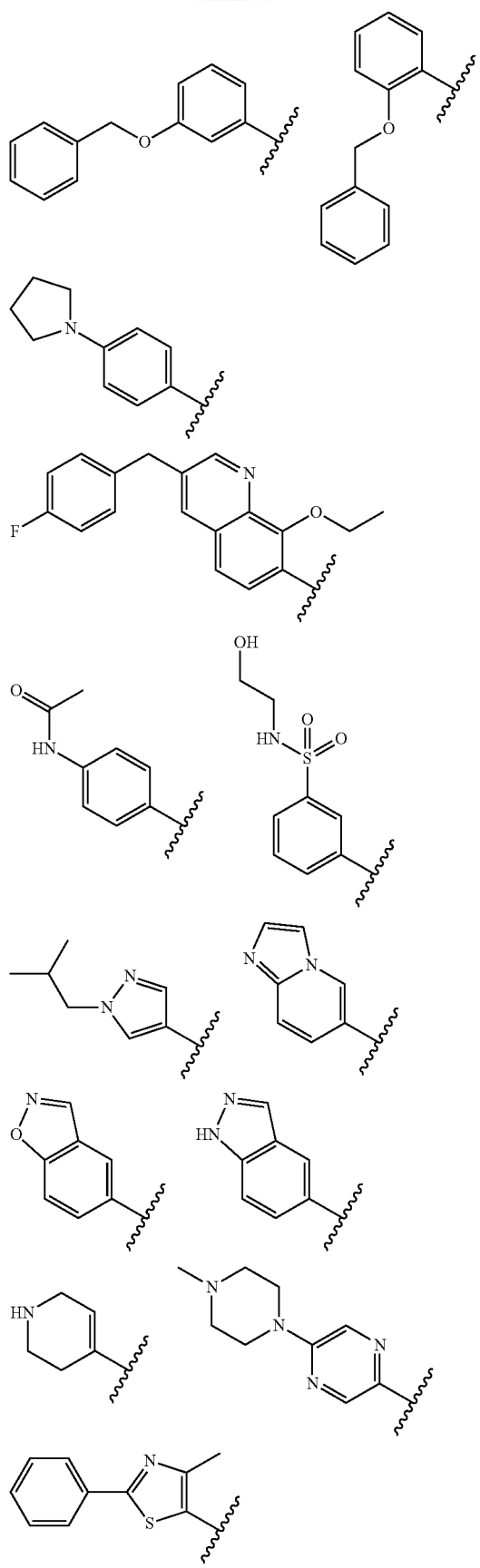
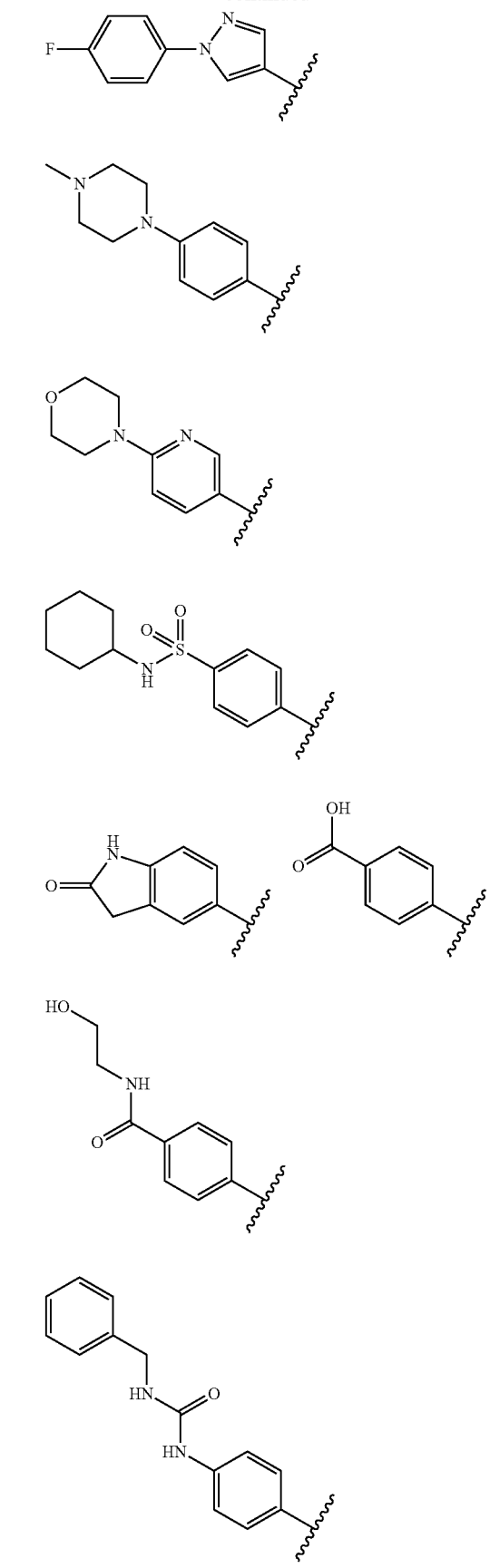

-continued
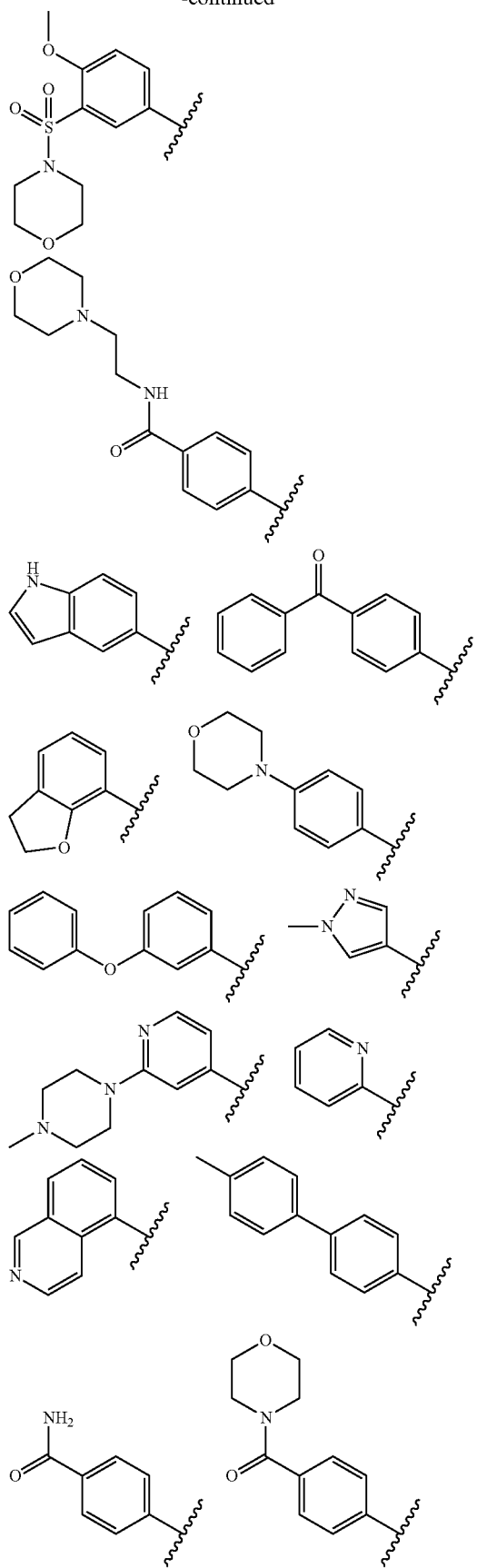
-continued
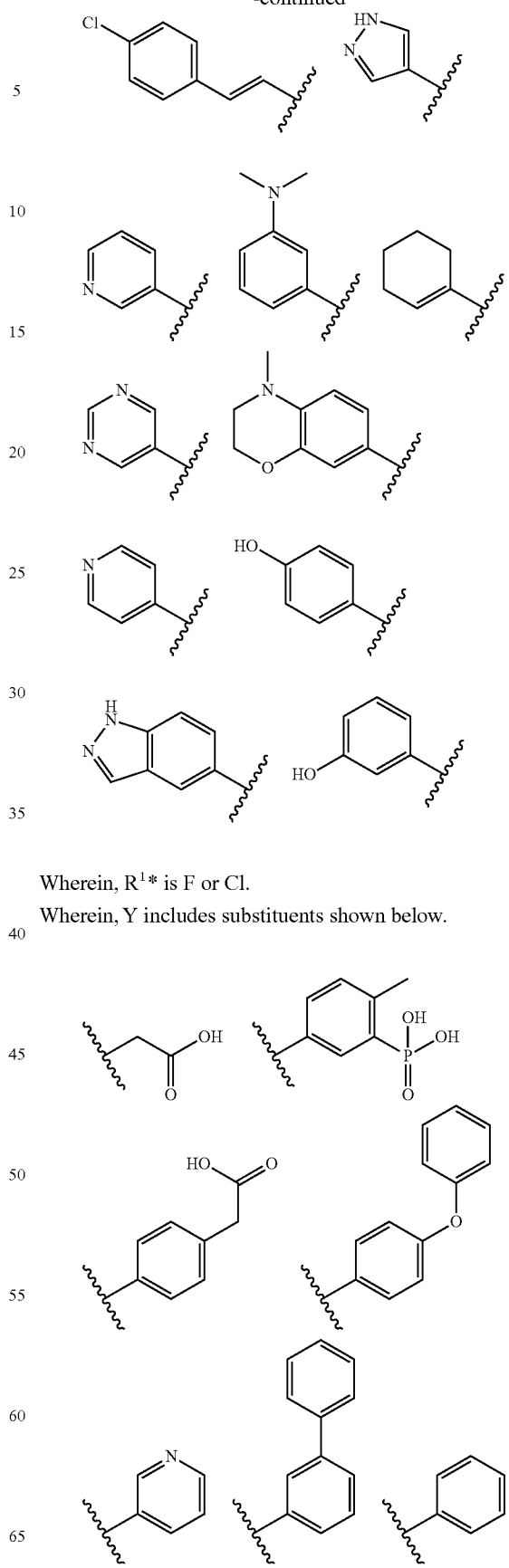
Wherein, R$^1$* is F or Cl.
Wherein, Y includes substituents shown below.

281
-continued
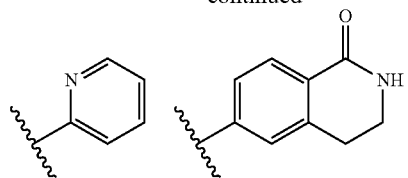
282
-continued
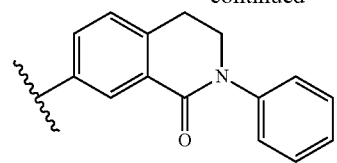
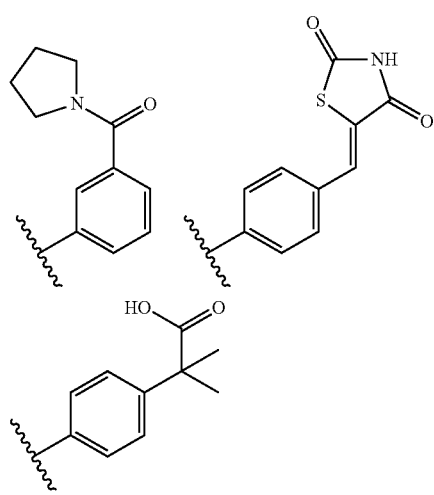
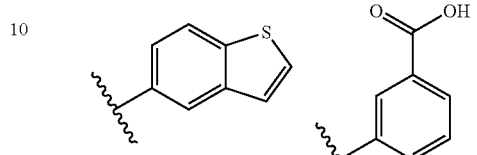
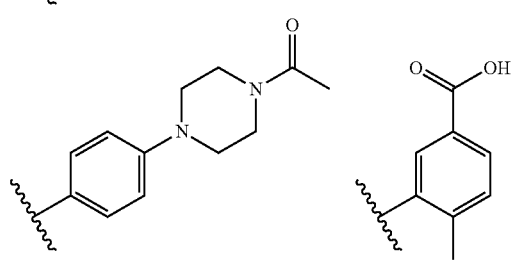
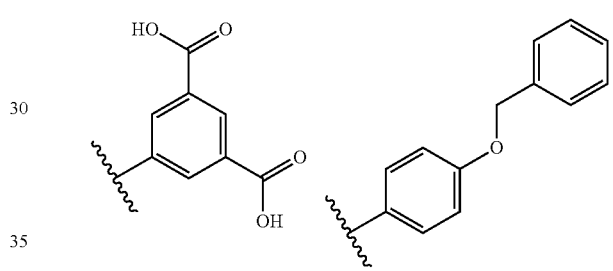
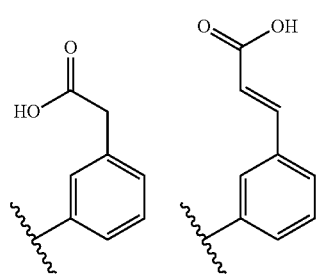
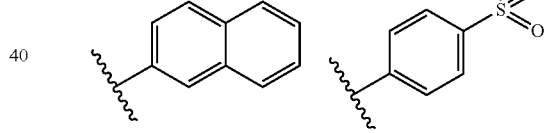
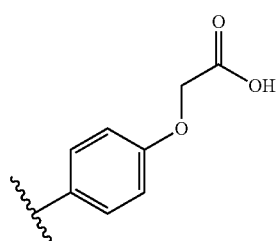
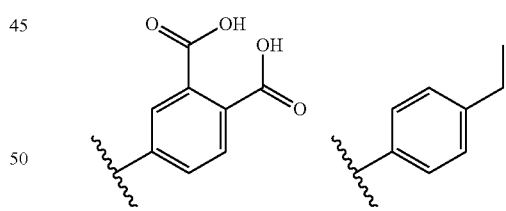
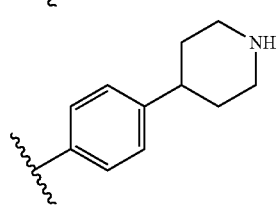
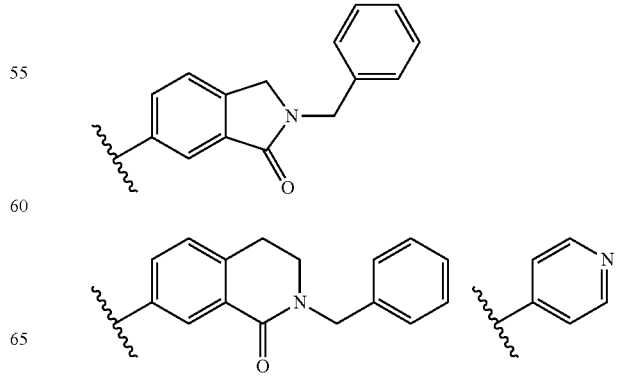

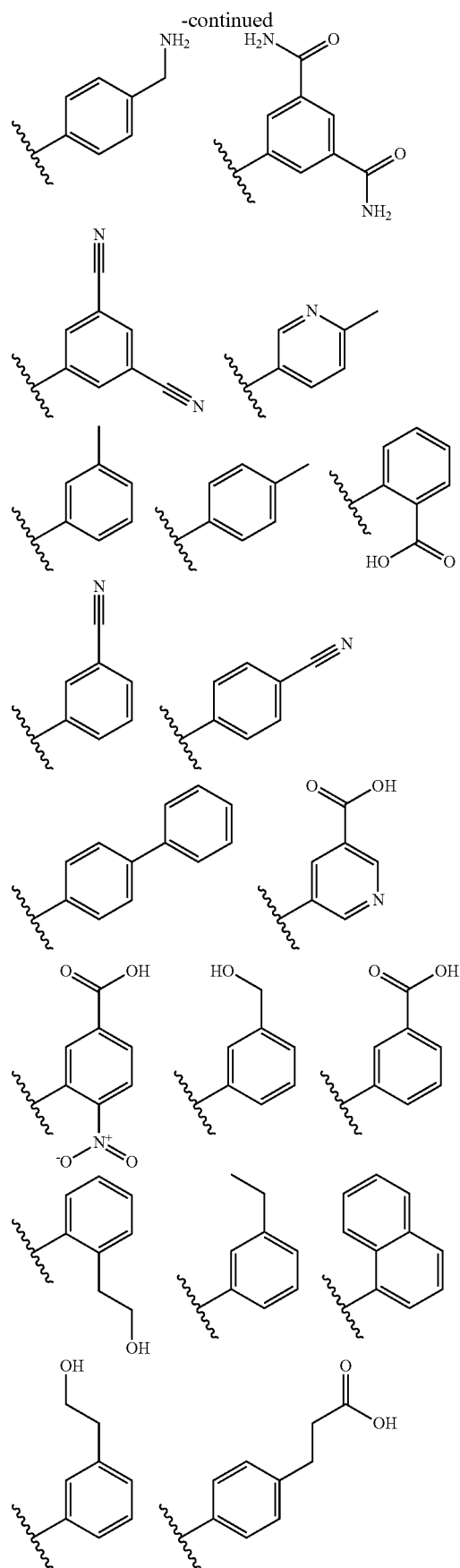
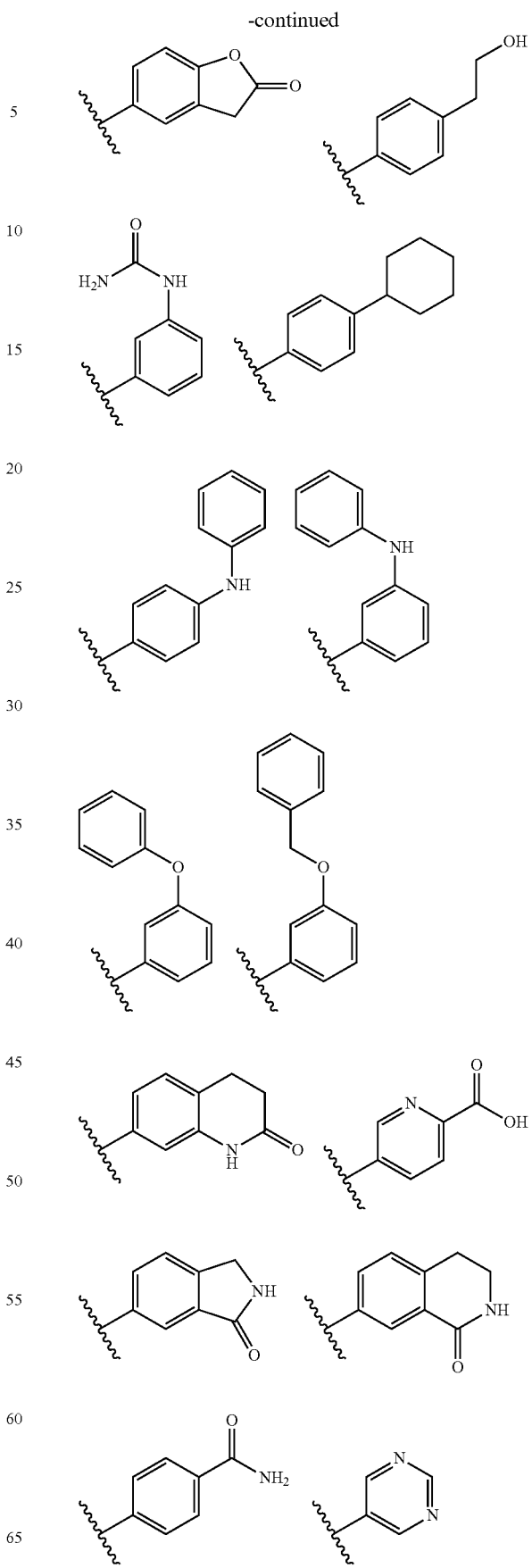

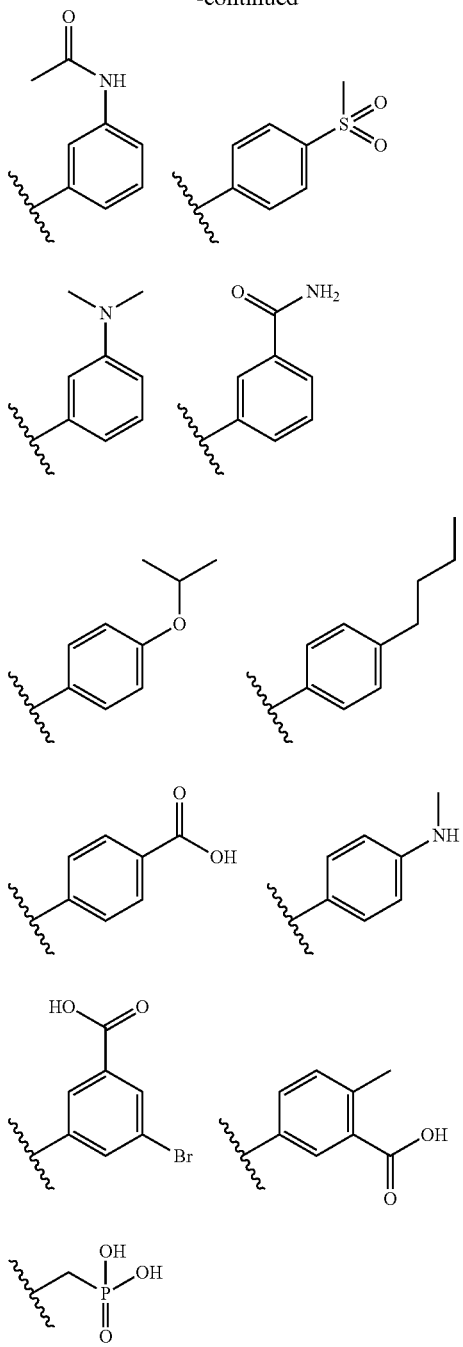

Particularly, compounds shown below are preferred.

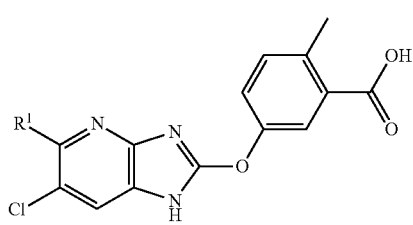

wherein, R¹ includes the substituents exemplified above.

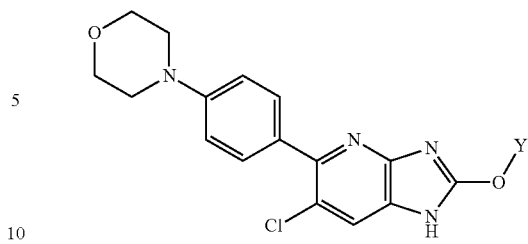

wherein, Y includes the substituents exemplified above.

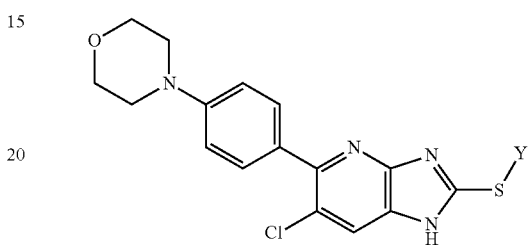

wherein, Y includes the substituents exemplified above.

Evaluation Method of an Activator for AMP-Activated Protein Kinase (AMPK)

Test Example 1

To a buffer solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium (3-glycerophosphate and 2 mM dithiothreitol, a human AMPK α1β1γ1 enzyme (manufactured by Carna Biosciences, Inc.) was added in an amount to give a conversion rate of approximately 10% by reaction for 2 hours, and a compound dissolved in DMSO was added thereto so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N' tetraacetic acid (EGTA), 5 mM disodium β-glycerophosphate, 2 mM dithiothreitol, 0.4 mM ATP and 3 µM FL-Peptide 7 (manufactured by Caliper Life Sciences, Inc.) was added in equal amount (10 µl in total). The obtained liquid was allowed to react at 25° C. for 2 hours, and 10 µl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 1 are shown below.
Compound A-1: EC150=4.5 nM, Emax=383%
Compound A-2: EC150=7 nM, Emax=408%
Compound B-2: EC150=3.6 nM, Emax=399%
Compound B-3: EC150=23 nM, Emax=313%
Compound B-5: EC150=4700 nM, Emax=176%
Compound B-7: EC150=5100 nM, Emax=246%
Compound B-10: EC150=280 nM, Emax=290%
Compound B-13: EC150=76 nM, Emax=311%
Compound B-22: EC150=13 nM, Emax=339%
Compound B-32: EC150=70 nM, Emax=301%
Compound B-40: EC150=110 nM, Emax=297%
Compound B-63: EC150=100 nM, Emax=321%
Compound B-81: EC150=25 nM, Emax=283%
Compound B-101: EC150=120 nM, Emax=269%
Compound B-104: EC150=190 nM, Emax=267%
Compound B-107: EC150=250 nM, Emax=249%
Compound B-108: EC150=27 nM, Emax=340%
Compound B-109: EC150=140 nM, Emax=315%
Compound B-110: EC150=160 nM, Emax=288%
Compound B-113: EC150=13 nM, Emax=316%
Compound B-117: EC150=370 nM, Emax=243%
Compound B-119: EC150=220 nM, Emax=265%
Compound B-121: EC150=97 nM, Emax=278%
Compound B-126: EC150=180 nM, Emax=262%
Compound B-131: EC150=44 nM, Emax=298%
Compound B-133: EC150=360 nM, Emax=234%
Compound B-136: EC150=27 nM, Emax=333%
Compound B-137: EC150=25 nM, Emax=301%
Compound B-141: EC150=61 nM, Emax=319%
Compound C-1: EC150=66 nM, Emax=295%
Compound C-4: EC150=0.42 nM, Emax=355%
Compound C-9: EC150=33 nM, Emax=322%
Compound C-11: EC150=7.4 nM, Emax=356%
Compound C-12: EC150=140 nM, Emax=256%
Compound C-21: EC150=36 nM, Emax=338%
Compound C-24: EC150=17 nM, Emax=237%
Compound C-29: EC150=8.3 nM, Emax=349%
Compound C-32: EC150=68 nM, Emax=253%
Compound C-33: EC150=52 nM, Emax=329%
Compound C-37: EC150=1.3 nM, Emax=349%
Compound C-39: EC150=35 nM, Emax=279%
Compound C-63: EC150=16 nM, Emax=331%
Compound C-70: EC150=4.2 nM, Emax=335%
Compound C-88: EC150=120 nM, Emax=298%
Compound C-89: EC150=470 nM, Emax=242%
Compound C-94: EC150=12 nM, Emax=352%
Compound C-95: EC150=17 nM, Emax=309%
Compound C-96: EC150=99 nM, Emax=326%
Compound C-98: EC150=1700 nM, Emax=165%
Compound C-99: EC150=170 nM, Emax=205%
Compound C-100: EC150=590 nM, Emax=212%
Compound C-106: EC150=690 nM, Emax=278%
Compound C-107: EC150=300 nM, Emax=232%
Compound C-118: EC150=2.1 nM, Emax=334%
Compound C-119: EC150=130 nM, Emax=237%
Compound D-1: EC150=430 nM, Emax=182%
Compound D-2: EC150=220 nM, Emax=255%
Compound D-3: EC150=220 nM, Emax=192%
Compound D-4: EC150=70 nM, Emax=207%
Compound D-7: EC150=1600 nM, Emax=285%
Compound D-8: EC150=39 nM, Emax=244%
Compound D-9: EC150=380 nM, Emax=186%
Compound D-12: EC150=69 nM, Emax=226%
Compound D-16: EC150=8.5 nM, Emax=280%
Compound D-17: EC150=11 nM, Emax=282%
Compound D-18: EC150=21 nM, Emax=325%
Compound D-21: EC150=41 nM, Emax=351%
Compound D-24: EC150=140 nM, Emax=198%
Compound D-25: EC150=31 nM, Emax=225%
Compound D-26: EC150=82 nM, Emax=282%
Compound D-31: EC150=19 nM, Emax=314%
Compound D-33: EC150=52 nM, Emax=220%
Compound D-39: EC150=0.6 nM, Emax=310%
Compound D-41: EC150=8300 nM, Emax=159%
Compound D-42: EC150=260 nM, Emax=187%
Compound D-43: EC150=8.4 nM, Emax=270%
Compound D-49: EC150=3.5 nM, Emax=263%
Compound D-50: EC150=11 nM, Emax=225%
Compound D-52: EC150=2800 nM, Emax=169%
Compound D-54: EC150=110 nM, Emax=252%
Compound D-55: EC150=2700 nM, Emax=177%
Compound D-56: EC150=68 nM, Emax=211%
Compound D-58: EC150=66 nM, Emax=224%
Compound D-62: EC150=80 nM, Emax=267%
Compound D-65: EC150=42 nM, Emax=252%
Compound D-70: EC150=180 nM, Emax=214%
Compound D-71: EC150=860 nM, Emax=174%
Compound D-72: EC150=220 nM, Emax=192%
Compound D-73: EC150=17 nM, Emax=254%
Compound D-102: EC150=4300 nM, Emax=172%
Compound D-103: EC150=110 nM, Emax=238%
Compound D-107: EC150=26 nM, Emax=249%
Compound D-108: EC150=3.3 nM, Emax=301%
Compound D-109: EC150=18 nM, Emax=270%
Compound D-110: EC150=270 nM, Emax=220%
Compound D-111: EC150=150 nM, Emax=238%

Preparation Method of Human AMPK α2γ2γ1

The full length cDNAs of human AMPK β2 (NM_005399.3) and human AMPK α2 (NM_006252.3) were inserted into the MCS1 and MCS2 of the pETDuet-1 vector to prepare a human AMPK β2 and human AMPK α2 (6×His tag at the 5' terminus) expressing plasmid. The plasmid was cotransfected with an expression plasmid, in which the full length cDNA of human AMPK γ1 (NM_002733.3) had been inserted into pET28b(+), into BL21 CodonPlus (DE3)-RIL to obtain an expression strain. The expression strain was cultured in TB medium, followed by induction with 0.5 mM IPTG, and cultured at 25° C. for 3 hours and then harvested. After ultrasonication, supernatant was collected and applied to Histrap column (GE) and RESOUECE Q 6 ml column (GE) to prepare 12.5 mg of purified sample containing three types of subunit from 1.8 L of broth.

Preparation Method of Human CaMKK2 Used to Impart Activity to AMPK

An expression vector, in which the full length cDNA of human CAMKK β (NM_172226.1) had been inserted into pGEX-6P-3, was transfected into BL21 Star (DE3). The expression strain was cultured in TB medium, followed by induction with 0.5 mM IPTG, and cultured at 25° C. for 3 hours and then harvested. After ultrasonication, supernatant was collected and applied to GSTrap FF column (GE) to prepare 14 mg of GST-fused CAMKK β from 720 ml of broth.

Evaluation Method of an Activator for AMP-Activated Protein Kinase (AMPK)

Test Example 2

Human AMPK α2β2γ1 prepared in *Escherichia coli* was not phosphorylated and did not exhibit activity. Thus, phosphorylation treatment was carried out as pretreatment.

Human AMPK α2β2γ1 in an amount to give a conversion rate of approximately 10% by reaction for 2 hours, and CaMKK2 in an amount capable of sufficiently imparting activity to AMPK for one hour were mixed in a buffer solution consisting of a 50 mM HEPES-NaOH buffer solution (pH 7.0), 100 mM NaCl, 5 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium β-glycerophosphate, 1 mM dithiothreitol and 0.2 mM ATP, and the obtained liquid was left to stand at 25° C. for 1 to 1.5 hours to sufficiently phosphorylate AMPK.

After that, to the enzyme liquid, which had been subjected to phosphorylation treatment, a compound dissolved in DMSO was added so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium glycerophosphate, 2 mM dithiothreitol, 0.4 mM ATP and 3 µM FL-Peptide 7 (manufactured by Caliper Life Sciences, Inc.) was added in equal amount (10 µl in total). The obtained liquid was allowed to react at 25° C. for 2 hours, and 10 µl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 2 are shown below.
Compound A-1: EC150=130 nM, Emax=394%
Compound A-2: EC150=74 nM, Emax=406%
Compound B-101: EC150=1300 nM, Emax=212%
Compound B-108: EC150=410 nM, Emax=341%
Compound B-119: EC150=240 nM, Emax=242%
Compound C-4: EC150=4.3 nM, Emax=292%
Compound C-12: EC150=130 nM, Emax=293%
Compound C-94: EC150=59 nM, Emax=325%
Compound C-106: EC150=580 nM, Emax=290%
Compound D-49: EC150=54 nM, Emax=420%

As can be seen from the above Test Examples, the compounds of the present invention have an excellent activating effect on both of an AMPK a1 trimer and an AMPK α2 trimer.

Usefulness as a medicament can be examined by the following tests etc. CYP3A4 fluorescent MBI test The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (enzyme expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 µmmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted with a substrate and a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane) =4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 mmol/L ethoxyresorufin (CYP1A2), 100 µmol/L tolbutamide (CYP2C9), 50 mmol/L S-mephenitoin (CYP2C19), 5 µmol/L dextromethorphan (CYP2D6), 1 mmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2C9 metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

FAT Test

Each 20 μL of freeze-stored *Salmonella typhimurium* (TA98 and TA100 strain) was inoculated in 10 mL of liquid nutrient medium (2.5% Oxoid nutrient broth No. 2), and the cultures were incubated at 37° C. under shaking for 10 hours. 9 mL of TA98 culture was centrifuged (2000×g, 10 minutes) to remove medium, and the bacteria was suspended in 9 mL of Micro F buffer ($K_2HPO_4$: 3.5 g/L, $KH2PO_4$: 1 g/L, $(NH_4)_2SO_4$: 1 g/L, trisodium citrate dihydrate: 0.25 g/L, $MgSO_4.7H_2O$: 0.1 g/L), and the suspension was added to 110 mL of Exposure medium (Micro F buffer containing Biotin: 8 μg/mL, histidine 0.2 μg/mL, glucose: 8 mg/mL). 3.16 mL of TA100 culture was added to 120 mL of Exposure medium to prepare the test bacterial solution. 588 μL of the test bacterial solution (or mixed solution of 498 μl of the test bacterial solution and 90 μL of the S9 mix in the case with metabolic activation system) was mixed with each 12 μL of the following solution: DMSO solution of the test substance (eight dose levels from maximum dose 50 mg/mL at 2-fold ratio); DMSO as negative control; 50 μg/mL of 4-nitroquinoline-1-oxide DMSO solution as positive control for TA98 without metabolic activation system; 0.25 μg/mL of 2-(2-furyl)-3-(5-nitro-2-furyl)acrylamide DMSO solution as positive control for TA100 without metabolic activation system; 40 μg/mL of 2-aminoanthracene DMSO solution as positive control for TA98 with metabolic activation system; or 20 μg/mL of 2-aminoanthracene DMSO solution as positive control for TA100 with metabolic activation system. 12 μL of the solution and 588 μL of the test bacterial solution (a mixed solution of 498 μl of the test bacterial solution and 90 μL of S9 mix with metabolic activation condition) were mixed and incubated at 37° C. under shaking for 90 minutes. 460 μL of the bacterial solution exposed to the test substance was mixed with 2300 μL of Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into 48 wells per dose in the microwell plates, and was subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose was counted, and evaluated the mutagenicity by comparing with the negative control group.

Solubility Test

The solubility of a compound was determined under a condition in which 1% DMSO was added. 10 mM compound solution was prepared using DMSO, and then 6 μL of the compound solution was added to 594 μL of artificial intestinal juice in pH 6.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (1/1), and then a concentration in the filtration was measured with HPLC or LC/MS/MS by the absolute calibration method.

Metabolic Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

Powder Solubility Test

Appropriate amounts of the test substances were put into appropriate containers. To the respective containers were added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 200 μL of 20 mmol/L TCA (sodium taurocholate)/JP-2 fluid (TCA 1.08 g and water to reach 100 mL). In the case that the test compound was dissolved after the addition of the test fluid, the bulk powder was added as appropriate. The containers were sealed, and shaken for 1 hour at 37° C. The mixtures were filtered, and 100 μL of methanol was added to each of the filtrate (100 μL) so that the filtrates were two-fold diluted. The dilution ratio was changed if necessary. After confirmation of no bubbles and precipitates, the containers were sealed and shaken. Quantification was performed by HPLC with an absolute calibration method.

BA Test

Materials and methods for studies on oral absorption
(1) Animals: mice or rats
(2) Animal Husbandry:
Mice and rats had free access to solid food and sterilized bottled tap water.
(3) Setting of Dose and Group Compositions:
orally or intravenously administered at a predetermined dose; Group compositions were as shown below (Dose depends on the compound)
Oral: 1 to 30 mg/kg (n=2 to 3)
Intravenous: 0.5 to 10 mg/kg (n=2 to 3)
(4) Preparation for Dosing Formulation:
for oral administration, in a solution or a suspension state; for intravenous administration, in a solubilized state
(5) Dosing Procedure:
In oral administration study, the test suspension was dosed to the stomach of rats by using a gavage tube In intravenous administration study, the test solution was dosed to rats via tail vein using a syringe with a needle.
(6) Evaluation Items:
Blood was collected at each time point, and plasma concentration of the test substance was determined by a LC/MS/MS system.
(7) Data Analysis:
Regarding the transition of the plasma concentration, area under the plasma concentration-time curve (AUC) was calculated by means of WinNonlin® program, respectively. Bioavailability (BA) was calculated by using AUC values in oral administration study and in intravenous administration study.

Fluctuation Ames Test

In 10 ml of nutrient liquid medium (2.5% Oxoid nutrient broth No. 2), 20 µL of freeze-stored *Salmonella typhimurium* (TA 98 strain, TA 100 strain) is seeded, and the medium is pre-cultured with shaking at 37° C. for 10 hours. For the TA 98 strain, 9 mL of bacterial liquid is centrifuged (2000×g, 10 min) to remove broth. The bacteria are suspended in 9 mL of Micro F buffer solution ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), and the suspension is added to 110 mL of Exposure medium (Micro F buffer solution containing biotin: 8 µg/mL, histidine: 0.2 µg/mL and glucose: 8 mg/mL). For the TA 100 strain, 3.16 mL of bacterial liquid is added to 120 mL of Exposure medium to prepare a test bacterial liquid. Each 12 µL of a solution of a compound of the present invention in DMSO (a few-stage dilution from a maximum dose of 50 mg/mL at a common ratio of 2 or 3), DMSO as a negative control, a 50 µg/mL solution of 4-nitroquinoline-1-oxide in DMSO for the TA 98 strain and a 0.25 µg/mL solution of 2-(2-furyl)-3-(5-nitro-2-furyl)acrylamide in DMSO for the TA 100 strain under non-metabolic activation conditions, a 40 µg/mL solution of 2-aminoanthracene in DMSO for the TA 98 strain and a 20 µg/mL solution of 2-aminoanthracene in DMSO for the TA 100 strain under metabolic activation conditions as positive controls is mixed with 588 µL of a test bacterial liquid (a mixed liquid of 498 µL of test bacterial liquid and 90 µL of S9 mix under metabolic activation conditions), and the obtained liquid is cultured with shaking at 37° C. for 90 minutes. A bacterial liquid exposed to a compound of the present invention, 460 µL, is mixed with 2300 µL of Indicator medium (Micro F buffer solution containing biotin: 8 µg/mL, histidine: 0.2 µg/mL, glucose: 8 mg/mL and bromocresol purple: 37.5 µg/mL), and 50 µL each of the obtained liquid is dispensed into a microplate 48 wells/dose. The plate is static-cultured at 37° C. for 3 days. A well which contains bacteria acquiring the ability to proliferate by mutation of an amino acid (histidine)-synthesizing enzyme gene is changed from purple to yellow by pH changes. Therefore, the number of bacteria-proliferation wells, whose color has been changed to yellow, of 48 wells per dose is counted, and compared with that of the negative control group for evaluation. Negative mutagenicity is shown as (−), and positive is shown as (+).

Formulation Example 1

A hard gelatin capsule is prepared using the following ingredients.

|  | Dose (mg/capsule) |
| --- | --- |
| Active ingredient | 250 |
| Starch (dry) | 200 |
| Magnesium stearate | 10 |
| Total | 460 mg |

Formulation Example 2

A tablet is prepared using the following ingredients.

|  | Dose (mg/tablet) |
| --- | --- |
| Active ingredient | 250 |
| Cellulose (microcrystal) | 400 |
| Silicon dioxide (fumed) | 10 |
| Stearic acid | 5 |
| Total | 665 mg |

The ingredients are mixed and compressed to form tablets, each of which has a weight of 665 mg.

Formulation Example 3

An aerosol solution containing the following ingredients is prepared.

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient and ethanol are mixed, and the mixture is added to a part of propellant 22. The obtained mixture is cooled to −30° C., and transferred to a packing machine. Thereafter, the amount to be required is supplied to a stainless steel container, and diluted with remaining propellant. A bubbling unit is attached to the container.

Formulation Example 4

A tablet containing 60 mg of active ingredient is prepared as follows.

| Active ingredient | 60 mg |
| --- | --- |
| Starch | 45 mg |

295
-continued

| Microcrystalline cellulose | 35 mg |
| Polyvinylpyrrolidone (a 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and then adequately mixed. An aqueous solution containing polyvinylpyrrolidone is mixed with the obtained powder, and the mixture is then passed through a No. 14 mesh U.S. sieve. Granules obtained in this manner are dried at 50° C. and passed through a No. 18 mesh U.S. sieve. The sodium carboxymethyl starch, magnesium stearate and talc that are passed through a No. 60 mesh U.S. sieve in advance, are added to the granules, and the obtained mixture is mixed and then compressed by a tablet machine to obtain tablets, each of which has a weight of 150 mg.

Formulation Example 5

A capsule containing 80 mg of active ingredient is prepared as follows.

| Active ingredient | 80 mg |
| Starch | 59 mg |
| Microcrystalline cellulose | 59 mg |
| Magnesium stearate | 2 mg |
| Total | 200 mg |

The active ingredient, starch, cellulose and magnesium stearate are mixed and passed through a No. 45 mesh U.S. sieve, and each 200 mg of the mixture is filled into a hard gelatin capsule.

Formulation Example 6

A suppository containing 225 mg of active ingredient is prepared as follows.

| Active ingredient | 225 mg |
| Saturated fatty acid glyceride | 2000 mg |
| Total | 2225 mg |

The active ingredient is passed through a No. 60 mesh U.S. sieve and suspended in a saturated fatty acid glyceride, which has been melted by minimum heating in advance. Thereafter, the resultant mixture is put into a mold with an apparent weight of 2 g and cooled.

Formulation Example 7

A suspension containing 50 mg of active ingredient is prepared as follows.

| Active ingredient | 50 mg |
| Sodium carboxymethyl cellulose | 50 mg |
| Syrup | 1.25 ml |
| Benzoic acid solution | 0.10 ml |
| Flavor | q.v. |

296
-continued

| Pigment | q.v. |
| Total after adding purified water | 5 ml |

The active ingredient is passed through a No. 45 mesh U.S. sieve and mixed with sodium carboxymethyl cellulose and syrup to form a smooth paste. The benzoic acid solution and the flavor diluted with part of water are added, and stirred. A sufficient amount of water is then added thereto to obtain a required volume.

Formulation Example 8

An intravenous formulation is prepared as follows.

| Active ingredient | 100 mg |
| Saturated fatty acid glyceride | 1000 ml |

A solution of the above-described ingredients is usually intravenously administered to a patient at a rate of 1 ml per 1 min.

INDUSTRIAL APPLICABILITY

As is apparent from the above test examples, the compounds of the present invention show an AMPK activating effect. Therefore, the compounds of the present invention are very useful as a therapeutic agent for type II diabetes, hyperglycemia, metabolic syndrome, obesity, hypercholesterolemia and hypertension.

The invention claimed is:
1. A compound represented by formula (I):

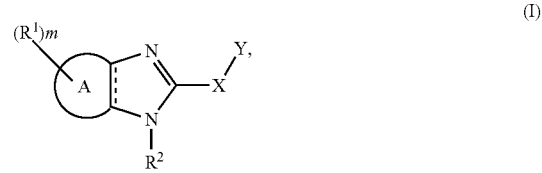

a pharmaceutically acceptable salt or solvate thereof, wherein a group represented by formula:

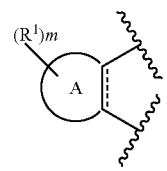

is a group represented by formula:

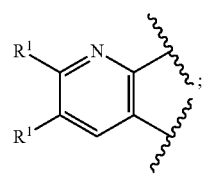

$R^1$ is each independently halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^2$ is hydrogen, or substituted or unsubstituted alkyl;

X is —O—; and

Y is substituted or unsubstituted aryl.

2. The compound according to claim 1, a pharmaceutically acceptable salt or solvate thereof, wherein Y is

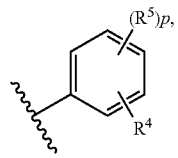

wherein $R^4$ is a group represented by formula: —$(CR^6R^7)$q-Z;

$R^6$ is each independently hydrogen, hydroxy, substituted or unsubstituted alkyl, or substituted or unsubstituted amino;

$R^7$ is each independently hydrogen, hydroxy, substituted or unsubstituted alkyl, or substituted or unsubstituted amino;

q is an integer of 0 to 4;

Z is —COOH, —COOR$^8$, —OH, —C(=O)—NR$^9$ R$^{10}$, —NR$^9$ —C(=O)—R$^{11}$, —NR$^9$ —SO$_2$ —R$^8$, —SO$_2$ —NR$^9$ R$^{10}$, —SO$_2$ —NR$^9$ —C(=O)—R$^8$, —SO$_2$ —NR$^9$ —COOR$^8$, —SO$_2$ —NR$^9$ —C(=O)—NR$^9$ R$^{10}$, —C(=O)—NR$^9$ —SO$_2$ —R$^8$, —NR$^9$ —C(=O)—NR$^9$ R$^{10}$, —P(=O)(—OH)$_2$, —P(=O)H(—OH), —P(=O)(—R$^{11}$)$_2$, —P(=O)(—OR$^{11}$)$_2$, —P(=O)(—OH)(—R$^{11}$), —P(=O)(—OH)(—OR$^{11}$), —P(=O)(—R$^{11}$)(—OR$^{11}$), —P(=O)(—OH)(—O—(CR$^6$ R$^7$)$_{0-4}$—R$^{12}$), —P(=O)(—NR$^9$ —CR$^{13}$ R$^{14}$ —COOH)$_2$, —P(=O)(—NR$^9$ —CR$^{13}$ R$^{14}$ —COOR$^{11}$)$_2$, —P(=O)(—OH)(—NR$^9$ —CR$^{13}$ R$^{14}$ —COOH), —P(=O)(—OH)(—NR$^9$ —CR$^{13}$ R$^{14}$ —COOR$^{11}$), —P(=O)(—NR$^9$ —CR$^{13}$ R$^{14}$ —COOR$^{11}$)(—O—R$^8$), —P(=O)(—O—CR$^{13}$ R$^{14}$ —O—C(=O)—R$^{11}$)$_2$, —P(=O)(—OH)(—O—CR$^{13}$ R$^{14}$ —O—C(=O)—R$^{11}$), —P(=O)(—OH)(—O—(CR$^6$ R$^7$)$_{1-4}$—S(=O)—R$^{11}$), —P(=O)(—O—(CR$^6$ R$^7$)$_{1-4}$—S(=O)—R$^{11}$)$_2$, —P(=O)(—OH)(—O—(CR$^6$ R$^7$)$_{1-4}$—S—C(=O)—R$^{11}$), —P(=O)(—O—(CR$^6$ R$^7$)$_{1-4}$—S—C(=O)—R$^{11}$)$_2$, —NR$^9$ —C(=O)—O—R$^{11}$ or

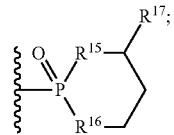

$R^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^9$ and $R^{10}$ are each independently hydrogen, or substituted or unsubstituted alkyl;

$R^{11}$ and $R^{12}$ are each independently substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^{13}$ and $R^{14}$ are each independently hydrogen, or substituted or unsubstituted alkyl;

$R^{15}$ and $R^{16}$ are each independently —O—or —NH—;

$R^{17}$ is substituted or unsubstituted aryl, or substituted or unsubstituted heteroaryl;

$R^5$ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and p is an integer of 0 to 2.

3. The compound according to claim 2, a pharmaceutically acceptable salt or solvate thereof, wherein q is 1.

4. The compound according to claim 3, a pharmaceutically acceptable salt or solvate thereof, wherein $R^6$ and $R^7$ are each independently substituted or unsubstituted alkyl.

5. The compound according to claim 2, a pharmaceutically acceptable salt or solvate thereof, wherein Z is —NR9—C(=O)—R$^{11}$.

6. The compound according to claim 1, a pharmaceutically acceptable salt or solvate thereof, wherein at least one of $R^1$ is halogen.

7. The compound according to claim 1, a pharmaceutically acceptable salt or solvate thereof, wherein at least one of $R^1$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

8. The compound according to claim 1, a pharmaceutically acceptable salt or solvate thereof, wherein at least one of $R^1$ is substituted or unsubstituted aryl.

9. The compound according to claim 1, a pharmaceutically acceptable salt or solvate thereof, wherein one of $R^1$ is halogen, and another of $R^1$ is substituted or unsubstituted aryl.

10. A pharmaceutical composition comprising a compound represented by formula (I):

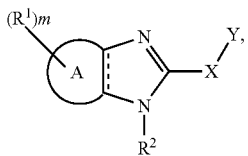
(I)

a pharmaceutically acceptable salt or solvate thereof, wherein
a group represented by formula:

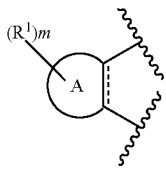

is a group represented by formula:

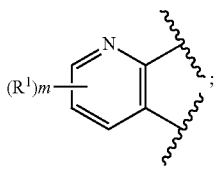

$R^1$ is each independently halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^2$ is hydrogen, or substituted or unsubstituted alkyl;

X is —O—; and

Y is substituted or unsubstituted aryl, substituted or unsubstituted cycloalkyl, substituted or unsubstituted cycloalkenyl, or substituted or unsubstituted heterocyclyl, wherein the pharmaceutical composition has an activating effect on adenosine monophosphate-activated protein kinase.

11. The pharmaceutical composition according to claim 10, wherein Y is substituted or unsubstituted aryl.

12. The pharmaceutical composition according to claim 11, wherein Y is a group represented by formula:

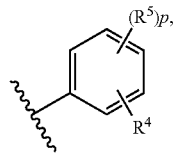

$R^4$ is a group represented by formula: —$(CR^6R^7)q$-Z;

$R^6$ is each independently hydrogen, hydroxy, substituted or unsubstituted alkyl, or substituted or unsubstituted amino;

$R^7$ is each independently hydrogen, hydroxy, substituted or unsubstituted alkyl, or substituted or unsubstituted amino;

q is an integer of 0 to 4;

Z is —COOH, —COOR$^8$, —OH, —C(=O)—NR$^9$ R$^{10}$, —NR$^9$ —C(=O)—R$^{11}$, —NR$^9$ —SO$_2$ —R$^8$, —SO$_2$ —NR$^9$ R$^{10}$, —SO$_2$ —NR$^9$ —C(=O)—R$^8$, —SO$_2$ —NR$^9$ —COOR$^8$, —SO$_2$ —NR$^9$ —C(=O)—NR$^9$ R$^{10}$, —C(=O)—NR$^9$ —SO$_2$ —R$^8$, —NR$^9$ —C(=O)—NR$^9$ R$^{10}$, —P(=O)(—OH)$_2$, —P(=O)H(—OH), —P(=O)(—R$^{11}$)$_2$, —P(=O)(—OR$^{11}$)$_2$, —P(=O)(—OH)(—R$^{11}$), —P(=O)(—OH)(—OR$^{11}$), —P(=O)(—R$^{11}$)(—OR$^{11}$), —P(=O)(—OH)(—O—(CR$^6$ R$^7$)$_{0-4}$ —R$^{12}$), —P(=O)(—NR$^9$ —CR$^{13}$ R$^{14}$ —COOH)$_2$, —P(=O)(—NR$^9$ —CR$^{13}$ R$^{14}$ —COOR$^{11}$)$_2$, —P(=O)(—OH)(—NR$^9$ —CR$^{13}$ R$^{14}$ —COOH), —P(=O)(—OH)(—NR$^9$ —CR$^{13}$ R$^{14}$ —COOR$^{11}$), —P(=O)(—NR$^9$ —CR$^{13}$ R$^{14}$ —COOR$^{11}$)(—O—R$^8$), —P(=O)(—O—CR$^{13}$ R$^{14}$ —O—C(=O)—R$^{11}$, —P(=O)(—OH)(—O—CR$^{13}$ R$^{14}$ —O—C(=O)—R$^{11}$), —P(=O)(—OH)(—O—(CR$^6$ R$^7$)$_{1-4}$ —S(=O)—R$^{11}$), —P(=O)(—O—(CR$^6$ R$^7$)$_{1-4}$ —S(=O)—R$^{11}$)$_2$, —P(=O)(—OH)(—O—(CR$^6$ R$^7$)$_{1-4}$ —S—C(=O)—R$^{11}$), —P(=O)(—O—(CR$^6$ R$^7$)$_{1-4}$ —S—C(=O)—R$^{11}$)$_2$, —NR$^9$ —C(=O)—O—R$^{11}$ or

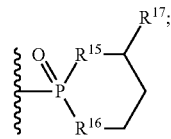

$R^8$ is substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^9$ and $R^{10}$ are each independently hydrogen, or substituted or unsubstituted alkyl;

$R^{11}$ and $R^{12}$ are each independently substituted or unsubstituted alkyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^{13}$ and $R^{14}$ are each independently hydrogen, or substituted or unsubstituted alkyl;

R¹⁵ and R¹⁶ are each independently —O— or —NH—;

R¹⁷ is substituted or unsubstituted aryl, or substituted or unsubstituted heteroaryl;

R⁵ is halogen, hydroxy, cyano, nitro, carboxy, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkylsulfonyl, substituted or unsubstituted carbamoyl, or substituted or unsubstituted amino; and p is an integer of 0 to 2.

13. The pharmaceutical composition according to claim 10, wherein Y is substituted or unsubstituted heterocyclyl.

14. The pharmaceutical composition according to claim 10,
wherein at least one of R¹ is halogen.

15. The pharmaceutical composition according to claim 10,
wherein at least one of R¹ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

16. The pharmaceutical composition according to claim 10, wherein R² is hydrogen.

17. The pharmaceutical composition according to claim 10,
wherein
one of R¹ is halogen, and another of R¹ is substituted or unsubstituted aryl;
R² is hydrogen;
X is —O—; and
Y is substituted or unsubstituted aryl.

18. A compound represented by formula (I):

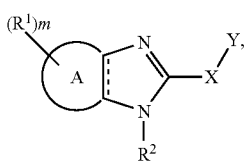

(I)

a pharmaceutically acceptable salt or solvate thereof, wherein a group represented by formula:

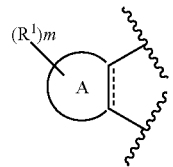

is a group represented by formula:

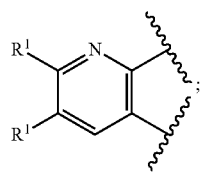

R¹ is each independently halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

R² is hydrogen, or substituted or unsubstituted alkyl;
X is —O—; and
Y is substituted or unsubstituted heterocyclyl.

* * * * *